(12) United States Patent
Cohen et al.

(10) Patent No.: US 9,057,734 B2
(45) Date of Patent: Jun. 16, 2015

(54) OPTOGENETIC PROBES FOR MEASURING MEMBRANE POTENTIAL

(75) Inventors: Adam E. Cohen, Cambridge, MA (US); Joel M. Kralj, Somerville, MA (US); Adam D. Douglass, Salt Lake City, UT (US)

(73) Assignee: President and Fellows of Harvard College, Cambridge, MA (US)

( * ) Notice: Subject to any disclaimer, the term of this patent is extended or adjusted under 35 U.S.C. 154(b) by 63 days.

(21) Appl. No.: 13/818,432

(22) PCT Filed: Aug. 23, 2011

(86) PCT No.: PCT/US2011/048793
§ 371 (c)(1),
(2), (4) Date: May 13, 2013

(87) PCT Pub. No.: WO2012/027358
PCT Pub. Date: Mar. 1, 2012

(65) Prior Publication Data
US 2013/0224756 A1    Aug. 29, 2013

Related U.S. Application Data

(60) Provisional application No. 61/376,049, filed on Aug. 23, 2010, provisional application No. 61/412,972, filed on Nov. 12, 2010.

(51) Int. Cl.
| | | |
|---|---|---|
| C12M 1/34 | (2006.01) |
| G01N 33/68 | (2006.01) |
| C07K 14/195 | (2006.01) |
| G01N 33/566 | (2006.01) |
| C12N 15/62 | (2006.01) |
| C12N 15/85 | (2006.01) |

(52) U.S. Cl.
CPC .......... *G01N 33/6872* (2013.01); *C07K 14/195* (2013.01); *G01N 33/566* (2013.01); *G01N 2333/726* (2013.01); *C12N 15/62* (2013.01); *C12N 15/625* (2013.01); *C12N 15/85* (2013.01)

(58) Field of Classification Search
CPC ................................................ G01N 33/6872
See application file for complete search history.

(56) References Cited

U.S. PATENT DOCUMENTS

| | | |
|---|---|---|
| 4,293,652 A | 10/1981 | Cohen |
| 5,290,699 A | 3/1994 | Oesterhelt et al. |
| 5,661,035 A | 8/1997 | Tsien et al. |
| 5,925,523 A | 7/1999 | Dove et al. |
| 6,107,066 A | 8/2000 | Tsien et al. |
| 6,200,759 B1 | 3/2001 | Dove et al. |
| 6,243,197 B1 | 6/2001 | Schalz |
| 6,885,492 B2 | 4/2005 | DeSimone et al. |
| 6,898,004 B2 | 5/2005 | Shimizu et al. |
| 6,972,892 B2 | 12/2005 | DeSimone et al. |
| 6,991,910 B2 | 1/2006 | Adorante et al. |
| 7,459,333 B2 | 12/2008 | Richards et al. |
| 7,560,709 B2 | 7/2009 | Kimura et al. |
| 7,736,897 B2 | 6/2010 | Tao et al. |
| 7,964,853 B2 | 6/2011 | Araya |
| 8,202,699 B2 | 6/2012 | Hegemann et al. |
| 8,401,609 B2 | 3/2013 | Deisseroth et al. |
| 8,532,398 B2 | 9/2013 | Filkins et al. |
| 8,562,658 B2 | 10/2013 | Shoham et al. |
| 8,580,937 B2 | 11/2013 | Spudich et al. |
| 8,603,790 B2 | 12/2013 | Deisseroth et al. |
| 8,617,876 B2 | 12/2013 | Farrar et al. |
| 8,647,870 B2 | 2/2014 | Hegemann et al. |
| 8,716,447 B2 | 5/2014 | Deisseroth et al. |
| 2002/0021490 A1 | 2/2002 | Kasahara et al. |
| 2005/0202398 A1 | 9/2005 | Hegemann et al. |
| 2009/0142852 A1 | 6/2009 | Friedrich et al. |
| 2009/0229669 A1 | 9/2009 | Birge et al. |
| 2009/0268511 A1 | 10/2009 | Birge et al. |
| 2011/0165681 A1 | 7/2011 | Boyden et al. |
| 2011/0200568 A1 | 8/2011 | Ikeda et al. |
| 2013/0170026 A1 | 7/2013 | Cohen et al. |
| 2014/0093907 A1 | 4/2014 | Miller et al. |
| 2014/0295413 A1 | 10/2014 | Cohen et al. |

FOREIGN PATENT DOCUMENTS

| | | |
|---|---|---|
| EP | 2 023 127 A1 | 2/2009 |
| EP | 2112510 A1 | 10/2009 |
| WO | WO 01/59446 A2 | 8/2001 |
| WO | 0183701 A2 | 11/2001 |

(Continued)

OTHER PUBLICATIONS

Sineshchekov et al, "Light-induced intramolecular charge movements in microbial rhodopsins in intact *E. coli* cells.", Photochemical & Photobiological Sciences: Official Journal of the European Photochemistry Association and the European Society for Photobiology, vol. 3, No. 6, pp. 548-554, 2004.
Dioumeav et al, "Proton transport by proteorhodopsin requires that the retinal Schiff base counterion Asp-97 be anionic", Biochemistry, American Chemical Society, vol. 42, No. 21, pp. 6582-6587, 2003.
Invitation to Pay Additional Fees for PCT/US2012/066303, mailed Mar. 21, 2013.
International Search Report and Written Opinion for PCT/US2012/066303, mailed May 28, 2013.
International Preliminary Report on Patentability for PCT/US2012/066303, mailed Jun. 5, 2014.
International Search Report and Written Opinion for PCT/US2011/048793, mailed Dec. 13, 2011.
International Preliminary Report on Patentability for PCT/US2011/048793, mailed Mar. 7, 2013,
GENBANK Submission; NIH/NCBI, Accession No. AAY82897. Ewers et al., Jun. 1, 2006.
GENBANK Submission; NIH/NCBI, Accesssion No. NC_010364.1. Pfeiffer et al., Jun. 10, 2013, 1 page.
GENBANK Submission; NIH/NCBI, Accesssion No. P29563. Uegaki et al., Oct. 29, 2014, 3 pages.
GENBANK Submission; NIH/NCBI, Accesssion No. P69051. Sugiyama et al., Oct. 29, 2014, 3 pages.

(Continued)

*Primary Examiner* — Albert Navarro
(74) *Attorney, Agent, or Firm* — Wolf, Greenfield & Sacks, P.C.; C. Hunter Baker; Gitrada A. Harmon

(57) ABSTRACT

The invention provides methods, cells and constructs for optical measurement of membrane potential. These methods can be used in cells that are not accessible to presently available methods using electrodes. The methods can be directed to, for example, high-throughput drug screening assays to determine agents that can affect membrane potential of a target cell.

35 Claims, 33 Drawing Sheets

(56) References Cited

FOREIGN PATENT DOCUMENTS

| WO | 2004063326 A2 | 7/2004 |
|---|---|---|
| WO | WO 2007/019398 A1 | 2/2007 |
| WO | 2007131180 A2 | 11/2007 |
| WO | WO 2008/149055 A1 | 12/2008 |
| WO | WO 2010/027446 A2 | 3/2010 |
| WO | 2010056970 A2 | 5/2010 |
| WO | WO 2012/027358 A1 | 3/2012 |

OTHER PUBLICATIONS

GENBANK Submission; NIH/NCBI, Accesssion No. P96787. Ibara et al., Oct. 29, 2014, 3 pages.
GENBANK Submission; NIH/NCBI, Accesssion No. Z35086.1. Seidel et al., Sep. 9, 2004, 2 pages.
GENBANK Submission; NIH/NCBI, Accesssion No. AAG01180. Idnurm et al., Mar. 21, 2001, 1 page.
GENBANK Submission; NIH/NCBI, Accesssion No. AAG42454. Wang et al., Dec. 26, 2000, 1 page.
GENBANK Submission; NIH/NCBI, Accesssion No. AF349981. Béjà et al., May 11, 2004, 1 page.
GENBANK Submission; NIH/NCBI, Accesssion No. AF349983. Béjà et al., May 11, 2004, 1 page.
GENBANK Submission; NIH/NCBI, Accesssion No. BAA06678. Tateno et al., Feb. 7, 1999, 1 page.
GENBANK Submission; NIH/NCBI, Accesssion No. GU045593.1. Chow et al., Jan. 6, 2010, 1 page.
GENBANK Submission; NIH/NCBI, Accesssion No. HM367071. Han et al., Apr. 13, 2011, 1 page.
GENBANK Submission; NIH/NCBI, Accesssion No. M11720.1. Dunn et al., Apr. 26, 1993, 1 page.
Akemann et al., Imaging neural circuit dynamics with a voltage-sensitive fluorescent protein. J Neurophysiol. Oct. 2012;108(8):2323-37. doi: 10.1152/jn.00452.2012. Epub Jul. 18, 2012.
Akemann et al., Two-photon voltage imaging using a genetically encoded voltage indicator. Sci Rep. 2013;3:2231. doi: 10.1038/srep02231.
Ataka et al., A genetically targetable fluorescent probe of channel gating with rapid kinetics. Biophys J. Jan. 2002;82(1 Pt 1):509-16.
Atasoy et al., A FLEX switch targets Channelrhodopsin-2 multiple cell types for imaging and long-range circuit mapping. J Neurosci. Jul. 9, 2008;28(28):7025-30. doi: 10.1523/JNEUROSCI.1954-08.2008.
Baker et al., Genetically encoded fluorescent sensors of membrane potential. Brain Cell Biol. Aug. 2008;36(1-4):53-67.
Baker et al., Three fluorescent protein voltage sensors exhibit low plasma membrane expression in mammalian cells. J. Neurosci Methods. Mar. 30, 2007;161(1):32-8.
Barondeau et al., Mechanism and energetics of green fluorescent protein chromophore synthesis revealed by trapped intermediate structures. Proc Natl Acad Sci U S A. Oct. 14, 2003;100(21):12111-6. Epub Oct. 1, 2003.
Bean, The action potential in mammalian central neurons. Nat Rev Neurosci. Jun. 2007;8(6):451-65.
Béjà et al., Proteorhodopsin phototrophy in the ocean. Nature Jun. 14, 2001;411(6839):786-9.
Béjà et al., Bacterial rhodopsin: evidence for a new type of phototrophy in the sea. Science. Sep. 15, 2000;289(5486):1902-6.
Bergo et al., Conformational changes detected in a sensor rhodopsin II-transducer complex. J Biol Chem. Sep. 19, 2003;278(38):36556-62.
Bernstein et al., Optogenetics and thermogenetics: technologies for controlling the activity of targeted cells within intact neural circuits. Curr Opin Neurobiol. Feb. 2012;22(1):61-71. doi: 10.1016/j.conb.2011.10.023. Epub Nov. 24, 2011.
Boyden et al., Millisecond-timescale, genetically targeted optical control of neural activity. Nat Neurosci. Sep. 2005;8(9):1263-8. Epub Aug. 14, 2005.
Brack et al., Picosecond time-resolved absorption and fluorescence dynamics in the artificial bacteriorhodopsin pigment BR6.11. Biophys J. Aug. 1993;65(2):964-72.
Canepari et al., Combining calcium imaging with other optical applications. Cold Spring Harbor Protocols. 2013. pbd. Top066167.
Cans et al., Positioning Lipid Membrane Domains in Giant Vesicles by Micro-organization of Aqueous Cytoplasm Mimic J. Am. Chem. Soc., 2008;130(23):7400-7406.
Cao et al., Genetically targeted optical electrophysiology in intact neural circuits. Cell. Aug. 15, 2013;154(4):904-13. doi: 10.1016/j.cell.2013.07.027. Epub Aug. 8, 2013.
Cardin et al., Targeted optogenetic stimulation and recording of neurons in vivo using cell-type-specific expression of Channelrhodopsin-2. Nat Protoc. Feb. 2010;5(2):247-54. doi: 10.1038/nprot.2009.228. Epub Jan. 21, 2010.
Carlson et al., Circular permutated red fluorescent proteins and calcium ion indicators based on mCherry. Protein Eng Des Sel. Dec. 2013;26(12):763-72. doi: 10.1093/proteins/gzt052. Epub Oct. 22, 2013.
Chanda et al., A hybrid approach to measuring electrical activity in genetically specified neurons. Nat Neurosci. Nov. 2005;8(11);1619-26. Epub Oct. 2, 2005.
Chen et al., Paired-pulse depression of unitary quantal amplitude at single hippocampal synapses. Proc Natl Acad Sci U S A Jan. 27, 2004;101(4):1063-8. Epub Jan. 13, 2004.
Chen et al., Ultrasensitive fluorescent proteins for imaging neuronal activity. Nature. Jul. 18, 2013;499(7458):295-300. doi: 10.1038/nature12354.
Chow et al., High-performance genetically targetable optical neural silencing by light-driven proton pumps. Nature. Jan. 7, 2010;463(7277):98-102.
Chung et al., Diagnostic potential of laser-induced autofluorescence emission in brain tissue. J Korean Med Sci. Apr. 1997;12(2):135-42.
Depry et al., Multiplexed visualization of dynamic signaling networks using genetically encoded fluorescent protein-based biosensors. Pflugers Arch. Mar. 2013;465(3):373-81, doi: 10.1007/s00424-012-1175-y. Epub Nov. 9, 2012.
Derossi et al., Cell internalization of the third helix of the Antennapedia homeodomain is receptor-independent. J Biol Chem. Jul. 26, 1996;271(30):18188-93.
Diester et al., An optogenetic toolbox designed for primates. Nat Neurosci Mar. 2011;14(3):387-97. doi: 10.1038/nn.2749. Epub Jan. 30, 2011.
Dioumaev et al., Proton transers in the photochemical reaction cycle of proteorhodopsin. Biochemistry. Apr. 30, 2002;41(17):5348-58.
Dooley et al., Imaging dynamic redox changes in mammalian cells with green fluorescent protein indicators. J Biol Chem May 21, 2004;279(21):22284-93. Epub Feb. 25, 2004.
Enami et al., Crystal structures of archaerhodopsin-1 and -2: Common structural motif in archaeal light-driven proton pumps. J Mol Biol. May 5, 2006;358(3):675-85.
Flock et al., Optical properties of Intralipid: a phantom medium for light propagation studies. Lasers Surg Med. 1992;12(5):510-9.
Friedrich et al., Proteorhodopsin is a light-driven proton pump with variable vectoriality. J Mol Biol. Aug. 30, 2002;321(5):821-38.
Fromherz et al., ANNINE-6plus, a voltage-sensitive dye with good solubility, strong membrane binding and high sensitivity. Eur Biophys J. Apr. 2008;37(4):509-14.
Furuta et al., Brominated 7-hydroxycoumarin-4-ylmethyls: photolabile protecting groups with biologically useful cross-sections for two photon photolysis. Proc Natl Acad Sci U S A. Feb. 16, 1999;96(4):1193-200.
Gabriel et al., Direct observation in the millisecond time range of fluorescent molecule asymmetrical interaction with the electropermeabilized cell membrane. Biophys J. Nov. 1997;73(5):2630-7.
Giovannoni et al., Proteorhodopsin in the ubiquitous marine bacterium SAR11, Nature. Nov. 3, 2005;438(7064);82-5.
Gong et al., Imaging neural spiking in brain tissue using FRET-opsin protein voltage sensors. Nat Commun Apr. 22, 2014;5:3674. doi: 10.1038/ncomms4674.
Gradinaru et al., Molecular and cellular approaches for diversifying and extending optogenetics. Cell Apr. 2, 2010;141(1):154-65.

(56) References Cited

OTHER PUBLICATIONS

Hochbaum et al., All-optical electrophysiology in mammalian neurons using engineered microbial rhodopsins. Nat Methods, Aug. 2014;11(8):825-33. doi: 10.1038/nmeth.3000. Epub Jun. 22, 2014.
Hoffmann et al., Photoactive mitochondria: in vivo transfer of a light-driven proton pump into the inner mitochondrial membrane of *Schizosaccharomyces pombe*. Proc Natl Acad Sci U S A Sep. 27, 1994;91(20):9367-71.
Hou et al., Temporal dynamics of microbial rhodopsin fluorescence reports absolute membrane voltage. Biophy J. Feb. 4, 2014;106(3):639-48. doi: 10.1016/j.bpj.2013.11.4493.
Huggins et al., Optimal experimental design for sampling voltage on dendritic trees in the low-SNR regime. J Comput Neurosci Apr. 2012;32(2):347-66. doi: 10.1007/s10827-011-0357-5. Epub Aug. 23, 2011.
Huys et al., Efficient estimation of detailed single-neuron models. J Neurophysiol. Aug. 2006;96(2):872-90. Epub Apr. 19, 2006.
Ichas et al., Mitochondria are excitable organelles capable of generating and conveying electrical and calcium signals. Cell. Jun. 27, 1997;89(7);1145-53.
Ihara et al., Evolution of the archeal rhodopsins: evolution rate changes by gene duplication and functional differentiation. J Mol Biol. Jan. 8, 1999;285(1):163-74.
Jin et al., Single action potentials and subthreshold electrical events imaged in neurons with a fluorescent protein voltage probe. Neuron Sep. 6, 2012;75(5):779-85. doi: 10.1016/j.neuron.2012.06.040.
Johnson et al., Localization of mitochondria in living cells with rhodamine 123. Proc Natl Acad Sci U S A. Feb. 1980;77(2):990-4.
Kirkton et al., Engineering biosynthetic excitable tissues from unexcitable cells for electrophysiological and cell therapy studies. Nat Commun. 2011;2:300. doi: 10.1038/ncomms1302.
Klapoetke et al., Independent optical excitation of distinct neural populations. Nat Methods. Mar. 2014;11(3):338-46. doi: 10.1038/nmeth.2836. Epub Feb. 9, 2014.
Kleinlogel et al., A gene-fusion strategy for stoichiometric and co-localized expression of light-gated membrane proteins. Nat Methods. Nov. 6, 2011;8(12):1083-8. doi: 10.1038/nmeth.1766.
Knöpfel et al., Toward the second generation of optogenetic tools. J Neurosci Nov. 10, 2010;30(45):14998-5004.
Kochendoerfer et al., How color visual pigments are tuned. Trends Biochem Sci. Aug. 1999;24(8):300-5.
Kolodner et al., Electric-field-induced Schiff-base deprotonation in D85N mutant bacteriorhodopsin. Proc Natl Acad Sci U S A. Oct. 15, 1996;93(21):11618-21.
Kralj et al., Electrical spiking in *Escherichia coli* probed with a fluorescent voltage-indicating protein. Science Jul. 15, 2011;333(6040):345-8.
Kralj et al., Optical recording of action potentials in mammalian neurons using a microbial rhodopsin. Nat methods. Nov. 27, 2011;9(1):90-5. doi: 10.1038/nmeth.1782.
Kramer et al., New photochemical tools for controlling neuronal activity. Curr Opin Neurobiol. Oct. 2009;19(5):544-52. doi: 10.1016/j.conb.2009.09.004. Epub Oct. 12, 2009.
Krauthamer et al., Action potential-induced fluorescence changes resolved with an optical fiber carrying excitation light. J Fluoresc. Dec. 1991;1(4):207-13.
Krylova et al., A versatile, bar-coded nuclear marketer/reporter for live cell fluorescent and multiplexed high content imaging. PLoS One. May 14, 2013;8(5):e63286. doi: 10.1371/journal.pone.0063286. Print 2013.
Kuner et al., A genetically encoded ratiometric indicator for chloride: capturing chloride transients in cultured hippocampal neurons. Neuron. Sep. 2000;27(3);447-59.
Lam et al., Improving FRET dynamic range with bright green and red fluorescent proteins. Nat Methods. Oct. 2012;9(10):1005-12. doi: 10.1038/nmeth.2171. Epub Sep. 9, 2012.
Lanyi, Proton translocation mechanism and energetics in the light-driven pump bacteriorhodopsin. Biochim Biophys Acta. Dec. 7, 1993;1183(2):241-61.

Lanyi, Bacteriorhodopsin. Annu Rev Physiol. 2004;66:665-88.
Lenz et al., First steps of retinal photoisomerization in proteorhodopsin. Biophys J. Jul. 1, 2006;91(1):255-62.
Liang et al., Patterned Photostimulation with Digital Micromirror Devices to Investigate Dendritic Integration Across Branch Points. J Vis Exp. 2011;49:e2003. Video Article.
Liem et al., The patch clamp technique. Neurosurgery Feb. 1995;36(2):382-92.
Lin et al., Brain tumor demarcation using optical spectroscopy: an in vitro. J Biomed Opt. Apr. 2000;5(2);214-20.
Lin et al., Characterization of engineered channelrhodopsin variants with improved properties and kinetics. Biophys J. Mar. 4, 2009;96(5):1803-14. doi: 10.1016/j.bpj.2008.11.034.
Lundby et al., Engineering of a genetically encodable fluorescent voltage sensor exploiting fast Ci-VSP voltage-sensing movements. PLoS One. Jun. 25, 2008;3(6);e2514. doi: 10.1371/journal.pone.0002514.
Ma et al., Role of ER export signals in controlling surface potassium channel numbers. Science. Jan. 12, 2001;291(5502):316-9.
MacLaurin et al., Mechanism of voltage-sensitive fluorescence in a microbial rhodopsin. Proc Natl Acad Sci U S A. Apr. 9, 2013;110(15):5939-44. doi: 10.1073/pnas.1215595110. Epub Mar. 25, 2013.
Man et al., Diversification and spectral tuning in marine proteorhodopsins. EMBO J. Apr. 15, 2003;22(8):1725-31.
Martinac et al., Ion channels in microbes. Physiol Rev. Oct. 2008;88(4):1449-90.
Maruyama et al., Detecting cells using non-negative matrix factorization on calcium imaging data. Neural Netw. Jul. 2014;55:11-9. doi: 10.1016/j.neunet.2014.03.007. Epub Mar. 24, 2014.
Marvin et al., An optimized fluorescent probe for visualizing glutamate neurotransmission. Nat Methods. Feb. 2013;10(2):162-70. doi: 10.1038/nmeth.2333. Epub Jan. 13, 2013.
Mattis et al., Principles for applying optogenetic tools derived from direct comparative analysis of microbial opsins. Nat Methods. Dec. 18, 2011;9(2):159-72. doi: 10.1038/nmeth.1808.
Melkonian et al., A light and electron microscopic study of *Scherffelia dubia*, a new member of the scaly green flagellates (Prasinophyceae). Nord J Bot. 1986;6(2):235-256.
Miller et al., Optically monitoring voltage in neurons by photo-induced electron transfer through molecular wires. Proc Natl Acad Sci U S A. Feb. 7, 2012;109(6):2114-9. doi: 10.1073/pnas.1120694109. Epub Jan. 24, 2012.
Mogi et al., Aspartic acid substitutions affect proton translocation by bacteriorhodopsin. Proc Natl Acad Sci U S A. Jan. 1988;85(12):4148-52.
Molokanova et al., Bright future of optical assays for ion channel drug discovery. Drug Discov Today Jan. 2008;13(1-2):14-22.
Muga et al., Membrane interaction and conformational properties of the putative fusion peptide of PH-30, a protein active in sperm-egg fusion. Biochemistry. Apr. 19, 1994;33(15):4444-8.
Mukamel et al., Automated analysis of cellular signals from large-scale calcium imaging data. Neuron. Sep. 24, 2009;63(6):747-60. doi: 10.1016/j.neuron.2009.08.009.
Murata et al., Phosphoinositide phosphatase activity coupled to an intrinsic voltage sensor. Nature. Jun. 30, 2005;435(7046):1239-43. Epub May 18, 2005.
Mutoh et al., Genetically engineered fluorescent voltage reports. ACS Chem Neurosci. Aug. 15, 2012;3(8):585-92. doi: 10.1021/cu300041b. Epub Jun. 6, 2012.
Mutoh et al., Spectrally-resolved response properties of the three most advanced FRET based fluorescent protein voltage probes. PLoS One. 2009;4(2):e4555.
Nagel et al., Light activation of channelrhodopsin-2 in excitable cells of *Caenorhabditis elegans* triggers rapid behavioral responses. Curr Biol. Dec. 20, 2005;15(24):2279-84.
Neutze et al., Bacteriorhodopsin: a high-resolution sructural view of vectorial proton transport. Biochim Biophys Acta. Oct. 11, 2002;1565(2):144-67.
Oldach et al., Genetically encoded fluorescent biosensors for live-cell visualization of protein phosphorylation. Chem Biol. Feb. 20, 2014;21(2):186-97. doi: 10.1016/j.chembiol.2013.12.012. Epub Jan. 30, 2014.

(56) References Cited

OTHER PUBLICATIONS

Park et al., Screening fluorescent voltage indicators with spontaneously spiking HEK cells. PLoS One. Dec. 31, 2013;8(12):e85221. doi: 10.1371/journal.pone.0085221. eCollection 2013.

Peron et al., From cudgel to scalpel: toward precise neural control with optogenetics. Nat Methods. Jan. 2011;8(1):30-4. doi: 10.1038/nmeth.f.325. Epub Dec. 20, 2010.

Perron et al., Second and third generation voltage-sensitive fluorescent proteins for monitoring membrane potential. Front Mol Neurosci. Jun. 22, 2009;2:5. doi: 10.3389/neuro.02.005.2009. eCollection 2009.

Popovic et al., The spatio-temporal characteristics of action potential initiation in layer 5 pyramidal neurons: a voltage imaging study. J Physiol. Sep. 1, 2011;589(Pt 17):4167-87. doi: 10.1113/jphysiol.2011.209015. Epub Jun. 13, 2011.

Przybylo et al., Fluorescence techniques for determination of the membrane potentials in high throughput screening. J Fluoresc. Nov. 2010;20(6):1139-57. doi: 10.1007/s10895-010-0665-6.

Puchar et al., Measuring the induced membrane voltage with Di-8-ANEPPS. J Vis Exp. Nov. 19, 2009;(33). pii: 1659, doi: 10.3791/1659. Video Article.

Rousso et al., pKa of the protonated Schiff base and aspartic 85 in the bacteriorhodopsin binding site is controlled by a specific geometry between the two residues. Biochemistry. Sep. 19, 1995;34(37):12059-65.

Sakai et al., Design and characterization of a DNA-encoded, voltage-sensitive fluorescent protein. Eur J Neurosci. Jun. 2001;13(12):2314-8.

San Martin et al., Imaging mitochondrial flux in single cells with a FRET sensor for pyruvate.PLoS One. Jan. 21, 2014;9(1):e85780. doi: 10.1371/journal.pone.0085780. eCollection 2014.

Scanziani et al., Electrophysiology in the age of light. Nature. Oct. 15, 2009;461(7266):930-9. doi: 10.1038/nature08540.

Schoenenberger et al., Optimizing the spatial resolution of Channelrhodopsin-2 activation. Brain Cell Biol. Aug. 2008;36(1-4):119-27. doi: 10.1007/s11068-008-9025-8. Epub Jul. 25, 2008.

Shaner et al., A guide to choosing fluorescent proteins. Nat Methods Dec. 2005;2(12):905-9.

Sheves et al., Controlling the pKa of the bacteriorhodopsin Schiff base by use of artificial retinal analogues. Proc Natl Acad Sci U S A. May 1986;83(10):3262-6.

Siegel et al., A genetically encoded optical probe of membrane voltage. Neuron. Oct. 1997;19(4):735-41.

Sjulson et al., Rational optimzation and imaging in vivo of a genetically encoded optical voltage reporter. J Neurosci May 21, 2008;28(21):5582-93.

Soppa et al., Bacteriorhodopsin mutants of *Halobacterium* sp. GRB. II. Characterization of mutants. J Biol Chem. Aug. 5, 1989;264(22):13049-56.

St-Pierre et al., High-fidelity optical reporting of neuronal electrical activity with an ultrafast fluorescent voltage sensor. Nat Neurosci Jun. 2014;17(6):884-9. doi: 10.1038/nm.3709. Epub Apr. 22, 2014.

Stuart et al., Active propagation of somatic action potentials into neocortical pyramidal cell dendrites. Nature. Jan. 6, 1994;367(6458):69-72.

Subramaniam et al., Protonation state of Asp (Glu)-85 regulates the purple-to-blue transition in bacteriorhodopsin mutants Arg-82—Ala and Asp-85—Glu: the blue form is inactive in proton translocation. Proc Natl Acad U S A. Feb. 1990;87(3):1013-7.

Takahashi et al., Light-addressed in single-neuron stimulation in dissociated neuronal cultures with sparse expression of ChR2. Biosystems. Feb. 2012;107(2):106-12. doi: 10.1016/j.biosystems.2011.10.002. Epub Oct. 14, 2011.

Tantama et al., Imaging energy status in live cells with a fluorescent biosensor of the intracellular ATP-to-ADP ratio. Nat Commun 2013;4:2550. doi: 10.1038/ncomms3550.

Tateno et al., The novel ion pump rhodopsins from *Haloarcula* form a family independent from both the bacteriorhodopsin and archaerhodopsin families/tribes. Arch Biochem Biophys. Nov. 15, 1994;315(1):127-32.

Tsuda et al., Probing the function of neuronal populations: combining micromirror-based optogenetic photostimulation with voltage-sensiive dye imaging. Neurosci Res. Jan. 2013;75(1):76-81. doi: 10.1016/j.neures.2012.11.006. Epub Dec. 17, 2012.

Venkatachalam et al., Flash memory: photochemical imprinting of neuronal action potentials onto a microbial rhodopsin. J Am Chem Soc. Feb. 12, 2014;136(6):2529-37. doi: 10.1021/ja411338t. Epub Jan. 27, 2014.

Verburg et al., Mitochondrial membrane potential in axons increases with local nerve growth factor or semaphorin signaling. J Neurosci. Aug. 13, 2008;28(33):8306-15.

Vogt et al., Combining membrane potential imaging with L-glutamate or GABA photorelease. PLoS One. 2011;6(10):e24911. doi: 10.1371/journal.pone.0024911. Epub Oct. 11, 2011.

Wachter, The family of GFP-like proteins: structure, function, photophysics and biosensor applications. Introduction and perspective. Photochem Photobiol. Mar.-Apr. 2006;82(2):339-44.

Wang et al., Laser-evoked synaptic transmission in cultured hippocampal neurons expressing channelrhodopsin-2 delivered by adeno-associated virus. J Neurosci Methods. Oct. 15, 2009;183(2):165-75. doi: 10.1016/j.jneumeth.2009.06.024. Epub Jun. 26, 2009.

Wardill et al., A neuron-based screening platform for optimizing genetically-encoded calcium indicators. PLoS One. Oct. 14, 2013;8(10):e77728. doi: 10.1371/journal.pone.0077728. eCollection 2013.

Waschuk et al., *Leptosphaeria* rhodopsin: bacteriorhodopsin-like proton pump from a eukaryote. Proc Natl Acad Sci U S A. May 10, 2005;102(19):6879-83. Epub Apr. 28, 2005.

White, Viral and cellular membrane fusion proteins. Annu Rev Physiol. 1990;52:675-97.

White, Membrane fusion. Science. Nov. 6, 1992;258(5084):917-24.

Williams et al., Computational optogenetics: empirically-derived voltage- and light-sensitive channelrhodopsin-2 model. PLoS Comput Biol. 2013;9(9):e1003220. doi: 10.1371/journal.pcbi.1003220. Epub Sep. 12, 2013.

Wu et al., Improved orange and red $Ca^{2+}$ indicators and photophysical considerations for optogenetic applications. ACS Chem Neurosci. Jun. 19, 2013;4(6):963-72. doi: 10.1021/cn400012b. Epub Mar. 19, 2013.

Yan et al., Palette of fluorinated voltage-sensitive hemicyanine dyes. Proc Natl Acad Sci U S A. Dec. 11, 2012;109(50):20443-8. doi: 10.1073/pnas.1214850109. Epub Nov. 20, 2012.

Yizhar et al., Optogenetics in neural systems. Neuron. Jul. 14, 2011;71(1):9-34. doi: 10.1016/j.neuron.2011.06.004.

Zhao et al., An expanded palette of genetically encoded $Ca^{2+}$ indicators. Science. Sep. 30, 2011;333(6051):1888-91. doi: 10.1126/science.1208592. Epub Sep. 8, 2011.

Zhao et al., Molecular evolution by staggered extension process (StEP) in vitro recombination. Nat Biotechnol. Mar. 1998;16(3):258-61.

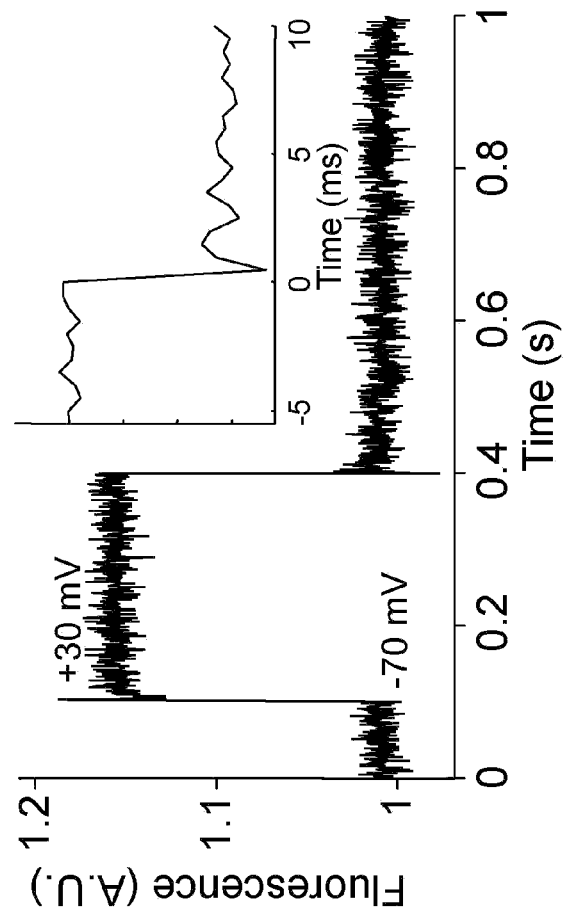
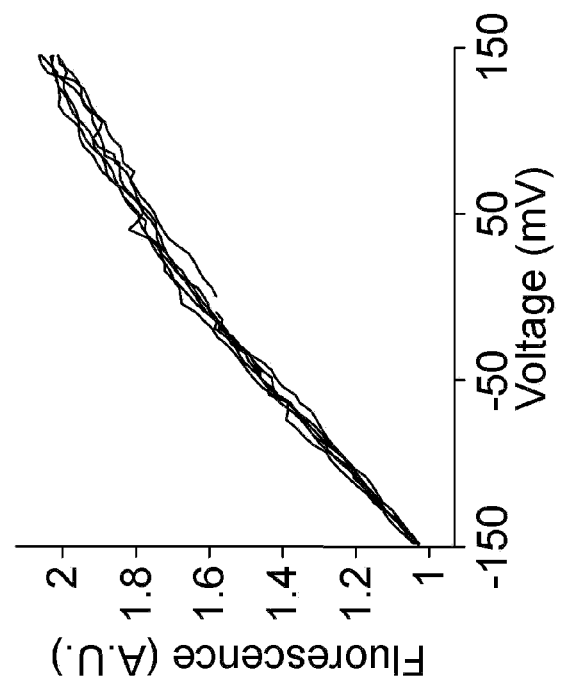
FIG. 6D
FIG. 6E

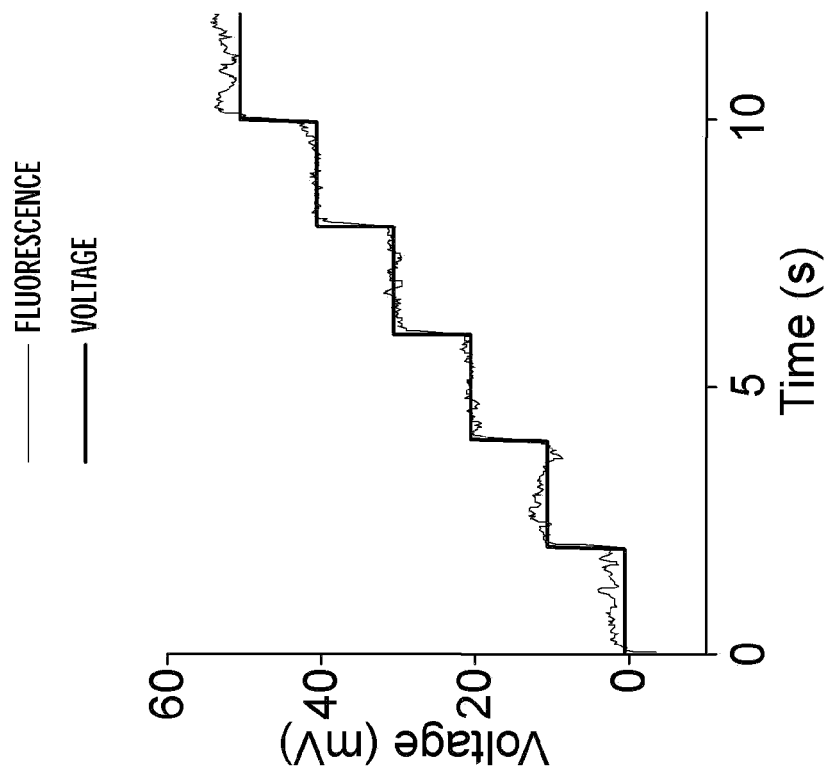
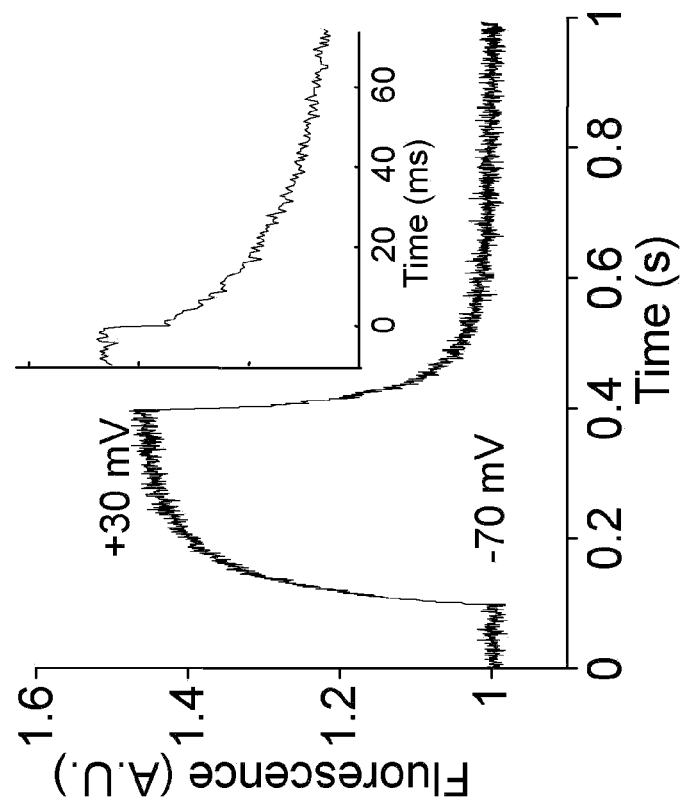
FIG. 8D
FIG. 8C

SEQUENCE LISTING

<160> NUMBER OF SEQ ID NOS: 87

<210> SEQ ID NO 1
<211> LENGTH: 8
<212> TYPE: PRT
<213> ORGANISM: Unknown
<220> FEATURE:
<223> OTHER INFORMATION: Description of Unknown: Nuclear
      import signal peptide

<400> SEQUENCE: 1

Pro Pro Lys Lys Lys Arg Lys Val
1               5

<210> SEQ ID NO 2
<211> LENGTH: 28
<212> TYPE: PRT
<213> ORGANISM: Unknown
<220> FEATURE:
<223> OTHER INFORMATION: Description of Unknown: Endoplasmic
      reticulum import signal peptide

<400> SEQUENCE: 2

Met Ser Phe Val Ser Leu Leu Leu Val Gly Ile Leu Phe Trp Ala Thr
1               5                   10                  15

Gly Ala Glu Asn Leu Thr Lys Cys Glu Val Phe Asn
            20                  25

<210> SEQ ID NO 3
<211> LENGTH: 4
<212> TYPE: PRT
<213> ORGANISM: Unknown
<220> FEATURE:
<223> OTHER INFORMATION: Description of Unknown: Endoplasmic
      reticulum retention signal peptide

<400> SEQUENCE: 3

Lys Asp Glu Leu
1

<210> SEQ ID NO 4
<211> LENGTH: 3
<212> TYPE: PRT

```
<213> ORGANISM: Unknown
<220> FEATURE:
<223> OTHER INFORMATION: Description of Unknown: Peroxisome
      import signal peptide

<400> SEQUENCE: 4

Ser Lys Leu
1

<210> SEQ ID NO 5
<211> LENGTH: 9
<212> TYPE: PRT
<213> ORGANISM: Unknown
<220> FEATURE:
<223> OTHER INFORMATION: Description of Unknown: Peroxisome
      import signal peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (2)..(2)
<223> OTHER INFORMATION: Leu, Val or Ile
<220> FEATURE:
<221> NAME/KEY: MOD_RES
<222> LOCATION: (3)..(7)
<223> OTHER INFORMATION: Any amino acid
<220> FEATURE:
<221> NAME/KEY: MOD_RES
<222> LOCATION: (8)..(8)
<223> OTHER INFORMATION: His or Gln
<220> FEATURE:
<221> NAME/KEY: MOD_RES
<222> LOCATION: (9)..(9)
<223> OTHER INFORMATION: Leu, Ala or Phe

<400> SEQUENCE: 5

Xaa Xaa Xaa Xaa Xaa Xaa Xaa Xaa Xaa
1               5

<210> SEQ ID NO 6
<211> LENGTH: 25
<212> TYPE: PRT
<213> ORGANISM: Unknown
<220> FEATURE:
<223> OTHER INFORMATION: Description of Unknown: Mitochondrial
      inner membrane peptide

<400> SEQUENCE: 6

Met Leu Ser Leu Arg Asn Ser Ile Arg Phe Phe Lys Pro Ala Thr Arg
1               5                   10                  15

Thr Leu Cys Ser Ser Arg Tyr Leu Leu
            20                  25

<210> SEQ ID NO 7
<211> LENGTH: 26
<212> TYPE: PRT
<213> ORGANISM: Unknown
<220> FEATURE:
<223> OTHER INFORMATION: Description of Unknown: Mitochondrial
      outer membrane peptide

<400> SEQUENCE: 7

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25
```

```
<210> SEQ ID NO 8
<211> LENGTH: 21
<212> TYPE: PRT
<213> ORGANISM: Unknown
<220> FEATURE:
<223> OTHER INFORMATION: Description of Unknown: Plasma
      membrane cytosolic face peptide

<400> SEQUENCE: 8

Met Gly Cys Ile Lys Ser Lys Arg Lys Asp Asn Leu Asn Asp Gly
1               5                   10                  15

Val Asp Met Lys Thr
            20

<210> SEQ ID NO 9
<211> LENGTH: 15
<212> TYPE: PRT
<213> ORGANISM: Unknown
<220> FEATURE:
<223> OTHER INFORMATION: Description of Unknown: Plasma
      membrane cytosolic face peptide

<400> SEQUENCE: 9

Lys Lys Lys Lys Lys Lys Ser Lys Thr Lys Cys Val Ile Met
1               5                   10                  15

<210> SEQ ID NO 10
<211> LENGTH: 77
<212> TYPE: PRT
<213> ORGANISM: Homo sapiens

<400> SEQUENCE: 10

Met Ala Val Arg Gln Ala Leu Gly Arg Gly Leu Gln Leu Gly Arg Ala
1               5                   10                  15

Leu Leu Leu Arg Phe Thr Gly Lys Pro Gly Arg Ala Tyr Gly Leu Gly
                20                  25                  30

Arg Pro Gly Pro Ala Ala Gly Cys Val Arg Gly Glu Arg Pro Gly Trp
            35                  40                  45

Ala Ala Gly Pro Gly Ala Glu Pro Arg Val Gly Leu Gly Leu Pro
        50                  55                  60

Asn Arg Leu Arg Phe Phe Arg Gln Ser Val Ala Gly Leu
65                  70                  75

<210> SEQ ID NO 11
<211> LENGTH: 31
<212> TYPE: PRT
<213> ORGANISM: Homo sapiens

<400> SEQUENCE: 11

Met Ala Ala Pro Arg Ala Gly Arg Gly Ala Gly Trp Ser Leu Arg Ala
1               5                   10                  15

Trp Arg Ala Leu Gly Gly Ile Arg Trp Gly Arg Arg Pro Arg Leu
                20                  25                  30

<210> SEQ ID NO 12
<211> LENGTH: 19
<212> TYPE: PRT
<213> ORGANISM: Homo sapiens

<400> SEQUENCE: 12

Met Phe Ala Asp Arg Trp Leu Phe Ser Thr Asn His Lys Asp Ile Gly
1               5                   10                  15

Thr Leu Tyr
```

<210> SEQ ID NO 13
<211> LENGTH: 26
<212> TYPE: PRT
<213> ORGANISM: Homo sapiens

<400> SEQUENCE: 13

Met Ala His Ala Ala Gln Val Gly Leu Gln Asp Ala Thr Ser Pro Ile
1               5                   10                  15

Met Glu Glu Leu Ile Thr Phe His Asp His
            20                  25

<210> SEQ ID NO 14
<211> LENGTH: 29
<212> TYPE: PRT
<213> ORGANISM: Homo sapiens

<400> SEQUENCE: 14

Met Ser Thr Ala Ala Leu Ile Thr Leu Val Arg Ser Gly Gly Asn Gln
1               5                   10                  15

Val Arg Arg Arg Val Leu Leu Ser Ser Arg Leu Leu Gln
            20                  25

<210> SEQ ID NO 15
<211> LENGTH: 43
<212> TYPE: PRT
<213> ORGANISM: Homo sapiens

<400> SEQUENCE: 15

Met Leu Ser Val Arg Val Ala Ala Ala Val Val Arg Ala Leu Pro Arg
1               5                   10                  15

Arg Ala Gly Leu Val Ser Arg Asn Ala Leu Gly Ser Ser Phe Ile Ala
            20                  25                  30

Ala Arg Asn Phe His Ala Ser Asn Thr His Leu
        35                  40

<210> SEQ ID NO 16
<211> LENGTH: 41
<212> TYPE: PRT
<213> ORGANISM: Homo sapiens

<400> SEQUENCE: 16

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly
        35                  40

<210> SEQ ID NO 17
<211> LENGTH: 18
<212> TYPE: PRT
<213> ORGANISM: Unknown
<220> FEATURE:
<223> OTHER INFORMATION: Description of Unknown: Beta2
      nicotinic acetylcholine receptor peptide

<400> SEQUENCE: 17

Met Arg Gly Thr Pro Leu Leu Leu Val Val Ser Leu Phe Ser Leu Leu
1               5                   10                  15

Gln Asp

<210> SEQ ID NO 18
<211> LENGTH: 7
<212> TYPE: PRT
<213> ORGANISM: Unknown
<220> FEATURE:
<223> OTHER INFORMATION: Description of Unknown: Endoplasmic
      reticulum export motif peptide

<400> SEQUENCE: 18

Phe Cys Tyr Glu Asn Glu Val
1               5

<210> SEQ ID NO 19
<211> LENGTH: 18
<212> TYPE: PRT
<213> ORGANISM: Unknown
<220> FEATURE:
<223> OTHER INFORMATION: Description of Unknown: Golgi
      export peptide

<400> SEQUENCE: 19

Arg Ser Arg Phe Val Lys Lys Asp Gly His Cys Asn Val Gln Phe Ile
1               5                   10                  15

Asn Val

<210> SEQ ID NO 20
<211> LENGTH: 20
<212> TYPE: PRT
<213> ORGANISM: Unknown
<220> FEATURE:
<223> OTHER INFORMATION: Description of Unknown: Membrane
      localization peptide

<400> SEQUENCE: 20

Lys Ser Arg Ile Thr Ser Glu Gly Glu Tyr Ile Pro Leu Asp Gln Ile
1               5                   10                  15

Asp Ile Asn Val
            20

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 21

His His His His His His
1               5

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttatgccagg tacgccaact ggctgtttac cac                                33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gtggtaaaca gccagttggc gtacctggca taa                                33

<210> SEQ ID NO 24
<211> LENGTH: 7933
<212> TYPE: DNA
<213> ORGANISM: Lentivirus sp.

<400> SEQUENCE: 24

| | | |
|---|---|---|
| gaattcgata tcaagcttat cgataatcaa cctctggatt acaaaatttg tgaaagattg | 60 |
| actggtattc ttaactatgt tgctcctttt acgctatgtg gatacgctgc tttaatgcct | 120 |
| ttgtatcatg ctattgcttc ccgtatggct ttcattttct cctccttgta taaatcctgg | 180 |
| ttgctgtctc tttatgagga gttgtggccc gttgtcaggc aacgtggcgt ggtgtgcact | 240 |
| gtgtttgctg acgcaacccc cactggttgg ggcattgcca ccacctgtca gctccttttcc | 300 |
| gggactttcg ctttccccct ccctattgcc acggcggaac tcatcgccgc ctgccttgcc | 360 |
| cgctgctgga caggggctcg gctgttgggc actgacaatt ccgtggtgtt gtcggggaaa | 420 |
| tcatcgtcct ttccttggct gctcgcctgt gttgccacct ggattctgcg cgggacgtcc | 480 |
| ttctgctacg tcccttcggc cctcaatcca gcggaccttc cttcccgcgg cctgctgccg | 540 |
| gctctgcggc ctcttccgcg tcttcgcctt cgccctcaga cgagtcggat ctccctttgg | 600 |
| gccgcctccc cgcatcgata ccgtcgacct cgagacctag aaaaacatgg agcaatcaca | 660 |
| agtagcaata cagcagctac caatgctgat tgtgcctggc tagaagcaca agaggaggag | 720 |
| gaggtgggtt ttccagtcac acctcaggta ccttttaagac caatgactta caaggcagct | 780 |
| gtagatctta gccactttt aaaagaaaag gggggactgg aagggctaat tcactcccaa | 840 |
| cgaagacaag atatccttga tctgtggatc taccacacac aaggctactt ccctgattgg | 900 |
| cagaactaca caccagggcc agggatcaga tatccactga cctttggatg gtgctacaag | 960 |
| ctagtaccag ttgagcaaga gaaggtagaa gaagccaatg aaggagagaa cacccgcttg | 1020 |
| ttacaccctg tgagcctgca tgggatggat gacccggaga gagaagtatt agagtggagg | 1080 |
| tttgacagcc gcctagcatt tcatcacatg gcccgagagc tgcatccgga ctgtactggg | 1140 |
| tctctctggt tagaccagat ctgagcctgg gagctctctg gctaactagg gaacccactg | 1200 |
| cttaagcctc aataaagctt gccttgagtg cttcaagtag tgtgtgcccg tctgttgtgt | 1260 |
| gactctggta actagagatc cctcagaccc ttttagtcag tgtggaaaat ctctagcagg | 1320 |
| gcccgtttaa acccgctgat cagcctcgac tgtgccttct agttgccagc catctgttgt | 1380 |
| ttgcccctcc cccgtgcctt ccttgaccct ggaaggtgcc actcccactg tcctttccta | 1440 |
| ataaaatgag gaaattgcat cgcattgtct gagtaggtgt cattctattc tggggggtgg | 1500 |
| ggtgggcag acagcaagg gggaggattg ggaagacaat agcaggcatg ctgggatgc | 1560 |
| ggtgggctct atggcttctg aggcggaaag aaccagctgg ggctctaggg gtatccccca | 1620 |
| cgcgccctgt agcggcgcat taagcgcggc gggtgtggtg gttacgcgca gcgtgaccgc | 1680 |
| tacacttgcc agcgccctag cgcccgctcc tttcgctttc ttcccttcct ttctcgccac | 1740 |
| gttcgccggc tttccccgtc aagctctaaa tcggggctc cctttagggt tccgatttag | 1800 |
| tgctttacgg cacctcgacc ccaaaaaact tgattaggt gatggttcac gtagtgggcc | 1860 |
| atcgccctga tagacggttt ttcgcccttt gacgttggag tccacgttct ttaatagtgg | 1920 |

```
actcttgttc caaactggaa caacactcaa ccctatctcg gtctattctt ttgatttata    1980
agggattttg ccgatttcgg cctattggtt aaaaaatgag ctgatttaac aaaaatttaa    2040
cgcgaattaa ttctgtggaa tgtgtgtcag ttagggtgtg aaagtcccc aggctcccca     2100
gcaggcagaa gtatgcaaag catgcatctc aattagtcag caaccaggtg tggaaagtcc    2160
ccaggctccc cagcaggcag aagtatgcaa agcatgcatc tcaattagtc agcaaccata    2220
gtcccgcccc taactccgcc catcccgccc ctaactccgc ccagttccgc ccattctccg    2280
ccccatggct gactaatttt ttttatttat gcagaggccg aggccgcctc tgcctctgag    2340
ctattccaga agtagtgagg aggctttttt ggaggcctag gcttttgcaa aaagctcccg    2400
ggagcttgta tatccatttt cggatctgat cagcacgtgt tgacaattaa tcatcggcat    2460
agtatatcgg catagtataa tacgacaagg tgaggaacta aaccatggcc aagttgacca    2520
gtgccgttcc ggtgctcacc gcgcgcgacg tcgccggagc ggtcgagttc tggaccgacc    2580
ggctcgggtt ctcccgggac ttcgtggagg acgacttcgc cggtgtggtc cgggacgacg    2640
tgaccctgtt catcagcgcg gtccaggacc aggtggtgcc ggacaacacc ctggcctggg    2700
tgtgggtgcg cggcctggac gagctgtacg ccgagtggtc ggaggtcgtg tccacgaact    2760
tccgggacgc ctccgggccg gccatgaccg agatcggcga gcagccgtgg gggcgggagt    2820
tcgccctgcg cgaccggccc ggcaactgcg tgcacttcgt ggccgaggag caggactgac    2880
acgtgctacg agatttcgat tccaccgccg ccttctatga aaggttgggc ttcggaatcg    2940
ttttccggga cgccggctgg atgatcctcc agcgcgggga tctcatgctg gagttcttcg    3000
cccacccccaa cttgtttatt gcagcttata atggttacaa ataaagcaat agcatcacaa    3060
atttcacaaa taaagcattt ttttcactgc attctagttg tggtttgtcc aaactcatca    3120
atgtatctta tcatgtctgt ataccgtcga cctctagcta gagcttggcg taatcatggt    3180
catagctgtt tcctgtgtga aattgttatc cgctcacaat tccacacaac atacgagccg    3240
gaagcataaa gtgtaaagcc tggggtgcct aatgagtgag ctaactcaca ttaattgcgt    3300
tgcgctcact gcccgctttc cagtcgggaa acctgtcgtg ccagctgcat taatgaatcg    3360
gccaacgcgc ggggagaggc ggtttgcgta ttgggcgctc ttccgcttcc tcgctcactg    3420
actcgctgcg ctcggtcgtt cggctgcggc gagcggtatc agctcactca aaggcggtaa    3480
tacggttatc cacagaatca ggggataacg caggaaagaa catgtgagca aaaggccagc    3540
aaaaggccag gaaccgtaaa aaggccgcgt tgctggcgtt tttccatagg ctccgccccc    3600
ctgacgagca tcacaaaaat cgacgctcaa gtcagaggtg gcgaaacccg acaggactat    3660
aaagatacca ggcgtttccc cctggaagct ccctcgtgcg ctctcctgtt ccgaccctgc    3720
cgcttaccgg atacctgtcc gcctttctcc cttcgggaag cgtggcgctt tctcatagct    3780
cacgctgtag gtatctcagt tcggtgtagg tcgttcgctc caagctgggc tgtgtgcacg    3840
aaccccccgt tcagcccgac cgctgcgcct tatccggtaa ctatcgtctt gagtccaacc    3900
cggtaagaca cgacttatcg ccactggcag cagccactgg taacaggatt agcagagcga    3960
ggtatgtagg cggtgctaca gagttcttga agtggtggcc taactacggc tacactagaa    4020
gaacagtatt tggtatctgc gctctgctga agccagttac cttcggaaaa agagttggta    4080
gctcttgatc cggcaaacaa accaccgctg gtagcggtgg tttttttgtt tgcaagcagc    4140
agattacgcg cagaaaaaaa ggatctcaag aagatccttt gatcttttct acggggtctg    4200
acgctcagtg gaacgaaaac tcacgttaag ggattttggt catgagatta tcaaaaagga    4260
```

```
tcttcaccta gatccttta aattaaaaat gaagttttaa atcaatctaa agtatatatg    4320
agtaaacttg gtctgacagt taccaatgct taatcagtga ggcacctatc tcagcgatct    4380
gtctatttcg ttcatccata gttgcctgac tccccgtcgt gtagataact acgatacggg    4440
agggcttacc atctggcccc agtgctgcaa tgataccgcg agaccacgc tcaccggctc     4500
cagatttatc agcaataaac cagccagccg aagggccga gcgcagaagt ggtcctgcaa    4560
ctttatccgc ctccatccag tctattaatt gttgccggga agctagagta agtagttcgc    4620
cagttaatag tttgcgcaac gttgttgcca ttgctacagg catcgtggtg tcacgctcgt    4680
cgtttggtat ggcttcattc agctccggtt cccaacgatc aaggcgagtt acatgatccc    4740
ccatgttgtg caaaaaagcg gttagctcct tcggtcctcc gatcgttgtc agaagtaagt    4800
tggccgcagt gttatcactc atggttatgg cagcactgca taattctctt actgtcatgc    4860
catccgtaag atgcttttct gtgactggtg agtactcaac caagtcattc tgagaatagt    4920
gtatgcggcg accgagttgc tcttgcccgg cgtcaatacg gataatacc gcgccacata    4980
gcagaacttt aaaagtgctc atcattggaa aacgttcttc gggcgaaaa ctctcaagga    5040
tcttaccgct gttgagatcc agttcgatgt aacccactcg tgcacccaac tgatcttcag    5100
catcttttac tttcaccagc gtttctgggt gagcaaaaac aggaaggcaa aatgccgcaa    5160
aaaagggaat aagggcgaca cggaaatgtt gaatactcat actcttcctt tttcaatatt    5220
attgaagcat ttatcagggt tattgtctca tgagcggata catatttgaa tgtatttaga    5280
aaaataaaca ataggggtt ccgcgcacat ttccccgaaa agtgccacct gactcgacgg     5340
atcgggagat ctcccgatcc cctatggtgc actctcagta caatctgctc tgatgccgca    5400
tagttaagcc agtatctgct ccctgcttgt gtgttggagg tcgctgagta gtgcgcgagc    5460
aaaatttaag ctacaacaag gcaaggcttg accgacaatt gcatgaagaa tctgcttagg    5520
gttaggcgtt ttgcgctgct tcgcgatgta cgggccagat atacgcgttg acattgatta    5580
ttgactagtt attaatagta atcaattacg gggtcattag ttcatagccc atatatggag    5640
ttccgcgtta cataacttac ggtaaatggc ccgcctggct gaccgcccaa cgacccccgc    5700
ccattgacgt caataatgac gtatgttccc atagtaacgc caatagggac tttccattga    5760
cgtcaatggg tggagtattt acggtaaact gcccacttgg cagtacatca agtgtatcat    5820
atgccaagta cgccccctat tgacgtcaat gacggtaaat ggcccgcctg gcattatgcc    5880
cagtacatga ccttatggga ctttcctact tggcagtaca tctacgtatt agtcatcgct    5940
attaccatgg tgatgcggtt ttggcagtac atcaatgggc gtggatagcg gtttgactca    6000
cggggatttc caagtctcca ccccattgac gtcaatggga gtttgttttg gcaccaaaat    6060
caacgggact ttccaaaatg tcgtaacaac tccgccccat tgacgcaaat gggcggtagg    6120
cgtgtacggt gggaggtcta tataagcagc gcgttttgcc tgtactgggt ctctctggtt    6180
agaccagatc tgagcctggg agctctctg ctaactaggg aacccactgc ttaagcctca     6240
ataaagcttg ccttgagtgc ttcaagtagt gtgtgcccgt ctgttgtgtg actctggtaa    6300
ctagagatcc ctcagaccct tttagtcagt gtggaaaatc tctagcagtg gcgcccgaac    6360
agggacttga aagcgaaagg gaaaccagag gagctctctc gacgcaggac tcggcttgct    6420
gaagcgcgca cggcaagagg cgaggggcgg cgactggtga gtacgccaaa aatttgact    6480
agcggaggct agaaggagag atgggtgc gagagcgtca gtattaagcg gggagaatt       6540
agatcgcgat gggaaaaaat tcggttaagg ccagggggaa agaaaaaata taaattaaaa    6600
catatagtat gggcaagcag ggagctagaa cgattcgcag ttaatcctgg cctgttagaa    6660
```

```
acatcagaag gctgtagaca aatactggga cagctacaac catcccttca gacaggatca    6720
gaagaactta gatcattata taatacagta gcaaccctct attgtgtgca tcaaaggata    6780
gagataaaag acaccaagga agctttagac aagatagagg aagagcaaaa caaaagtaag    6840
accaccgcac agcaagcggc cgctgatctt cagacctgga ggaggagata tgagggacaa    6900
ttggagaagt gaattatata aatataaagt agtaaaaatt gaaccattag gagtagcacc    6960
caccaaggca aagagaagag tggtgcagag agaaaaaaga gcagtgggaa taggagcttt    7020
gttccttggg ttcttgggag cagcaggaag cactatgggc gcagcgtcaa tgacgctgac    7080
ggtacaggcc agacaattat tgtctggtat agtgcagcag cagaacaatt tgctgagggc    7140
tattgaggcg caacagcatc tgttgcaact cacagtctgg ggcatcaagc agctccaggc    7200
aagaatcctg gctgtggaaa gatacctaaa ggatcaacag ctcctgggga tttgggttg    7260 ctctggaaaa ctcatttgca ccactgctgt gccttggaat gctagttgga gtaataaatc    7320
tctggaacag atttggaatc acacgacctg gatggagtgg gacagagaaa ttaacaatta    7380
cacaagctta atacactcct taattgaaga atcgcaaaac cagcaagaaa agaatgaaca    7440
agaattattg gaattagata aatgggcaag tttgtggaat tggtttaaca taacaaattg    7500
gctgtggtat ataaaattat tcataatgat agtaggaggc ttggtaggtt taagaatagt    7560
ttttgctgta ctttctatag tgaatagagt taggcaggga tattcaccat tatcgtttca    7620
gacccacctc ccaaccccga ggggacccga caggcccgaa ggaatagaag aagaaggtgg    7680
agagagagac agagacagat ccattcgatt agtgaacgga tcggcactgc gtgcgccaat    7740
tctgcagaca aatggcagta ttcatccaca attttaaaag aaaaggggg attgggggt    7800 acagtgcagg ggaaagaata gtagacataa tagcaacaga catacaaact aaagaattac    7860
aaaaacaaat tacaaaaatt caaaattttc gggtttatta cagggacagc agagatccag    7920
tttggttaat taa                                                      7933
```

<210> SEQ ID NO 25
<211> LENGTH: 1293
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
cattatggcc ttaggtcact tcatctccat ggggttcttc ttctgatttt ctagaaaatg      60 agatggggt gcagagagct tcctcagtga cctgcccagg gtcacatcag aaatgtcaga     120
gctagaactt gaactcagat tactaatctt aaattccatg ccttgggggc atgcaagtac     180
gatatacaga aggagtgaac tcattagggc agatgaccaa tgagtttagg aaagaagagt     240
ccagggcagg gtcatctac accacccgcc cagccctggg tgagtccagc cacgttcacc      300
tcattatagt tgcctctctc cagtcctacc ttgacgggaa gcacaagcag aaactgggac     360
aggagcccca ggagaccaaa tcttcatggt ccctctggga ggatgggtgg ggagagctgt     420
ggcagaggcc tcaggagggg ccctgctgct cagtggtgac agatagggt gagaaagcag     480 acagagtcat tccgtcagca ttctgggtct gtttggtact tcttctcacg ctaaggtggc     540
ggtgtgatat gcacaatggc taaaaagcag ggagagctgg aaagaaacaa ggacagagac     600
agaggccaag tcaaccagac caattcccag aggaagcaaa gaaaccatta cagagactac     660
aagggggaag ggaaggagag atgaattagc ttcccctgta aaccttagaa cccagctgtt     720
```

```
gccagggcaa cggggcaata cctgtctctt cagaggagat gaagttgcca gggtaactac    780
atcctgtctt tctcaaggac catcccagaa tgtggcaccc actagccgtt accatagcaa    840
ctgcctcttt gccccactta atcccatccc gtctgttaaa agggccctat agttggaggt    900
gggggaggta ggaagagcga tgatcacttg tggactaagt tgttcacat ccccttctcc     960 aaccccctca gtacatcacc ctgggagaac aaggtccact tgcttctggg cccacacagt   1020
cctgcagtat tgtgtatata aggccagggc aacggaggag caggttttga agtgaaaggc   1080
aggcaggtgt tggggaggca gttaccgggg caacgggaac agggcgtttc ggaggtggtt   1140
gccatgggga cctggatgct gacgaaggct cgcgaggctg tgagcagcca cagtgccctg   1200
ctcagaagcc ccaagctcgt caatcaagct ggttctccat ttgcactcag gagcacgggc   1260
aggcgagtgg cccctagttc tgggggcagc ggg                                1293

<210> SEQ ID NO 26
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
acataactta cggtaaatgg cccgcctggc tgaccgccca acgaccccg cccattgacg      60 tcaataatga cgtatgttcc catagtaacg ccaatagggga ctttccattg acgtcaatgg   120
gtggactatt tacggtaaac tgcccacttg gcagtacatc aagtgtatca tatgccaagt   180 acgccccta ttgacgtcaa tgacggtaaa tggcccgcct ggcattatgc ccagtacatg    240 acctatggg actttcctac ttggcagtac atctacgtat tagtcatc                  288

<210> SEQ ID NO 27
<211> LENGTH: 527
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cgttacataa cttacggtaa atggcccgcc tggctgaccg cccaacgacc cccgcccatt     60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccacccca ttgacgtcaa tgggagtttg ttttggcacc aaaatcaacg   420
ggactttcca aaatgtcgta caactccgc cccattgacg caaatgggcg gtaggcgtgt    480
acggtgggag gtctatataa gcagagctcg tttagtgaac cgtcaga                  527

<210> SEQ ID NO 28
<211> LENGTH: 1181
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 28

```
gggtgcagcg gcctccgcgc cgggttttgg cgcctcccgc gggcgccccc ctcctcacgg      60
cgagcgctgc cacgtcagac gaagggcgca gcgagcgtcc tgatccttcc gcccggacgc     120
tcaggacagc ggcccgctgc tcataagact cggcctaga accccagtat cagcagaagg     180
acattttagg acgggacttg ggtgactcta gggcactggt tttctttcca gagagcggaa     240
caggcgagga aaagtagtcc cttctcggcg attctgcgga gggatctccg tggggcggtg     300
aacgccgatg attatataag gacgcgccgg gtgtggcaca gctagttccg tcgcagccgg     360
gatttgggtc gcggttcttg tttgtggatc gctgtgatcg tcacttggtg agtagcgggc     420
tgctgggctg gccggggctt tcgtggccgc cgggccgctc ggtgggacgg aagcgtgtgg     480
agagaccgcc aagggctgta gtctgggtcc gcgagcaagg ttgccctgaa ctggggggttg     540
gggggagcgc agcaaaatgg cggctgttcc cgagtcttga atggaagacg cttgtgaggc     600
gggctgtgag gtcgttgaaa caaggtgggg ggcatggtgg gcggcaagaa cccaaggtct     660
tgaggccttc gctaatgcgg gaaagctctt attcgggtga gatgggctgg ggcaccatct     720
ggggaccctg acgtgaagtt tgtcactgac tggagaactc ggtttgtcgt ctgttgcggg     780
ggcggcagtt atggcggtgc cgttgggcag tgcacccgta cctttgggag cgcgcgccct     840
cgtcgtgtcg tgacgtcacc cgttctgttg gcttataatg cagggtgggg ccacctgccg     900
gtaggtgtgc ggtaggcttt tctccgtcgc aggacgcagg gttcgggcct agggtaggct     960
ctcctgaatc gacaggcgcc ggacctctgg tgagggagg gataagtgag gcgtcagttt    1020
ctttggtcgg ttttatgtac ctatcttctt aagtagctga agctccggtt ttgaactatg    1080
cgctcggggt tggcgagtgt gttttgtgaa gttttttagg caccttttga aatgtaatca    1140
tttgggtcaa tatgtaattt tcagtgttag actagtaaag g                        1181
```

<210> SEQ ID NO 29
<211> LENGTH: 776
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atggacccca tcgctctgca ggctggttac gacctgctgg gtgacggcag acctgaaact      60
ctgtggctgg gcatcggcac tctgctgatg ctgattggaa ccttctactt tctggtccgc     120
ggatggggag tcaccgataa ggatgcccgg gaatattacg ctgtgactat cctggtgccc     180
ggaatcgcat ccgccgcata tctgtctatg ttctttggta tcgggcttac tgaggtgacc     240
gtcgggggcg aaatgttgga tatctattat gccaggtacg ccaactggct gtttaccacc     300
ccacttctgc tgctggatct ggcccttctc gctaaggtgg atcgggtgac catcggcacc     360
ctggtggggtg tggacgccct gatgatcgtc actggcctca tcggagcctt gagccacacg     420
gccatagcca gatacagttg gtggttgttc tctacaattt gcatgatagt ggtgctctat     480
tttctggcta catccctgcg atctgctgca aaggagcggg gccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc ggtgccgatg tcagtgccgc cgaccg         776
```

<210> SEQ ID NO 30
<211> LENGTH: 744
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 30

| | |
|---|---|
| atggacccca tcgctctgca ggcaggatac gacctgctgg gcgacggaag gccagagacc | 60 |
| ctgtggctgg gaatcggaac cctgctgatg ctgatcggca ccttctactt catcgtgaag | 120 |
| ggctggggcg tgaccgacaa ggaggccagg gagtactaca gcatcacaat cctggtgccc | 180 |
| ggcatcgcca gcgccgccta cctgagcatg ttcttcggca tcggcctgac cgaggtgacc | 240 |
| gtggccggcg aggtgctgga catctactac gccagatacg ccaactggct gttcaccacc | 300 |
| cctttgcttc tgctcgacct ggccctgctg gctaaggtgg acagggtgag catcggaacc | 360 |
| ctggtgggag tggacgccct gatgatcgtg accggcctga tcgcgccct gagccacacc | 420 |
| ccactggcta ggtacagctg gtggctgttc agcaccatct gcatgatcgt ggtgctgtac | 480 |
| ttcctggcta ccagcctgag ggctgctgct aaggagaggg gaccagaggt ggctagcacc | 540 |
| ttcaacaccc tgaccgccct ggtgctggtg ctgtggaccg cctacccccat cctgtggatc | 600 |
| atcggaaccg agggagctgg agtggtggga ctggaatcg agaccctgct gttcatggtg | 660 |
| ctggacgtga ccgccaaagt gggcttcggc ttcatcctgc tgaggagcag ggccatcctg | 720 |
| ggcgacaccg aggcccccga gccc | 744 |

<210> SEQ ID NO 31
<211> LENGTH: 655
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 31

| | |
|---|---|
| cgatgtacgg gccagatata cgcgttgaca ttgattattg actagttatt aatagtaatc | 60 |
| aattacgggg tcattagttc atagcccata tatggagttc cgcgttacat aacttacggt | 120 |
| aaatggcccg cctggctgac cgcccaacga ccccgccca ttgacgtcaa taatgacgta | 180 |
| tgttcccata gtaacgccaa tagggacttt ccattgacgt caatgggtgg actatttacg | 240 |
| gtaaactgcc cacttggcag tacatcaagt gtatcatatg ccaagtacgc cccctattga | 300 |
| cgtcaatgac ggtaaatggc ccgcctggca ttatgcccag tacatgacct tatgggactt | 360 |
| tcctacttgg cagtacatct acgtattagt catcgctatt accatggtga tgcggttttg | 420 |
| gcagtacatc aatgggcgtg atagcggtt tgactcacgg ggatttccaa gtctccaccc | 480 |
| cattgacgtc aatgggagtt tgttttggca ccaaaatcaa cgggactttc caaaatgtcg | 540 |
| taacaactcc gccccattga cgcaaatggg cggtaggcgt gtacggtggg aggtctatat | 600 |
| aagcagagct ctctggctaa ctagagaacc cactgcttac tggcttatcg aaatt | 655 |

<210> SEQ ID NO 32
<211> LENGTH: 419
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 32

```
cggagtactg tcctccgggc tggcggagta ctgtcctccg gcaaggtcgg agtactgtcc      60
tccgacacta gaggtcggag tactgtcctc cgacgcaagg cggagtactg tcctccgggc     120
tgcggagtac tgtcctccgg caaggtcgga gtactgtcct ccgacactag aggtcggagt     180
actgtcctcc gacgcaaggt cggagtactg tcctccgaca ctagaggtcg gagtactgtc     240
ctccgacgca aggtcggagt actgtcctcc gacactagag gtcggagtac tgtcctccga     300
cgcaaggcgg agtactgtcc tccgggctgg cggagtactg tcctccggca agggtcgact     360
ctagagggta taatggat cccatcgcgt ctcagcctca ctttgagctc ctccacacg        419
```

<210> SEQ ID NO 33
<211> LENGTH: 8703
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

```
ctattcctaa agaccttggg tgaccaaaat cttatttaa taaataaaac tgtttattaa       60
aacttttttg tttcaaagaa ccatatgtat agtgaaattt ataaaaatat caatttttaa    120
aaagctggtg tactcattta tgttatgaac tctaaaacca tatactgact gcaagtgatg    180
atgtatagag tgatgtttac gagtaaacat atttagttgt atacatccta ctgagcacat    240
tttgatgtat gaaataacat tacaagcttt atccaaatta agccatttta aaacactgcc    300
aattgaaaat acaaatcctg gaaaaaatcg tctttagcgc agtcatttga gccatcctaa    360
tccgttacct cagaccataa taagaaggga taacactagc tgtagcaatg gaacacatct    420
gtttcacaca atcatatctc ctgcgccggt gctaagcaga ttcagcgtga tcataacatg    480
cttttccactc ataaatgtaa atttacaatt tgcacatgta aaacagacac ttttgagata    540
ttggataaaa aaacaagagt atattgctta gtttcatcca ccagtcatcc ccacagcgtt    600
tggaaggcca taaaaagtgt ctaaaatcaa tgatcattga aagagcacaa gagagactct    660
tacgctgtaa tgccactggg acaaaagtg acagtctctt aatgggctct tctggagggg    720
ctcctgaaca ttaaaaatta tcagcgaaat taccgaaaga gcttcaagca actggcatgc    780
ttgatcctct gcgtcggggc ggtgaatagg tgcttcagat gccctcttac ccacgggctg    840
gattcagctg ccccgctacc agcggagacc ccctaatgag cctctgcaat taagtttatt    900
catgttaagt gtgaacgggg tgcgtgcgga actgtgggca gctaacagac ctgggttctt    960
tgtgccacaa gtgctgcctt tattcggctc acaaagcaga aaacaacacc cgcacctata   1020
atggcgccct cggctgggtc taagaaacgt ggcgagttga cagagcagag tgggcggggt   1080
taagacagac tgacagcggg acccatctcc atcctcttat taacgcttaa cgagtgcctt   1140
cctcatgcaa tattcatcgc cactaatatc atccaagctc tgagctgagc tggccactta   1200
tgtaaggcaa ttatgtaaaa tatcagacag ggcccacact cagaatctga ctggggtaga   1260
gacgcgggac gagaaccgag agcaagaact gaaagtgaaa gtgaccacta aagggaggag   1320
aggacagagg ggcaggatgt gtcaagatta ccagagaaca cttggccaga aatgcgcaac   1380
cattggagct ctccggatta cccaaaggtt aacgagtttg aacgcctctg cccactcgcc   1440
catctctgat ggtttcccaa gaactcctca agcaaaatat atataattgt gtgtattatg   1500
cacagacacg agaaaatgct gttttctga tctgcattac agcacatttg cccgccaacg   1560
```

```
acaataccac ccactcggta cctcgctgac tcctgatgcc tgatacctgc gcggtgactg    1620
tctacaatct gcataatcaa gagaagttgt gttgaagacg agcgccacac aaccgtttcc    1680
acaaggtcac ccaaggccgg tgcagatgta ggtgaggtct ccataaacag actgaaataa    1740
acacatcctc cgctgggaac aacaaccccc tcacgcctca tgcatttcca taagcctaca    1800
tgcatctctt ccaacttatg gagactcgca cctaccaaca tccgcacaac aaagatatac    1860
agagcgcgct ccctcaggtc aaggccctgt ggggtctgt gcagaaatag gtcatttgtc     1920
acacatcaag tcctggggca ggagatgcat tatagatgag accaaacagc ctgtctcggt    1980
gagctctacc cactccctga gactagaaat ggggaaggg agcttgagat aacaaccgct     2040
gcaatcactg tgtcgatgtt taatatcagc accaaccggg aacaataagg agatgggtgc    2100
attcatgttc acatcttacc agtcaagtat catcgaaccg gcttgataac cacacctcgt    2160
gtaatagctg agcagatagt tgtcatttta aagcgttggc ctttgtcgat tatgtaatgc    2220
gcacattcaa cacatggtaa tatagaaacg gttatgtcga ggttgttttg tccagagatg    2280
accttcacac agttacagcc gctctgcatc cacacaaatg gaggacttaa tcgtggactg    2340
cattcttaga aatgatctac aaagacaaat aatgtgaaat caagaaagga caaaatttaa    2400
gtaaggggat gagggagaga gagaacgagg ggcaaggaga aagcatggct cctgtctttt    2460
tctgcaccca tctgttcgga gtgcaggtgg agctctattc actcagctct gcatgtgtgt    2520
ttgggggggg caggaagaaa gggagggcaa aaggaagagt ggagagatgg tgggggctgg    2580
agggatgggg ggttctcggt gatctctcct gaagggata atgggagagc agcgctttgc     2640
aatggctgcc atgtagtacc ctccctgcac aattagccaa tcagcagcaa gctctgccag    2700
ccagaaggac acataaaaga gaacattgc agcagaggca cagaaggagc ctgcgaggag     2760
ctgggaaata cacacacaac agcagaacca caacaccctc ccctggacac accctactgg    2820
ggatcactgc ttttctttt ttctgaacca tcgcccacgc cacacggaga gaaatctctc     2880
tctcatcatc atcctgaaga aaaccccctt atcctcattt tcacactgct gaggaaaacc    2940
tacaatcgca cgggctgaga tttcctggcg aagactgtcc ttttccttt tcttttttt     3000 ttcttttcct ttggaaactg acatttgcat ttctccattc caagccacgg cgtaataata    3060
tctgcaatcc agcctgaaga cctgcaaatc gaaggaccta gatcactatc atctttgtac    3120
gtcaagaatg gttactgtac gtataacctt tcttcttt gctctgacca atatgaaaca      3180
ctaaaatcga ttcgagcagc ctctcagcat caattacagt gcgtgaaaaa cattcaaata    3240
gaggcagcaa atattacatg tgaaaataca ggctggctaa atccaagcta atttagaaat    3300
gtggtcaaaa cgcatactgg cacgtctaat cgcggattca gtaaacaaga ttaacgatta    3360
gcccagtgta taagtcatat gatacaggca tgcgcgagag catcgctaca cccgagctgg    3420
cttcattttc ggaggaaaat caaaacattg ctttctcctg ccgtgcgaac cattcgtcat    3480
aaaccgtaat acgcaacata catttattac tacatccgtt aattagcgat aattagccgt    3540
tattaacaaa gagcgctgag gaattcctct caaatagcgg aggtgcggcg gaggcagagg    3600
ggcgtaaaag ggcacatgcg tgcctggctc aaaaaaggat gctccagact gaaactcaga    3660
gacaaaacac gatgcctcgg aggctgagag cccatcgaga ggaaaggcaa agaaaagggt    3720
cgagtcactc agaggggggag gggagatatt gtgcatccat tggtttgaat tgaagcaggc    3780
agaataaaaa tccttgcgat tatgcttcgt gagagatcgc gagagaggaa aaggctaaat    3840
gccacgtatg caaatggata aatgtcatct atttcttcgc gagtagacat tttgtggaca    3900
```

```
acgagagtgt aaataagcga tatgagggga atacaaaggc cttgagggaa agcgttttgg    3960
gcgtgtcttg tcgaaaagaa gacagcgatg gcacgcgctc agaaccacca tcttcacgta    4020
gataatccgc gtgaaaacaa taacaaaact gctcatttta acacgagcag gtgtttgaaa    4080
ccacccaaaa aagattgtct aaaatattaa gattaattaa tgacgtttaa atgtccaggc    4140
ctgatataaa tgaagcgtgt agtaagagta atcgcctttg tttcttttca gagatacgtt    4200
ttcagagatt cagggaatta tatcttcaat aaaataatgt ttgatttcat tattttaaag    4260
cttttttaaga agtaaaaata cacattattc atttacattt tattttatttt aaaggcctat    4320
ggtcttgaaa ataataagtg gaatatatag gctatatatt cgtctaagga cagccggtgt    4380
tattttatag tgacctcaga caaaagccga gacaaaacga ggcgcttgcc tttcatttta    4440
atccttaata gacggtgtga tgaatgaatg aatgaatgaa taaatgaatg aatgacgggc    4500
ccttcggcat gttgttccgc agtcctccgt gagcacgagt ctctaccgca gtgccaagca    4560
cataaaaccg ttgagtcaga taaccttctc caggcgcgta tacacaattc aaggacaagc    4620
acatcacaac tatacacaac acaacacaac cgcctaaacg cacgagctca tcaatcgcaa    4680
tttaaaggca tgtcagtcaa agaaaaaggc ggcgttattt aaaaccaatg ttcaacaata    4740
tttgtatgct gactagcccg ggcgcgcacg ctataagatc acaaggcctt gttttttccc    4800
tttattcaaa atatcattaa ttattacagg tcataaaaca aaacaatgca aattacaatg    4860
atttaaagac tattgattta acaataatca gttaattata gaataatatt ataatatttt    4920
acatacaaat gaaagatgac attatttgat gacattgtaa ttaaaatata tgcaatatat    4980
ttttacgttt ttattaatta ggctattact attattataa ttatcattat ttttattatt    5040
attattatta ttaaatagtc ttgcgaaata agagtgaagg cagttgcaat gttcattgtt    5100
cccggagagt cccgcagcct ctggcctcaa cacaaagcgc tactgtttac attaatattc    5160
atagtgctgc catggtctct gtagaggagg aacgggtggc tcttttgttc gctagtgtca    5220
atacgtttat tcagcaaaaa gcagctcgga tttgtgaatg cccaacaagc acacgcgcac    5280
tccaatcaaa ggacgagagg ataacgattt taaacgattc gcaaacgtgt ttatttgtaa    5340
agacgacatc aagagcttaa tgtccacttg aaaagaaata aatatgcccg cggcgccaag    5400
gatattttga atgtagtcgt tcatggtgag ccactcccga attcagcact ctggagagcg    5460
accaaagagg aatagcggaa tagcaactac ttgagccatt tctctccgtt tgatggcgtt    5520
catgattaaa aatataatca cgtgattttt tatacatata taaatatata cataaagtaa    5580
cgctttcctt ttgagaatac ataaatattt attcgcgtga taaatcaatg atcttatatt    5640
tatttgcacg accgaaatta gccaaattca ccaattaaaa aaaaaataag ccaacaaaaa    5700
agaagggttt atccgttcag ttttgacttg tgtcctgttg ttttacagct gccactgtga    5760
tcccttaagc tgcagtgaga gtgtggctaa tgccttttgt ttaagataat cctgtaatct    5820
gttaccgaaa cggcctattg acaagccggc attcacattt cagtcaggag gcccgtccag    5880
acatgtacat ttatgaatta cgaatgataa aattaagatc tgcattaggc gtcagaaatg    5940
tcacgaacac ccattcattt cccacagcca ataatggatc atgctgggaa gcgctatcct    6000
cgcagtctca aaattaatgt tgacatgttg cgtagagcta cagattagat cagccatatg    6060
ctttatgtgt ttacctcagc ggatcttcag caagatgtgt ttattttaag aaaatggctt    6120
cctcgctgcc tgcacagggg cattaaggaa gtgacgtgag cgtcctcaca gtcaaattac    6180
tttatctcat gctgctttca ggcctctgct tatttttatta ttattatttt aaattagggg    6240
gaatcacggt ggcgttgtgg gtagggtagc gcgatcacct tacagcaaga aggtcgctgg    6300
```

```
ttcgagctct ggctgggtca gttggcattt ctgtgtggag tttaaattga attgaaattg    6360
aataaactaa attggcccta gtgtatgtgt gtgaatgtaa gtgtgcatgg gtgtttccca    6420
gtgttgggtt tgactggaag agcatccgct tcgtaaaaca tatgctggat aagttggcgg    6480
ttcatttcac tgtggtgacc gctgattaat aaagggacta agctgaaaat gaatgaatt    6540
aatacatttt aaatgagctt ttgctgacat gtttatgatt acaaatagtg aaattgtatg    6600
ttaatttacg ataagtgcat tgttctaaat tcattttat gtagcagctg gttttcttc      6660
catttgtgtc attcaacaga acattttct aaaaagtga acttaaattt tctcctccct      6720
ctgacaaggc ttgatggtaa tttcagccga ctctaattac agactcacta aaaggaatcg    6780
gtgcagtcat ttatctttat cagcgcgctg gtgggaaggt aataggtttt gcttatgagt    6840
tgtttgcgtg cgagtctggg tccttgtgta ggcgatgctg atgcactgca ttaaatattg    6900
agggagaagt cgctcaaaaa tagcaaagta caggctgggg caggaacgtc aaagcccgct    6960
cagtggccac gtttcttgtt tcgtaagtcc tattttaat agcgataatt caggctcagt     7020
agaaggaact ccagcactat aagcagtctc tcgcctgtct cggcgagtta tgtatttgg     7080
gatgaagtgc tcttccacct ctacctctgc tgtgctggcg ccagtatctg ggctgtaaga    7140
tagtgtacgt gtcagtctgt gtggccgaag agcctgtgtg ttgtgtaact cactacattc    7200
gtcgctgtgg atggctgact tgccatgggg aggtttactt cagttcacga atcacattcg    7260
ccacgatctt gtcactttgt gtcaagactc gctctctgtg tgtcaacagc tctgctgttt    7320
gaggttgaaa ttctgaactt gagatatatc ccaggatata ttagggctac tgccaacgga    7380
aaaagcaaat ggtgccatgg ccatttgatt gatcaaacaa acacccttt gcttgggtga     7440
cagtgaaatg tcagatccat gtttgtactg ctttaataac ttgcctctct gagctttctc    7500
cttgtcagtg tcaatttgcc tgagatataa attccggttg ccccgaaagc ttatttatt     7560
aaaaaaagc taacatgcac tcatacaacg tgcgcacata catgtgaggc ttgctaaaag     7620
tcaagaagca agccaatagc aagagtcgtc agactgctgt tacctgggca acctggttag    7680
aggtaaggct caaggcaaga ataaatcatt ccactgaaga gacacagcgt tacagcgaga    7740
tgagagcaag aggcgatagt gaaggagaa caaaagaaca gcctacccac actagtgcag     7800
atctacctgt ttgagctact gattgttcag tttgattaga tatcagacaa ttctgctatc    7860
tccaattgca ttgctgcatg aattcctaga aatcatttta atcaccaaaa actagtaggg    7920
acacttgtgg cgtatatgat tctgcctgtt gattgtgggg atccaacaga aagatcatga    7980
atgcattgtt aattaagtcg gtgagacacc ctgttccacc ctaggggccg ttctggggaa    8040
agagtgcttt cagtcagcta agatgactaa atatgtgaac atatattact acacatgcca    8100
atttgtacat tctggatagt taccagcct gggaaaacat cgaaaaaat aaatcaacat       8160
agataaaatt ggcaaatccc ttctggtacg atgcagagtg cttgctctga gaacttgtgc    8220
attgtgacag aaagcgaccg ttaaaaactg aaagtagcat ctacaacctg catacatctg    8280
ttctttgaaa atcccctgta ggccaaatta agcatcacgc tgtgctccac agcaacacgg    8340
atgaaccgaa aacccagaca caaacgcaca cacttttcac ataaacaagg tttagttatg    8400
ctagctatgc tttttcgtcc tcccttgtc atcagcggcg agtgacgtaa cacagtttga     8460
ccctggacag cgtaaagggg gggttgggaa tgagtgaaag gactgtgaca tctgcagggc    8520
caggggctga tggagagagc tgaagtgagg gaggtcagag gaggaggaag ggtgggatat    8580
tgtcctcctc aggccctatc cctctcagac gcattgattt ttaacctctc agcgagaatg    8640
```

```
ccaagcatta cacccctcaa attatggttc ctcacccaac ctgttatatt ttccacctgc    8700
agc                                                                  8703
```

<210> SEQ ID NO 34
<211> LENGTH: 28
<212> TYPE: DNA
<213> ORGANISM: Artificial Sequence
<220> FEATURE:
<221> NAME/KEY: source
<223> OTHER INFORMATION: Description of Artificial Sequence: Synthetic
      oligonucleotide

<400> SEQUENCE: 34

```
ctgacgcttt ttatcgcaac tctctact                                         28
```

<210> SEQ ID NO 35
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
atgaaactgc tgctgatctt gggaagcgta attgccttgc cgacattcgc agctggggga     60
ggggatctgg acgccagcga ttacacgggt gtcagttttt ggctcgtgac tgcggcgctc    120
ctggcatcga ccgtgttttt cttcgtggaa agagacaggg tgtcggcgaa gtggaaaacc    180
tcgttgactg tctccgggtt ggtgacaggc atcgcgtttt ggcactacat gtatatgcga    240
ggggtctgga ttgagacagg tgattcaccg acggtgtttc gttacatcaa ttggttgctc    300
actgtaccac tcctcatttg cgagttttac cttattcttg cggcagccac gaatgtggcg    360
ggttcgttgt tcaaaaagct ccttgttggc tcgttggtta tgctggtatt tggctatatg    420
ggggaagccg gtatcatggc tgcgtggcct gcgtttatca ttggatgcct ggcttgggtc    480
tatatgatct atgagttgtg ggccggagaa ggaaaatccg cgtgtaatac ggcctcgccc    540
gcagtgcagt ccgcctataa cacgatgatg tatatcatca tctttggatg gcaatctat     600 cccgtcggat actttaccgg gtacctcatg ggtgacggtg atctgccct caatcttaat    660 ctcatctaca accttgcaga cttcgtcaac aagattcttt tcgggctgat tatctggaac    720
gtcgcagtaa aagaatcctc aaatgcgtga                                    750
```

<210> SEQ ID NO 36
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
atgaaactgc tgctgatctt gggaagcgta attgccttgc cgacattcgc agctggggga     60
ggggatctgg acgccagcga ttacacgggt gtcagttttt ggctcgtgac tgcggcgctc    120
ctggcatcga ccgtgttttt cttcgtggaa agagacaggg tgtcggcgaa gtggaaaacc    180
tcgttgactg tctccgggtt ggtgacaggc atcgcgtttt ggcactacat gtatatgcga    240
ggggtctgga ttgagacagg tgattcaccg acggtgtttc gttacatcaa ttggttgctc    300
actgtaccac tcctcatttg ccagttttac cttattcttg cggcagccac gaatgtggcg    360
ggttcgttgt tcaaaaagct ccttgttggc tcgttggtta tgctggtatt tggctatatg    420
```

```
gggcaagccg gtatcatggc tgcgtggcct gcgtttatca ttggatgcct ggcttgggtc    480
tatatgatct atgagttgtg ggccggagaa ggaaaatccg cgtgtaatac ggcctcgccc    540
gcagtgcagt ccgcctataa cacgatgatg tatatcatca tctttggatg ggcaatctat    600
cccgtcggat actttaccgg gtacctcatg ggtgacggtg gatctgccga caatcttaat    660
ctcatctaca accttgcaga cttcgtcaac aagattcttt tcgggctgat tatctggaac    720
gtcgcagtaa aagaatcctc aaatgcgtga                                     750
```

<210> SEQ ID NO 37
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atgggtaagc ttctcctgat tctaggaagt gctattgctt tgccatcttt tgcagcggcc     60
gggggagatc tcgacataag cgacacagtc ggggtgagtt tttggcttgt caccgcaggg    120
atgttggcag ctacggtctt ttttttcgtg gagcgggatc aggtgtccgc aaagtggaag    180
acttcactga ccgtttctgg attgataacg gggatcgcct tttggcatta tctctacatg    240
cgaggagtgt ggattgatac cggggatact cccacggtat ttcgatacat caattggcta    300
ctgacagttc ccctgcaggt tgtagagttc tatctgatac tggctgcatg cacaagcgtc    360
gcggcctctc tcttcaagaa actgctggct ggttcattag ttatgttggg ggctgggttc    420
gccggagagg cggggctggc cccagtgctg ccagcgttta ttatcggtat ggcaggatgg    480
ctctatatga tttacgagtt gtatatgggg gaagggaagg ccgctgtgag cacagccagc    540
ccagctgtga attccgcgta caatgccatg atgatgatta tgttgttggg gtgggccatc    600
tatccagccg ggtatgcagc agggtatctg atgggcggag aaggagtgta tgcatctaac    660
ttgaacctga tctacaatct cgccgacttc gttaacaaga tcctattcgg tttgatcatt    720
tggaacgttg ccgtgaaaga atcaagtaat gca                                 753
```

<210> SEQ ID NO 38
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
atggtgggcc tcaccaccct tttctggctg ggcgctattg ggatgttggt tgggaccctg     60
gcttttgcat gggccggcag ggacgccggg tcaggtgaga ggcggtacta cgtgacgctc    120
gtgggaatta gcggtatcgc cgccgtagca tatgtcgtaa tggcccttgg ggttggctgg    180
gtccccgtgg ccgagcggac cgttttttgca cctcgataca ttaattggat tctcactact    240
ccacttatcg tttacttcct tgggctgctg gctggcctgg acagccgcga atttggaata    300
gttataactt tgaatacagt ggtgatgttg gcggcttcg ctgggccat ggtgccaggc    360
```

```
gggcccccg  gcgtcgcctt  actgactccc  acagtcgacg  tggcgctgat  cgtctatctg    600
gacctggtca  ctaaagtggg  gtttggcttc  attgctctgg  acgccgctgc  cactttgaga    660
gctgaacacg  gagaatcact  cgcaggagtg  gataccgacg  ctcccgccgt  ggcagat      717
```

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
atgaggggta  cgcccctgct  cctcgtcgtc  tctctgttct  ctctgcttca  ggac           54
```

<210> SEQ ID NO 40
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
atgatggaca  gcaaaggttc  gtcgcagaaa  gggtcccgcc  tgctcctgct  gctggtggtg     60
tcaaatctac  tcttgtgcca  gggtgtggtc  tccacccccg  tcgggatc                  108
```

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
ttctgctacg  agaacgaggt  g                                                 21
```

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
aagagcagga  tcaccagcga  gggcgagtac  atcccctgg   accagatcga  catcaacgtg     60
```

<210> SEQ ID NO 43
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atggtgagca  agggcgagga  gctgttcacc  ggggtggtgc  ccatcctggt  cgagctggac     60
ggcgacgtaa  acggccacaa  gttcagcgtg  tccggcgagg  gcgagggcga  tgccacctac    120
ggcaagctga  ccctgaagct  gatctgcacc  accggcaagc  tgcccgtgcc  ctggcccacc    180
ctcgtgacca  ccctgggcta  cggcctgcag  tgcttcgccc  gctaccccga  ccacatgaag    240
```

| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca ccgccgacaa gcagaagaac | 480 |
| ggcatcaagg ccaacttcaa gatccgccac aacatcgagg acggcggcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagtga | 720 |

```
<210> SEQ ID NO 44
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
```

| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccttcggcta cggcctgcag tgcttcgccc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagct accagtccgc cctgagcaaa gaccccaacg agaagcgcga tcacatggtc | 660 |
| ctgctggagt tcgtgaccgc cgccgggatc actctcggca tggacgagct gtacaagtaa | 720 |

```
<210> SEQ ID NO 45
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
```

| atggtgtcta agggcgaaga gctgattaag gagaacatgc acatgaagct gtacatggag | 60 |
| ggcaccgtga acaaccacca cttcaagtgc acatccgagg gcgaaggcaa gccctacgag | 120 |
| ggcacccaga ccatgagaat caaggtggtc gagggcggcc ctctccccett cgccttcgac | 180 |
| atcctggcta ccagcttcat gtacggcagc agaaccttca tcaaccacac ccagggcatc | 240 |
| cccgacttct ttaagcagtc cttccctgag ggcttcacat gggagagagt caccacatac | 300 |
| gaagacgggg gcgtgctgac cgctacccag gacaccagcc tccaggacgg ctgcctcatc | 360 |
| tacaacgtca agatcagagg ggtgaacttc ccatccaacg ccctgtgat gcagaagaaa | 420 |
| acactcggct gggaggccaa caccgagatg ctgtaccccg ctgacggcgg cctggaaggc | 480 |
| agaaccgaca tggccctgaa gctcgtgggc ggggccacc tgatctgcaa cttcaagacc | 540 |

| | | |
|---|---|---|
| acatacagat ccaagaaacc cgctaagaac ctcaagatgc ccggcgtcta ctatgtggac | 600 | |
| cacagactgg aaagaatcaa ggaggccgac aaagagacct acgtcgagca gcacgaggtg | 660 | |
| gctgtggcca gatactgcga cctccctagc aaactggggc acaaacttaa ttaa | 714 | |

<210> SEQ ID NO 46
<211> LENGTH: 5492
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

| | |
|---|---|
| aagaaaccaa ttgtccatat tgcatcagac attgccgtca ctgcgtcttt tactggctct | 60 |
| tctcgctaac caaaccggta accccgctta ttaaaagcat tctgtaacaa agcgggacca | 120 |
| aagccatgac aaaaacgcgt aacaaaagtg tctataatca cggcagaaaa gtccacattg | 180 |
| attatttgca cggcgtcaca ctttgctatg ccatagcatt tttatccata agattagcgg | 240 |
| atcctacctg acgctttta tcgcaactct ctactgtttc tccatacccg ttttttggg | 300 |
| ctagaaataa ttttgtttaa ctttaagaag agatataca tacccatggg taaattatta | 360 |
| ctgatattag gtagtgttat tgcacttcct acatttgctg caggtggtgg tgaccttgat | 420 |
| gctagtgatt acactggtgt ttctttttgg ttagttactg ctgctttatt agcatctact | 480 |
| gtatttttct ttgttgaaag agatagagtt tctgcaaaat ggaaaacatc attaactgta | 540 |
| tctggtcttg ttactggtat tgctttctgg cattacatgt acatgagagg ggtatggatt | 600 |
| gaaactggtg attcgccaac tgtatttaga tacattaatt ggttactaac agttcctcta | 660 |
| ttaatatgtg aattctactt aattcttgct gctgcaacta atgttgctgg atcattattt | 720 |
| aagaaattac tagttggttc tcttgttatg cttgtgtttg gttacatggg tgaagcagga | 780 |
| atcatggctg catggcctgc attcattatt gggtgtttag cttgggtata catgatttat | 840 |
| gaattatggg ctggagaagg aaaatctgca tgtaatactg caagtcctgc tgtgcaatca | 900 |
| gcttacaaca caatgatgta tattatcatc tttggttggg cgatttatcc tgtaggttat | 960 |
| ttcacaggtt acctgatggg tgacggtgga tcagctctta acttaaacct tatctataac | 1020 |
| cttgctgact tgttaacaa gattctattt ggtttaatta tatggaatgt tgctgttaaa | 1080 |
| gaatcttcta atgctcacca tcaccatcac catagcggca tggtgagcaa gggcgaggag | 1140 |
| ctgttcaccg gggtggtgcc catcctggtc gagctggacg gcgacgtaaa cggccacaag | 1200 |
| ttcagcgtgt ccggcgaggg cgagggcgat gccacctacg gcaagctgac cctgaagctg | 1260 |
| atctgcacca ccggcaagct gcccgtgccc tggcccaccc tcgtgaccac cctgggctac | 1320 |
| ggcctgcagt gcttcgcccg ctaccccgac cacatgaagc agcacgactt cttcaagtcc | 1380 |
| gccatgcccg aaggctacgt ccaggagcgc accatcttct tcaaggacga cggcaactac | 1440 |
| aagacccgcg ccgaggtgaa gttcgagggc gacaccctgg tgaaccgcat cgagctgaag | 1500 |
| ggcatcgact tcaaggagga cggcaacatc ctggggcaca agctggagta caactacaac | 1560 |
| agccacaacg tctatatcac cgccgacaag cagaagaacg gcatcaaggc caacttcaag | 1620 |
| atccgccaca acatcgagga cggcggcgtg cagctcgccg accactacca gcagaacacc | 1680 |
| cccatcggcg acggccccgt gctgctgccc gacaaccact acctgagcta ccagtccgcc | 1740 |
| ctgagcaaag accccaacga gaagcgcgat cacatggtcc tgctggagtt cgtgaccgcc | 1800 |
| gccgggatca ctctcggcat ggacgagctg tacaagtgag tttaaacggt ctccagcttg | 1860 |

```
gctgttttgg cggatgagag aagattttca gcctgataca gattaaatca gaacgcagaa   1920
gcggtctgat aaaacagaat tgcctggcg gcagtagcgc ggtggtccca cctgacccca    1980
tgccgaactc agaagtgaaa cgccgtagcg ccgatggtag tgtggggtct ccccatgcga   2040
gagtagggaa ctgccaggca tcaaataaaa cgaaaggctc agtcgaaaga ctgggccttt   2100
cgttttatct gttgtttgtc ggtgaacgct ctcctgagta ggacaaatcc gccgggagcg   2160
gatttgaacg ttgcgaagca acggcccgga gggtggcggg caggacgccc gccataaact   2220
gccaggcatc aaattaagca gaaggccatc ctgacggatg ccttttttgc gtttctacaa   2280 actcttttg tttattttc taaatacatt caaatatgta tccgctcatg agacaataac    2340
cctgataaat gcttcaataa tattgaaaaa ggaagagtat gagtattcaa catttccgtg   2400
tcgcccttat tcccttttt gcggcatttt gccttcctgt ttttgctcac ccagaaacgc    2460
tggtgaaagt aaaagatgct gaagatcagt tgggtgcacg agtgggttac atcgaactgg   2520
atctcaacag cggtaagatc cttgagagtt ttcgccccga agaacgtttt ccaatgatga   2580 gcactttta agttctgcta tgtggcgcgg tattatcccg tgttgacgcc gggcaagagc    2640
aactcggtcg ccgcatacac tattctcaga atgacttggt tgagtactca ccagtcacag   2700
aaaagcatct tacggatggc atgacagtaa gagaattatg cagtgctgcc ataaccatga   2760
gtgataacac tgcggccaac ttacttctga acgatcgg aggaccgaag gagctaaccg     2820
cttttttgca caacatgggg gatcatgtaa ctcgccttga tcgttgggaa ccggagctga   2880
atgaagccat accaaacgac gagcgtgaca ccacgatgcc tgtagcaatg caacaacgt    2940 tgcgcaaact attaactggc gaactactta ctctagcttc ccggcaacaa ttaatagact   3000
ggatggaggc ggataaagtt gcaggaccac ttctgcgctc ggcccttccg gctggctggt   3060
ttattgctga taaatctgga gccggtgagc gtgggtctcg cggtatcatt gcagcactgg   3120
ggccagatgg taagccctcc cgtatcgtag ttatctacac gacggggagt caggcaacta   3180
tggatgaacg aaatagacag atcgctgaga taggtgcctc actgattaag cattggtaac   3240
tgtcagacca gtttactca tatatacttt agattgattt aaaacttcat ttttaattta   3300
aaaggatcta ggtgaagatc ctttttgata atctcatgac caaaatccct taacgtgagt   3360
tttcgttcca ctgagcgtca gaccccgtag aaaagatcaa aggatcttct tgagatcctt   3420 ttttttctgcg cgtaatctgc tgcttgcaaa caaaaaaacc accgctacca gcggtggttt   3480
gtttgccgga tcaagagcta ccaactcttt ttccgaaggt aactggcttc agcagagcgc   3540
agataccaaa tactgtcctt ctagtgtagc cgtagttagg ccaccacttc aagaactctg   3600
tagcaccgcc tacatacctc gctctgctaa tcctgttacc agtggctgct gccagtggcg   3660
ataagtcgtg tcttaccggg ttggactcaa gacgatagtt accggataag gcgcagcggt   3720
cgggctgaac ggggggttcg tgcacacagc ccagcttgga gcgaacgacc tacaccgaac   3780
tgagatacct acagcgtgag ctatgagaaa gcgccacgct cccgaaggg agaaaggcgg    3840 acaggtatcc ggtaagcggc agggtcggaa caggagagcg cacgagggag cttccagggg   3900
gaaacgcctg gtatctttat agtcctgtcg ggtttcgcca cctctgactt gagcgtcgat   3960
ttttgtgatg ctcgtcaggg gggcggagcc tatgaaaaa cgccagcaac gcggcctttt    4020
tacggttcct ggccttttgc tggccttttg ctcacatgtt cttcctgcg ttatcccctg    4080 attctgtgga taaccgtatt accgcctttg agtgagctga taccgctcgc cgcagccgaa   4140
cgaccgagcg cagcgagtca gtgagcgagg aagcggaaga gcgcctgatg cggtattttc   4200
```

```
tccttacgca tctgtgcggt atttcacacc gcatatggtg cactctcagt acaatctgct    4260
ctgatgccgc atagttaagc cagtatacac tccgctatcg ctacgtgact gggtcatggc    4320
tgcgccccga cacccgccaa cacccgctga cgcgccctga cgggcttgtc tgctcccggc    4380
atccgcttac agacaagctg tgaccgtctc cgggagctgc atgtgtcaga ggttttcacc    4440
gtcatcaccg aaacgcgcga ggcagcagat caattcgcgc gcgaaggcga agcggcatgc    4500
ataatgtgcc tgtcaaatgg acgaagcagg gattctgcaa accctatgct actccgtcaa    4560
gccgtcaatt gtctgattcg ttaccaatta tgacaacttg acggctacat cattcacttt    4620
ttcttcacaa ccggcacgga actcgctcgg gctggcccg  gtgcattttt taaatacccg    4680
cgagaaatag agttgatcgt caaaaccaac attgcgaccg acggtggcga taggcatccg    4740
ggtggtgctc aaaagcagct tcgcctggct gatacgttgg tcctcgcgcc agcttaagac    4800
gctaatccct aactgctggc ggaaaagatg tgacagacgc gacggcgaca agcaaacatg    4860
ctgtgcgacg ctggcgatat caaaattgct gtctgccagg tgatcgctga tgtactgaca    4920
agcctcgcgt acccgattat ccatcggtgg atggagcgac tcgttaatcg cttccatgcg    4980
ccgcagtaac aattgctcaa gcagatttat cgccagcagc tccgaatagc gcccttcccc    5040
ttgcccggcg ttaatgattt gcccaaacag gtcgctgaaa tgcggctggt gcgcttcatc    5100
cgggcgaaag aacccgtat  tggcaaatat tgacggccag ttaagccatt catgccagta    5160
ggcgcgcgga cgaaagtaaa cccactggtg ataccattcg cgagcctccg gatgacgacc    5220
gtagtgatga atctctcctg gcgggaacag caaaatatca cccggtcggc aaacaaattc    5280
tcgtccctga ttttcacca  cccctgacc  gcgaatggtg agattgagaa  ataacctttt    5340
cattcccagc ggtcggtcga taaaaaaatc gagataaccg ttggcctcaa tcggcgttaa    5400
acccgccacc agatgggcat taaacgagta tcccggcagc aggggatcat tttgcgcttc    5460
agccatactt ttcatactcc cgccattcag ag                                  5492

<210> SEQ ID NO 47
<211> LENGTH: 13764
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gtacaaaaaa gcaggctcta ttcctaaaga ccttgggtga ccaaaatctt attttaataa     60
ataaaactgt ttattaaaac ttttttgttt caaagaacca tatgtatagt gaaatttata    120
aaaatatcaa ttttttaaaa gctggtgtac tcatttatgt tatgaactct aaaaccatat    180
actgactgca agtgatgatg tatagagtga tgtttacgag taaacatatt tagttgtata    240
catcctactg agcacatttt gatgtatgaa ataacattac aagctttatc caaattaagc    300
cattttaaaa cactgccaat tgaaaataca aatcctggaa aaaatcgtct ttagcgcagt    360 cattttgagcc atcctaatcc gttacctcag accataataa gaagggataa cactagctgt    420
agcaatggaa cacatctgtt tcacacaatc atatctcctg cgccggtgct aagcagattc    480
agcgtgatca taacatgctt tccactcata atgtaaatt  acaatttgc  acatgtaaaa    540 cagacacttt tgagatattg gataaaaaaa caagagtata ttgcttagtt tcatccacca    600
gtcatcccca cagcgtttgg aaggccataa aaagtgtcta aaatcaatga tcattgaaag    660
agcacaagag agactcttac gctgtaatgc cactgggggac aaaagtgaca gtctcttaat    720
```

-continued

```
gggctcttct ggaggggctc ctgaacatta aaaattatca gcgaaattac cgaaagagct    780
tcaagcaact ggcatgcttg atcctctgcg tcggggcggt gaataggtgc ttcagatgcc    840
ctcttaccca cgggctggat tcagctgccc cgctaccagc ggagaccccc taatgagcct    900
ctgcaattaa gtttattcat gttaagtgtg aacggggtgc gtgcggaact gtgggcagct    960
aacagacctg ggttctttgt gccacaagtg ctgcctttat tcggctcaca aagcagaaaa   1020
caacaccgc acctataatg cgccctcgg ctgggtctaa gaaacgtggc gagttgacag     1080
agcagagtgg gcggggttaa gacagactga cagcgggacc catctccatc ctcttattaa   1140
cgcttaacga gtgccttcct catgcaatat tcatcgccac taatatcatc caagctctga   1200
gctgagctgg ccacttatgt aaggcaatta tgtaaaatat cagacagggc ccacactcag   1260
aatctgactg gggtagagac gcgggacgag aaccgagagc aagaactgaa agtgaaagtg   1320
accactaaag ggaggagagg acagaggggc aggatgtgtc aagattacca gagaacactt   1380
ggccagaaat gcgcaaccat tggagctctc cggattaccc aaaggttaac gagtttgaac   1440
gcctctgccc actcgcccat ctctgatggt ttcccaagaa ctcctcaagc aaaatatata   1500
taattgtgtg tattatgcac agacacgaga aaatgctgtt tttctgatct gcattacagc   1560
acatttgccc gccaacgaca ataccaccca ctcggtacct cgctgactcc tgatgcctga   1620
tacctgcgcg gtgactgtct acaatctgca taatcaagag aagttgtgtt gaagacgagc   1680
gccacacaac cgtttccaca aggtcaccca aggccggtgc agatgtaggt gaggtctcca   1740
taaacagact gaaataaaca catcctccgc tgggaacaac aaccccctca cgcctcatgc   1800
atttccataa gcctacatgc atctcttcca acttatggag actcgcacct accaacatcc   1860
gcacaacaaa gatatacaga gcgcgctccc tcaggtcaag gccctgtggg ggtctgtgca   1920
gaaataggtc atttgtcaca catcaagtcc tggggcagga gatgcattat agatgagacc   1980
aaacagcctg tctcggtgag ctctacccac tccctgagac tagaaatggg ggaagggagc   2040
ttgagataac aaccgctgca atcactgtgt cgatgtttaa tatcagcacc aaccgggaac   2100
aataaggaga tgggtgcatt catgttcaca tcttaccagt caagtatcat cgaaccggct   2160
tgataaccac acctcgtgta atagctgagc agatagttgt cattttaaag cgttggcctt   2220
tgtcgattat gtaatgcgca cattcaacac atggtaatat agaaacggtt atgtcgaggt   2280
tgttttgtcc agagatgacc ttcacacagt tacagccgct ctgcatccac acaaatggag   2340
gacttaatcg tggactgcat tcttagaaat gatctacaaa gacaaataat gtgaaatcaa   2400
gaaaggacaa aatttaagta aggggatgag ggagagagag aacagagggc aaggagaaag   2460
catggctcct gtcttttttct gcacccatct gttcggagtg caggtggagc tctattcact   2520
cagctctgca tgtgtgtttg ggggggcag aagaaaggg agggcaaaag gaagagtgga    2580
gagatggtgg gggctggagg gatgggggt tctcggtgat ctctcctgaa ggggataatg    2640
ggagagcagc gctttgcaat ggctgccatg tagtaccctc cctgcacaat tagccaatca   2700
gcagcaagct ctgccagcca gaaggacaca taaaagaaga acattgcagc agaggcacag   2760
aaggagcctg cgaggagctg ggaaatacac acacaacagc agaaccacaa caccctcccc   2820
tggacacacc ctactgggga tcactgcttt tcttttttc tgaaccatcg cccacgccac    2880
acggagagaa atctctctct catcatcatc ctgaagaaaa ccccctatc ctcatttca    2940
cactgctgag gaaaacctac aatcgcacgg gctgagattt cctggcgaag actgtccttt   3000
ttccttttc ttttttttc ttttccttg gaaactgaca tttgcatttc tccattccaa     3060
gccacggcgt aataatatct gcaatccagc ctgaagacct gcaaatcgaa ggacctagat   3120
```

```
cactatcatc tttgtacgtc aagaatggtt actgtacgta taaccttcct ttcttttgct    3180
ctgaccaata tgaaacacta aaatcgattc gagcagcctc tcagcatcaa ttacagtgcg    3240
tgaaaaacat tcaaatagag gcagcaaata ttacatgtga aaatacaggc tggctaaatc    3300
caagctaatt tagaaatgtg gtcaaaacgc atactggcac gtctaatcgc ggattcagta    3360
aacaagatta acgattagcc cagtgtataa gtcatatgat acaggcatgc gcgagagcat    3420
cgctacaccc gagctggctt cattttcgga ggaaaatcaa aacattgctt tctcctgccg    3480
tgcgaaccat tcgtcataaa ccgtaatacg caacatacat ttattactac atccgttaat    3540
tagcgataat tagccgttat taacaaagag cgctgaggaa ttcctctcaa atagcggagg    3600
tgcggcggag gcagaggggc gtaaaagggc acatgcgtgc ctggctcaaa aaaggatgct    3660
ccagactgaa actcagagac aaaacacgat gcctcggagg ctgagagccc atcgagagga    3720
aaggcaaaga aaagggtcga gtcactcaga gggggagggg agatattgtg catccattgg    3780
tttgaattga agcaggcaga ataaaaatcc ttgcgattat gcttcgtgag agatcgcgag    3840
agaggaaaag gctaaatgcc acgtatgcaa atggataaat gtcatctatt tcttcgcgag    3900
tagacatttt gtggacaacg agagtgtaaa taagcgatat gaggggaata caaaggcctt    3960
gagggaaagc gttttgggcg tgtcttgtcg aaaagaagac agcgatggca cgcgctcaga    4020
accaccatct tcacgtagat aatccgcgtg aaaacaataa caaaactgct catttaaca     4080
cgagcaggtg tttgaaacca cccaaaaaag attgtctaaa atattaagat taattaatga    4140
cgtttaaatg tccaggcctg atataaatga acgtgtagt aagagtaatc gcctttgttt     4200
cttttcagag atacgttttc agagattcag ggaattatat cttcaataaa ataatgtttg    4260
atttcattat tttaaagctt tttaagaagt aaaaatacac attattcatt tacatttat     4320
tttatttaaa ggcctatggt cttgaaaata ataagtggaa tatataggct atatattcgt    4380
ctaaggacag ccggtgttat tttatagtga cctcagacaa aagccgagac aaaacgaggc    4440
gcttgccttt catttaatc cttaatagac ggtgtgatga atgaatgaat gaatgaataa     4500
atgaatgaat gacgggccct tcggcatgtt gttccgcagt cctccgtgag cacgagtctc    4560
taccgcagtg ccaagcacat aaaaccgttg agtcagataa ccttctccag gcgcgtatac    4620
acaattcaag gacaagcaca tcacaactat acacaacaca acacaaccgc ctaaacgcac    4680
gagctcatca atcgcaattt aaaggcatgt cagtcaaaga aaaaggcggc gttatttaaa    4740
accaatgttc aacaatattt gtatgctgac tagcccgggc gcgcacgcta taagatcaca    4800
aggccttgtt ttttcccttt attcaaaata tcattaatta ttacaggtca taaaacaaaa    4860
caatgcaaat tacaatgatt taaagactat tgatttaaca ataatcagtt aattatagaa    4920
taatattata atatttaca tacaaatgaa agatgacatt atttgatgac attgtaatta     4980
aaatatatgc aatatatttt tacgtttta ttaattaggc tattactatt attataatta      5040
tcattatttt tattattatt attattatta aatagtcttg cgaaataaga gtgaaggcag    5100
ttgcaatgtt cattgttccc ggagagtccc gcagcctctg gcctcaacac aaagcgctac    5160
tgtttacatt aatattcata gtgctgccat ggtctctgta gaggaggaac gggtggctct    5220
tttgttcgct agtgtcaata cgtttattca gcaaaaagca gctcggattt gtgaatgccc    5280
aacaagcaca cgcgcactcc aatcaaagga cgagaggata acgattttaa acgattcgca    5340
aacgtgttta tttgtaaaga cgacatcaag agcttaatgt ccacttgaaa agaaataaat    5400
atgcccgcgg cgccaaggat attttgaatg tagtcgttca tggtgagcca ctcccgaatt    5460
```

```
cagcactctg gagagcgacc aaagaggaat agcggaatag caactacttg agccatttct    5520
ctccgtttga tggcgttcat gattaaaaat ataatcacgt gatttttat  acatatataa    5580 atatatacat aaagtaacgc tttccttttg agaatacata aatatttatt cgcgtgataa    5640
atcaatgatc ttatatttat ttgcacgacc gaaattagcc aaattcacca attaaaaaaa    5700
aaataagcca acaaaaaaga agggtttatc cgttcagttt tgacttgtgt cctgttgttt    5760
tacagctgcc actgtgatcc cttaagctgc agtgagagtg tggctaatgc cttttgttta    5820
agataatcct gtaatctgtt accgaaacgg cctattgaca agccggcatt cacatttcag    5880
tcaggaggcc cgtccagaca tgtacattta tgaattacga atgataaaat taagatctgc    5940
attaggcgtc agaaatgtca cgaacaccca ttcatttccc acagccaata atggatcatg    6000
ctgggaagcg ctatcctcgc agtctcaaaa ttaatgttga catgttgcgt agagctacag    6060
attagatcag ccatatgctt tatgtgttta cctcagcgga tcttcagcaa gatgtgttta    6120
ttttaagaaa atggcttcct cgctgcctgc acagggcat  taaggaagtg acgtgagcgt    6180
cctcacagtc aaattacttt atctcatgct gctttcaggc ctctgcttat tttattatta    6240
ttattttaaa ttaggggaa  tcacggtggc gttgtgggta gggtagcgcg atcaccttac    6300
agcaagaagg tcgctggttc gagctctggc tgggtcagtt ggcatttctg tgtggagttt    6360
aaattgaatt gaaattgaat aaactaaatt ggccctagtg tatgtgtgtg aatgtaagtg    6420
tgcatgggtg tttcccagtg ttgggtttga ctggaagagc atccgcttcg taaaacatat    6480
gctggataag ttggcggttc atttcactgt ggtgaccgct gattaataaa gggactaagc    6540
tgaaaatgaa atgaattaat acattttaaa tgagcttttg ctgacatgtt tatgattaca    6600
aatagtgaaa ttgtatgtta atttacgata agtgcattgt tctaaattca tttttatgta    6660
gcagctggtt tttcttccat ttgtgtcatt caacagaaca ttttctaaa  aaagtgaact    6720 taaattttct cctccctctg acaaggcttg atggtaattt cagccgactc taattacaga    6780
ctcactaaaa ggaatcggtg cagtcattta tctttatcag cgcgctggtg ggaaggtaat    6840
aggttttgct tatgagttgt ttgcgtgcga gtctgggtcc ttgtgtaggc gatgctgatg    6900
cactgcatta aatattgagg gagaagtcgc tcaaaaatag caaagtacag gctggggcag    6960
gaacgtcaaa gcccgctcag tggccacgtt tcttgtttcg taagtcctat ttttaatagc    7020
gataattcag gctcagtaga aggaactcca gcactataag cagtctctcg cctgtctcgg    7080
cgagttatgt attttgggat gaagtgctct tccacctcta cctctgctgt gctggcgcca    7140
gtatctgggc tgtaagatag tgtacgtgtc agtctgtgtg gccgaagagc ctgtgtgttg    7200
tgtaactcac tacattcgtc gctgtggatg gctgacttgc catggggagg tttacttcag    7260
ttcacgaatc acattcgcca cgatcttgtc actttgtgtc aagactcgct ctctgtgtgt    7320
caacagctct gctgtttgag gttgaaattc tgaacttgag atatatccca ggatatatta    7380
gggctactgc caacggaaaa agcaaatggt gccatggcca tttgattgat caaacaaaca    7440
cccttttgct tgggtgacag tgaaatgtca gatccatgtt tgtactgctt taataacttg    7500
cctctctgag ctttctcctt gtcagtgtca atttgcctga gatataaatt ccggttgccc    7560
cgaaagctta ttttattaaa aaaaagctaa catgcactca tacaacgtgc gcacatacat    7620
gtgaggcttg ctaaaagtca agaagcaagc caatagcaag agtcgtcaga ctgctgttac    7680
ctgggcaacc tggttagagg taaggctcaa ggcaagaata aatcattcca ctgaagagac    7740
acagcgttac agcgagatga gagcaagagg cgatagtgaa gggagaacaa aagaacagcc    7800
tacccacact agtgcagatc tacctgtttg agctactgat tgttcagttt gattagatat    7860
```

```
cagacaattc tgctatctcc aattgcattg ctgcatgaat tcctagaaat cattttaatc   7920
accaaaaact agtagggaca cttgtggcgt atatgattct gcctgttgat tgtggggatc   7980
caacagaaag atcatgaatg cattgttaat taagtcggtg agacaccctg ttccaccccta  8040 ggggccgttc tgggggaaaga gtgctttcag tcagctaaag atgactaata tgtgaacata  8100
tattactaca catgccaatt tgtacattct ggatagttac cagccctggg aaaacatcga   8160
aaaaaataaa tcaacataga taaaattggc aaatcccttc tggtacgatg cagagtgctt   8220
gctctgagaa cttgtgcatt gtgacagaaa gcgaccgtta aaaactgaaa gtagcatcta   8280
caacctgcat acatctgttc tttgaaaatc ccctgtaggc caaattaagc atcacgctgt   8340
gctccacagc aacacggatg aaccgaaaac ccagacacaa acgcacacac ttttcacata   8400
aacaaggttt agttatgcta gctatgcttt ttcgtcctcc ctttgtcatc agcggcgagt   8460
gacgtaacac agtttgaccc tggacagcgt aaaggggggg ttgggaatga gtgaaaggac   8520
tgtgacatct gcagggccag gggctgatgg agagagctga agtgagggag gtcagaggag   8580
gaggaagggt gggatattgt cctcctcagg ccctatccct ctcagacgca ttgattttta   8640
acctctcagc gagaatgcca agcattacac ccctcaaatt atggttcctc acccaacctg   8700
ttatattttc cacctgcagc acccagcttt cttgtacaaa gtggtcacta gtcgccacca   8760
tgaggggtac gcccctgctc ctcgtcgtct ctctgttctc tctgcttcag gacgctgggg   8820
gaggggatct ggacgccagc gattacacgg gtgtcagttt ttggctcgtg actgcggcgc   8880
tcctggcatc gaccgtgttt ttcttcgtgg aaagagacag ggtgtcggcg aagtggaaaa   8940
cctcgttgac tgtctccggg ttggtgacag gcatcgcgtt ttggcactac atgtatatgc   9000
gaggggtctg gattgagaca ggtgattcac cgacggtgtt tcgttacatc aattggttgc   9060
tcactgtacc actcctcatt tgcgagtttt accttattct tgcggcagcc acgaatgtgg   9120
cgggttcgtt gttcaaaaag ctccttgttg gctcgttggt tatgctggta tttggctata   9180
tgggggaagc cggtatcatg gctgcgtggc ctgcgtttat cattggatgc ctggcttggg   9240
tctatatgat ctatgagttg tgggccggag aaggaaaatc cgcgtgtaat acggcctcgc   9300
ccgcagtgca gtccgcctat aacacgatga tgtatatcat catctttgga tgggcaatct   9360
atcccgtcgg atactttacc gggtacctca tgggtgacgg tggatctgcc ctcaatctta   9420
atctcatcta caaccttgca gacttcgtca acaagattct tttcgggctg attatctgga   9480
acgtcgcagt aaaagaatcc tcaaatgcga gcggcatggt gagcaagggc gaggagctgt   9540
tcaccggggt ggtgcccatc ctggtcgagc tggacggcga cgtaaacggc cacaagttca   9600
gcgtgtccgg cgagggcgag ggcgatgcca cctacggcaa gctgaccctg aagctgatct   9660
gcaccaccgg caagctgccc gtgccctggc ccaccctcgt gaccaccctg ggctacggcc   9720
tgcagtgctt cgcccgctac cccgaccaca tgaagcagca cgacttcttc aagtccgcca   9780
tgcccgaagg ctacgtccag gagcgcacca tcttcttcaa ggacgacggc aactacaaga   9840
cccgcgccga ggtgaagttc gagggcgaca ccctggtgaa ccgcatcgag ctgaagggca   9900
tcgacttcaa ggaggacggc aacatcctgg ggcacaagct ggagtacaac tacaacagcc   9960
acaacgtcta tatcaccgcc gacaagcaga gaaacggcat caaggccaac ttcaagatcc   10020
gccacaacat cgaggacggc ggcgtgcagc tcgccgacca ctaccagcag aacaccccca   10080
tcggcgacgg ccccgtgctg ctgcccgaca ccactacct gagctaccag tccgccctga   10140
gcaaagaccc caacgagaag cgcgatcaca tggtcctgct ggagttcgtg accgccgccg   10200
```

```
ggatcactct cggcatggac gagctgtaca agttctgcta cgagaacgag gtgtaaccgc   10260
ggtggagctc gaattaattc atcgatgatg atccagacat gataagatac attgatgagt   10320
ttggacaaac cacaactaga atgcagtgaa aaaaatgctt tatttgtgaa atttgtgatg   10380
ctattgcttt atttgtaacc attataagct gcaataaaca agttaacaac aacaattgca   10440
ttcattttat gtttcaggtt caggggagg tgtgggaggt tttttaaagc aagtaaaacc     10500
tctacaaatg tggtatggct gattatgatc ctctagatca gatctaatct gatcattcag   10560
gcgcgccaac acgtgaatac cacgcgtgat ctgcgaagat acggccacgg gtgctcttga   10620
tcctgtggct gattttggac tgtgctgctc gcagctgctg atgaatcaca tacttcctcc   10680
attttcttcc actgattgac tgttataatt tccctaattt ccaggtcaag gtgctgtgca   10740
ttgtggtaat agatgtgaca tgacgtcact tccaaaggac caatgaacat gtctgaccaa   10800
tttcatataa tgtgaaaacg atttcatag gcagaataaa taacatttaa attaaactgg    10860
gcatcagcgc aattcaattg gtttggtaat agcaagggaa aatagaatga agtgatctcc   10920
aaaaaataag tacttttga ctgtaaataa aattgtaagg agtaaaaagt acttttttt     10980 ctaaaaaat gtaattaagt aaaagtaaaa gtattgattt ttaattgtac tcaagtaaag    11040
taaaaatccc caaaaataat acttaagtac agtaatcaag taaaattact caagtactttt 11100 acacctctgg ttcttgaggt acctcttccg cttcctcgct cactgactcg ctgcgctcgg   11160
tcgttcggct gcggcgagcg gtatcagctc actcaaaggc ggtaatacgg ttatccacag   11220
aatcagggga taacgcagga agaacatgt gagcaaaagg ccagcaaaag gccaggaacc    11280
gtaaaaggcc gcgttgctg gcgttttcc ataggctccg ccccctgac gagcatcaca      11340 aaaatcgacg ctcaagtcag aggtggcgaa acccgacagg actataaaga taccaggcgt   11400 ttcccctgg aagctccctc gtgcgctctc ctgttccgac cctgccgctt accggatacc    11460
tgtccgcctt tctcccttcg ggaagcgtgg cgctttctca tagctcacgc tgtaggtatc   11520
tcagttcggt gtaggtcgtt cgctccaagc tgggctgtgt gcacgaaccc cccgttcagc   11580
ccgaccgctg cgccttatcc ggtaactatc gtcttgagtc caacccggta agacacgact   11640
tatcgccact ggcagcagcc actggtaaca ggattagcag agcgaggtat gtaggcggtg   11700
ctacagagtt cttgaagtgg tggcctaact acggctacac tagaaggaca gtatttggta   11760
tctgcgctct gctgaagcca gttaccttcg gaaaaagagt tggtagctct tgatccggca   11820
aacaaaccac cgctggtagc ggtggttttt ttgtttgcaa gcagcagatt acgcgcagaa   11880
aaaaaggatc tcaagaagat cctttgatct tttctacggg gtctgacgct cagtggaacg   11940
aaaactcacg ttaagggatt ttggtcatga gattatcaaa aaggatcttc acctagatcc   12000
ttttaaatta aaaatgaagt tttaaatcaa tctaaagtat atatgagtaa acttggtctg   12060
acagttacca atgcttaatc agtgaggcac ctatctcagc gatctgtcta tttcgttcat   12120
ccatagttgc ctgactcccc gtcgtgtaga taactacgat acgggagggc ttaccatctg   12180
gccccagtgc tgcaatgata ccgcgagacc cacgctcacc ggctccagat ttatcagcaa   12240
taaaccagcc agccggaagg gccgagcgca gaagtggtcc tgcaacttta tccgcctcca   12300
tccagtctat taattgttgc cgggaagcta gagtaagtag ttcgccagtt aatagtttgc   12360
gcaacgttgt tgccattgct acaggcatcg tggtgtcacg ctcgtcgttt ggtatggctt   12420
cattcagctc cggttcccaa cgatcaaggc gagttacatg atccccatg ttgtgcaaaa     12480 aagcggttag ctccttcggt cctccgatcg ttgtcagaag taagttggcc gcagtgttat   12540
cactcatggt tatggcagca ctgcataatt ctcttactgt catgccatcc gtaagatgct   12600
```

```
tttctgtgac tggtgagtac tcaaccaagt cattctgaga atagtgtatg cggcgaccga    12660
gttgctcttg cccggcgtca atacgggata ataccgcgcc acatagcaga actttaaaag    12720
tgctcatcat tggaaaacgt tcttcggggc gaaaactctc aaggatctta ccgctgttga    12780
gatccagttc gatgtaaccc actcgtgcac ccaactgatc ttcagcatct tttactttca    12840
ccagcgtttc tgggtgagca aaaacaggaa ggcaaaatgc cgcaaaaaag ggaataaggg    12900
cgacacggaa atgttgaata ctcatactct tcctttttca atattattga agcatttatc    12960
agggttattg tctcatgagc ggatacatat ttgaatgtat ttagaaaaat aaacaaatag    13020
gggttccgcg cacatttccc cgaggtacct gtccaggagt tcttgacaga ggtgtaaaaa    13080
gtactcaaaa attttactca agtgaaagta caagtactta gggaaaattt tactcaatta    13140
aaagtaaaag tatctggcta gaatcttact tgagtaaaag taaaaaagta ctccattaaa    13200
attgtacttg agtattaagg aagtaaaagt aaaagcaaga agaaaacta gagattcttg    13260 tttaagcttt taatctcaaa aaacattaaa tgaaatgcat acaaggtttt atcctgcttt    13320
agaactgttt gtatttaatt atcaaactat aagacagaca atctaatgcc agtacacgct    13380
actcaaagtt gtaaaacctc agatttaact tcagtagaag ctgattctca aaattgttag    13440
tgtcaagcct agctcttttg gggctgaaaa gcaatcctgc agtgctgaaa agcctctcac    13500
aggcagccga tgcgggaaga ggtgtattag tcttgataga gaggctgcaa atagcaggaa    13560
acgtgagcag agactccctg tgtctgaaa cacaggccag atgggccatt cgtacgctta    13620
atttcgaata tcgatatcaa gggcccatct cgagtatccg acacctagg tagcatgcat    13680 ggcgccttgt cgactagcta gcatcccggg aagaattcct cgacggatcc accggtgtgg    13740
aattctgcag atatcaacaa gttt                                          13764
```

<210> SEQ ID NO 48
<211> LENGTH: 1497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
atggacccca tcgctctgca ggctggttac gacctgctgg gtgacggcag acctgaaact      60
ctgtggctgg gcatcggcac tctgctgatg ctgattggaa ccttctactt tctggtccgc     120
ggatggggag tcaccgataa ggatgcccgg gaatattacg ctgtgactat cctggtgccc     180
ggaatcgcat ccgccgcata tctgtctatg ttctttggta tcgggcttac tgaggtgacc     240 gtcggggcg aaatgttgga tatctattat gccaggtacg ccgactggct gtttaccacc     300
ccacttctgc tgctggatct ggcccttctc gctaaggtgg atcgggtgac catcggcacc     360
ctggtgggtg tggacgccct gatgatcgtc actggcctca tcggagcctt gagccacacg     420
gccatagcca gatacagttg gtggttgttc tctacaattt gcatgatagt ggtgctctat     480
tttctggcta catccctgcg atctgctgca aaggagcggg ccccgaggt ggcatctacc     540 tttaacaccc tgcagctct ggtcttgtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
ggcgacaccg aggcaccaga acccagtgcc ggtgccgatg tcagtgccgc cgaccgaccg     780
gtagtagcag tgagcaaggg cgaggagaat aacatggcca tcatcaagga gttcatgcgc     840
```

```
ttcaaggtgc gcatggaggg ctccgtgaac ggccacgagt tcgagatcga gggcgagggc      900
gagggccgcc cctacgaggg cttccagacc gctaagctga aggtgaccaa gggtggcccc      960
ctgcccttcg cctgggacat cctgtcccct catttcacct acggctccaa ggcctacgtg     1020
aagcaccccg ccgacatccc cgactacttc aagctgtcct tccccgaggg cttcaagtgg     1080
gagcgcgtga tgaactacga ggacggcggc gtggtgaccg tgacccagga ctcctccctg     1140
caggacggca gttcatctca aggtgaagc tgcgcggca ccaacttccc ctccgacggc       1200
cccgtgatgc agaagaagac catgggctgg gaggcctcct ccgagcggat gtaccccgag     1260
gacggtgccc tgaagggcaa gatcaagatg aggctgaagc tgaaggacgg cggccactac     1320
acctccgagg tcaagaccac ctacaaggcc aagaagcccg tgcagctgcc cggcgcctac     1380
atcgtcgaca tcaagttgga catcacctcc cacaacgagg actacaccat cgtggaacag     1440
tacgaacgcg ccgagggccg ccactccacc ggcggcatgg acgagctgta caagtga      1497
```

<210> SEQ ID NO 49
<211> LENGTH: 1494
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atggacccca tcgctctgca ggctggttac gacctgctgg gtgacggcag acctgaaact       60
ctgtggctgg gcatcggcac tctgctgatg ctgattggaa ccttctactt tctggtccgc      120
ggatggggag tcaccgataa ggatgcccgg gaatattacg ctgtgactat cctggtgccc      180
ggaatcgcat ccgccgcata tctgtctatg ttctttggta tcgggcttac tgaggtgacc      240
gtcgggggcg aaatgttgga tatctattat gccaggtacg ccgactggct gtttaccacc      300
ccacttctgc tgctggatct ggcccttctc gctaaggtgg atcgggtgac catcggcacc      360
ctggtgggtg tggacgcccct gatgatcgtc actggcctca tcggagcctt gagccacacg      420
gccatagcca gatacagttg gtggttgttc tctacaattt gcatgatagt ggtgctctat      480
tttctggcta catccctgcg atctgctgca aaggagcggg gccccgaggt ggcatctacc      540
tttaacaccc tgcacagctct ggtcttggtg ctgtggaccg cttaccctat cctgtggatc      600
ataggcactg agggcgctgg cgtggtgggc ctgggcatcg aaactctgct gtttatggtg      660
ttggacgtga ctgccaaggt cggctttggc tttatcctgt tgagatcccg ggctattctg      720
ggcgacaccg aggcaccaga acccagtgcc ggtgccgatg tcagtgccgc cgactcaggc      780
agtaaaggag aagaactttt cactggagtt gtcccaattc ttgttgaatt agatggtgat      840
gttaatgggc acaaattttc tgtcagtgga gagggtgaag tgatgcaac atacggaaaa      900 cttacccta aattattttg cactactgga aaactacctg ttccttggcc aacactgtc      960 actactttaa cttatggtgt tcaatgcttt tcaagatacc cagatcatat gaaacggcat     1020
gactttttca agagtgccat gcccgaaggt tatgtacagg aagaactat atttttcaaa     1080 gatgacggga actacaagac acgtgctgaa gtcaagtttg aaggtgatac ccttgttaat     1140
agaatcgagt taaaggtat tgattttaaa gaagatggaa acattcttgg acacaaattg     1200
gaatacaact ataacgatca ccaggtgtac atcatggcag acaaacaaaa gaatggaatc     1260
aaagctaact tcaaaattag acacaacatt gaagatggaa gcgttcaact agcagaccat     1320
tatcaacaaa atactccaat tggcgatggg cccgtccttt taccagacaa ccattacctg     1380
```

```
ttcacaactt ctactctttc gaaagatccc aacgaaaaga gagaccacat ggtccttctt    1440
gagtttgtaa cagctgctgg gattacacat ggcatggatg aactatacaa ataa          1494
```

<210> SEQ ID NO 50
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atggacccca tcgctctgca ggctggttac gacctgctgg gtgacggcag acctgaaact      60
ctgtggctgg gcatcggcac tctgctgatg ctgattggaa ccttctactt tctggtccgc     120
ggatggggag tcaccgataa ggatgcccgg gaatattacg ctgtgactat cctggtgccc     180
ggaatcgcat ccgccgcata tctgtctatg ttctttggta tcgggcttac tgaggtgacc     240 gtcggggggcg aaatgttgga tatctattat gccaggtacg ccgactggct gtttaccacc     300
ccacttctgc tgctggatct ggcccttctc gctaaggtgg atcgggtgac catcggcacc     360
ctggtgggtg tggacgccct gatgatcgtc actggcctca tcgagccctt gagccacacg     420
gccatagcca gatacagttg gtggttgttc tctacaattt gcatgatagt ggtgctctat     480
tttctggcta catccctgcg atctgctgca aaggagcggg gccccgaggt ggcatctacc     540
tttaacaccc tgacagctct ggtcttggtg ctgtggaccg cttaccctat cctgtggatc     600
ataggcactg agggcgctgg cgtggtgggc ctgggcatcg aaactctgct gtttatggtg     660
ttggacgtga ctgccaaggt cggctttggc tttatcctgt tgagatcccg ggctattctg     720
tcaggcgtga gcaagggcga ggagaataac atggccatca tcaaggagtt catgcgcttc     780
aaggtgcgca tggagggctc cgtgaacggc cacgagttcg agatcgaggg cgagggcgag     840
ggccgcccct acgagggctt tcagaccgct aagctgaagg tgaccaaggg tggcccctg      900 ccccttcgcct gggacatcct gtcccctcat ttcacctacg gctccaaggc ctacgtgaag     960
caccccgccg acatccccga ctacttcaag ctgtccttcc ccgagggctt caagtgggag    1020
cgcgtgatga actacgagga cggcggcgtg gtgaccgtga cccaggactc ctccctgcag    1080
gacggcgagt tcatctacaa ggtgaagctg cgcggcacca acttcccctc cgacggcccc    1140
gtgatgcaga agaagaccat gggctgggag gcctcctccg agcggatgta ccccgaggac    1200
ggtgccctga agggcaagat caagatgagg ctgaagctga aggacggcgg ccactacacc    1260
tccgaggtca agaccaccta caaggccaag aagcccgtgc agctgccccgg cgcctacatc    1320 gtcgacatca gttggacat cacctcccac aacgaggact acaccatcgt ggaacagtac    1380
gaacgcgccg agggccgcca ctccaccggc ggcatggacg agctgtacaa gtga          1434
```

<210> SEQ ID NO 51
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
atggacccca tcgctctgca ggctggttac gacctgctgg gtgacggcag acctgaaact      60
ctgtggctgg gcatcggcac tctgctgatg ctgattggaa ccttctactt tctggtccgc     120
```

| | |
|---|---|
| ggatggggag tcaccgataa ggatgcccgg gaatattacg ctgtgactat cctggtgccc | 180 |
| ggaatcgcat ccgccgcata tctgtctatg ttctttggta tcgggcttac tgaggtgacc | 240 |
| gtcggggcg aaatgttgga tatctattat gccaggtacg ccgactggct gtttaccacc | 300 |
| ccacttctgc tgctggatct ggcccttctc gctaaggtgg atcgggtgac catcggcacc | 360 |
| ctggtgggtg tggacgccct gatgatcgtc actggcctca tcggagcctt gagccacacg | 420 |
| gccatagcca gatacagttg gtggttgttc tctacaattt gcatgatagt ggtgctctat | 480 |
| tttctggcta catccctgcg atctgctgca aaggagcggg gccccgaggt ggcatctacc | 540 |
| tttaacaccc tgacagctct ggtcttggtg ctgtggaccg cttaccctat cctgtggatc | 600 |
| ataggcactg agggcgctgg cgtggtgggc ctgggcatcg aaactctgct gtttatggtg | 660 |
| ttggacgtga ctgccaaggt cggctttggc tttatcctgt tgagatcccg ggctattctg | 720 |
| tcaggcatgg ccatcatcaa ggagttcatg cgcttcaagg tgcgcatgga gggctccgtg | 780 |
| aacggccacg agttcgagat cgagggcgag ggcgagggcc gccctacga gggctttcag | 840 |
| accgctaagc tgaaggtgac caagggtggc cccctgccct cgcctggga catcctgtcc | 900 |
| cctcatttca cctacggctc caaggcctac gtgaagcacc ccgccgacat ccccgactac | 960 |
| ttcaagctgt ccttccccga gggcttcaag tgggagcgcg tgatgaacta cgaggacggc | 1020 |
| ggcgtggtga ccgtgaccca ggactcctcc ctgcaggacg gcgagttcat ctacaaggtg | 1080 |
| aagctgcgcg gcaccaactt ccctcccgac ggccccgtga tgcagaagaa gaccatgggc | 1140 |
| tgggaggcct cctccgagcg gatgtacccc gaggacggtg ccctgaaggg caagatcaag | 1200 |
| atgaggctga gctgaagga cggcggccac tacacctccg aggtcaagac cacctacaag | 1260 |
| gccaagaagc ccgtgcagct gcccggcgcc tacatcgtcg acatcaagtt ggacatcacc | 1320 |
| tcccacaacg aggactacac catcgtggaa cagtacgaac gcgccgaggg ccgccactcc | 1380 |
| accggcggca tggacgagct gtacaagtga | 1410 |

<210> SEQ ID NO 52
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

| | |
|---|---|
| atggacccca tcgctctgca ggctggttac gacctgctgg gtgacggcag acctgaaact | 60 |
| ctgtggctgg gcatcggcac tctgctgatg ctgattggaa ccttctactt tctggtccgc | 120 |
| ggatggggag tcaccgataa ggatgcccgg gaatattacg ctgtgactat cctggtgccc | 180 |
| ggaatcgcat ccgccgcata tctgtctatg ttctttggta tcgggcttac tgaggtgacc | 240 |
| gtcggggcg aaatgttgga tatctattat gccaggtacg ccgactggct gtttaccacc | 300 |
| ccacttctgc tgctggatct ggcccttctc gctaaggtgg atcgggtgac catcggcacc | 360 |
| ctggtgggtg tggacgccct gatgatcgtc actggcctca tcggagcctt gagccacacg | 420 |
| gccatagcca gatacagttg gtggttgttc tctacaattt gcatgatagt ggtgctctat | 480 |
| tttctggcta catccctgcg atctgctgca aaggagcggg gccccgaggt ggcatctacc | 540 |
| tttaacaccc tgacagctct ggtcttggtg ctgtggaccg cttaccctat cctgtggatc | 600 |
| ataggcactg agggcgctgg cgtggtgggc ctgggcatcg aaactctgct gtttatggtg | 660 |
| ttggacgtga ctgccaaggt cggctttggc tttatcctgt tgagatcccg ggctattctg | 720 |

-continued

```
tcaggcatgg tgagcaaggg cgaggagctg ttcaccgggg tggtgcccat cctggtcgag    780
ctggacggcg acgtaaacgg ccacaagttc agcgtgtccg gcgagggcga gggcgatgcc    840
acctacggca agctgaccct gaagctgatc tgcaccaccg gcaagctgcc cgtgccctgg    900 cccacccctcg tgaccaccct gggctacggc ctgcagtgct cgcccgcta ccccgaccac    960 atgaagcagc acgacttctt caagtccgcc atgcccgaag gctacgtcca ggagcgcacc    1020
atcttcttca aggacgacgg caactacaag cccgcgccg aggtgaagtt cgagggcgac    1080
accctggtga accgcatcga gctgaagggc atcgacttca aggaggacgg caacatcctg    1140
gggcacaagc tggagtacaa ctacaacagc cacaacgtct atatcaccgc cgacaagcag    1200
aagaacggca tcaaggccaa cttcaagatc cgccacaaca tcgaggacgg cggcgtgcag    1260
ctcgccgacc actaccagca gaacaccccc atcggcgacg gccccgtgct gctgcccgac    1320
aaccactacc tgagctacca gtccgccctg agcaaagacc ccaacgagaa gcgcgatcac    1380
atggtcctgc tggagttcgt gaccgccgcc gggatcactc tcggcatgga cgagctgtac    1440
aagtaa                                                               1446
```

<210> SEQ ID NO 53
<211> LENGTH: 1488
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
atggacccca tcgctctgca ggctggttac gacctgctgg gtgacggcag acctgaaact     60
ctgtggctgg gcatcggcac tctgctgatg ctgattggaa ccttctactt tctggtccgc    120
ggatggggag tcaccgataa ggatgcccgg aatattacg ctgtgactat cctggtgccc    180
ggaatcgcat ccgccgcata tctgtctatg ttctttggta tcgggcttac tgaggtgacc    240 gtcggggcg aaatgttgga tatctattat gccaggtacg ccgactggct gtttaccacc    300
ccacttctgc tgctggatct ggcccttctc gctaaggtgg atcgggtgac catcggcacc    360
ctggtgggtg tggacgccct gatgatcgtc actggcctca tcggagcctt gagccacacg    420
gccatagcca gatacagttg gtggttgttc tctacaattt gcatgatagt ggtgctctat    480
tttctggcta catcctgcg atctgctgca aaggagcggg ccccgaggt ggcatctacc    540 tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgactcaggc    780
gtgagcaagg gcgaggagaa taacatggcc atcatcaagg agttcatgcg cttcaaggtg    840
cgcatggagg gctccgtgaa cggccacgag ttcgagatcg agggcgaggg cgagggccgc    900
ccctacgagg gctttcagac cgctaagctg aaggtgacca agggtggccc cctgcccttc    960
gcctgggaca tcctgtcccc tcatttcacc tacggctcca aggcctacgt gaagcacccc    1020
gccgacatcc ccgactactt caagctgtcc ttccccgagg gcttcaagtg ggagcgcgtg    1080
atgaactacg aggacggcgg cgtggtgacc gtgacccagg actcctccct gcaggacggc    1140
gagttcatct acaaggtgaa gctgcgcggg accaacttcc cctccgacgg ccccgtgatg    1200
cagaagaaga ccatgggctg ggaggcctcc tccgagcgga tgtaccccga ggacggtgcc    1260
```

| | |
|---|---|
| ctgaagggca agatcaagat gaggctgaag ctgaaggacg gcggccacta cacctccgag | 1320 |
| gtcaagacca cctacaaggc caagaagccc gtgcagctgc ccggcgccta catcgtcgac | 1380 |
| atcaagttgg acatcacctc ccacaacgag gactacacca tcgtggaaca gtacgaacgc | 1440 |
| gccgagggcc gccactccac cggcggcatg gacgagctgt acaagtga | 1488 |

<210> SEQ ID NO 54
<211> LENGTH: 1422
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

| | |
|---|---|
| atggacccca tcgctctgca ggctggttac gacctgctgg gtgacggcag acctgaaact | 60 |
| ctgtggctgg gcatcggcac tctgctgatg ctgattggaa ccttctactt tctggtccgc | 120 |
| ggatggggag tcaccgataa ggatgcccgg gaatattacg ctgtgactat cctggtgccc | 180 |
| ggaatcgcat ccgccgcata tctgtctatg ttctttggta tcgggcttac tgaggtgacc | 240 |
| gtcggggcg aaatgttgga tatctattat gccaggtacg ccaactggct gtttaccacc | 300 |
| ccacttctgc tgctggatct ggcccttctc gctaaggtgg atcgggtgac catcggcacc | 360 |
| ctggtgggtg tggacgccct gatgatcgtc actggcctca tcggagcctt gagccacacg | 420 |
| gccatagcca gatacagttg gtggttgttc tctacaattt gcatgatagt ggtgctctat | 480 |
| tttctggcta catccctgcg atctgctgca aaggagcggg gccccgaggt ggcatctacc | 540 |
| tttaacaccc tgacagctct ggtcttggtg ctgtggaccg cttaccctat cctgtggatc | 600 |
| ataggcactg agggcgctgg cgtggtgggc ctgggcatcg aaactctgct gtttatggtg | 660 |
| ttggacgtga ctgccaaggt cggctttggc tttatcctgt tgagatcccg ggctattctg | 720 |
| ggcgacaccg agtcaggcat ggccatcatc aaggagttca tgcgcttcaa ggtgcgcatg | 780 |
| gagggctccg tgaacggcca cgagttcgag atcgagggcg agggcgaggg ccgcccctac | 840 |
| gagggctttc agaccgctaa gctgaaggtg accaagggtg gccccctgcc cttcgcctgg | 900 |
| gacatcctgt cccctcattt cacctacggc tccaaggcct acgtgaagca ccccgccgac | 960 |
| atccccgact acttcaagct gtccttcccc gagggcttca gtgggagcg cgtgatgaac | 1020 |
| tacgaggacg gcgcgtggt gaccgtgacc caggactcct ccctgcagga cggcgagttc | 1080 |
| atctacaagg tgaagctgcg cggcaccaac ttccctccg acggccccgt gatgcagaag | 1140 |
| aagaccatgg gctgggaggc ctcctccgag cggatgtacc ccgaggacgg tgccctgaag | 1200 |
| ggcaagatca gatgaggct gaagctgaag gacggcggcc actacacctc gaggtcaag | 1260 |
| accacctaca aggccaagaa gcccgtgcag ctgcccggcg cctacatcgt cgacatcaag | 1320 |
| ttggacatca cctcccacaa cgaggactac accatcgtgg aacagtacga acgcgccgag | 1380 |
| ggccgccact ccaccggcgg catggacgag ctgtacaagt ga | 1422 |

<210> SEQ ID NO 55
<211> LENGTH: 1500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

| | |
|---|---|
| atggacccca tcgctctgca ggctggttac gacctgctgg gtgacggcag acctgaaact | 60 |

```
ctgtggctgg gcatcggcac tctgctgatg ctgattggaa ccttctactt tctggtccgc    120
ggatggggag tcaccgataa ggatgcccgg gaatattacg ctgtgactat cctggtgccc    180
ggaatcgcat ccgccgcata tctgtctatg ttctttggta tcgggcttac tgaggtgacc    240 gtcggggcg aaatgttgga tatctattat gccaggtacg ccaactggct gtttaccacc    300
ccacttctgc tgctggatct ggcccttctc gctaaggtgg atcgggtgac catcggcacc    360
ctggtgggtg tggacgccct gatgatcgtc actggcctca tcgagccctt gagccacacg    420
gccatagcca gatacagttg gtggttgttc tctacaattt gcatgatagt ggtgctctat    480
tttctggcta catccctgcg atctgctgca aggagcggg ccccgaggt ggcatctacc    540 tttaacaccc tgacagctct ggtcttggtg ctgtggaccg cttaccctat cctgtggatc    600
ataggcactg agggcgctgg cgtggtgggc ctgggcatcg aaactctgct gtttatggtg    660
ttggacgtga ctgccaaggt cggctttggc tttatcctgt tgagatcccg ggctattctg    720
ggcgacaccg aggcaccaga acccagtgcc ggtgccgatg tcagtgccgc cgacagcggc    780
atggtgagca agggcgagga gctgttcacc ggggtggtgc ccatcctggt cgagctggac    840
ggcgacgtaa acgccacaa gttcagcgtg tccggcgagg gcgagggcga tgccacctac    900
ggcaagctga ccctgaagct gatctgcacc accggcaagc tgcccgtgcc ctggcccacc    960
ctcgtgacca ccctgggcta cggcctgcag tgcttcgccc gctacccga ccacatgaag   1020 cagcacgact tcttcaagtc cgccatgccc gaaggctacg tccaggagcg caccatcttc   1080
ttcaaggacg acggcaacta caagacccgc gccgaggtga agttcgaggg cgacaccctg   1140
gtgaaccgca tcgagctgaa gggcatcgac ttcaaggagg acggcaacat cctggggcac   1200
aagctggagt acaactacaa cagccacaac gtctatatca ccgccgacaa gcagaagaac   1260
ggcatcaagg ccaacttcaa gatccgccac aacatcgagg acggcggcgt gcagctcgcc   1320
gaccactacc agcagaacac ccccatcggc gacggccccg tgctgctgcc cgacaaccac   1380
tacctgagct accagtccgc cctgagcaaa gaccccaacg agaagcgcga tcacatggtc   1440
ctgctggagt tcgtgaccgc cgccgggatc actctcggca tggacgagct gtacaagtga   1500
```

<210> SEQ ID NO 56
<211> LENGTH: 10745
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360 accccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg cccctattg acgtcaatga cggtaaatgg cccgcctggc    540
attatgccca gtacatgacc ttatgggact ttcctacttg gcagtacatc tacgtattag    600
```

```
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taagcagcgc gttttgcctg tactgggtct   840
ctctggttag accagatctg agcctgggag ctctctggct aactagggaa cccactgctt   900
aagcctcaat aaagcttgcc ttgagtgctt caagtagtgt gtgcccgtct gttgtgtgac   960
tctggtaact agagatccct cagacccttt tagtcagtgt ggaaaatctc tagcagtggc  1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga gaacttaga tcattatata atacagtagc aaccctctat tgtgtgcatc   1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtgaaaga tacctaaagg atcaacagct cctgggatt   1920 tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
tcgtttcaga cccacctccc aaccccgagg ggacccgaca ggcccgaagg aatagaagaa  2340
gaaggtggag agagacag agacagatcc attcgattag tgaacggatc ggcactgcgt  2400
gcgccaattc tgcagacaaa tggcagtatt catccacaat tttaaaagaa aagggggat   2460 tggggggtac agtgcagggg aaagaatagt agacataata gcaacagaca tacaaactaa  2520
agaattacaa aaacaaatta caaaaattca aaattttcgg gtttattaca gggacagcag  2580
agatccagtt tggttaatta acattatggc cttaggtcac ttcatctcca tggggttctt  2640
cttctgattt tctagaaaat gagatggggg tgcagagagc ttcctcagtg acctgcccag  2700
ggtcacatca gaaatgtcag agctagaact tgaactcaga ttactaatct taaattccat  2760
gccttggggg catgcaagta cgatatacag aaggagtgaa ctcattaggg cagatgacca  2820
atgagtttag gaaagaagag tccagggcag ggtacatcta caccacccgc ccagccctgg  2880
gtgagtccag ccacgttcac ctcattatag ttgcctctct ccagtcctac cttgacggga  2940
```

```
agcacaagca gaaactggga caggagcccc aggagaccaa atcttcatgg tccctctggg   3000
aggatgggtg gggagagctg tggcagaggc ctcaggaggg gccctgctgc tcagtggtga   3060
cagatagggg tgagaaagca gacagagtca ttccgtcagc attctgggtc tgtttggtac   3120
ttcttctcac gctaaggtgg cggtgtgata tgcacaatgg ctaaaaagca gggagagctg   3180
gaaagaaaca aggacagaga cagaggccaa gtcaaccaga ccaattccca gaggaagcaa   3240
agaaaccatt acagagacta caaggtggaa gggaaggaga gatgaattag cttcccctgt   3300
aaaccttaga acccagctgt tgccagggca acggggcaat acctgtctct tcagaggaga   3360
tgaagttgcc agggtaacta catcctgtct ttctcaagga ccatcccaga atgtggcacc   3420
cactagccgt taccatagca actgcctctt tgccccactt aatcccatcc cgtctgttaa   3480
aagggcccta tagttggagg tgggggaggt aggaagagcg atgatcactt gtggactaag   3540
tttgttcaca tcccttctc caacccctc agtacatcac cctgggagaa caaggtccac   3600
ttgcttctgg gcccacacag tcctgcagta ttgtgtatat aaggccaggg caacggagga   3660
gcaggttttg aagtgaaagg caggcaggtg ttggggaggc agttaccggg gcaacgggaa   3720
cagggcgttt cggaggtggt tgccatgggg acctggatgc tgacgaaggc tcgcgaggct   3780
gtgagcagcc acagtgccct gctcagaagc cccaagctcg tcaatcaagc tggttctcca   3840
tttgcactca ggagcacggg caggcgagtg gcccctagtt ctgggggcag cgggggatcc   3900
gccaccatgg accccatcgc tctgcaggct ggttacgacc tgctgggtga cggcagacct   3960
gaaactctgt ggctgggcat cggcactctg ctgatgctga ttggaacctt ctactttctg   4020
gtccgcggat gggagtcac cgataaggat gcccgggaat attacgctgt gactatcctg   4080
gtgcccggaa tcgcatccgc cgcatatctg tctatgttct ttggtatcgg cttactgag   4140
gtgaccgtcg ggggcgaaat gttggatatc tattatgcca ggtacgccga ctggctgttt   4200
accaccccac ttctgctgct ggatctggcc cttctcgcta aggtggatcg ggtgaccatc   4260
ggcaccctgg tgggtgtgga cgccctgatg atcgtcactg gcctcatcgg agccttgagc   4320
cacacggcca tagccagata cagttggtgg ttgttctcta caatttgcat gatagtggtg   4380
ctctattttc tggctacatc cctgcgatct gctgcaaagg agcggggccc cgaggtggca   4440
tctaccttta acaccctgac agctctggtc ttggtgctgt ggaccgctta ccctatcctg   4500
tggatcatag gcactgaggg cgctggcgtg gtgggcctgg gcatcgaaac tctgctgttt   4560
atggtgttgg acgtgactgc caaggtcggc tttggctta tcctgttgag atcccgggct   4620
attctgggcg acaccgaggc accagaaccc agtgccggtg ccgatgtcag tgccgccgac   4680
cgaccggtag tagcagtgag caagggcgag gagctgttca ccggggtggt gcccatcctg   4740
gtcgagctgg acggcgacgt aaacggccac aagttcagcg tgtccggcga gggcgagggc   4800
gatgccacct acggcaagct gaccctgaag ttcatctgca ccaccggcaa gctgcccgtg   4860
ccctggccca cctcgtgac cacccctgacc tacggcgtgc agtgcttcag ccgctacccc   4920
gaccacatga agcagcacga cttcttcaag tccgccatgc ccgaaggcta cgtccaggag   4980
cgcaccatct tcttcaagga cgacggcaac tacaagaccc gcgccgaggt gaagttcgag   5040
ggcgacaccc tggtgaaccg catcgagctg aagggcatcg acttcaagga ggacggcaac   5100
atcctggggc acaagctgga gtacaactac aacagccaca acgtctatat catggccgac   5160
aagcagaaga acggcatcaa ggtgaacttc aagatccgcc acaacatcga ggacggcagc   5220
gtgcagctcg ccgaccacta ccagcagaac accccatcg cgacggccc cgtgctgctg   5280
cccgacaacc actacctgag cacccagtcc gccctgagca agaccccaa cgagaagcgc   5340
```

```
gatcacatgg tcctgctgga gttcgtgacc gccgccggga tcactctcgg catggacgag   5400
ctgtacaagt aagaattcga tatcaagctt atcgataatc aacctctgga ttacaaaatt   5460
tgtgaaagat tgactggtat tcttaactat gttgctcctt ttacgctatg tggatacgct   5520
gctttaatgc ctttgtatca tgctattgct tcccgtatgg ctttcatttt ctcctccttg   5580
tataaatcct ggttgctgtc tctttatgag gagttgtggc ccgttgtcag caacgtggc    5640 gtggtgtgca ctgtgtttgc tgacgcaacc cccactggtt ggggcattgc caccacctgt   5700
cagctccttt ccgggactttt cgctttcccc ctccctattg ccacggcgga actcatcgcc   5760
gcctgccttg cccgctgctg acaggggct cggctgttgg gcactgacaa ttccgtggtg   5820
ttgtcgggga aatcatcgtc ctttccttgg ctgctcgcct gtgttgccac ctggattctg   5880
cgcgggacgt ccttctgcta cgtcccttcg gccctcaatc cagcggacct tccttcccgc   5940
ggcctgctgc cggctctgcg gcctcttccg cgtcttcgcc ttcgccctca gacgagtcgg   6000
atctcccttt gggccgcctc cccgcatcga taccgtcgac ctcgagacct agaaaaacat   6060
ggagcaatca caagtagcaa tacagcagct accaatgctg attgtgcctg gctagaagca   6120
caagaggagg aggaggtggg ttttccagtc acacctcagg tacctttaag accaatgact   6180
tacaaggcag ctgtagatct tagccacttt ttaaaagaaa agggggact ggaagggcta    6240 attcactccc aacgaagaca agatatcctt gatctgtgga tctaccacac aaggctac     6300 ttccctgatt ggcagaacta cacaccaggg ccagggatca gatatccact gacctttgga   6360
tggtgctaca agctagtacc agttgagcaa gagaaggtag aagaagccaa tgaaggagag   6420
aacacccgct tgttacaccc tgtgagcctg catgggatgg atgacccgga gagaagta     6480 ttagagtgga ggtttgacag ccgcctagca tttcatcaca tggcccgaga gctgcatccg   6540
gactgtactg ggtctctctg gttagaccag atctgagcct gggagctctc tggctaacta   6600
gggaacccac tgcttaagcc tcaataaagc ttgccttgag tgcttcaagt agtgtgtgcc   6660
cgtctgttgt gtgactctgg taactagaga tccctcagac ccttttagtc agtgtggaaa   6720
atctctagca gggcccgttt aaacccgctg atcagcctcg actgtgcctt ctagttgcca   6780
gccatctgtt gtttgcccct cccccgtgcc ttccttgacc ctggaaggtg ccactcccac   6840 tgtccttttcc taataaaatg aggaaattgc atcgcattgt ctgagtaggt gtcattctat   6900 tctgggggt gggtgggc aggacagcaa ggggaggat tgggaagaca atagcaggca       6960
tgctggggat gcggtgggct ctatggcttc tgaggcggaa agaaccagct ggggctctag   7020
ggggtatccc cacgcgccct gtagcggcgc attaagcgcg gcgggtgtgg tggttacgcg   7080
cagcgtgacc gctacacttg ccagcgccct agcgcccgct cctttcgctt tcttcccttc   7140
ctttctcgcc acgttcgccg gctttccccg tcaagctcta aatcggggc tccctttagg    7200 gttccgattt agtgctttac ggcacctcga ccccaaaaaa cttgattagg gtgatggttc   7260
acgtagtggg ccatcgccct gatagacggt ttttcgccct ttgacgttgg agtccacgtt   7320
ctttaatagt ggactcttgt tccaaactgg aacaacactc aaccctatct cggtctattc   7380
ttttgattta agggatttt tgccgatttc ggcctattgg ttaaaaatg agctgattta     7440 acaaaaattt aacgcgaatt aattctgtgg aatgtgtgtc agttagggtg tggaaagtcc   7500
ccaggctccc cagcaggcag aagtatgcaa agcatgcatc tcaattagtc agcaaccagg   7560
tgtggaaagt cccaggctc cccagcaggc agaagtatgc aaagcatgca tctcaattag    7620
tcagcaacca tagtcccgcc cctaactccg cccatcccgc ccctaactcc gcccagttcc   7680
```

```
gcccattctc cgccccatgg ctgactaatt ttttttattt atgcagaggc cgaggccgcc    7740
tctgcctctg agctattcca gaagtagtga ggaggctttt ttggaggcct aggcttttgc    7800
aaaaagctcc cgggagcttg tatatccatt ttcggatctg atcagcacgt gttgacaatt    7860
aatcatcggc atagtatatc ggcatagtat aatacgacaa ggtgaggaac taaaccatgg    7920
ccaagttgac cagtgccgtt ccggtgctca ccgcgcgcga cgtcgccgga gcggtcgagt    7980
tctggaccga ccggctcggg ttctcccggg acttcgtgga ggacgacttc gccggtgtgg    8040
tccgggacga cgtgaccctg ttcatcagcg cggtccagga ccaggtggtg ccggacaaca    8100
ccctggcctg ggtgtgggtg cgcggcctgg acgagctgta cgccgagtgg tcggaggtcg    8160
tgtccacgaa cttccgggac gcctccgggc cggccatgac cgagatcggc gagcagccgt    8220
ggggcggga gttcgccctg cgcgaccgg ccggcaactg cgtgcacttc gtggccgagg    8280
agcaggactg acacgtgcta cgagatttcg attccaccgc cgccttctat gaaaggttgg    8340
gcttcggaat cgttttccgg gacgccggct ggatgatcct ccagcgcggg gatctcatgc    8400
tggagttctt cgcccacccc aacttgttta ttgcagctta taatggttac aaataaagca    8460
atagcatcac aaatttcaca aataaagcat ttttttcact gcattctagt tgtggttttgt    8520
ccaaactcat caatgtatct tatcatgtct gtataccgtc gacctctagc tagagcttgg    8580
cgtaatcatg gtcatagctg tttcctgtgt gaaattgtta tccgctcaca attccacaca    8640
acatacgagc cggaagcata aagtgtaaag cctggggtgc ctaatgagtg agctaactca    8700
cattaattgc gttgcgctca ctgcccgctt tccagtcggg aaacctgtcg tgccagctgc    8760
attaatgaat cggccaacgc gcggggagag cggtttgcg tattgggcgc tcttccgctt    8820
cctcgctcac tgactcgctg cgctcggtcg ttcggctgcg gcgagcggta tcagctcact    8880
caaaggcggt aatacggtta tccacagaat caggggataa cgcaggaaag aacatgtgag    8940
caaaaggcca gcaaaaggcc aggaaccgta aaaaggccgc gttgctggcg ttttttccata    9000
ggctccgccc ccctgacgag catcacaaaa atcgacgctc aagtcagagg tggcgaaacc    9060
cgacaggact ataaagatac caggcgtttc ccctggaag ctccctcgtg cgctctcctg    9120
ttccgaccct gccgcttacc ggatacctgt ccgcctttct cccttcggga agcgtggcgc    9180
tttctcatag ctcacgctgt aggtatctca gttcggtgta ggtcgttcgc tccaagctgg    9240
gctgtgtgca cgaaccccc gttcagcccg accgctgcgc cttatccggt aactatcgtc    9300
ttgagtccaa cccggtaaga cacgacttat cgccactggc agcagccact ggtaacagga    9360
ttagcagagc gaggtatgta ggcggtgcta cagagttctt gaagtggtgg cctaactacg    9420
gctacactag aagaacagta tttggtatct gcgctctgct gaagccagtt accttcggaa    9480
aaagagttgg tagctcttga tccggcaaac aaaccaccgc tggtagcggt ggtttttttg    9540
tttgcaagca gcagattacg cgcagaaaaa aaggatctca agaagatcct ttgatctttt    9600
ctacggggtc tgacgctcag tggaacgaaa actcacgtta agggattttg gtcatgagat    9660
tatcaaaaag gatcttcacc tagatccttt taaattaaaa atgaagtttt aaatcaatct    9720
aaagtatata tgagtaaact tggtctgaca gttaccaatg cttaatcagt gaggcaccta    9780
tctcagcgat ctgtctattt cgttcatcca tagttgcctg actccccgtc gtgtagataa    9840
ctacgatacg ggagggctta ccatctggcc ccagtgctgc aatgataccg cgagacccac    9900
gctcaccggc tccagattta tcagcaataa accagccagc cggaagggcc gagcgcagaa    9960
gtggtcctgc aactttatcc gcctccatcc agtctattaa ttgttgccgg gaagctagag   10020
taagtagttc gccagttaat agtttgcgca acgttgttgc cattgctaca ggcatcgtgg   10080
```

| | | | |
|---|---|---|---|
| tgtcacgctc gtcgtttggt atggcttcat tcagctccgg ttcccaacga tcaaggcgag | 10140 |
| ttacatgatc ccccatgttg tgcaaaaaag cggttagctc cttcggtcct ccgatcgttg | 10200 |
| tcagaagtaa gttggccgca gtgttatcac tcatggttat ggcagcactg cataattctc | 10260 |
| ttactgtcat gccatccgta agatgctttt ctgtgactgg tgagtactca accaagtcat | 10320 |
| tctgagaata gtgtatgcgg cgaccgagtt gctcttgccc ggcgtcaata cgggataata | 10380 |
| ccgcgccaca tagcagaact taaaagtgc tcatcattgg aaaacgttct cgggcgaa | 10440 |
| aactctcaag gatcttaccg ctgttgagat ccagttcgat gtaacccact cgtgcaccca | 10500 |
| actgatcttc agcatctttt actttcacca gcgtttctgg gtgagcaaaa acaggaaggc | 10560 |
| aaaatgccgc aaaaaaggga ataagggcga cacggaaatg ttgaatactc atactcttcc | 10620 |
| ttttcaata ttattgaagc atttatcagg gttattgtct catgagcgga tacatatttg | 10680 |
| aatgtattta gaaaaataaa caaatagggg ttccgcgcac atttccccga aaagtgccac | 10740 |
| ctgac | 10745 |

<210> SEQ ID NO 57
<211> LENGTH: 10745
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

| | | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagaccctt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |

```
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctgggatt     1920 tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aacccgagg ggacccgaca ggcccgaagg aatagaagaa     2340
gaaggtggag agagacag agacagatcc attcgattag tgaacggatc ggcactgcgt      2400
gcgccaattc tgcagacaaa tggcagtatt catccacaat tttaaaagaa aagggggggat   2460 tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060 cagataggg tgagaaagca gacagagtca ttccgtcagc attctgggtc tgtttggtac     3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt     3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tgggggaggt aggaagagcg atgatcactt gtggactaag    3540
tttgttcaca tccccttctc caaccccctc agtacatcac cctgggagaa caaggtccac    3600
ttgcttctgg gcccacacag tcctgcagta ttgtgtatat aaggccaggg caacggagga    3660
```

```
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cgggggatcc    3900
gccaccatgg accccatcgc tctgcaggct ggttacgacc tgctgggtga cggcagacct    3960
gaaactctgt ggctgggcat cggcactctg ctgatgctga ttggaacctt ctactttctg    4020
gtccgcggat ggggagtcac cgataaggat gcccgggaat attacgctgt gactatcctg    4080
gtgcccggaa tcgcatccgc cgcatatctg tctatgttct ttggtatcgg gcttactgag    4140
gtgaccgtcg ggggcgaaat gttggatatc tattatgcca ggtacgccaa ctggctgttt    4200
accaccccac ttctgctgct ggatctggcc cttctcgcta aggtggatcg ggtgaccatc    4260
ggcaccctgg tgggtgtgga cgccctgatg atcgtcactg gcctcatcgg agccttgagc    4320
cacacggcca tagccagata cagttggtgg ttgttctcta caatttgcat gatagtggtg    4380 ctctatttc tggctacatc cctgcgatct gctgcaaagg agcggggccc cgaggtggca    4440 tctacctta acaccctgac agctctggtc ttggtgctgt ggaccgctta ccctatcctg    4500
tggatcatag gcactgaggg cgctggcgtg gtgggcctgg gcatcgaaac tctgctgttt    4560
atggtgttgg acgtgactgc caaggtcggc tttggctta tcctgttgag atcccgggct    4620
attctgggcg acaccgaggc accagaaccc agtgccggtg ccgatgtcag tgccgccgac    4680
cgaccggtag tagcagtgag caagggcgag gagctgttca ccggggtggt gcccatcctg    4740
gtcgagctgg acggcgacgt aaacggccac aagttcagcg tgtccggcga gggcgagggc    4800
gatgccacct acggcaagct gaccctgaag ttcatctgca ccaccggcaa gctgcccgtg    4860
ccctggccca ccctcgtgac caccctgacc tacggcgtgc agtgcttcag ccgctacccc    4920
gaccacatga agcagcacga cttcttcaag tccgccatgc ccgaaggcta cgtccaggag    4980
cgcaccatct tcttcaagga cgacggcaac tacaagaccc gcgccgaggt gaagttcgag    5040
ggcgacaccc tggtgaaccg catcgagctg aagggcatcg acttcaagga ggacggcaac    5100
atcctggggc acaagctgga gtacaactac aacagccaca acgtctatat catggccgac    5160
aagcagaaga acggcatcaa ggtgaacttc aagatccgcc acaacatcga ggacggcagc    5220
gtgcagctcg ccgaccacta ccagcagaac ccccccatcg gcgacggccc cgtgctgctg    5280
cccgacaacc actacctgag cacccagtcc gccctgagca agacccccaa cgagaagcgc    5340
gatcacatgg tcctgctgga gttcgtgacc gccgccggga tcactctcgg catggacgag    5400
ctgtacaagt aagaattcga tatcaagctt atcgataatc aacctctgga ttacaaaatt    5460
tgtgaaagat tgactggtat tcttaactat gttgctcctt ttacgctatg tggatacgct    5520
gctttaatgc ctttgtatca tgctattgct tcccgtatgg ctttcatttt ctcctccttg    5580
tataaatcct ggttgctgtc tctttatgag gagttgtggc ccgttgtcag gcaacgtggc    5640
gtggtgtgca ctgtgtttgc tgacgcaacc cccactggtt ggggcattgc caccacctgt    5700
cagctccttt ccgggacttt cgctttcccc ctccctattg ccacggcgga actcatcgcc    5760
gcctgccttg cccgctgctg gacaggggct cggctgttgg gcactgacaa ttccgtggtg    5820
ttgtcgggga atcatcgtc ctttccttgg ctgctcgcct gtgttgccac ctggattctg    5880
cgcgggacgt ccttctgcta cgtcccttcg ccctcaatc cagcggacct tccttcccgc    5940
ggcctgctgc cggctctgcg gcctcttccg cgtcttcgcc ttcgccctca gacgagtcgg    6000
atctcccttt gggccgcctc cccgcatcga taccgtcgac ctcgagacct agaaaaacat    6060
```

```
ggagcaatca caagtagcaa tacagcagct accaatgctg attgtgcctg gctagaagca    6120
caagaggagg aggaggtggg ttttccagtc acacctcagg tacctttaag accaatgact    6180
tacaaggcag ctgtagatct tagccacttt ttaaaagaaa agggggggact ggaagggcta   6240 attcactccc aacgaagaca agatatcctt gatctgtgga tctaccacac acaaggctac    6300
ttccctgatt ggcagaacta cacaccaggg ccagggatca gatatccact gacctttgga    6360
tggtgctaca agctagtacc agttgagcaa gagaaggtag aagaagccaa tgaaggagag    6420
aacacccgct tgttacaccc tgtgagcctg catgggatgg atgacccgga gagagaagta    6480
ttagagtgga ggtttgacag ccgcctagca tttcatcaca tggcccgaga gctgcatccg    6540
gactgtactg ggtctctctg gttagaccag atctgagcct gggagctctc tggctaacta    6600
gggaacccac tgcttaagcc tcaataaagc ttgccttgag tgcttcaagt agtgtgtgcc    6660
cgtctgttgt gtgactctgg taactagaga tccctcagac ccttttagtc agtgtggaaa    6720
atctctagca gggcccgttt aaacccgctg atcagcctcg actgtgcctt ctagttgcca    6780
gccatctgtt gtttgcccct cccccgtgcc ttccttgacc ctggaaggtg ccactcccac    6840 tgtccttttcc taataaaatg aggaaattgc atcgcattgt ctgagtaggt gtcattctat    6900 tctgggggt ggggtgggc aggacagcaa ggggggaggat tgggaagaca atagcaggca    6960
tgctggggat gcggtgggct ctatggcttc tgaggcggaa agaaccagct ggggctctag    7020
ggggtatccc cacgcgccct gtagcggcgc attaagcgcg gcgggtgtgg tggttacgcg    7080
cagcgtgacc gctacacttg ccagcgccct agcgcccgct cctttcgctt tcttcccttc    7140
ctttctcgcc acgttcgccg gctttccccg tcaagctcta aatcggggc tccctttagg    7200 gttccgattt agtgctttac ggcacctcga ccccaaaaaa cttgattagg gtgatggttc    7260
acgtagtggg ccatcgccct gatagacggt ttttcgccct ttgacgttgg agtccacgtt    7320
ctttaatagt ggactcttgt tccaaactgg aacaacactc aaccctatct cggtctattc    7380
ttttgattta aagggatttt tgccgatttc ggcctattgg ttaaaaaatg agctgattta    7440
acaaaaattt aacgcgaatt aattctgtgg aatgtgtgtc agttagggtg tggaaagtcc    7500
ccaggctccc cagcaggcag aagtatgcaa agcatgcatc tcaattagtc agcaaccagg    7560
tgtggaaagt ccccaggctc cccagcaggc agaagtatgc aaagcatgca tctcaattag    7620
tcagcaacca tagtcccgcc cctaactccg cccatcccgc ccctaactcc gcccagttcc    7680
gcccattctc cgccccatgg ctgactaatt ttttttattt atgcagaggc cgaggccgcc    7740
tctgcctctg agctattcca gaagtagtga ggaggctttt ttggaggcct aggcttttgc    7800
aaaaagctcc cgggagcttg tatatccatt ttcggatctg atcagcacgt gttgacaatt    7860
aatcatcggc atagtatatc ggcatagtat aatacgacaa ggtgaggaac taaaccatgg    7920
ccaagttgac cagtgccgtt ccggtgctca ccgcgcgcga cgtcgccgga gcggtcgagt    7980
tctggaccga ccggctcggg ttctcccggg acttcgtgga ggacgacttc gccggtgtgg    8040
tccgggacga cgtgaccctg ttcatcagcg cggtccagga ccaggtggtg ccggacaaca    8100
ccctggcctg ggtgtgggtg cgcggcctgg acgagctgta cgccgagtgg tcggaggtcg    8160
tgtccacgaa cttccgggac gcctccggcc ggccatgac cgagatcggc gagcagccgt    8220
gggggcggga gttcgccctg cgcgacccgg ccggcaactg cgtgcacttc gtggccgagg    8280
agcaggactg acacgtgcta cgagatttcg attccaccgc cgccttctat gaaaggttgg    8340
gcttcggaat cgttttccgg gacgccggct ggatgatcct ccagcgcggg gatctcatgc    8400
```

```
tggagttctt cgcccacccc aacttgttta ttgcagctta taatggttac aaataaagca    8460
atagcatcac aaatttcaca aataaagcat tttttttcact gcattctagt tgtggtttgt   8520
ccaaactcat caatgtatct tatcatgtct gtataccgtc gacctctagc tagagcttgg    8580
cgtaatcatg gtcatagctg tttcctgtgt gaaattgtta tccgctcaca attccacaca    8640
acatacgagc cggaagcata agtgtaaag cctggggtgc ctaatgagtg agctaactca     8700
cattaattgc gttgcgctca ctgcccgctt tccagtcggg aaacctgtcg tgccagctgc    8760
attaatgaat cggccaacgc gcggggagag gcggtttgcg tattgggcgc tcttccgctt    8820
cctcgctcac tgactcgctg cgctcggtcg ttcggctgcg gcgagcggta tcagctcact    8880
caaaggcggt aatacggtta ccacagaat caggggataa gcaggaaag aacatgtgag      8940 caaaaggcca gcaaaaggcc aggaaccgta aaaaggccgc gttgctggcg ttttccata     9000 ggctccgccc ccctgacgag catcacaaaa atcgacgctc aagtcagagg tggcgaaacc    9060
cgacaggact ataaagatac caggcgtttc ccctggaag ctccctcgtg cgctctcctg     9120
ttccgaccct gccgcttacc ggatacctgt ccgcctttct cccttcggga agcgtggcgc    9180
tttctcatag ctcacgctgt aggtatctca gttcggtgta ggtcgttcgc tccaagctgg    9240
gctgtgtgca cgaaccccc gttcagcccg accgctgcgc cttatccggt aactatcgtc    9300
ttgagtccaa cccggtaaga cacgacttat cgccactggc agcagccact ggtaacagga    9360
ttagcagagc gaggtatgta ggcggtgcta cagagttctt gaagtggtgg cctaactacg    9420
gctacactag aagaacagta tttggtatct gcgctctgct gaagccagtt accttcggaa    9480
aaagagttgg tagctcttga tccggcaaac aaaccaccgc tggtagcggt ggtttttttg    9540
tttgcaagca gcagattacg cgcagaaaaa aaggatctca agaagatcct ttgatctttt    9600
ctacggggtc tgacgctcag tggaacgaaa actcacgtta agggattttg gtcatgagat    9660
tatcaaaaag gatcttcacc tagatccttt taaattaaaa atgaagtttt aaatcaatct    9720
aaagtatata tgagtaaact tggtctgaca gttaccaatg cttaatcagt gaggcaccta    9780
tctcagcgat ctgtctattt cgttcatcca tagttgcctg actccccgtc gtgtagataa    9840
ctacgatacg ggagggctta ccatctggcc ccagtgctgc aatgataccg cgagacccac    9900
gctcaccggc tccagattta tcagcaataa accagccagc cggaagggcc gagcgcagaa    9960
gtggtcctgc aactttatcc gcctccatcc agtctattaa ttgttgccgg gaagctagag    10020
taagtagttc gccagttaat agtttgcgca acgttgttgc cattgctaca ggcatcgtgg    10080
tgtcacgctc gtcgtttggt atggcttcat tcagctccgg ttcccaacga tcaaggcgag    10140
ttacatgatc ccccatgttg tgcaaaaaag cggttagctc cttcggtcct ccgatcgttg    10200
tcagaagtaa gttggccgca gtgttatcac tcatggttat ggcagcactg cataattctc    10260
ttactgtcat gccatccgta agatgctttt ctgtgactgg tgagtactca accaagtcat    10320
tctgagaata gtgtatgcgg cgaccgagtt gctcttgccc ggcgtcaata cgggataata    10380
ccgcgccaca tagcagaact ttaaaagtgc tcatcattgg aaaacgttct cggggcgaa    10440 aactctcaag gatcttaccg ctgttgagat ccagttcgat gtaacccact cgtgcaccca    10500
actgatcttc agcatctttt actttcacca gcgtttctgg gtgagcaaaa acaggaaggc    10560
aaaatgccgc aaaaaaggga ataagggcga cacggaaatg ttgaatactc atactcttcc    10620
tttttcaata ttattgaagc atttatcagg gttattgtct catgagcgga tacatatttg    10680
aatgtattta gaaaaataaa caaatagggg ttccgcgcac atttccccga aaagtgccac    10740
ctgac                                                               10745
```

-continued

<210> SEQ ID NO 58
<211> LENGTH: 9812
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
caggtggcac ttttcgggga aatgtgcgcg gaacccctat ttgtttattt ttctaaatac        60
attcaaatat gtatccgctc atgagacaat aaccctgata aatgcttcaa taatattgaa       120
aaaggaagag tatgagtatt caacatttcc gtgtcgccct tattcccttt tttgcggcat       180
tttgccttcc tgttttttgct cacccagaaa cgctggtgaa agtaaaagat gctgaagatc      240
agttgggtgc acgagtgggt tacatcgaac tggatctcaa cagcggtaag atccttgaga       300
gttttcgccc cgaagaacgt tttccaatga tgagcacttt taaagttctg ctatgtggcg       360
cggtattatc ccgtattgac gccgggcaag agcaactcgg tcgccgcata cactattctc       420
agaatgactt ggttgagtac tcaccagtca cagaaaagca tcttacggat ggcatgacag       480
taagagaatt atgcagtgct gccataacca tgagtgataa cactgcggcc aacttacttc       540
tgacaacgat cggaggaccg aaggagctaa ccgcttttt gcacaacatg ggggatcatg        600
taactcgcct tgatcgttgg gaaccggagc tgaatgaagc cataccaaac gacgagcgtg       660
acaccacgat gcctgtagca atggcaacaa cgttgcgcaa actattaact ggcgaactac       720
ttactctagc ttcccggcaa caattaatag actggatgga ggcggataaa gttgcaggac       780
cacttctgcg ctcggccctt ccggctggct ggtttattgc tgataaatct ggagccggtg       840
agcgtgggtc tcgcggtatc attgcagcac tggggccaga tggtaagccc tcccgtatcg       900
tagttatcta cacgacgggg agtcaggcaa ctatggatga acgaaataga cagatcgctg       960
agataggtgc ctcactgatt aagcattggt aactgtcaga ccaagtttac tcatatatac      1020
tttagattga tttaaaactt catttttaat ttaaaaggat ctaggtgaag atcctttttg      1080
ataatctcat gaccaaaatc ccttaacgtg agttttcgtt ccactgagcg tcagaccccg      1140
tagaaaagat caaaggatct cttgagatc ctttttttct gcgcgtaatc tgctgcttgc       1200
aaacaaaaaa accaccgcta ccagcggtgg tttgtttgcc ggatcaagag ctaccaactc      1260
tttttccgaa ggtaactggc ttcagcagag cgcagatacc aaatactgtc cttctagtgt      1320
agccgtagtt aggccaccac ttcaagaact ctgtagcacc gcctacatac ctcgctctgc      1380
taatcctgtt accagtggct gctgccagtg gcgataagtc gtgtcttacc gggttggact      1440
caagacgata gttaccggat aaggcgcagc ggtcgggctg aacggggggt tcgtgcacac      1500
agcccagctt ggagcgaacg acctacaccg aactgagata cctacagcgt gagctatgag      1560
aaagcgccac gcttcccgaa gggagaaagg cggacaggta tccggtaagc ggcagggtcg      1620
gaacaggaga gcgcacgagg gagcttccag ggggaaacgc ctggtatctt tatagtcctg      1680
tcgggtttcg ccacctctga cttgagcgtc gatttttgtg atgctcgtca gggggggcgga     1740
gcctatggaa aaacgccagc aacgcggcct ttttacggtt cctggccttt tgctggcctt      1800
ttgctcacat gttctttcct gcgttatccc ctgattctgt ggataaccgt attaccgcct      1860
ttgagtgagc tgataccgct cgccgcagcc gaacgaccga gcgcagcgag tcagtgagcg      1920
aggaagcgga gagcgcccca atacgcaaac cgcctctccc cgcgcgttgg ccgattcatt      1980
aatgcagctg gcacgacagg tttcccgact ggaaagcggg cagtgagcgc aacgcaatta      2040
```

```
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgcc   2400
gcattgcaga gatattgtat ttaagtgcct agctcgatac aataaacggg tctctctggt   2460
tagaccagat ctgagcctgg gagctctctg gctaactagg gaacccactg cttaagcctc   2520
aataaagctt gccttgagtg cttcaagtag tgtgtgcccg tctgttgtgt gactctggta   2580
actagagatc cctcagaccc ttttagtcag tgtggaaaat ctctagcagt ggcgcccgaa   2640
cagggacctg aaagcgaaag ggaaaccaga gctctctcga cgcaggactc ggcttgctga   2700
agcgcgcacg gcaagaggcg aggggcggcg actggtgagt acgccaaaaa ttttgactag   2760
cggaggctag aaggagagag atgggtgcga gagcgtcagt attaagcggg ggagaattag   2820
atcgcgatgg gaaaaaattc ggttaaggcc agggggaaag aaaaaatata aattaaaaca   2880
tatagtatgg gcaagcaggg agctagaacg attcgcagtt aatcctggcc tgttagaaac   2940
atcagaaggc tgtagacaaa tactgggaca gctacaacca tcccttcaga caggatcaga   3000
agaacttaga tcattatata atacagtagc aaccctctat tgtgtgcatc aaaggataga   3060
gataaaagac accaaggaag ctttagacaa gatagaggaa gagcaaaaca aaagtaagac   3120
caccgcacag caagcggccg ctgatcttca gacctggagg aggagatatg agggacaatt   3180
ggagaagtga attatataaa tataaagtag taaaaattga accattagga gtagcaccca   3240
ccaaggcaaa gagaagagtg gtgcagagag aaaaaagagc agtgggaata ggagctttgt   3300
tccttgggtt cttgggagca gcaggaagca ctatgggcgc agcctcaatg acgctgacgg   3360
tacaggccag acaattattg tctggtatag tgcagcagca gaacaatttg ctgagggcta   3420
ttgaggcgca acagcatctg ttgcaactca cagtctgggg catcaagcag ctccaggcaa   3480
gaatcctggc tgtggaaaga tacctaaagg atcaacagct cctggggatt tggggttgct   3540
ctggaaaact catttgcacc actgctgtgc cttggaatgc tagttggagt aataaatctc   3600
tggaacagat tggaatcaca cgacctggat ggagtgggac agagaaatta acaattacac   3660
aagcttaata cactccttaa ttgaagaatc gcaaaaccag caagaaaaga atgaacaaga   3720
attattggaa ttagataaat gggcaagttt gtggaattgg tttaacataa caaattggct   3780
gtggtatata aaattattca taatgatagt aggaggcttg gtaggtttaa gaatagtttt   3840
tgctgtactt tctatagtga atagagttag gcagggatat tcaccattat cgtttcagac   3900
ccacctccca accccgaggg gacccgacag gcccgaagga atagaagaag aaggtggaga   3960
gagagacaga gacagatcca ttcgattagt gaacggatct cgacggttaa cttttaaaag   4020
aaaaggggggg attgggggggt acagtgcagg ggaaagaata gtagacataa tagcaacaga   4080
catacaaact aaagaattac aaaaacaaat tacaaaaatt caaaatttta tcgataagct   4140
tgggagttcc gcgttacata acttacggta aatggcccgc ctggctgacc gcccaacgac   4200
ccccgcccat tgacgtcaat aatgacgtat gttcccatag taacgccaat agggactttc   4260
cattgacgtc aatgggtgga gtatttacgg taaactgccc acttggcagt acatcaagtg   4320
tatcatatgc caagtacgcc ccctattgac gtcaatgacg gtaaatggcc cgcctggcat   4380
```

```
tatgcccagt acatgacctt atgggacttt cctacttggc agtacatcta cgtattagtc    4440
atcgctatta ccatggtgat gcggttttgg cagtacatca atgggcgtgg atagcggttt    4500
gactcacggg gatttccaag tctccacccc attgacgtca atgggagttt gttttggcac    4560
caaaatcaac gggactttcc aaaatgtcgt aacaactccg ccccattgac gcaaatgggc    4620
ggtaggcgtg tacggtggga ggtctatata agcagagctc gtttagtgaa ccgtcagatc    4680
gcctggagac gccatccacg ctgttttgac ctccatagaa gacaccgact ctagagatgg    4740
accccatcgc tctgcaggct ggttacgacc tgctgggtga cggcagacct gaaactctgt    4800
ggctgggcat cggcactctg ctgatgctga ttggaacctt ctactttctg gtccgcggat    4860
ggggagtcac cgataaggat gcccgggaat attacgctgt gactatcctg gtgcccggaa    4920
tcgcatccgc cgcatatctg tctatgttct ttggtatcgg gcttactgag gtgaccgtcg    4980
ggggcgaaat gttggatatc tattatgcca ggtacgccaa ctggctgttt accacccccac   5040
ttctgctgct ggatctggcc cttctcgcta aggtggatcg ggtgaccatc ggcaccctgg    5100
tgggtgtgga cgccctgatg atcgtcactg gcctcatcgg agccttgagc cacacggcca    5160
tagccagata cagttggtgg ttgttctcta caatttgcat gatagtggtg ctctattttc    5220
tggctacatc cctgcgatct gctgcaaagg agcggggccc cgaggtggca tctacccttta   5280
acaccctgac agctctggtc ttggtgctgt ggaccgctta ccctatcctg tggatcatag    5340
gcactgaggg cgctggcgtg gtgggcctgg gcatcgaaac tctgctgttt atggtgttgg    5400
acgtgactgc caaggtcggc tttggcttta tcctgttgag atcccgggct attctgggcg    5460
acaccgaggc accagaaccc agtgccggtg ccgatgtcag tgccgccgac cgaaccggta    5520
acgtctatat caaggccgac aagcagaaga acggcatcaa ggcgaacttc aagatccgcc    5580
acaacatcga ggacggcggc gtgcagctcg cctaccacta ccagcagaac ccccccatcg    5640
gcgacggccc cgtgctgctg cccgacaacc actacctgag cgtgcagtcc aaactttcga    5700
aagaccccaa cgagaagcgc gatcacatgg tcctgctgga gttcgtgacc gccgccggga    5760
tcactctcgg catggacgag ctgtacaagg gcggtaccgg agggagcatg gtgagcaagg    5820
gcgaggagct gttcaccggg gtggtgccca tcctggtcga gctggacggc gacgtaaacg    5880
gccacaagtt cagcgtgtcc ggcgagggcg agggcgatgc cacctacggc aagctgaccc    5940
tgaagttcat ctgcaccacc ggcaagctgc ccgtgccctg gcccaccctc gtgaccaccc    6000
tgacctacgg cgtgcagtgc ttcagccgct accccgacca catgaagcag cacgacttct    6060
tcaagtccgc catgcccgaa ggctacatcc aggagcgcac catcttcttc aaggacgacg    6120
gcaactacaa gacccgcgcc gaggtgaagt tcgagggcga caccctggtg aaccgcatcg    6180
agctgaaggg catcgacttc aaggaggacg gcaacatcct ggggcacaag ctggagtaca    6240
acacgcgtga ccaactgact aagagcagat cgcagaatt taaagaggct ttctccctat    6300
ttgacaagga cggggatggg acaataacaa ccaaggagct ggggacggtg atgcggtctc    6360
tggggcagaa ccccacagaa gcagagctgc aggacatgat caatgaagta gatgccgacg    6420
gtgacggcac aatcgacttc cctgagttcc tgacaatgat ggcaagaaaa atgaaagaca    6480
cagcagtga agaagaaatt agagaagcgt tccgtgtgtt tgataaggat ggcaatggct     6540
acatcagtgc agcagagctt cgccacgtga tgacaaacct tggagagaag ttaacagatg    6600
aagaggttga tgaaatgatc agggaagcag acatcgatgg ggatggtcag gtaaactacg    6660
aagagtttgt acaaatgatg acagcgaagt aacaatcaac ctctggatta caaaatttgt    6720
gaaagattga ctggtattct taactatgtt gctcctttta cgctatgtgg atacgctgct    6780
```

```
ttaatgcctt tgtatcatgc tattgcttcc cgtatggctt tcattttctc ctccttgtat    6840
aaatcctggt tgctgtctct ttatgaggag ttgtggcccg ttgtcaggca acgtggcgtg    6900
gtgtgcactg tgtttgctga cgcaaccccc actggttggg gcattgccac cacctgtcag    6960
ctcctttccg ggactttcgc tttcccctc cctattgcca cggcggaact catcgccgcc    7020
tgccttgccc gctgctggac aggggctcgg ctgttgggca ctgacaattc cgtggtgttg    7080
tcggggaagc tgacgtcctt tccatggctg ctcgcctgtg ttgccacctg gattctgcgc    7140
gggacgtcct tctgctacgt cccttcggcc ctcaatccag cggaccttcc ttcccgcggc    7200
ctgctgccgc ctctgcggcc tcttccgcgt cttcgccttc gccctcagac gagtcggatc    7260
tccctttggg ccgcctcccc gcctggaatt ctaccgggta ggggaggcgc ttttcccaag    7320
gcagtctgga gcatgcgctt tagcagcccc gctgggcact tggcgctaca caagtggcct    7380
ctggcctcgc acacattcca catccaccgg taggcgccaa ccggctccgt tctttggtgg    7440 cccctttcgcg ccaccttcta ctcctcccct agtcaggaag ttccccccg ccccgcagct    7500 cgcgtcgtgc aggacgtgac aaatggaagt agcacgtctc actagtctcg tgcagatgga    7560
cagcaccgct gagcaatgga agcgggtagg cctttggggc agcggccaat agcagctttg    7620
ctccttcgct ttctgggctc agaggctggg aaggggtggg tccggggcg ggctcagggg    7680 cgggctcagg ggcggggcgg gcgcccgaag gtcctccgga ggcccggcat tctgcacgct    7740
tcaaaagcgc acgtctgccg cgctgttctc ctcttcctca tctccgggcc tttcgacctg    7800
cagcccaagc ttaccatgac cgagtacaag cccacggtgc gcctcgccac ccgcgacgac    7860
gtccccaggg ccgtacgcac cctcgccgcc gcgttcgccg actaccccgc cacgcgccac    7920
accgtcgatc cggaccgcca catcgagcgg gtcaccgagc tgcaagaact cttcctcacg    7980
cgcgtcgggc tcgacatcgg caaggtgtgg gtcgcggacg acggcgccgc ggtggcggtc    8040
tggaccacgc cggagagcgt cgaagcgggg gcggtgttcg ccgagatcgg cccgcgcatg    8100
gccgagttga gcggttcccg gctggccgcg cagcaacaga tggaaggcct cctggcgccg    8160
caccggccca aggagcccgc gtggttcctg gccaccgtcg gcgtctcgcc cgaccaccag    8220
ggcaagggtc tgggcagcgc cgtcgtgctc cccggagtgg aggcggccga gcgcgccggg    8280
gtgcccgcct tcctggagac ctccgcgccc cgcaacctcc ccttctacga gcggctcggc    8340
ttcaccgtca ccgccgacgt cgaggtgccc gaaggaccgc gcacctggtg catgacccgc    8400
aagcccggtg cctgacgccc gccccacgac ccgcagcgcc cgaccgaaag gagcgcacga    8460
ccccatgcat ctcgagggcc cggtaccttt aagaccaatg acttacaagg cagctgtaga    8520
tcttagccac ttttttaaaag aaaaggggg actggaaggg ctagctcact cccaacgaag    8580
acaagatctg ctttttgctt gtactgggtc tctctggtta daccagatct gagcctggga    8640
gctctctggc tgcctaggga acccactgct taagcctcaa taaagcttgc cttgagtgct    8700
tcaagtagtg tgtgcccgtc tgttgtgtga ctctggtaac tagagatccc tcagaccctt    8760
ttagtcagtg tggaaaatct ctagcagtag tagttcatgt catcttatta ttcagtattt    8820
ataacttgca aagaaatgaa tatcagagag tgagaggaac ttgtttattg cagcttataa    8880
tggttacaaa taaagcaata gcatcacaaa tttcacaaat aaagcatttt ttcactgca    8940 ttctagttgt ggtttgtcca aactcatcaa tgtatcttat catgtctggc tctagctatc    9000
ccgcccctaa ctccgcccag ttccgcccat tctccgcccc atggctgact aattttttt    9060 atttatgcag aggccgaggc cgcctcggcc tctgagctat tccagaagta gtgaggaggc    9120
```

| | |
|---|---|
| ttttttggag gcctaggctt ttgcgtcgag acgtacccaa ttcgccctat agtgagtcgt | 9180 |
| attacgcgcg ctcactggcc gtcgttttac aacgtcgtga ctgggaaaac cctggcgtta | 9240 |
| cccaacttaa tcgccttgca gcacatcccc ctttcgccag ctggcgtaat agcgaagagg | 9300 |
| cccgcaccga tcgcccttcc caacagttgc gcagcctgaa tggcgaatgg cgcgacgcgc | 9360 |
| cctgtagcgg cgcattaagc gcggcgggtg tggtggttac gcgcagcgtg accgctacac | 9420 |
| ttgccagcgc cctagcgccc gctcctttcg ctttcttccc ttcctttctc gccacgttcg | 9480 |
| ccggctttcc ccgtcaagct ctaaatcggg ggctcccttt agggttccga tttagtgctt | 9540 |
| tacggcacct cgaccccaaa aaacttgatt agggtgatgg ttcacgtagt gggccatcgc | 9600 |
| cctgatagac ggtttttcgc cctttgacgt tggagtccac gttctttaat agtggactct | 9660 |
| tgttccaaac tggaacaaca ctcaacccta tctcggtcta ttcttttgat ttataaggga | 9720 |
| ttttgccgat ttcggcctat tggttaaaaa atgagctgat ttaacaaaaa tttaacgcga | 9780 |
| attttaacaa atattaacg tttacaattt cc | 9812 |

<210> SEQ ID NO 59
<211> LENGTH: 9811
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

| | |
|---|---|
| caggtggcac ttttcgggga aatgtgcgcg gaacccctat ttgtttattt ttctaaatac | 60 |
| attcaaatat gtatccgctc atgagacaat aaccctgata aatgcttcaa taatattgaa | 120 |
| aaaggaagag tatgagtatt caacatttcc gtgtcgccct tattcccttt tttgcggcat | 180 |
| tttgccttcc tgttttgct cacccagaaa cgctggtgaa agtaaaagat gctgaagatc | 240 |
| agttgggtgc acgagtgggt tacatcgaac tggatctcaa cagcggtaag atccttgaga | 300 |
| gttttcgccc cgaagaacgt tttccaatga tgagcacttt taaagttctg ctatgtggcg | 360 |
| cggtattatc ccgtattgac gccgggcaag agcaactcgg tcgccgcata cactattctc | 420 |
| agaatgactt ggttgagtac tcaccagtca cagaaaagca tcttacggat ggcatgacag | 480 |
| taagagaatt atgcagtgct gccataacca tgagtgataa cactgcggcc aacttacttc | 540 |
| tgacaacgat cggaggaccg aaggagctaa ccgcttttt gcacaacatg ggggatcatg | 600 |
| taactcgcct tgatcgttgg gaaccggagc tgaatgaagc cataccaaac gacgagcgtg | 660 |
| acaccacgat gcctgtagca atggcaacaa cgttgcgcaa actattaact ggcgaactac | 720 |
| ttactctagc ttcccggcaa caattaatag actggatgga ggcggataaa gttgcaggac | 780 |
| cacttctgcg ctcggccctt ccggctggct ggtttattgc tgataaatct ggagccggtg | 840 |
| agcgtgggtc tcgcggtatc attgcagcac tggggccaga tggtaagccc tcccgtatcg | 900 |
| tagttatcta cacgacgggg agtcaggcaa ctatggatga acgaaataga cagatcgctg | 960 |
| agataggtgc ctcactgatt aagcattggt aactgtcaga ccaagtttac tcatatatac | 1020 |
| tttagattga tttaaaactt cattttaat ttaaaaggat ctaggtgaag atcctttttg | 1080 |
| ataatctcat gaccaaaatc ccttaacgtg agttttcgtt ccactgagcg tcagaccccg | 1140 |
| tagaaaagat caaaggatct tcttgagatc cttttttct gcgcgtaatc tgctgcttgc | 1200 |
| aaacaaaaaa accaccgcta ccagcggtgg tttgtttgcc ggatcaagag ctaccaactc | 1260 |
| tttttccgaa ggtaactggc ttcagcagag cgcagatacc aaatactgtc cttctagtgt | 1320 |

```
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gattttgtg atgctcgtca gggggcgga    1740 gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgcc   2400
gcattgcaga gatattgtat ttaagtgcct agctcgatac aataaacggg tctctctggt   2460
tagaccagat ctgagcctgg gagctctctg gctaactagg gaacccactg cttaagcctc   2520
aataaagctt gccttgagtg cttcaagtag tgtgtgcccg tctgttgtgt gactctggta   2580
actagagatc cctcagaccc ttttagtcag tgtggaaaat ctctagcagt ggcgcccgaa   2640
cagggacctg aaagcgaaag ggaaaccaga gctctctcga cgcaggactc ggcttgctga   2700
agcgcgcacg gcaagaggcg aggggcggcg actggtgagt acgccaaaaa ttttgactag   2760
cggaggctag aaggagagag atgggtgcga gagcgtcagt attaagcggg ggagaattag   2820
atcgcgatgg gaaaaaattc ggttaaggcc agggggaaag aaaaaatata aattaaaaca   2880
tatagtatgg gcaagcaggg agctagaacg attcgcagtt aatcctggcc tgttagaaac   2940
atcagaaggc tgtagacaaa tactgggaca gctacaacca tcccttcaga caggatcaga   3000
agaacttaga tcattatata atacagtagc aaccctctat tgtgtgcatc aaaggataga   3060
gataaaagac accaaggaag ctttagacaa gatagaggaa gagcaaaaca aaagtaagac   3120
caccgcacag caagcggccg ctgatcttca gacctggagg aggagatatg agggacaatt   3180
ggagaagtga attatataaa tataaagtag taaaaattga accattagga gtagcaccca   3240
ccaaggcaaa gagaagagtg gtgcagagag aaaaagagc agtgggaata ggagctttgt   3300
tccttgggtt cttgggagca gcaggaagca ctatgggcgc agcctcaatg acgctgacgg   3360
tacaggccag acaattattg tctggtatag tgcagcagca gaacaatttg ctgagggcta   3420
ttgaggcgca acagcatctg ttgcaactca cagtctgggg catcaagcag ctccaggcaa   3480
gaatcctggc tgtggaaaga tacctaaagg atcaacagct cctggggatt ggggttgct    3540 ctggaaaact catttgcacc actgctgtgc cttggaatgc tagttggagt aataaatctc   3600
tggaacagat tggaatcaca cgacctggat ggagtgggac agagaaatta acaattacac   3660
aagcttaata cactccttaa ttgaagaatc gcaaaaccag caagaaaaga atgaacaaga   3720
```

```
attattggaa ttagataaat gggcaagttt gtggaattgg tttaacataa caaattggct    3780
gtggtatata aaattattca taatgatagt aggaggcttg gtaggtttaa gaatagtttt    3840
tgctgtactt tctatagtga atagagttag gcagggatat tcaccattat cgtttcagac    3900
ccacctccca accccgaggg gacccgacag gcccgaagga atagaagaag aaggtggaga    3960
gagagacaga gacagatcca ttcgattagt gaacggatct cgacggttaa cttttaaaag    4020
aaaagggggg attgggggt acagtgcagg ggaaagaata gtagacataa tagcaacaga    4080
catacaaact aaagaattac aaaaacaaat tacaaaaatt caaaatttta tcgataagct    4140
tgggagttcc gcgttacata acttacggta aatggcccgc ctggctgacc gcccaacgac    4200
ccccgcccat tgacgtcaat aatgacgtat gttcccatag taacgccaat agggactttc    4260
cattgacgtc aatgggtgga gtatttacgg taaactgccc acttggcagt acatcaagtg    4320
tatcatatgc caagtacgcc ccctattgac gtcaatgacg gtaaatggcc cgcctggcat    4380
tatgcccagt acatgacctt atgggacttt cctacttggc agtacatcta cgtattagtc    4440
atcgctatta ccatggtgat gcggttttgg cagtacatca atgggcgtgg atagcggttt    4500
gactcacggg gatttccaag tctccacccc attgacgtca atgggagttt gttttggcac    4560
caaaatcaac gggactttcc aaaatgtcgt aacaactccg ccccattgac gcaaatgggc    4620
ggtaggcgtg tacggtggga ggtctatata agcagagctc gtttagtgaa ccgtcagatc    4680
gcctggagac gccatccacg ctgttttgac ctccatagaa gacaccgact ctagagatgg    4740
accccatcgc tctgcaggct ggttacgacc tgctgggtga cggcagacct gaaactctgt    4800
ggctgggcat cggcactctg ctgatgctga ttggaaccct tctactttctg gtccgcggat    4860
ggggagtcac cgataaggat gcccgggaat attacgctgt gactatcctg gtgcccggaa    4920
tcgcatccgc cgcatatctg tctatgttct ttggtatcgg gcttactgag gtgaccgtcg    4980
ggggcgaaat gttggatatc tattatgcca ggtacgccaa ctggctgttt accaccccac    5040
ttctgctgct ggatctggcc cttctcgcta aggtggatcg ggtgaccatc ggcaccctgg    5100
tgggtgtgga cgccctgatg atcgtcactg gcctcatcgg agccttgagc cacacggcca    5160
tagccagata cagttggtgg ttgttctcta caatttgcat gatagtggtg ctctatttc    5220
tggctacatc cctgcgatct gctgcaaagg agcggggccc cgaggtggca tctaccttta    5280
acaccctgac agctctggtc ttggtgctgt ggaccgctta ccctatcctg tggatcatag    5340
gcactgaggg cgctggcgtg gtgggcctgg gcatcgaaac tctgctgttt atggtgttgg    5400
acgtgactgc caaggtcggc tttggctta tcctgttgag atcccgggct attctgggcg    5460
acaccgaggc accagaaccc agtgccggtg ccgatgtcag tgccgccgac cgaccggtaa    5520
cgtctatatc aaggccgaca agcagaagaa cggcatcaag gcgaacttca agatccgcca    5580
caacatcgag gacggcggcg tgcagctcgc ctaccactac cagcagaaca cccccatcgg    5640
cgacggcccc gtgctgctgc ccgacaacca ctacctgagc gtgcagtcca acttttcgaa    5700
agaccccaac gagaagcgcg atcacatggt cctgctggag ttcgtgaccg ccgccgggat    5760
cactctcggc atggacgagc tgtacaaggg cggtaccgga gggagcatgg tgagcaaggg    5820
cgaggagctg ttcaccgggg tggtgcccat cctggtcgag ctggacggcg acgtaaacgg    5880
ccacaagttc agcgtgtccg gcgagggcga gggcgatgcc acctacggca agctgaccct    5940
gaagttcatc tgcaccaccg gcaagctgcc cgtgccctgg cccaccctcg tgaccaccct    6000
gacctacggc gtgcagtgct tcagccgcta ccccgaccac atgaagcagc acgacttctt    6060
```

```
caagtccgcc atgcccgaag ctacatcca ggagcgcacc atcttcttca aggacgacgg    6120
caactacaag acccgcgccg aggtgaagtt cgagggcgac accctggtga accgcatcga    6180
gctgaagggc atcgacttca aggaggacgg caacatcctg ggcacaagc tggagtacaa    6240 cacgcgtgac caactgactg aagagcagat cgcagaattt aaagaggctt ctccctatt    6300 tgacaaggac ggggatggga caataacaac caaggagctg ggacggtga tgcggtctct    6360 ggggcagaac cccacagaag cagagctgca ggacatgatc aatgaagtag atgccgacgg    6420
tgacggcaca atcgacttcc ctgagttcct gacaatgatg gcaagaaaaa tgaaagacac    6480
agacagtgaa gaagaaatta gagaagcgtt ccgtgtgttt gataaggatg caatggcta    6540 catcagtgca gcagagcttc gccacgtgat gacaaacctt ggagagaagt taacagatga    6600
agaggttgat gaaatgatca gggaagcaga catcgatggg gatggtcagg taaactacga    6660
agagtttgta caaatgatga cagcgaagta acaatcaacc tctggattac aaaatttgtg    6720
aaagattgac tggtattctt aactatgttg ctccttttac gctatgtgga tacgctgctt    6780
taatgccttt gtatcatgct attgcttccc gtatggcttt cattttctcc tccttgtata    6840
aatcctggtt gctgtctctt tatgaggagt tgtggcccgt tgtcaggcaa cgtggcgtgg    6900
tgtgcactgt gtttgctgac gcaaccccca ctggttgggg cattgccacc acctgtcagc    6960
tcctttccgg gactttcgct ttccccctcc ctattgccac ggcggaactc atcgccgcct    7020
gccttgcccg ctgctggaca ggggctcggc tgttgggcac tgacaattcc gtggtgttgt    7080
cggggaagct gacgtccttt ccatggctgc tcgcctgtgt tgccacctgg attctgcgcg    7140
ggacgtcctt ctgctacgtc ccttcggccc tcaatccagc ggaccttcct tcccgcggcc    7200
tgctgccggc tctgcggcct cttccgcgtc ttcgccttcg ccctcagacg agtcggatct    7260 cccttgggc cgcctccccg cctggaattc taccgggtag gggaggcgct tttcccaagg    7320
cagtctggag catgcgcttt agcagcccg ctgggcactt ggcgctacac aagtggcctc    7380
tggcctcgca cacattccac atccaccggt aggcgccaac cggctccgtt ctttggtggc    7440
cccttcgcgc caccttctac tcctccccta gtcaggaagt tccccccgc cccgcagctc    7500 gcgtcgtgcg ggacgtgaca aatggaagta gcacgtctca ctagtctcgt gcagatggac    7560
agcaccgctg agcaatggaa gcgggtaggc ctttgggca gcggccaata gcagctttgc    7620
tccttcgctt tctgggctca gaggctggga aggggtgggt ccggggcgg gctcaggggc    7680 gggctcaggg gcgggcggg cgcccgaagg tcctccggag gcccggcatt ctgcacgctt    7740
caaaagcgca cgtctgccgc gctgttctcc tcttcctcat ctccgggcct ttcgacctgc    7800
agcccaagct taccatgacc gagtacaagc ccacggtgcg cctcgccacc cgcgacgacg    7860
tccccagggc cgtacgcacc ctcgccgccg cgttcgccga ctaccccgcc acgcgccaca    7920
ccgtcgatcc ggaccgccac atcgagcggg tcaccgagct gcaagaactc ttcctcacgc    7980
gcgtcgggct cgacatcggc aaggtgtggg tcgcggacga cggcgccgcg gtggcggtct    8040
ggaccacgcc ggagagcgtc gaagcggggg cgtgttcgc cgagatcggc ccgcgcatgg    8100
ccgagttgag cggttcccgg ctggccgcgc agcaacagat ggaaggcctc ctggcgccgc    8160
accgccccaa ggagcccgcg tggttcctgg ccaccgtcgg cgtctcgccc gaccaccagg    8220
gcaagggtct gggcagcgcc gtcgtgctcc ccggagtgga ggcggccgag cgcgccgggg    8280
tgcccgcctt cctggagacc tccgcgcccc gcaacctccc cttctacgag cggctcggct    8340
tcaccgtcac cgccgacgtc gaggtgcccg aaggaccgcg cacctggtgc atgacccgca    8400
agcccggtgc ctgacgcccg ccccacgacc cgcagcgccc gaccgaaagg agcgcacgac    8460
```

-continued

```
cccatgcatc tcgagggccc ggtacccttta agaccaatga cttacaaggc agctgtagat    8520
cttagccact tttttaaaaga aaaggggggga ctggaagggc tagctcactc ccaacgaaga    8580
caagatctgc tttttgcttg tactgggtct ctctggttag accagatctg agcctgggag    8640
ctctctggct gccttaggggaa cccactgctt aagcctcaat aaagcttgcc ttgagtgctt    8700
caagtagtgt gtgcccgtct gttgtgtgac tctggtaact agagatccct cagacccttt    8760
tagtcagtgt ggaaaatctc tagcagtagt agttcatgtc atcttattat tcagtattta    8820
taacttgcaa agaaatgaat atcagagagt gagaggaact tgtttattgc agcttataat    8880
ggttacaaat aaagcaatag catcacaaat ttcacaaata aagcatttttt ttcactgcat    8940
tctagttgtg gtttgtccaa actcatcaat gtatcttatc atgtctggct ctagctatcc    9000
cgcccctaac tccgcccagt tccgcccatt ctccgcccca tggctgacta atttttttta    9060
tttatgcaga ggccgaggcc gcctcggcct ctgagctatt ccagaagtag tgaggaggct    9120
tttttggagg cctaggcttt tgcgtcgaga cgtacccaat tcgccctata gtgagtcgta    9180
ttacgcgcgc tcactggccg tcgttttaca acgtcgtgac tgggaaaacc ctggcgttac    9240
ccaacttaat cgccttgcag cacatccccc tttcgccagc tggcgtaata gcgaagaggc    9300
ccgcaccgat cgcccttccc aacagttgcg cagcctgaat ggcgaatggc gcgacgcgcc    9360
ctgtagcggc gcattaagcg cggcgggtgt ggtggttacg cgcagcgtga ccgctacact    9420
tgccagcgcc ctagcgcccg ctcctttcgc tttcttccct cctttctcg ccacgttcgc    9480
cggctttccc cgtcaagctc taaatcgggg gctcccttta gggttccgat ttagtgcttt    9540
acggcacctc gaccccaaaa aacttgatta gggtgatggt tcacgtagtg gccatcgcc    9600
ctgatagacg ttttttcgcc ctttgacgtt ggagtccacg ttctttaata gtggactctt    9660
gttccaaact ggaacaacac tcaaccctat ctcggtctat tcttttgatt tataagggat    9720
tttgccgatt tcggcctatt ggttaaaaaa tgagctgatt taacaaaaat ttaacgcgaa    9780
ttttaacaaa atattaacgt ttacaatttc c                                   9811
```

<210> SEQ ID NO 60
<211> LENGTH: 313
<212> TYPE: PRT
<213> ORGANISM: Leptosphaeria maculans

<400> SEQUENCE: 60

```
Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Th

```
Tyr Arg Gln Val Tyr Tyr Ala Arg Tyr Ile Asp Trp Ala Ile Thr Thr
        130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
            195                 200                 205

Leu Asn Gly Gly Ala Asn Ala Arg Val Lys Gly Glu Lys Leu Arg Ser
210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
                260                 265                 270

Phe Gly Ala Trp Leu Leu Val Thr His Ala Asn Leu Arg Glu Ser Asp
            275                 280                 285

Val Glu Leu Asn Gly Phe Trp Ala Asn Gly Leu Asn Arg Glu Gly Ala
290                 295                 300

Ile Arg Ile Gly Glu Asp Asp Gly Ala
305                 310

<210> SEQ ID NO 61
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
                20                  25                  30

Pro Val Pro Thr Val Leu Pro Asp Thr Pro Ile Tyr Glu Thr Val Gly
            35                  40                  45

Asp Ser Gly Ser Lys Thr Leu Trp Val Phe Val Leu Met Leu Ile
50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Thr Leu Thr Ala Ala Leu
                85                  90                  95

Ser Tyr Phe Ala Met Ala Thr Gly His Gly Val Ala Leu Asn Lys Ile
                100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asn Trp Ala Ile Thr Thr
        130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175
```

```
Leu Phe Ala Ala Phe Gly Ser Glu Gly Thr Pro Gln Lys Trp Gly Trp
                180                 185                 190

Tyr Thr Ile Ala Cys Ile Ala Tyr Ile Phe Val Val Trp His Leu Val
            195                 200                 205

Leu Asn Gly Gly Ala Asn Ala Arg Val Lys Gly Glu Lys Leu Arg Ser
        210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310

<210> SEQ ID NO 62
<211> LENGTH: 250
<212> TYPE: PRT
<213> ORGANISM: Haloarcula argentinensis

<400> SEQUENCE: 62

Met Pro Glu Pro Gly Ser Glu Ala Ile Trp Leu Trp Leu Gly Thr Ala
1               5                   10                  15

Gly Met Phe Leu Gly Met Leu Tyr Phe Ile Ala Arg Gly Trp Gly Glu
            20                  25                  30

Thr Asp Ser Arg Arg Gln Lys Phe Tyr Ile Ala Thr Ile Leu Ile Thr
        35                  40                  45

Ala Ile Ala Phe Val Asn Tyr Leu Ala Met Ala Leu Gly Phe Gly Leu
    50                  55                  60

Thr Ile Val Glu Phe Ala Gly Glu Glu His Pro Ile Tyr Trp Ala Arg
65                  70                  75                  80

Tyr Ser Asp Trp Leu Phe Thr Thr Pro Leu Leu Leu Tyr Asp Leu Gly
                85                  90                  95

Leu Leu Ala Gly Ala Asp Arg Asn Thr Ile Thr Ser Leu Val Ser Leu
            100                 105                 110

Asp Val Leu Met Ile Gly Thr Gly Leu Val Ala Thr Leu Ser Pro Gly
        115                 120                 125

Ser Gly Val Leu Ser Ala Gly Ala Glu Arg Leu Val Trp Trp Gly Ile
    130                 135                 140

Ser Thr Ala Phe Leu Leu Val Leu Leu Tyr Phe Leu Phe Ser Ser Leu
145                 150                 155                 160

Ser Gly Arg Val Ala Asp Leu Pro Ser Asp Thr Arg Ser Thr Phe Lys
                165                 170                 175

Thr Leu Arg Asn Leu Val Thr Val Val Trp Leu Val Tyr Pro Val Trp
            180                 185                 190

Trp Leu Ile Gly Thr Glu Gly Ile Gly Leu Val Gly Ile Gly Ile Glu
        195                 200                 205

Thr Ala Gly Phe Met Val Ile Asp Leu Thr Ala Lys Val Gly Phe Gly
    210                 215                 220

Ile Ile Leu Leu Arg Ser His Gly Val Leu Asp Gly Ala Ala Glu Thr
```

```
                225                 230                 235                 240

Thr Gly Thr Gly Ala Thr Pro Ala Asp Asp
                245                 250

<210> SEQ ID NO 63
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Pro Glu Pro Gly Ser Glu Ala Ile Trp Leu Trp Leu Gly Thr Ala
1               5                   10                  15

Gly Met Phe Leu Gly Met Leu Tyr Phe Ile Ala Arg Gly Trp Gly Glu
                20                  25                  30

Thr Asp Ser Arg Arg Gln Lys Phe Tyr Ile Ala Thr Ile Leu Ile Thr
            35                  40                  45

Ala Ile Ala Phe Val Asn Tyr Leu Ala Met Ala Leu Gly Phe Gly Leu
        50                  55                  60

Thr Ile Val Glu Phe Ala Gly Glu Glu His Pro Ile Tyr Trp Ala Arg
65                  70                  75                  80

Tyr Ser Asn Trp Leu Phe Thr Thr Pro Leu Leu Leu Tyr Asp Leu Gly
                85                  90                  95

Leu Leu Ala Gly Ala Asp Arg Asn Thr Ile Thr Ser Leu Val Ser Leu
                100                 105                 110

Asp Val Leu Met Ile Gly Thr Gly Leu Val Ala Thr Leu Ser Pro Gly
                115                 120                 125

Ser Gly Val Leu Ser Ala Gly Ala Glu Arg Leu Val Trp Trp Gly Ile
        130                 135                 140

Ser Thr Ala Phe Leu Leu Val Leu Leu Tyr Phe Leu Phe Ser Ser Leu
145                 150                 155                 160

Ser Gly Arg Val Ala Asp Leu Pro Ser Asp Thr Arg Ser Thr Phe Lys
                165                 170                 175

Thr Leu Arg Asn Leu Val Thr Val Val Trp Leu Val Tyr Pro Val Trp
                180                 185                 190

Trp Leu Ile Gly Thr Glu Gly Ile Gly Leu Val Gly Ile Gly Ile Glu
            195                 200                 205

Thr Ala Gly Phe Met Val Ile Asp Leu Thr Ala Lys Val Gly Phe Gly
        210                 215                 220

Ile Ile Leu Leu Arg Ser His Gly Val Leu Asp Gly Ala Ala Glu Thr
225                 230                 235                 240

Thr Gly Thr Gly Ala Thr Pro Ala Asp Asp
                245                 250

<210> SEQ ID NO 64
<211> LENGTH: 279
<212> TYPE: PRT
<213> ORGANISM: Acetabularia acetabulum

<400> SEQUENCE: 64

Met Ser Asn Pro Asn Pro Phe Gln Thr Thr Leu Gly Thr Asp Ala Gln
1               5                   10                  15

Trp Val Val Phe Ala Val Met Ala Leu Ala Ala Ile Val Phe Ser Ile
                20                  25                  30

Ala Val Gln Phe Arg Pro Leu Pro Leu Arg Leu Thr Tyr Tyr Val Asn
```

```
                35                  40                  45

Ile Ala Ile Cys Thr Ile Ala Ala Thr Ala Tyr Tyr Ala Met Ala Val
         50                  55                  60

Asn Gly Gly Asp Asn Lys Pro Thr Ala Gly Thr Gly Ala Asp Glu Arg
 65                  70                  75                  80

Gln Val Ile Tyr Ala Arg Tyr Ile Asp Trp Val Phe Thr Thr Pro Leu
                 85                  90                  95

Leu Leu Leu Asp Leu Val Leu Leu Thr Asn Met Pro Ala Thr Met Ile
                100                 105                 110

Ala Trp Ile Met Gly Ala Asp Ile Ala Met Ile Ala Phe Gly Ile Ile
            115                 120                 125

Gly Ala Phe Thr Val Gly Ser Tyr Lys Trp Phe Tyr Phe Val Val Gly
        130                 135                 140

Cys Ile Met Leu Ala Val Leu Ala Trp Gly Met Ile Asn Pro Ile Phe
145                 150                 155                 160

Lys Glu Glu Leu Gln Lys His Lys Glu Tyr Thr Gly Ala Tyr Thr Thr
                165                 170                 175

Leu Leu Ile Tyr Leu Ile Val Leu Trp Val Ile Tyr Pro Ile Val Trp
            180                 185                 190

Gly Leu Gly Ala Gly Gly His Ile Ile Gly Val Asp Val Glu Ile Ile
        195                 200                 205

Ala Met Gly Val Leu Asp Leu Leu Ala Lys Pro Leu Tyr Ala Ile Gly
    210                 215                 220

Val Leu Ile Thr Val Glu Val Val Tyr Gly Lys Val Gly Gln Gly Gly
225                 230                 235                 240

Ser Leu Ala Phe Asp Cys Leu Lys Ile Leu Lys Trp Trp Lys Leu Leu
                245                 250                 255

Trp Phe Gln Leu Val Ser Ile His Phe Ser Leu Cys Val Cys Arg Val
            260                 265                 270

Thr Ser Tyr Phe Leu Leu Asn
        275

<210> SEQ ID NO 65
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Ser Asn Pro Asn Pro Phe Gln Thr Thr Leu Gly Thr Asp Ala Gln
 1               5                  10                  15

Trp Val Val Phe Ala Val Met Ala Leu Ala Ala Ile Val Phe Ser Ile
                20                  25                  30

Ala Val Gln Phe Arg Pro Leu Pro Leu Arg Leu Thr Tyr Tyr Val Asn
            35                  40                  45

Ile Ala Ile Cys Thr Ile Ala Ala Thr Ala Tyr Tyr Ala Met Ala Val
        50                  55                  60

Asn Gly Gly Asp Asn Lys Pro Thr Ala Gly Thr Gly Ala Asp Glu Arg
65                  70                  75                  80

Gln Val Ile Tyr Ala Arg Tyr Ile Asn Trp Val Phe Thr Thr Pro Leu
                85                  90                  95

Leu Leu Leu Asp Leu Val Leu Leu Thr Asn Met Pro Ala Thr Met Ile
                100                 105                 110
```

```
Ala Trp Ile Met Gly Ala Asp Ile Ala Met Ile Ala Phe Gly Ile Ile
            115                 120                 125

Gly Ala Phe Thr Val Gly Ser Tyr Lys Trp Phe Tyr Phe Val Val Gly
        130                 135                 140

Cys Ile Met Leu Ala Val Leu Ala Trp Gly Met Ile Asn Pro Ile Phe
145                 150                 155                 160

Lys Glu Glu Leu Gln Lys His Lys Glu Tyr Thr Gly Ala Tyr Thr Thr
                165                 170                 175

Leu Leu Ile Tyr Leu Ile Val Leu Trp Val Ile Tyr Pro Ile Val Trp
            180                 185                 190

Gly Leu Gly Ala Gly Gly His Ile Ile Gly Val Asp Val Glu Ile Ile
        195                 200                 205

Ala Met Gly Val Leu Asp Leu Leu Ala Lys Pro Leu Tyr Ala Ile Gly
    210                 215                 220

Val Leu Ile Thr Val Glu Val Val Tyr Gly Lys Val Gly Gln Gly Gly
225                 230                 235                 240

Ser Leu Ala Phe Asp Cys Leu Lys Ile Leu Lys Trp Trp Lys Leu Leu
                245                 250                 255

Trp Phe Gln Leu Val Ser Ile His Phe Ser Leu Cys Val Cys Arg Val
            260                 265                 270

Thr Ser Tyr Phe Leu Leu Asn
        275

<210> SEQ ID NO 66
<211> LENGTH: 260
<212> TYPE: PRT
<213> ORGANISM: Halobacterium sp.

<400> SEQUENCE: 66

Met Asp Pro Ile Ala Leu Thr Ala Ala Val Gly Ala Asp Leu Leu Gly
1               5                   10                  15

Asp Gly Arg Pro Glu Thr Leu Trp Leu Gly Ile Gly Thr Leu Leu Met
            20                  25                  30

Leu Ile Gly Thr Phe Tyr Phe Ile Val Lys Gly Trp Gly Val Thr Asp
        35                  40                  45

Lys Glu Ala Arg Glu Tyr Tyr Ser Ile Thr Ile Leu Val Pro Gly Ile
50                  55                  60

Ala Ser Ala Ala Tyr Leu Ser Met Phe Phe Gly Ile Gly Leu Thr Glu
65                  70                  75                  80

Val Gln Val Gly Ser Glu Met Leu Asp Ile Tyr Tyr Ala Arg Tyr Ala
                85                  90                  95

Asp Trp Leu Phe Thr Thr Pro Leu Leu Leu Leu Asp Leu Ala Leu Leu
            100                 105                 110

Ala Lys Val Asp Arg Val Ser Ile Gly Thr Leu Val Gly Val Asp Ala
        115                 120                 125

Leu Met Ile Val Thr Gly Leu Val Gly Ala Leu Ser His Thr Pro Leu
    130                 135                 140

Ala Arg Tyr Thr Trp Trp Leu Phe Ser Thr Ile Cys Met Ile Val Val
145                 150                 155                 160

Leu Tyr Phe Leu Ala Thr Ser Leu Arg Ala Ala Lys Glu Arg Gly
                165                 170                 175

Pro Glu Val Ala Ser Thr Phe Asn Thr Leu Thr Ala Leu Val Leu Val
            180                 185                 190

Leu Trp Thr Ala Tyr Pro Ile Leu Trp Ile Ile Gly Thr Glu Gly Ala
        195                 200                 205
```

Gly Val Val Gly Leu Gly Ile Glu Thr Leu Leu Phe Met Val Leu Asp
            210                 215                 220

Val Thr Ala Lys Val Gly Phe Gly Phe Ile Leu Leu Arg Ser Arg Ala
225                 230                 235                 240

Ile Leu Gly Asp Thr Glu Ala Pro Glu Pro Ser Ala Gly Ala Glu Ala
            245                 250                 255

Ser Ala Ala Asp
            260

<210> SEQ ID NO 67
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Asp Pro Ile Ala Leu Thr Ala Ala Val Gly Ala Asp Leu Leu Gly
1               5                   10                  15

Asp Gly Arg Pro Glu Thr Leu Trp Leu Gly Ile Gly Thr Leu Leu Met
            20                  25                  30

Leu Ile Gly Thr Phe Tyr Phe Ile Val Lys Gly Trp Gly Val Thr Asp
        35                  40                  45

Lys Glu Ala Arg Glu Tyr Tyr Ser Ile Thr Ile Leu Val Pro Gly Ile
50                  55                  60

Ala Ser Ala Ala Tyr Leu Ser Met Phe Phe Gly Ile Gly Leu Thr Glu
65                  70                  75                  80

Val Gln Val Gly Ser Glu Met Leu Asp Ile Tyr Tyr Ala Arg Tyr Ala
                85                  90                  95

Asn Trp Leu Phe Thr Thr Pro Leu Leu Leu Leu Asp Leu Ala Leu Leu
            100                 105                 110

Ala Lys Val Asp Arg Val Ser Ile Gly Thr Leu Val Gly Val Asp Ala
        115                 120                 125

Leu Met Ile Val Thr Gly Leu Val Gly Ala Leu Ser His Thr Pro Leu
130                 135                 140

Ala Arg Tyr Thr Trp Trp Leu Phe Ser Thr Ile Cys Met Ile Val Val
145                 150                 155                 160

Leu Tyr Phe Leu Ala Thr Ser Leu Arg Ala Ala Lys Glu Arg Gly
                165                 170                 175

Pro Glu Val Ala Ser Thr Phe Asn Thr Leu Thr Ala Leu Val Leu Val
            180                 185                 190

Leu Trp Thr Ala Tyr Pro Ile Leu Trp Ile Ile Gly Thr Glu Gly Ala
        195                 200                 205

Gly Val Val Gly Leu Gly Ile Glu Thr Leu Leu Phe Met Val Leu Asp
210                 215                 220

Val Thr Ala Lys Val Gly Phe Gly Phe Ile Leu Leu Arg Ser Arg Ala
225                 230                 235                 240

Ile Leu Gly Asp Thr Glu Ala Pro Glu Pro Ser Ala Gly Ala Glu Ala
            245                 250                 255

Ser Ala Ala Asp
            260

<210> SEQ ID NO 68
<211> LENGTH: 259
<212> TYPE: PRT

<213> ORGANISM: Halobacterium sp.

<400> SEQUENCE: 68

```
Met Asp Pro Ile Ala Leu Gln Ala Gly Phe Asp Leu Leu Asn Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Ala Arg Gly Trp Gly Val Thr Asp Lys Glu
        35                  40                  45

Ala Arg Glu Tyr Tyr Ala Ile Thr Ile Leu Val Pro Gly Ile Ala Ser
    50                  55                  60

Ala Ala Tyr Leu Ala Met Phe Phe Gly Ile Gly Val Thr Glu Val Glu
65                  70                  75                  80

Leu Ala Ser Gly Thr Val Leu Asp Ile Tyr Tyr Ala Arg Tyr Ala Asp
                85                  90                  95

Trp Leu Phe Thr Thr Pro Leu Leu Leu Asp Leu Ala Leu Leu Ala
            100                 105                 110

Lys Val Asp Arg Val Thr Ile Gly Thr Leu Ile Gly Val Asp Ala Leu
            115                 120                 125

Met Ile Val Thr Gly Leu Ile Gly Ala Leu Ser Lys Thr Pro Leu Ala
130                 135                 140

Arg Tyr Thr Trp Trp Leu Phe Ser Thr Ile Ala Phe Leu Phe Val Leu
145                 150                 155                 160

Tyr Tyr Leu Leu Thr Ser Leu Arg Ser Ala Ala Ala Lys Arg Ser Glu
                165                 170                 175

Glu Val Arg Ser Thr Phe Asn Thr Leu Thr Ala Leu Val Ala Val Leu
            180                 185                 190

Trp Thr Ala Tyr Pro Ile Leu Trp Ile Val Gly Thr Glu Gly Ala Gly
            195                 200                 205

Val Val Gly Leu Gly Ile Glu Thr Leu Ala Phe Met Val Leu Asp Val
        210                 215                 220

Thr Ala Lys Val Gly Phe Gly Phe Val Leu Leu Arg Ser Arg Ala Ile
225                 230                 235                 240

Leu Gly Glu Thr Glu Ala Pro Glu Pro Ser Ala Gly Ala Asp Ala Ser
                245                 250                 255

Ala Ala Asp
```

<210> SEQ ID NO 69
<211> LENGTH: 259
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Met Asp Pro Ile Ala Leu Gln Ala Gly Phe Asp Leu Leu Asn Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Ala Arg Gly Trp Gly Val Thr Asp Lys Glu
        35                  40                  45

Ala Arg Glu Tyr Tyr Ala Ile Thr Ile Leu Val Pro Gly Ile Ala Ser
    50                  55                  60

Ala Ala Tyr Leu Ala Met Phe Phe Gly Ile Gly Val Thr Glu Val Glu
65                  70                  75                  80
```

```
Leu Ala Ser Gly Thr Val Leu Asp Ile Tyr Tyr Ala Arg Tyr Ala Asn
                85                  90                  95

Trp Leu Phe Thr Thr Pro Leu Leu Leu Asp Leu Ala Leu Leu Ala
           100                 105                 110

Lys Val Asp Arg Val Thr Ile Gly Thr Leu Ile Gly Val Asp Ala Leu
           115                 120                 125

Met Ile Val Thr Gly Leu Ile Gly Ala Leu Ser Lys Thr Pro Leu Ala
    130                 135                 140

Arg Tyr Thr Trp Trp Leu Phe Ser Thr Ile Ala Phe Leu Phe Val Leu
145                 150                 155                 160

Tyr Tyr Leu Leu Thr Ser Leu Arg Ser Ala Ala Lys Arg Ser Glu
                165                 170                 175

Glu Val Arg Ser Thr Phe Asn Thr Leu Thr Ala Leu Val Ala Val Leu
            180                 185                 190

Trp Thr Ala Tyr Pro Ile Leu Trp Ile Val Gly Thr Glu Gly Ala Gly
            195                 200                 205

Val Val Gly Leu Gly Ile Glu Thr Leu Ala Phe Met Val Leu Asp Val
    210                 215                 220

Thr Ala Lys Val Gly Phe Gly Phe Val Leu Leu Arg Ser Arg Ala Ile
225                 230                 235                 240

Leu Gly Glu Thr Glu Ala Pro Glu Pro Ser Ala Gly Ala Asp Ala Ser
                245                 250                 255

Ala Ala Asp

<210> SEQ ID NO 70
<211> LENGTH: 258
<212> TYPE: PRT
<213> ORGANISM: Halorubrum sodomense

<400> SEQUENCE: 70

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190
```

```
Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
            245                 250                 255

Ala Asp

<210> SEQ ID NO 71
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asn Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 72
<211> LENGTH: 255
```

<212> TYPE: PRT
<213> ORGANISM: Halobacterium salinarum

<400> SEQUENCE: 72

```
Met Gly Met Asp Pro Ile Ala Leu Gln Ala Gly Phe Asp Leu Leu Gly
1               5                   10                  15

Asp Gly Arg Pro Glu Thr Leu Trp Leu Gly Ile Gly Thr Leu Leu Met
            20                  25                  30

Ile Ile Gly Thr Phe Tyr Phe Ile Ala Gln Gly Trp Gly Val Thr Asp
        35                  40                  45

Lys Glu Ala Arg Glu Tyr Tyr Ala Ile Thr Ile Leu Val Pro Gly Ile
    50                  55                  60

Ala Ser Ala Ala Tyr Leu Ala Met Phe Phe Gly Ile Gly Val Thr Glu
65                  70                  75                  80

Val Glu Leu Ala Ser Gly Ala Val Leu Asp Ile Tyr Tyr Ala Arg Tyr
                85                  90                  95

Ala Asp Trp Leu Phe Thr Thr Pro Leu Leu Leu Asp Leu Ala Leu
            100                 105                 110

Leu Ala Lys Val Asp Arg Val Ser Ile Gly Thr Leu Ile Gly Val Asp
        115                 120                 125

Ala Leu Met Ile Val Thr Gly Leu Ile Gly Ala Leu Ser Lys Thr Pro
    130                 135                 140

Leu Ala Arg Tyr Thr Trp Trp Leu Phe Ser Thr Ile Ala Phe Leu Phe
145                 150                 155                 160

Val Leu Tyr Tyr Leu Leu Thr Ser Leu Arg Ser Ala Ala Ala Gln Arg
                165                 170                 175

Ser Glu Glu Val Gln Ser Thr Phe Asn Thr Leu Thr Ala Leu Val Ala
            180                 185                 190

Val Leu Trp Thr Ala Tyr Pro Ile Leu Trp Ile Val Gly Thr Glu Gly
        195                 200                 205

Ala Gly Val Val Gly Leu Gly Val Glu Thr Leu Ala Phe Met Val Leu
    210                 215                 220

Asp Val Thr Ala Lys Val Gly Phe Gly Phe Ala Leu Leu Arg Ser Arg
225                 230                 235                 240

Ala Ile Leu Gly Glu Thr Glu Ala Pro Glu Pro Ser Ala Gly Thr
                245                 250                 255
```

<210> SEQ ID NO 73
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Met Gly Met Asp Pro Ile Ala Leu Gln Ala Gly Phe Asp Leu Leu Gly
1               5                   10                  15

Asp Gly Arg Pro Glu Thr Leu Trp Leu Gly Ile Gly Thr Leu Leu Met
            20                  25                  30

Ile Ile Gly Thr Phe Tyr Phe Ile Ala Gln Gly Trp Gly Val Thr Asp
        35                  40                  45

Lys Glu Ala Arg Glu Tyr Tyr Ala Ile Thr Ile Leu Val Pro Gly Ile
    50                  55                  60

Ala Ser Ala Ala Tyr Leu Ala Met Phe Phe Gly Ile Gly Val Thr Glu
65                  70                  75                  80
```

Val Glu Leu Ala Ser Gly Ala Val Leu Asp Ile Tyr Tyr Ala Arg Tyr
            85                  90                  95

Ala Asn Trp Leu Phe Thr Thr Pro Leu Leu Leu Asp Leu Ala Leu
            100                 105                 110

Leu Ala Lys Val Asp Arg Val Ser Ile Gly Thr Leu Ile Gly Val Asp
            115                 120                 125

Ala Leu Met Ile Val Thr Gly Leu Ile Gly Ala Leu Ser Lys Thr Pro
        130                 135                 140

Leu Ala Arg Tyr Thr Trp Trp Leu Phe Ser Thr Ile Ala Phe Leu Phe
145                 150                 155                 160

Val Leu Tyr Tyr Leu Leu Thr Ser Leu Arg Ser Ala Ala Ala Gln Arg
                165                 170                 175

Ser Glu Glu Val Gln Ser Thr Phe Asn Thr Leu Thr Ala Leu Val Ala
            180                 185                 190

Val Leu Trp Thr Ala Tyr Pro Ile Leu Trp Ile Val Gly Thr Glu Gly
            195                 200                 205

Ala Gly Val Val Gly Leu Gly Val Glu Thr Leu Ala Phe Met Val Leu
        210                 215                 220

Asp Val Thr Ala Lys Val Gly Phe Gly Phe Ala Leu Leu Arg Ser Arg
225                 230                 235                 240

Ala Ile Leu Gly Glu Thr Glu Ala Pro Glu Pro Ser Ala Gly Thr
                245                 250                 255

<210> SEQ ID NO 74
<211> LENGTH: 753
<212> TYPE: DNA
<213> ORGANISM: Unknown
<220> FEATURE:
<223> OTHER INFORMATION: Description of Unknown: Green-absorbing
      proteorhodopsin polynucleotide from an uncultured
      marine bacterium

<400> SEQUENCE: 74
accatgggta aattattact gatattaggt agtgttattg cacttcctac atttgctgca        60
ggtggtggtg accttgatgc tagtgattac actggtgttt cttttttggtt agttactgct      120 gctctattag catctactgt atttttcttt gttgaaagag atagagtttc tgcaaaatgg       180
aaaacatcat taactgtatc tggtcttgtt actggtattg ctttctggca ttacatgtac       240
atgagagggg tatggattga gactggtgat tcgccaactg tatttagata cattgattgg       300
ttactaacag ttcctctatt gatatgtgaa ttctacttaa ttcttgctgc tgcaacaaat       360
gttgctgctg gcctgtttaa gaaattattg gttggttctc ttgttatgct tgtgtttggt       420
tacatgggtg aggcaggaat tatgaacgct tggcctgcat tcattattgg gtgtttagct       480
tgggtataca tgatttatga actatatgct ggagaaggaa atctgcatg taatactgca        540 agtccttcgg ttcaatcagc ttacaacaca atgatggcta tcatagtctt cggttgggca       600
atttatcctg taggttattt cacaggttac ctaatgggtg acggtggatc agctcttaac       660
ttaaaccgta tttataacct tgctgacttt gttaacaaga ttctatttgg tttaattata       720
tggaatgttg ctgttaaaga atcttctaat gct                                    753

<210> SEQ ID NO 75
<211> LENGTH: 251
<212> TYPE: PRT
<213> ORGANISM: Unknown
<220> FEATURE:
<223> OTHER INFORMATION: Description of Unknown: Green-absorbing
      proteorhodopsin polypeptide from an uncultured marine bacterium

<400> SEQUENCE: 75

Thr Met Gly Lys Leu Leu Ile Leu Gly Ser Val Ile Ala Leu Pro
1               5                   10                  15

Thr Phe Ala Ala Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg
            85                  90                  95

Tyr Ile Asp Trp Leu Leu Thr Val Pro Leu Leu Ile Cys Glu Phe Tyr
            100                 105                 110

Leu Ile Leu Ala Ala Ala Thr Asn Val Ala Ala Gly Leu Phe Lys Lys
            115                 120                 125

Leu Leu Val Gly Ser Leu Val Met Leu Val Phe Gly Tyr Met Gly Glu
130                 135                 140

Ala Gly Ile Met Asn Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
            165                 170                 175

Cys Asn Thr Ala Ser Pro Ser Val Gln Ser Ala Tyr Asn Thr Met Met
            180                 185                 190

Ala Ile Ile Val Phe Gly Trp Ala Ile Tyr Pro Val Gly Tyr Phe Thr
            195                 200                 205

Gly Tyr Leu Met Gly Asp Gly Gly Ser Ala Leu Asn Leu Asn Leu Ile
            210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
            245                 250

<210> SEQ ID NO 76
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Thr Met Gly Lys Leu Leu Ile Leu Gly Ser Val Ile Ala Leu Pro
1               5                   10                  15

Thr Phe Ala Ala Gly Gly Asp Leu Asp Ala Ser Asp Tyr Thr Gly
            20                  25                  30

Val Ser Phe Trp Leu Val Thr Ala Ala Leu Leu Ala Ser Thr Val Phe
        35                  40                  45

Phe Phe Val Glu Arg Asp Arg Val Ser Ala Lys Trp Lys Thr Ser Leu
50                  55                  60

Thr Val Ser Gly Leu Val Thr Gly Ile Ala Phe Trp His Tyr Met Tyr
65                  70                  75                  80

Met Arg Gly Val Trp Ile Glu Thr Gly Asp Ser Pro Thr Val Phe Arg

```
                  85                  90                  95
Tyr Ile Asn Trp Leu Leu Thr Val Pro Leu Leu Ile Cys Glu Phe Tyr
                100                 105                 110

Leu Ile Leu Ala Ala Ala Thr Asn Val Ala Ala Gly Leu Phe Lys Lys
                115                 120                 125

Leu Leu Val Gly Ser Leu Val Met Leu Val Phe Gly Tyr Met Gly Glu
            130                 135                 140

Ala Gly Ile Met Asn Ala Trp Pro Ala Phe Ile Ile Gly Cys Leu Ala
145                 150                 155                 160

Trp Val Tyr Met Ile Tyr Glu Leu Tyr Ala Gly Glu Gly Lys Ser Ala
                165                 170                 175

Cys Asn Thr Ala Ser Pro Ser Val Gln Ser Ala Tyr Asn Thr Met Met
                180                 185                 190

Ala Ile Ile Val Phe Gly Trp Ala Ile Tyr Pro Val Gly Tyr Phe Thr
                195                 200                 205

Gly Tyr Leu Met Gly Asp Gly Gly Ser Ala Leu Asn Leu Asn Leu Ile
            210                 215                 220

Tyr Asn Leu Ala Asp Phe Val Asn Lys Ile Leu Phe Gly Leu Ile Ile
225                 230                 235                 240

Trp Asn Val Ala Val Lys Glu Ser Ser Asn Ala
                245                 250

<210> SEQ ID NO 77
<211> LENGTH: 756
<212> TYPE: DNA
<213> ORGANISM: Unknown
<220> FEATURE:
<223> OTHER INFORMATION: Description of Unknown: Blue-absorbing
      proteorhodopsin polynucleotide from an uncultured
      marine bacterium

<400> SEQUENCE: 77
accatgggta aattattact gatattaggt agtgctattg cacttccatc atttgctgct      60
gctggtggcg atctagatat aagtgatact gttggtgttt cattctggct ggttacagct    120
ggtatgttag cggcaactgt gttctttttt gtagaaagag accaagtcag cgctaagtgg    180
aaaacttcac ttactgtatc tggtttaatt actggtatag cttttttggca ttatctctat    240 atgagaggtg tttggataga cactggtgat accccaacag tattcagata tattgattgg    300
ttattaactg ttccattaca agtggttgag ttctatctaa ttcttgctgc ttgtacaagt    360
gttgctgctt cattatttaa gaagcttcta gctggttcat tagtaatgtt aggtgctgga    420
tttgcaggcg aagctggatt agctcctgta ttacctgctt tcattattgg tatggctgga    480
tggttataca tgatttatga gctatatatg ggtgaaggta aggctgctgt aagtactgca    540
agtcctgctg ttaactctgc atacaacgca atgatgatga ttattgttgt tggatgggca    600
atttatcctg ctggatatgc tgctggttac ctaatgggtg gcgaaggtgt atacgcttca    660 aacttaaaacc ttatatataa ccttgctgac tttgttaaca agattctatt tggtttgatc    720
atttggaatg ttgctgttaa agaatcttct aatgct                               756

<210> SEQ ID NO 78
<211> LENGTH: 252
<212> TYPE: PRT
<213> ORGANISM: Unknown
<220> FEATURE:
<221> NAME/KEY: source
<223> OTHER INFORMATION: Description of Unknown: Blue-absorbing
      proteorhodopsin polypeptide from an uncultured
``` marine bacterium

<400> SEQUENCE: 78

Thr Met Gly Lys Leu Leu Ile Leu Gly Ser Ala Ile Ala Leu Pro
1               5                   10                  15

Ser Phe Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg
                85                  90                  95

Tyr Ile Asp Trp Leu Leu Thr Val Pro Leu Gln Val Val Glu Phe Tyr
            100                 105                 110

Leu Ile Leu Ala Ala Cys Thr Ser Val Ala Ala Ser Leu Phe Lys Lys
        115                 120                 125

Leu Leu Ala Gly Ser Leu Val Met Leu Gly Ala Gly Phe Ala Gly Glu
130                 135                 140

Ala Gly Leu Ala Pro Val Leu Pro Ala Phe Ile Ile Gly Met Ala Gly
145                 150                 155                 160

Trp Leu Tyr Met Ile Tyr Glu Leu Tyr Met Gly Glu Gly Lys Ala Ala
                165                 170                 175

Val Ser Thr Ala Ser Pro Ala Val Asn Ser Ala Tyr Asn Ala Met Met
            180                 185                 190

Met Ile Ile Val Val Gly Trp Ala Ile Tyr Pro Ala Gly Tyr Ala Ala
        195                 200                 205

Gly Tyr Leu Met Gly Gly Glu Gly Val Tyr Ala Ser Asn Leu Asn Leu
    210                 215                 220

Ile Tyr Asn Leu Ala Asp Phe Val Asn Lys Ile Leu Phe Gly Leu Ile
225                 230                 235                 240

Ile Trp Asn Val Ala Val Lys Glu Ser Ser Asn Ala
                245                 250

<210> SEQ ID NO 79
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Thr Met Gly Lys Leu Leu Ile Leu Gly Ser Ala Ile Ala Leu Pro
1               5                   10                  15

Ser Phe Ala Ala Gly Gly Asp Leu Asp Ile Ser Asp Thr Val Gly
            20                  25                  30

Val Ser Phe Trp Leu Val Thr Ala Gly Met Leu Ala Ala Thr Val Phe
        35                  40                  45

Phe Phe Val Glu Arg Asp Gln Val Ser Ala Lys Trp Lys Thr Ser Leu
    50                  55                  60

Thr Val Ser Gly Leu Ile Thr Gly Ile Ala Phe Trp His Tyr Leu Tyr
65                  70                  75                  80

Met Arg Gly Val Trp Ile Asp Thr Gly Asp Thr Pro Thr Val Phe Arg

|  |  |  |  | 85 |  |  |  |  | 90 |  |  |  |  | 95 |  |
|--|--|--|--|--|--|--|--|--|--|--|--|--|--|--|--|

Tyr Ile Asn Trp Leu Leu Thr Val Pro Leu Gln Val Val Glu Phe Tyr
                  100                       105                   110

Leu Ile Leu Ala Ala Cys Thr Ser Val Ala Ala Ser Leu Phe Lys Lys
        115                   120                  125

Leu Leu Ala Gly Ser Leu Val Met Leu Gly Ala Gly Phe Ala Gly Glu
    130                   135                  140

Ala Gly Leu Ala Pro Val Leu Pro Ala Phe Ile Ile Gly Met Ala Gly
145                150                  155              160

Trp Leu Tyr Met Ile Tyr Glu Leu Tyr Met Gly Glu Gly Lys Ala Ala
             165                  170              175

Val Ser Thr Ala Ser Pro Ala Val Asn Ser Ala Tyr Asn Ala Met Met
        180                   185                  190

Met Ile Ile Val Val Gly Trp Ala Ile Tyr Pro Ala Gly Tyr Ala Ala
             195                  200              205

Gly Tyr Leu Met Gly Gly Glu Gly Val Tyr Ala Ser Asn Leu Asn Leu
    210                   215                  220

Ile Tyr Asn Leu Ala Asp Phe Val Asn Lys Ile Leu Phe Gly Leu Ile
225                230                  235              240

Ile Trp Asn Val Ala Val Lys Glu Ser Ser Asn Ala
             245                  250

<210> SEQ ID NO 80
<211> LENGTH: 3058
<212> TYPE: DNA
<213> ORGANISM: Natronomonas pharaonis

<400> SEQUENCE: 80

```
gtcgacgagt acgccggttc cctgccactt gcgggcatct gtctcggcca gcaggtcatc      60
gccaacgccc tcggcggcga gaccgaaaag atggagttcg ccaccgcgg cgttaaccaa     120
ccggtcatgg acctccggac cgaaaaggtc gtcatgacga cccagaacca cggctacacc     180
gtctccgaac cgggcgagct tgatgtcacg caggtcaacg tcaacgacga cacgccgaa     240
ggtcgaaagc gacgaactcg atgtcatcac ccgccagtac caccccgaag ccaacccgg     300
tccccacgac acctcgggt tcttcgacga cgttctcgga atggtcgagg agccggcggc     360
aacccagtag cgccacggga tatctgcttg gtacctttc acaagaaaaa gagcttatta     420
gcgctttcta cctatagatt gcggtcgttt cgctccggcg attcggtttc gggtttttat     480
gtgcagtcgc gtcaataaca ccctatgtcg ctgaacgtat cacggctcct tctcccccagc     540
cgtgtccggc acagttatac ggggaagatg ggtgccgttt tcatcttcgt cggcgcgttg     600
acggtgcttt ttggtgccat cgcgtacggt gaggtaaccg ccgccgccgc gaccggtgat     660
gccgcagccg tacaggaggc ggcagtatcg gccattctcg ggctcatcat cctgctcggg     720
atcaacctcg gactcgttgc tgccacgctg gcggtgacca ccgccgcctc gctttcaacg     780
ctggccgcga aggcctcgcg gatgggcgac ggcgacctcg atgtcgagct tgagacccgt     840
cgcgaggacg aaatcggcga cctctatgcg gccttcgacg agatgcgcca atcggtgcgg     900
acatcgctgg aggacgccaa gaacgctcgc gaggacgcag agcaggcaca aaagcgggca     960
gaggagatca acacggaact acaggccgaa gccgagcgct cggcgaggt gatggaccgc    1020
tgtgccgacg cgactttac ccagcggctc gacgccgaaa cggacaacga agcaatgcag    1080
tccatcgagg ggtcatttaa cgagatgatg acggcatcg aggcgcttgt cgggcgcatc    1140
gagcgcttcg ccgacgcggt ctccgaggac gcagaggccg tccgtgcgaa cgccgaatcg    1200
```

```
gtcatggagg ccagcgagga cgtaaaccgc gccgtacaga acatctctga tgcagccggc   1260
gaccagaccg aaaccgtcca gcagatcgca ctggagatgg acgacgtctc ggcgacgacc   1320
gaagaggtcg ccgccagcgc cgacgacatc gccaagacgg ctcggcaggc cgccgaaacg   1380
ggcgaagccg gcgggagac cgccgagacg gccatcaccg agatgaacga ggtcgagtcg   1440
aggaccgaac aggcagtcgc gtcgatggaa gagctcaacg aagacgtccg cgaaatcggc   1500
gaggtatccg agatgattgc ggatatcgcc gagcagacga acatcctcgc gctgaacgcc   1560
tctatcgagg cagcacgggc ggacggcaac agcgagggct cgcggtcgt cgccgacgag   1620 gtcaaggcgc tcgccgagga cgacgaaggcg gcgaccgagg aaatcgacga cctcatcggg   1680
accgtccagg acagaacaca gacaacggtc gacgacatcc gcgagacaag cgaccaagtt   1740
tcggagggcg tcgagacggt cgaagatacc gtcgacgctc tcgaacgtat tgtcgacagc   1800
gtcgagcgga ccaacgacgg gattcaagag atcaaccagt cgacagacgc acaggctgac   1860
gccgcacaga aggcaacaac gatggtcgaa gatatggctg cgacatccga acagactgca   1920
agcgacgccg agacggccgc ggaaacgacg gagacacagg ccgagtctgt caaagaggtc   1980
ttcgacctca tcgatggtct ttccgagcag gccgactcac tcagcgaaac gctcagtcgg   2040
accgacaccg aagaggcgtc agcggccgac cttgatgacc agccgacgct cgcggcgggg   2100
gatgattaac gatggtggga cttacgaccc tcttttggct cggcgcaatc ggcatgctcg   2160
tcggcacgct cgcgttcgcg tgggccggcc gtgacgccgg aagcggcgag cgacggtact   2220
acgtgacgct tgtcggcatc agtggtatcg cagcagtcgc ctacgtcgtc atggcgctgg   2280
gcgtcggctg ggttcccgtg gccgaacgga ctgttttgc cccccggtac attgactgga   2340
ttctcacaac cccgctcatc gtctacttcc tcgggctgct tgcggggctt gatagtcggg   2400
agttcggcat cgtcatcacg ctcaacaccg tggtcatgct cgccggcttc gccggggcga   2460
tggtgcccgg tatcgagcgc tacgcgctgt tcggcatggg ggcggtcgca ttcctcggac   2520
tggtctacta cctcgtcggg ccgatgaccg aaagtgccag ccagcggtcc tccggaatca   2580
agtcgctgta cgtccgcctc cgaaacctga cggtcatcct ctgggcgatt tatccgttca   2640
tctggctgct tggaccgccg ggcgtggcgc tgctgacacc gactgtcgac gtggcgctta   2700
tcgtctacct tgacctcgtc acgaaggtcg gattcggctt catcgcactc gatgctgcgg   2760
cgacacttcg ggccgaacac ggcgaatcgc tcgctggcgt cgatactgac gcgcctgcgg   2820
tcgccgacta aaaagcgcct gttttccgc gaacgtcccg tcgttattct acgtagcggt   2880
actgccgttc gcccattcgc ccccagccgt cgaagacgaa ctccgagtca ggggccgtga   2940
actcctcgac ggccgtctcc tcgtcgtagt tgtgggcgtc gtggacgtcc tcgtactcct   3000
cgaaatcgag gtcgtagcgc gattcgagct gctcgtcgat gttcagcgca tcgagctc     3058
```

<210> SEQ ID NO 81
<211> LENGTH: 239
<212> TYPE: PRT
<213> ORGANISM: Natronomonas pharaonis

<400> SEQUENCE: 81

Met Val Gly Leu Thr Thr Leu Phe Trp Leu Gly Ala Ile Gly Met Leu
1               5                   10                  15

Val Gly Thr Leu Ala Phe Ala Trp Ala Gly Arg Asp Ala Gly Ser Gly
            20                  25                  30

Glu Arg Arg Tyr Tyr Val Thr Leu Val Gly Ile Ser Gly Ile Ala Ala
        35                  40                  45

```
Val Ala Tyr Val Val Met Ala Leu Gly Val Gly Trp Val Pro Val Ala
         50                  55                  60

Glu Arg Thr Val Phe Ala Pro Arg Tyr Ile Asp Trp Ile Leu Thr Thr
 65                  70                  75                  80

Pro Leu Ile Val Tyr Phe Leu Gly Leu Leu Ala Gly Leu Asp Ser Arg
                 85                  90                  95

Glu Phe Gly Ile Val Ile Thr Leu Asn Thr Val Val Met Leu Ala Gly
                100                 105                 110

Phe Ala Gly Ala Met Val Pro Gly Ile Glu Arg Tyr Ala Leu Phe Gly
            115                 120                 125

Met Gly Ala Val Ala Phe Leu Gly Leu Val Tyr Tyr Leu Val Gly Pro
        130                 135                 140

Met Thr Glu Ser Ala Ser Gln Arg Ser Ser Gly Ile Lys Ser Leu Tyr
145                 150                 155                 160

Val Arg Leu Arg Asn Leu Thr Val Ile Leu Trp Ala Ile Tyr Pro Phe
                165                 170                 175

Ile Trp Leu Leu Gly Pro Pro Gly Val Ala Leu Leu Thr Pro Thr Val
                180                 185                 190

Asp Val Ala Leu Ile Val Tyr Leu Asp Leu Val Thr Lys Val Gly Phe
            195                 200                 205

Gly Phe Ile Ala Leu Asp Ala Ala Ala Thr Leu Arg Ala Glu His Gly
        210                 215                 220

Glu Ser Leu Ala Gly Val Asp Thr Asp Ala Pro Ala Val Ala Asp
225                 230                 235

<210> SEQ ID NO 82
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Val Gly Leu Thr Thr Leu Phe Trp Leu Gly Ala Ile Gly Met Leu
 1               5                  10                  15

Val Gly Thr Leu Ala Phe Ala Trp Ala Gly Arg Asp Ala Gly Ser Gly
                20                  25                  30

Glu Arg Arg Tyr Tyr Val Thr Leu Val Gly Ile Ser Gly Ile Ala Ala
            35                  40                  45

Val Ala Tyr Val Val Met Ala Leu Gly Val Gly Trp Val Pro Val Ala
         50                  55                  60

Glu Arg Thr Val Phe Ala Pro Arg Tyr Ile Asn Trp Ile Leu Thr Thr
 65                  70                  75                  80

Pro Leu Ile Val Tyr Phe Leu Gly Leu Leu Ala Gly Leu Asp Ser Arg
                 85                  90                  95

Glu Phe Gly Ile Val Ile Thr Leu Asn Thr Val Val Met Leu Ala Gly
                100                 105                 110

Phe Ala Gly Ala Met Val Pro Gly Ile Glu Arg Tyr Ala Leu Phe Gly
            115                 120                 125

Met Gly Ala Val Ala Phe Leu Gly Leu Val Tyr Tyr Leu Val Gly Pro
        130                 135                 140

Met Thr Glu Ser Ala Ser Gln Arg Ser Ser Gly Ile Lys Ser Leu Tyr
145                 150                 155                 160

Val Arg Leu Arg Asn Leu Thr Val Ile Leu Trp Ala Ile Tyr Pro Phe
```

```
                  165                 170                 175
Ile Trp Leu Leu Gly Pro Pro Gly Val Ala Leu Leu Thr Pro Thr Val
            180                 185                 190

Asp Val Ala Leu Ile Val Tyr Leu Asp Leu Val Thr Lys Val Gly Phe
        195                 200                 205

Gly Phe Ile Ala Leu Asp Ala Ala Ala Thr Leu Arg Ala Glu His Gly
    210                 215                 220

Glu Ser Leu Ala Gly Val Asp Thr Asp Ala Pro Ala Val Ala Asp
225                 230                 235

<210> SEQ ID NO 83
<211> LENGTH: 1229
<212> TYPE: DNA
<213> ORGANISM: Halobacterium salinarum

<400> SEQUENCE: 83
gggtgcaacc gtgaagtccg ccacgaccgc gtcacgacag gagccgacca gcgacaccca      60
gaaggtgcga acggttgagt gccgcaacga tcacgagttt ttcgtgcgct tcgagtggta     120
acacgcgtgc acgcatcgac ttcaccgcgg gtgtttcgac gccagccggc cgttgaacca     180
gcaggcagcg ggcatttaca gccgctgtgg cccaaatggt ggggtgcgct attttggtat     240
ggtttggaat ccgcgtgtcg gctccgtgtc tgacggttca tcggttctaa attccgtcac     300
gagcgtacca tactgattgg gtcgtagagt tacacacata tcctcgttag gtactgttgc     360
atgttggagt tattgccaac agcagtggag ggggtatcgc aggcccagat caccggacgt     420
ccggagtgga tctggctagc gctcggtacg gcgctaatgg gactcgggac gctctatttc     480
ctcgtgaaag ggatgggcgt ctcggaccca gatgcaaaga aattctacgc catcacgacg     540
ctcgtcccag ccatcgcgtt cacgatgtac ctctcgatgc tgctgggta tggcctcaca     600 atggtaccgt tcggtgggga gcagaacccc atctactggg cgcggtacgc tgactggctg     660
ttcaccacgc cgctgttgtt gttagacctc gcgttgctcg ttgacgcgga tcagggaacg     720
atccttgcgc tcgtcggtgc cgacggcatc atgatcggga ccggcctggt cggcgcactg     780
acgaaggtct actcgtaccg cttcgtgtgg tgggcgatca gcaccgcagc gatgctgtac     840
atcctgtacg tgctgttctt cgggttcacc tcgaaggccg aaagcatgcg ccccgaggtc     900
gcatccacgt tcaaagtact gcgtaacgtt accgttgtgt tgtggtccgc gtatcccgtc     960
gtgtggctga tcggcagcga aggtgcggga atcgtgccgc tgaacatcga gacgctgctg    1020
ttcatggtgc ttgacgtgag cgcgaaggtc ggcttcgggc tcatcctcct gcgcagtcgt    1080
gcgatcttcg gcgaagccga agcgccggag ccgtccgccg gcgacggcgc ggccgcgacc    1140
agcgactgat cgcacacgca ggacagcccc acaaccggcg cggctgtgtt caacgacaca    1200
cgatgagtcc cccactcggt cttgtactc                                      1229

<210> SEQ ID NO 84
<211> LENGTH: 262
<212> TYPE: PRT
<213> ORGANISM: Halobacterium salinarum

<400> SEQUENCE: 84

Met Leu Glu Leu Leu Pro Thr Ala Val Glu Gly Val Ser Gln Ala Gln
1               5                   10                  15

Ile Thr Gly Arg Pro Glu Trp Ile Trp Leu Ala Leu Gly Thr Ala Leu
            20                  25                  30

Met Gly Leu Gly Thr Leu Tyr Phe Leu Val Lys Gly Met Gly Val Ser
```

```
                35                  40                  45
Asp Pro Asp Ala Lys Lys Phe Tyr Ala Ile Thr Thr Leu Val Pro Ala
 50                  55                  60
Ile Ala Phe Thr Met Tyr Leu Ser Met Leu Leu Gly Tyr Gly Leu Thr
 65                  70                  75                  80
Met Val Pro Phe Gly Gly Glu Gln Asn Pro Ile Tyr Trp Ala Arg Tyr
                 85                  90                  95
Ala Asp Trp Leu Phe Thr Thr Pro Leu Leu Leu Asp Leu Ala Leu
            100                 105                 110
Leu Val Asp Ala Asp Gln Gly Thr Ile Leu Ala Leu Val Gly Ala Asp
            115                 120                 125
Gly Ile Met Ile Gly Thr Gly Leu Val Gly Ala Leu Thr Lys Val Tyr
        130                 135                 140
Ser Tyr Arg Phe Val Trp Trp Ala Ile Ser Thr Ala Ala Met Leu Tyr
145                 150                 155                 160
Ile Leu Tyr Val Leu Phe Phe Gly Phe Thr Ser Lys Ala Glu Ser Met
                165                 170                 175
Arg Pro Glu Val Ala Ser Thr Phe Lys Val Leu Arg Asn Val Thr Val
            180                 185                 190
Val Leu Trp Ser Ala Tyr Pro Val Val Trp Leu Ile Gly Ser Glu Gly
        195                 200                 205
Ala Gly Ile Val Pro Leu Asn Ile Glu Thr Leu Leu Phe Met Val Leu
        210                 215                 220
Asp Val Ser Ala Lys Val Gly Phe Gly Leu Ile Leu Leu Arg Ser Arg
225                 230                 235                 240
Ala Ile Phe Gly Glu Ala Glu Ala Pro Glu Pro Ser Ala Gly Asp Gly
                245                 250                 255
Ala Ala Ala Thr Ser Asp
            260

<210> SEQ ID NO 85
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Leu Glu Leu Leu Pro Thr Ala Val Glu Gly Val Ser Gln Ala Gln
 1               5                  10                  15
Ile Thr Gly Arg Pro Glu Trp Ile Trp Leu Ala Leu Gly Thr Ala Leu
                 20                  25                  30
Met Gly Leu Gly Thr Leu Tyr Phe Leu Val Lys Gly Met Gly Val Ser
             35                  40                  45
Asp Pro Asp Ala Lys Lys Phe Tyr Ala Ile Thr Thr Leu Val Pro Ala
 50                  55                  60
Ile Ala Phe Thr Met Tyr Leu Ser Met Leu Leu Gly Tyr Gly Leu Thr
 65                  70                  75                  80
Met Val Pro Phe Gly Gly Glu Gln Asn Pro Ile Tyr Trp Ala Arg Tyr
                 85                  90                  95
Ala Asn Trp Leu Phe Thr Thr Pro Leu Leu Leu Asp Leu Ala Leu
            100                 105                 110
Leu Val Asp Ala Asp Gln Gly Thr Ile Leu Ala Leu Val Gly Ala Asp
            115                 120                 125
```

Gly Ile Met Ile Gly Thr Gly Leu Val Gly Ala Leu Thr Lys Val Tyr
            130                 135                 140

Ser Tyr Arg Phe Val Trp Trp Ala Ile Ser Thr Ala Ala Met Leu Tyr
145                 150                 155                 160

Ile Leu Tyr Val Leu Phe Phe Gly Phe Thr Ser Lys Ala Glu Ser Met
                165                 170                 175

Arg Pro Glu Val Ala Ser Thr Phe Lys Val Leu Arg Asn Val Thr Val
                180                 185                 190

Val Leu Trp Ser Ala Tyr Pro Val Val Trp Leu Ile Gly Ser Glu Gly
            195                 200                 205

Ala Gly Ile Val Pro Leu Asn Ile Glu Thr Leu Leu Phe Met Val Leu
            210                 215                 220

Asp Val Ser Ala Lys Val Gly Phe Gly Leu Ile Leu Leu Arg Ser Arg
225                 230                 235                 240

Ala Ile Phe Gly Glu Ala Glu Ala Pro Glu Pro Ser Ala Gly Asp Gly
                245                 250                 255

Ala Ala Ala Thr Ser Asp
            260

<210> SEQ ID NO 86
<211> LENGTH: 258
<212> TYPE: PRT
<213> ORGANISM: Halobacterium salinarum

<400> SEQUENCE: 86

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
            130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

```
Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 87
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asn Trp
                85                  90                  95

Leu Phe Thr Thr Pro Leu Leu Leu Asp Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp
```

OPTOGENETIC PROBES FOR MEASURING MEMBRANE POTENTIAL

CROSS-REFERENCE TO RELATED APPLICATIONS

This application is a 35 U.S.C. §371 National Phase Entry Application of International Application No. PCT/US2011/048793, filed Aug. 23, 2011, which designates the Unites States, and which claims benefit under 35 U.S.C. 119(e) of provisional applications No. 61/412,972, filed on Nov. 12, 2010, and 61/376,049, filed on Aug. 23, 2010, the contents of which are herein incorporated into this application by reference in their entirety.

GOVERNMENT SUPPORT

This invention was made with Government support under grant no. EB012498 awarded by National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created Dec. 21, 2011 is named ReplacementSL00280PCT.txt and is 208,779 bytes in size.

FIELD OF THE INVENTION

The field of the invention relates to methods, constructs, and compositions for optically measuring electrical potential across a phospholipid bilayer.

BACKGROUND

Membrane-enclosed biological structures can support a voltage difference between the inside and the outside of the membrane. This voltage, also called membrane potential, serves a variety of biological functions, including carrying information (e.g., in neurons), acting as an intermediate in production of ATP (e.g., in bacteria and mitochondria), powering the flagellar motor (e.g., in bacteria), and controlling transport of nutrients, toxins, and signaling molecules across the cell membrane (in bacteria and eukaryotic cells).

In spite of its fundamental biological role, membrane potential is very difficult to measure. Electrophysiology involves positioning electrodes on both sides of the membrane to record voltage directly. Electrophysiological experiments are slow to set up, can only be performed on one or a few cells at a time, cannot access deeply buried tissues (e.g., in vivo), do not work for cells that are too small (e.g. bacteria) or are enclosed in a hard cell wall (e.g. yeast), or are motile (e.g., sperm) cannot be applied to long-term measurements, and usually damage or kill the cell under study.

Accordingly, novel methods for measuring membrane potential are needed.

SUMMARY OF THE INVENTION

Described herein are methods of harnessing microbial rhodopsins as optical sensors to detect voltage across phospholipid layers. We have discovered that our novel system allows us to optically measure membrane potential of a cell or membrane bound cellular compartment, such as intracellular organelles and artificial cells or other lipid membrane bound structures.

The methods comprise expressing a microbial rhodopsin in the cell or cellular organelle, exposing the cell to a light source and detecting the emitted fluorescence from the microbial rhodopsin, wherein the intensity of the emitted fluorescence reflects membrane potential. The method allows measurement of membrane potential without the use of electrodes. The method further allows monitoring membrane potential changes in response to external stimulus or stimuli. This is important not only for research but also, for example, if one wants to screen candidate agents for their capacity to affect membrane potential, e.g., in drug screens.

Also provided are cells expressing microbial rhodopsins and modified microbial rhodopsins as well as nucleic acids constructs encoding modified archaerhodopsins useful in measuring membrane potential and changes thereof in eukaryotic cells. In some embodiments, the optical sensors described herein have their endogenous ion pump activity reduced or inhibited partially or substantially completely compared to the native microbial rhodopsin protein. This permits the optical sensors to sense voltage but not to participate in altering voltage through establishing ionic gradients. The detection of the voltage and its changes can be visualized and measured using optical systems.

The present invention is based, at least in part, on the discovery that microbial rhodopsin proteins, such as archaerhodopsins or proteorhodopsins and modified versions thereof having reduced ion pumping activity (compared to the natural microbial rhodopsin protein from which it is derived) can be used as optical sensors to sense voltage across membranes in a cell. That is, the microbial rhodopsin and the modified microbial rhodopsin proteins can be used to measure membrane potential of a cell and changes in the membrane potential. The constructs and methods can also be used for in vivo imaging of organs and organisms, such as a zebrafish, that could not be studied due to electrode size constraints. This is important not only in research but also for screening novel candidate agents for their capacity to affect membrane potential in cells.

We have developed Proteorhodopsin Optical Proton Sensor (PROPS), which function primarily in bacterial cells, and a family of archaerhodopsin-based fluorescent voltage-indicating proteins (VIPs) that also function in mammalian cells, including neurons and human stem cell-derived cardiomyocytes. The VIPs are based on voltage indicators derived from Archaerhodopsin 3 (Arch) and its homologues. These proteins indicate electrical dynamics with sub-millisecond temporal resolution and sub-micron spatial resolution. Using VIPs, we demonstrated non-contact, high-throughput, and high-content methods for measuring by using optical detection of electrical dynamics in mammalian cells and tissues.

The optical sensors described herein are not constrained by the need for electrodes and permit electrophysiological studies to be performed in e.g., subcellular compartments (e.g., mitochondria) or in small cells (e.g., bacteria). The optical sensors described herein can be used in drug screening, research settings, and for in vitro and in vivo imaging of voltage changes in both eukaryotic and prokaryotic cells.

We describe voltage indicator proteins and constructs expressing such proteins. The constructs have optionally a cell-type specific promoter that turns on when the cells are differentiated, e.g., to neuronal cells, such as neurons, or to cardiac cells, such as cardiomyocytes, purkinje cells, or sinusoidal cells. The constructs may further include targeting signals such as mitochondrial targeting signals to direct the voltage indicator protein to a desired membrane location. We provide cells and cell lines transiently and stably expressing these proteins, including human stem cells, such as induced pluripotent cells (iPSC) or embryonal stem cells (ESC), neural progenitor cells and neural cells, and cardiac progenitor cells and cardiac myocytes. We also describe methods for screening drugs using the described voltage indicator proteins.

The cells, whether they be prokaryotic or eukaryotic cells, used in the methods of the invention are typically engineered to express the microbial rhodopsin or the modified microbial rhodopsin as they do not naturally express the microbial rhodopsin protein that is used in the methods of the invention.

Accordingly, in one embodiment, the invention provides a method for measuring membrane potential in a cell expressing a nucleic acid encoding a microbial rhodopsin protein, the method comprising the steps of (a) exciting, in vitro, ex vivo or in vivo, at least one cell comprising a nucleic acid encoding a microbial rhodopsin protein with light of at least one wave length; and (b) detecting, in vitro, ex vivo or in vivo, at least one optical signal from the at least one cell, wherein the level of fluorescence emitted by the at least one cell compared to a reference is indicative of the membrane potential of the cell.

In some aspects of any embodiment or aspect of the invention, the microbial rhodopsin protein is a modified microbial rhodopsin protein with reduced ion pumping activity compared to a natural microbial rhodopsin protein from which it is derived.

In some aspects of any embodiment or aspect of the invention, the microbial rhodopsin protein is a member of a proteorhodopsin family of proteins.

In some aspects of any embodiment or aspect of the invention, the microbial rhodopsin protein is a member of an archaerhodopsin family of proteins.

In some aspects of any embodiment or aspect of the invention, the at least one wave length is a wave length between $\lambda$=594-645. Range of wave length between $\lambda$=630-645 nm can also be used.

In some aspects of any embodiment or aspect of the invention, the cell is a prokaryotic cell. The prokaryotic cell can be Gram negative or Gram positive. The prokaryotic cell can be pathogenic or non-pathogenic.

In some aspects of any embodiment or aspect of the invention, the cell is a eukaryotic cell.

In some aspects of any embodiment or aspect of the invention, the eukaryotic cell is a mammalian cell.

In some aspects of any embodiment or aspect of the invention, the eukaryotic cell is a stem cell or a pluripotent or a progenitor cell.

In some aspects of any embodiment or aspect of the invention, the eukaryotic cell is an induced pluripotent cell.

In some aspects of any embodiment or aspect of the invention, the eukaryotic cell is a neural cell.

In some aspects of any embodiment or aspect of the invention, the eukaryotic cell is a cardiomyocyte.

The cells can be cultured in vitro, ex vivo or the cells can be part of an organ or organism. Exemplary cells include bacteria, yeast, a plant cell, and a cell from vertebrate and non-vertebrate animal. In some embodiments, the eukaryotic cells are human cells. In some embodiments, the eukaryotic cells are non-human cells. In some embodiments, the cells do not naturally express the microbial proteorhodopsin used in the methods.

In some aspects of any embodiment or aspect of the invention, the method further comprises a step of transfecting, in vitro, ex vivo or in vivo, the at least one cell with a vector comprising the nucleic acid encoding the microbial rhodopsin protein. The cells can be transfected transiently or stably.

In some aspects of any embodiment or aspect of the invention, the nucleic acid encoding the microbial rhodopsin protein is operably linked to a cell-type specific promoter.

In some aspects of any embodiment or aspect of the invention, the nucleic acid encoding the microbial rhodopsin protein is operably linked to a membrane-targeting sequence.

In some aspects of any embodiment or aspect of the invention, the membrane-targeting sequence is a plasma membrane targeting sequence.

In some aspects of any embodiment or aspect of the invention, the membrane-targeting sequence is a subcellular compartment-targeting sequence.

In some aspects of any embodiment or aspect of the invention, the subcellular compartment is selected from a mitochondrial membrane, an endoplasmic reticulum, a sarcoplastic reticulum, a synaptic vesicle, an endosome and a phagosome.

In some aspects of any embodiment or aspect of the invention, the microbial rhodopsin gene is operably linked to a nucleic acid encoding an additional fluorescent protein or a chromophore.

In some aspects of any embodiment or aspect of the invention, the at least one additional fluorescent protein is a protein capable for indicating ion concentration in the cell.

In some aspects of any embodiment or aspect of the invention, the at least one additional fluorescent protein capable for indicating ion concentration is a calcium indicator.

In some aspects of any embodiment or aspect of the invention, the fluorescent protein capable for indicating ion concentration is a pH indicator.

In some aspects of any embodiment or aspect of the invention, the fluorescent protein is capable of undergoing nonradiative fluorescence resonance energy transfer to the microbial rhodopsin, with a rate of energy transfer dependent on the membrane potential.

In some aspects of any embodiment or aspect of the invention, brightness of the fluorescent protein is insensitive to membrane potential and local chemical environment, and thereby serves as a reference against which to compare the fluorescence of the microbial rhodopsin In some aspects of any embodiment or aspect of the invention, the method further comprises steps of exciting, in vitro, ex vivo or in vivo, the at least one cell with light of at least a first and a second wavelength; and detecting, in vitro, ex vivo, or in vivo, the at least first and the second optical signal resulting from the excitation with the at least the first and the second wavelength, which is different from the at least first wave length, from the at least one cell.

In some aspects of any embodiment or aspect of the invention, the at least second wave length is between $\lambda$=447-594 nm.

In some aspects of any embodiment or aspect of the invention, the method further comprises a step of calculating the ratio of the fluorescence emission from the microbial rhodopsin to the fluorescence emission of the fluorescent protein to obtain a measurement of membrane potential independent of variations in expression level.

In some aspects of any embodiment or aspect of the invention, the method further comprises the step of exposing, in vitro, ex vivo, or in vivo, the at least one cell to a stimulus capable of or suspected to be capable of changing membrane potential.

In some aspects of any embodiment or aspect of the invention, the stimulus a candidate agent. In some embodiments, at least one candidate agent is administered. In some embodiments a combination of at least two candidate agents are administered simultaneously or in series.

In some aspects of any embodiment or aspect of the invention, the stimulus is a change to the composition of the cell culture medium.

In some aspects of any embodiment or aspect of the invention, the stimulus is an electrical current.

In some aspects of any embodiment or aspect of the invention, the method further comprises the step of measuring, in vitro, ex vivo or in vivo, the at least one optical signal at least at a first and at least at a second time point.

In some aspects of any embodiment or aspect of the invention, the at least first time point is before exposing the at least one cell to a stimulus and the at least second time point is after exposing the at least one cell to the stimulus.

In some aspects of any embodiment or aspect of the invention, the method further comprises a step of measuring the ratio of fluorescence between the optical signals from the exposure to the at least first wave length and the at least second wave length.

In some aspects of any embodiment or aspect of the invention, the method comprises use of a plurality of cells. For example in a high-throughput assay format. For example, in such embodiments, a plurality of cells expressing the microbial rhodopsin proteins can be exposed to a number of candidate agents, such as drug candidates, and screened for the candidate agents' ability to affect the membrane potential of the cell.

In some aspects of any embodiment or aspect of the invention, the eukaryotic cell is a human cell. In some embodiments, the eukaryotic cell is a non-human cell.

In another embodiment, the invention provides an isolated and purified nucleic acid encoding a modified member of an archaerhodopsin family of proteins with reduced ion pumping activity compared to a natural member of an archaerhodopsin family of proteins from which it is derived.

In some aspects of any embodiment or aspect of the invention, the modified member of an archaerhodopsin family of proteins with reduced ion pumping activity compared to a natural member of an archaerhodopsin family of proteins from which it is derived comprises a mutated proton acceptor proximal to the Schiff Base.

In some aspects of any embodiment or aspect of the invention, the isolated and purified nucleic acid is operably linked to a nucleic acid encoding a membrane-targeting sequence.

In some aspects of any embodiment or aspect of the invention, the membrane-targeting sequence is a subcellular membrane-targeting sequence.

In some aspects of any embodiment or aspect of the invention, the subcellular membrane is a mitochondrial membrane, an endoplasmic reticulum, a sarcoplastic reticulum, a synaptic vesicle, an endosome or a phagosome.

In some aspects of any embodiment or aspect of the invention, the isolated and purified nucleic acid is operably linked to a cell-type specific promoter.

In some aspects of any embodiment or aspect of the invention, the isolated and purified nucleic acid is operably linked to at least one nucleic acid encoding an additional fluorescent protein or a chromophore.

In some aspects of any embodiment or aspect of the invention, the additional fluorescent protein is green fluorescent protein or a homolog thereof.

In some aspects of any embodiment or aspect of the invention, the isolated and purified nucleic acid is operably linked to a nucleic acid encoding a fluorescent protein capable of undergoing fluorescence resonance energy transfer to the microbial rhodopsin, with the rate of energy transfer dependent on the membrane potential.

In some aspects of any embodiment or aspect of the invention, the isolated and purified nucleic acid further comprises a vector.

In some aspects of any embodiment or aspect of the invention, the vector is a viral vector, such as a lentiviral vector or an adeno-associated virus (AAV) vector.

In another embodiment, the invention provides a kit comprising the isolated and purified nucleic acid as described above. The nucleic acid may be provided in a buffer solution or in a dried, such as lyophilized form in a suitable container. In some embodiments the kit further comprises buffers and solutions for performing the methods or the assays of the invention. Based on the description provided in the specification, a skilled artisan will be able to pick and choose the appropriate reagents for such a kit. The kit may comprise one or more transfection agents, one or more buffers, one or more cell culture media, and one or more containers, such as cell culture plates or arrays, to perform the methods and assays of the invention. Instruction manuals comprising instructions for performing the assay may also be included with the kits.

In another embodiment, the invention provides an isolated cell comprising a nucleic acid encoding a microbial rhodopsin protein. The cell is typically engineered to express the microbial rhodopsin protein.

In some aspects of any embodiment or aspect of the invention, the microbial rhodopsin protein is a modified microbial rhodopsin protein with reduced ion pumping activity compared to a natural microbial rhodopsin protein from which it is derived.

In some aspects of any embodiment or aspect of the invention, the modified microbial rhodopsin protein comprises a mutated proton acceptor proximal to the Schiff Base.

In some aspects of any embodiment or aspect of the invention, the microbial rhodopsin is a member of a proteorhodopsin family.

In some aspects of any embodiment or aspect of the invention, the microbial rhodopsin is a member of a archaerhodopsin family.

In some aspects of any embodiment or aspect of the invention, the cell is a eukaryotic cell.

In some aspects of any embodiment or aspect of the invention, the cell is a prokaryotic cell. In some embodiments, the prokaryotic cell is a Gram positive cell. In some embodiments, the prokaryotic cell is a Gram negative cell. In some embodiments, the prokaryotic cell is a pathogenic cell.

In some aspects of any embodiment or aspect of the invention, the modified microbial rhodopsin gene is operably linked to a promoter.

In some aspects of any embodiment or aspect of the invention, the promoter is a cell-type specific promoter.

In some aspects of any embodiment or aspect of the invention, the nucleic acid encoding the modified microbial rhodopsin protein is operably linked to a membrane-targeting nucleic acid.

In some aspects of any embodiment or aspect of the invention, the nucleic acid encoding the modified microbial rhodopsin protein is operably linked to a nucleic acid encoding at least one additional fluorescent protein or a chromophore.

In some aspects of any embodiment or aspect of the invention, at least one additional fluorescent protein is a green fluorescent protein or a homolog thereof.

In some aspects of any embodiment or aspect of the invention, the at least one additional fluorescent protein is a fluorescent protein capable of undergoing fluorescence resonance energy transfer to the microbial rhodopsin, with a rate of energy transfer dependent on the membrane potential.

In some aspects of any embodiment or aspect of the invention, the at least one additional fluorescent protein is a fluorescent protein whose brightness is insensitive to membrane potential and local chemical environment In some aspects of any embodiment or aspect of the invention, the cell further comprises a nucleic acid encoding a fluorescent protein capable of indicating ion concentration in the cell.

In some aspects of any embodiment or aspect of the invention, the cell is a stem cell, a pluripotent cell, or an induced pluripotent cell, or differentiated or undifferentiated progeny thereof.

In some aspects of any embodiment or aspect of the invention, the differentiated cell is a neuron.

In some aspects of any embodiment or aspect of the invention, the differentiated cell is a cardiomyocyte.

In one embodiment, the invention provides a kit comprising a cell or a plurality of cells of as described above in a suitable cell culture medium and a container. The kit may comprise frozen cells in a suitable medium. Other reagents, such as one or more buffers, one or more cell culture media, and one or more containers may be included in the kit. The kit may also include instructions for the methods of using the cells in the methods as described herein.

In another embodiment, the invention provides a method of making an engineered cell for optical measurement of membrane potential comprising the steps of transfecting a cell with a nucleic acid encoding a microbial rhodopsin protein. The transfection may be a transient transfection or a stable transfection.

In some embodiments, the cell is a prokaryotic cell. The prokaryotic cell may be Gram positive or Gram negative. In some aspects, the prokaryotic cell is a pathogenic bacterium. The cell can also be a stem cell, a pluripotent cell, a differentiated cell or an immortalized cell or a cell line. The cell can be an isolated cell or a part of an organ or an organism, such as a zebrafish or a non-human embryo or a human embryo.

In one aspect of this embodiment, and any aspect of this embodiment, the microbial rhodopsin protein is a modified microbial rhodopsin protein.

In one aspect of this embodiment, and any aspect of this embodiment, the nucleic acid encoding the microbial rhodopsin protein is operably linked to the differentiated cell type-specific promoter.

In one aspect of this embodiment, and any aspect of this embodiment, the nucleic acid encoding the microbial rhodopsin protein is operably linked to at least one additional gene encoding a fluorescent protein or a chromophore.

In one aspect of this embodiment, the at least one additional gene encoding a fluorescent protein is a green fluorescent protein or a homolog thereof.

In one aspect of this embodiment, and any aspect of this embodiment, the nucleic acid encoding the microbial rhodopsin protein is operably linked to a fluorescent protein capable of indicating ion concentration in the cell.

Exemplary nucleic acids and nucleic acid constructs are provided throughout this specification and their nucleic acid sequences are provided in the accompanying Sequence Listing. Typically, the modified microbial rhodopsins are modified to at least reduce the ion pumping activity of such proteins by mutating the proton acceptor proximal to the Schiff Base. However, the invention is not intended to be limited to these examples, as similar optical measurement is possible for any number of the existing microbial rhodopsin proteins.

Any such protein may be used in the methods of the invention and any such protein may also be modified to reduce its ion pumping activity.

BRIEF DESCRIPTION OF THE FIGURES

FIG. 2A shows visible absorption spectra of GPR D97N in whole *E. coli* at pH 7 and pH 11; FIG. 2B shows fluorescence emission spectra of purified GPR D97N protein solubulized in octyl-glucoside at pH 7 and pH 11; FIG. 2C shows photobleaching curves of GPR D97N and the organic dye Alexa 647 (Molecular Probes) under identical illumination conditions. GPR D97N is more photostable than any other known fluorescent protein under comparable illumination intensities. FIG. 2D shows pH titration of the Schiff base as monitored by visible absorption, in the wild-type and D97N mutants of GPR. The pKa of the D97N mutant is 9.8 and the pKa of the wild-type protein is >12.

FIG. 4A shows a film strip of three *E. coli* at pH 7.5. Each exposure is 100 ms. The brightness of individual cells varies with time. FIG. 4B shows a blinking pattern from a single cell at pH 7.5. Each trace is a 50 second (s) record of the intensity. The time after the start of the experiment is indicated on the right. Cells continued to blink throughout the 1 hour experiment. The same cell shows fast blinks (0 and 7 minutes), slow blinks (28 minutes), and 'ringing' behavior (18 minutes).

FIGS. 6A-6E show that Arch is a fluorescent voltage indicator. FIG. 6A shows a model of Arch as a voltage sensor. pH and membrane potential can both alter the protonation of the Schiff base. The crystal structure shown is bacteriorhodopsin; the structure of Arch has not been solved. FIG. 6B shows absorption (solid line) and fluorescence emission (Em, see, dashed line) spectra of purified Arch at neutral and high pH. FIG. 6C top shows a HEK cell expressing Arch, visualized via Arch fluorescence. FIG. 6C bottom shows a pixel-weight matrix regions of voltage-dependent fluorescence. Scale bar 10 μm. FIG. 6D shows fluorescence of Arch as a function of membrane potential. The fluorescence was divided by its value at −150 mV. FIG. 6E shows dynamic response of Arch to steps in membrane potential between −70 mV and +30 mV. The overshoots on the rising and falling edges were an artifact of electronic compensation circuitry. Data were an average of 20 cycles. Inset shows that step response occurred in less than the 0.5 ms resolution of the imaging system.

FIG. 7A shows whole-cell membrane potential determined via direct voltage recording (bottom, dotted line) and weighted Arch3 fluorescence (top, solid line) during a single-trial recording of a train of action potentials. Inset shows an averaged spike response for 269 events in a single cell, showing voltage (dotted line) and fluorescence (solid line). FIG. 7B shows recording of multiple spike-trains from a single cell. Current injections (shown in black dotted line) of 200 pA were applied to a neuron expressing Arch WT. Action potentials (shown in grey line) were readily detected via fluorescence over multiple rounds of current injection. FIG. 7C shows sub-cellular localization of an action potential. We took an image of a field of neuronal processes expressing Arch and created a weight matrix indicating pixels, shown as images in the Figure, whose fluorescence co-varied with the recorded potential in red, overlaid on the time-average Arch fluorescence which was shown in cyan. We detected sub-cellular regions within the electrically active cell. The figure shows a timecourse of an action potential determined via fluorescence (F) on the top graph (averaged over n=100 spikes) corresponding to each of the regions indicated. Also shown is the electrical recording of the action potential (V, bottom graph). FIG. 7D shows heterogeneous dynamics of an action potential within a single neuron, computed from an average of n=33 spikes. The region indicated by the arrow in the pixel map (see also graph) lags behind the rest of the cell by ~1 ms (black arrows). Scale bar 5 μm.

FIGS. 8A-8D demonstrate that Arch D95N shows voltage-dependent fluorescence but no photocurrent. FIG. 8A shows photocurrents in Arch 3 WT and Arch 3 D95N mutant, expressed in HEK cells clamped at V=0. Cells were illuminated with pulses of light at λ=640 nm, 1800 W/cm². FIG. 8B shows that Arch D95N fluorescence increased 3-fold between −150 mV and +150 mV, with nearly linear sensitivity from −120 to +120 mV. Inset shows a map of voltage sensitivity. Scale bar 5 μm. FIG. 8C shows that the step response comprised a component faster than 500 μs (20% of the response) and a component with a time constant of 41 ms. FIG. 8D shows that Arch D95N provided highly accurate estimates of membrane potential, clearly resolving voltage steps of 10 mV, with a noise in the voltage estimated from fluorescence of 260 μV/(Hz)^{1/2} over timescales<12 s.

FIG. 9A shows electrically recorded membrane potential of a neuron expressing Arch WT, subjected to pulses of current injection and laser illumination (I=1800 W/cm2, λ=640 nm). Illumination generated sufficient photocurrent to suppress action potentials when the cell was near threshold. Grey bars indicate laser illumination. FIG. 9B is same as FIG. 9A in a neuron expressing Arch D95N, showing no effect of illumination on spiking or resting potential. We showed a neuron expressing Arch D95N, showing Arch D95N fluorescence (shows in cyan in the experiment), and regions of voltage-dependent fluorescence (shown in red in the experiment). FIG. 9C shows whole-cell membrane potential determined via electrical recording (bottom, voltage line) and weighted ArchD95N fluorescence (top, fluorescence line) during a single-trial recording of a train of action potentials.

FIG. 11A shows a comparison of the action potential determined from patch clamp recording (dashed line) and fluorescence (solid line). FIGS. 11B-11D show optical recordings of the action potentials in a single HL-1 cell over increasingly long intervals. Data in 11D have been corrected for photobleaching.

| | |
|---|---|
| pADD247/248 | SEQ ID NO: 48 |
| pADD286/287 | SEQ ID NO: 53 |
| pADD292/293 | SEQ ID NO: 50 |
| pADD294 (D95N only) | SEQ ID NO: 54 |
| pADD297/300 | SEQ ID NO: 51 |
| pADD259/298 | SEQ ID NOS: 55 and 52, respectively |
| Pfck: Arch3(WT/D95N)-EGFP | SEQ ID NOS: 56-57, respectively |
| pADD269/270 | SEQ ID NO: 49 |
| Pcmv: Arch3(WT/D95N)-GCaMP | SEQ ID NOS: 58-59, respectively |

Figure 14B:
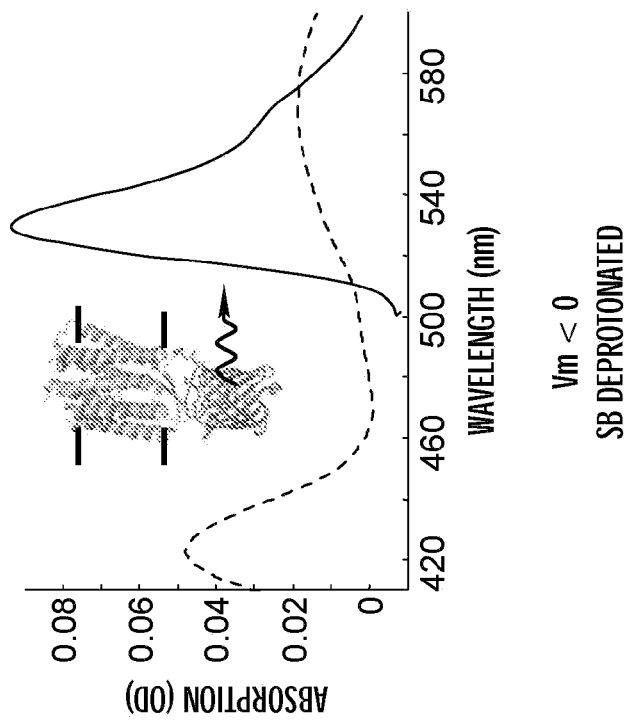
Figure 14A:
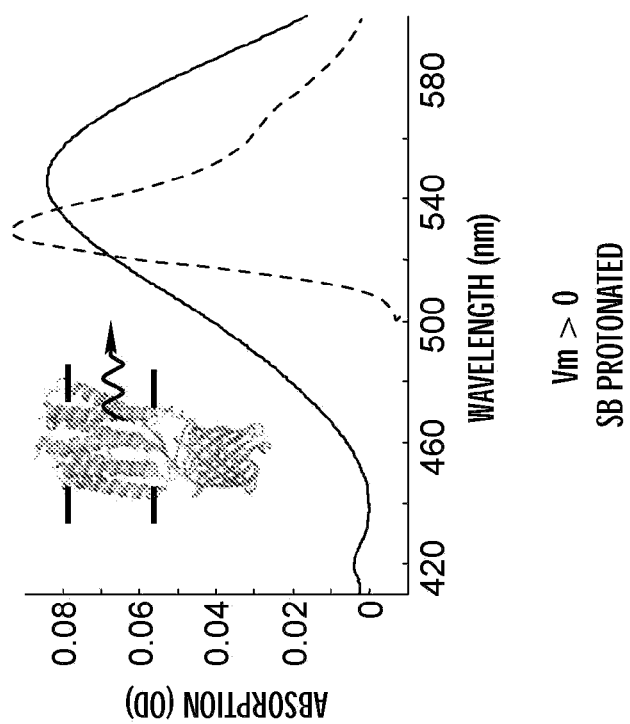

FIGS. 14A-14B illustrate mechanism of ssFRET. FIG. 14A shows that when the Schiff Base (SB) on the retinal is protonated, the absorption spectrum of the retinal (solid) overlaps with the emission spectrum of the GFP (dotted), and the fluorescence of the GFP is quenched. However, the retinal itself is fluorescent in this state. FIG. 14B shows that when the SB is deprotonated, the GFP fluorescence (solid line) becomes de-quenched and the retinal fluorescence vanishes.

Figure 15:
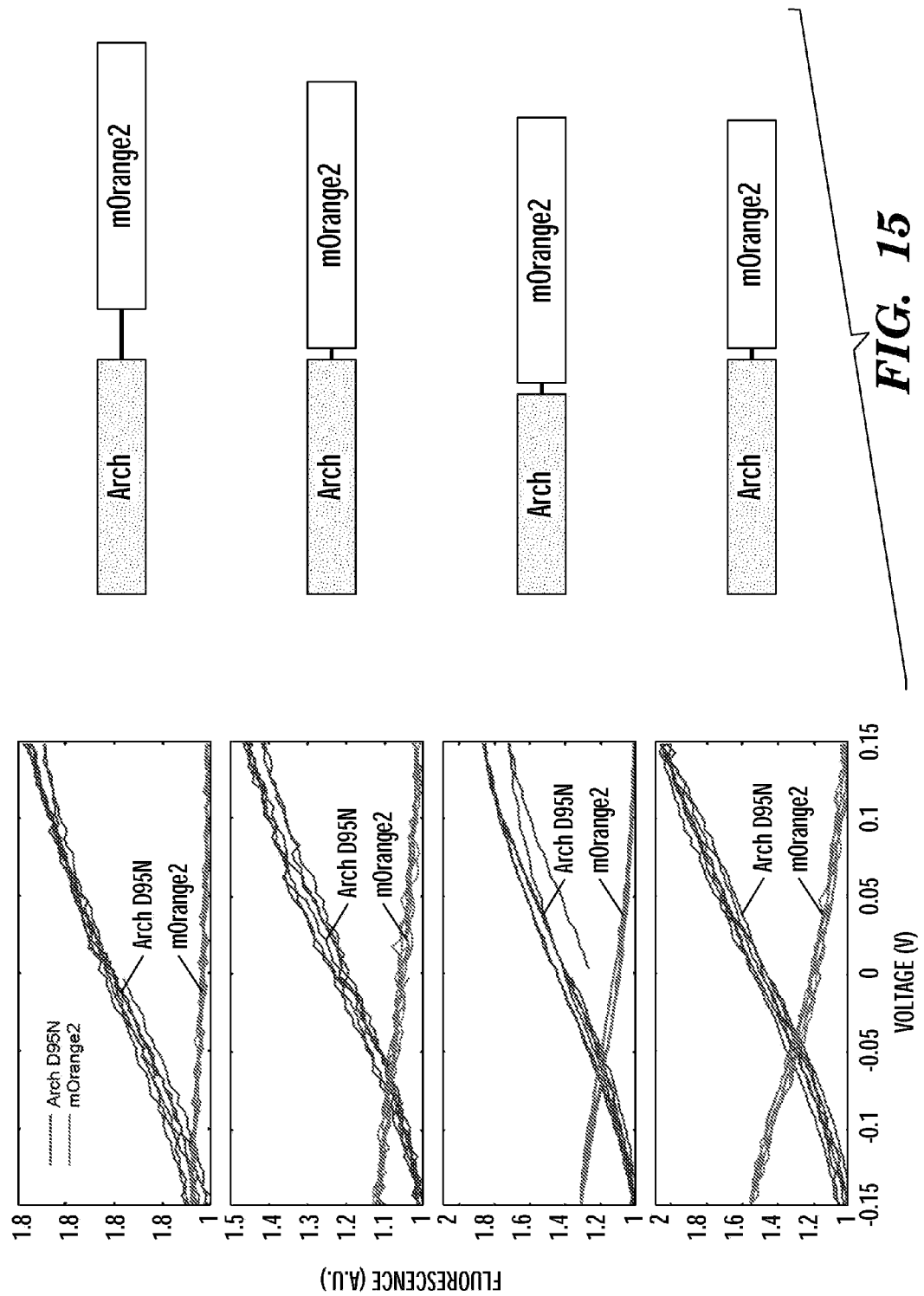

FIG. 15 shows distance dependence of ssFRET signal. As the distance between the mOrange2 and the Arch chromophores decreased, the magnitude of the ssFRET signal increased.

Figure 16:
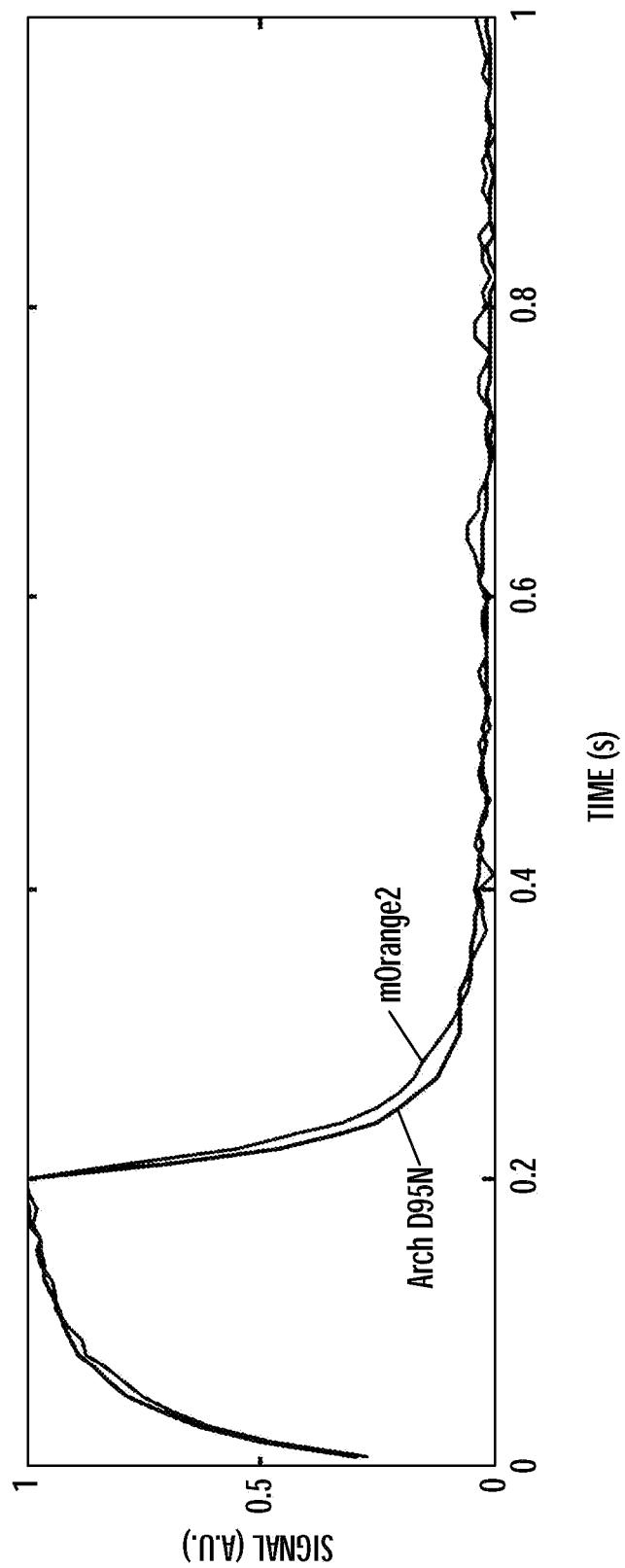

FIG. 16 shows a step response of Arch 3 fluorescence and mOrange fluorescence in pADD294. Here the mOrange2 signal has been inverted to facilitate comparison with the Arch 3 signal. The similarity of the timecourses is consistent with modulation of the mOrange2 fluorescence via ssFRET. The voltage step is from −70 mV to +30 mV.

Figure 17A:
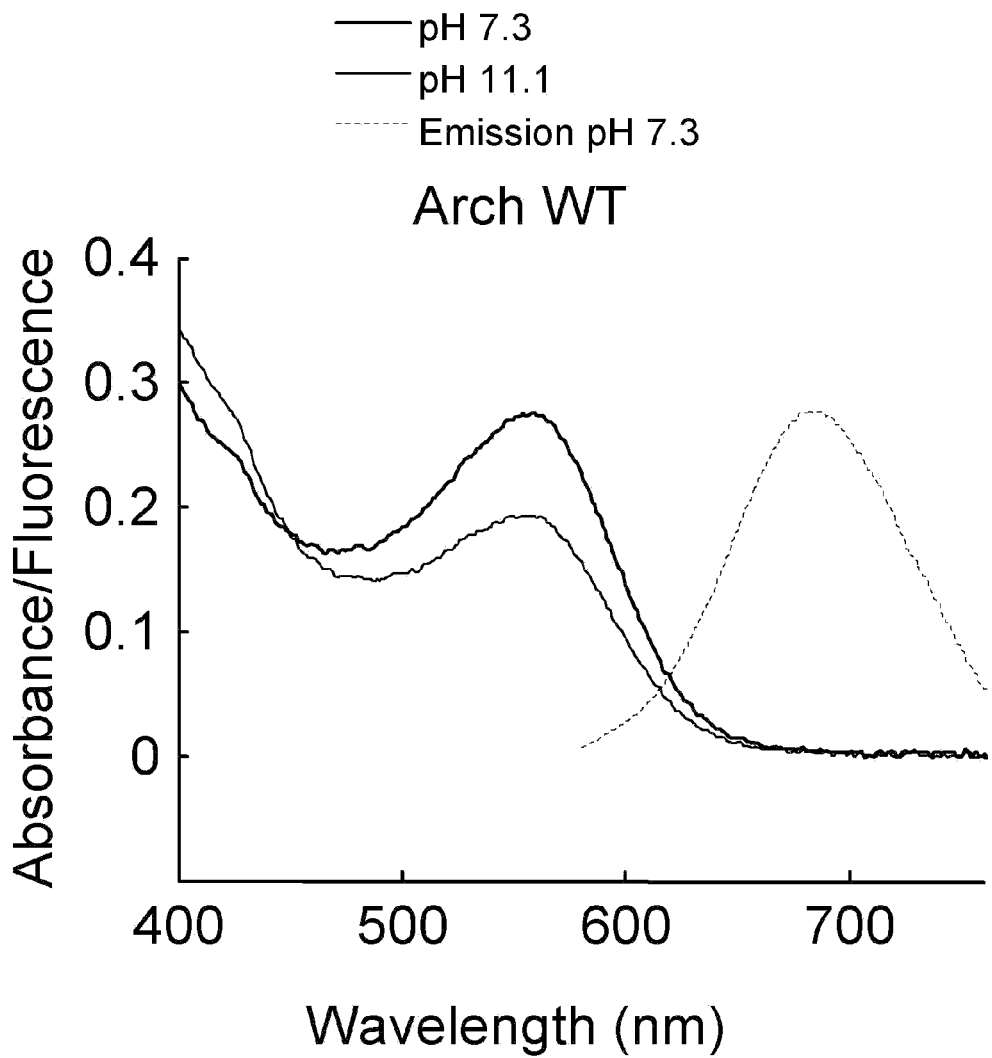
Figure 17B:
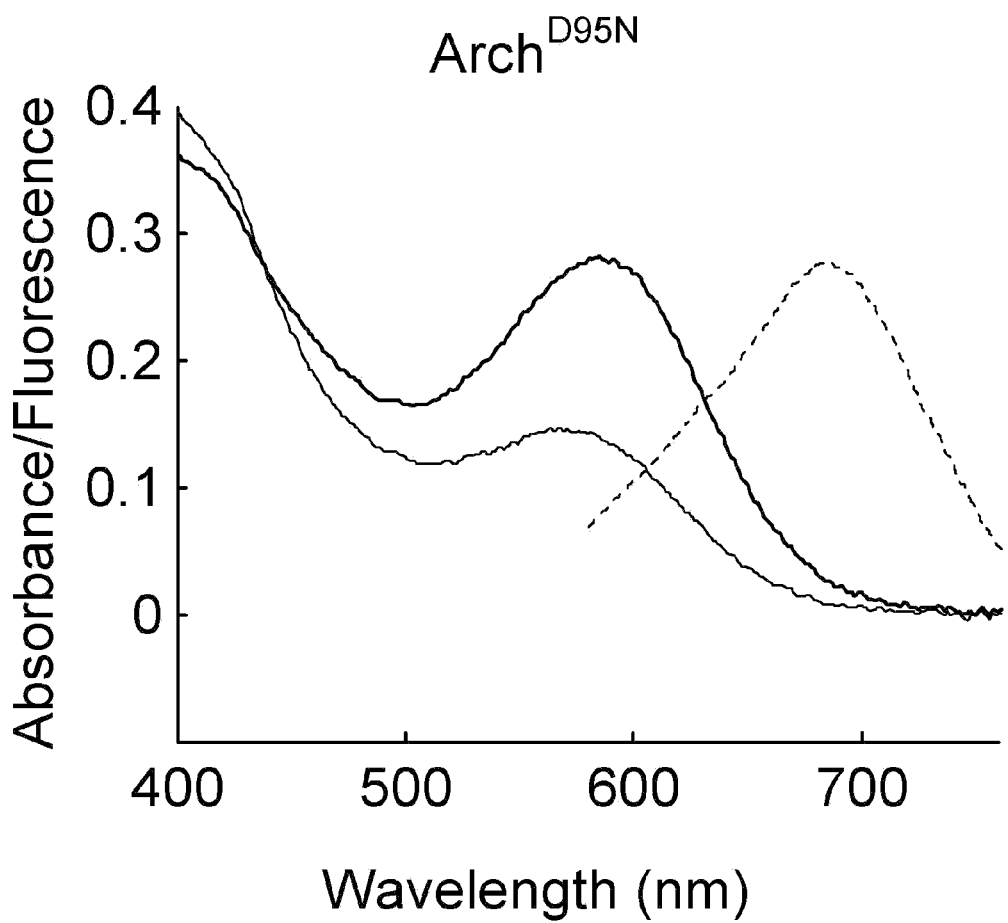
Figure 17C:
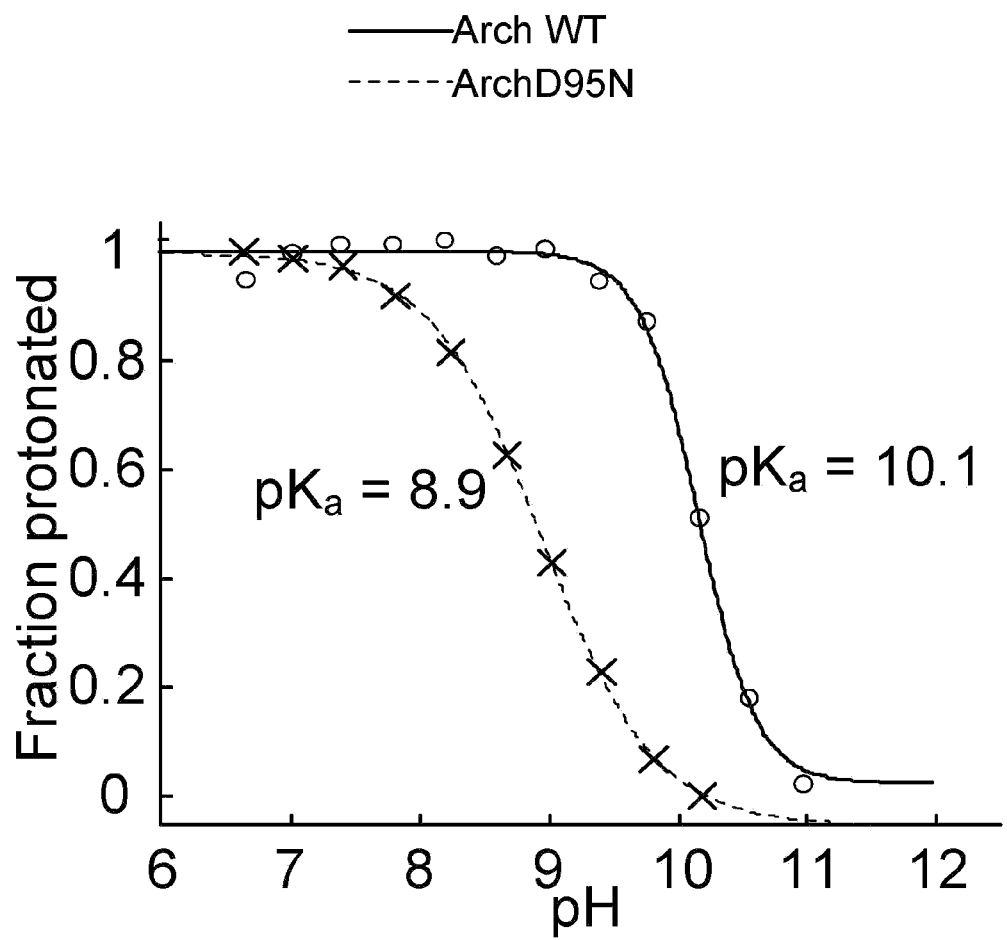

FIGS. 17A-17C show pH-dependent spectra of Arch 3 WT and D95N. FIG. 17A shows Arch WT absorption at neutral (bold line) and high (this line) pH. At neutral pH, Arch absorbed maximally at 558 nm. Fluorescence emission (dashed line) was recorded on 2 µM protein solubilized in 1% DM, with λexc=532 nm. FIG. 17B shows Arch D95N spectra under the same conditions as in FIG. 17A. The absorption maximum was at 585 nm. FIG. 17C shows absorption spectra that were recorded on purified protein between pH 6-11. Singular Value Decomposition of absorption spectra between 400-750 nm was used to calculate the fraction of the SB in the protonated state as a function of pH. The result was fit to a Hill function to determine the pKa of the SB.

Figure 18:
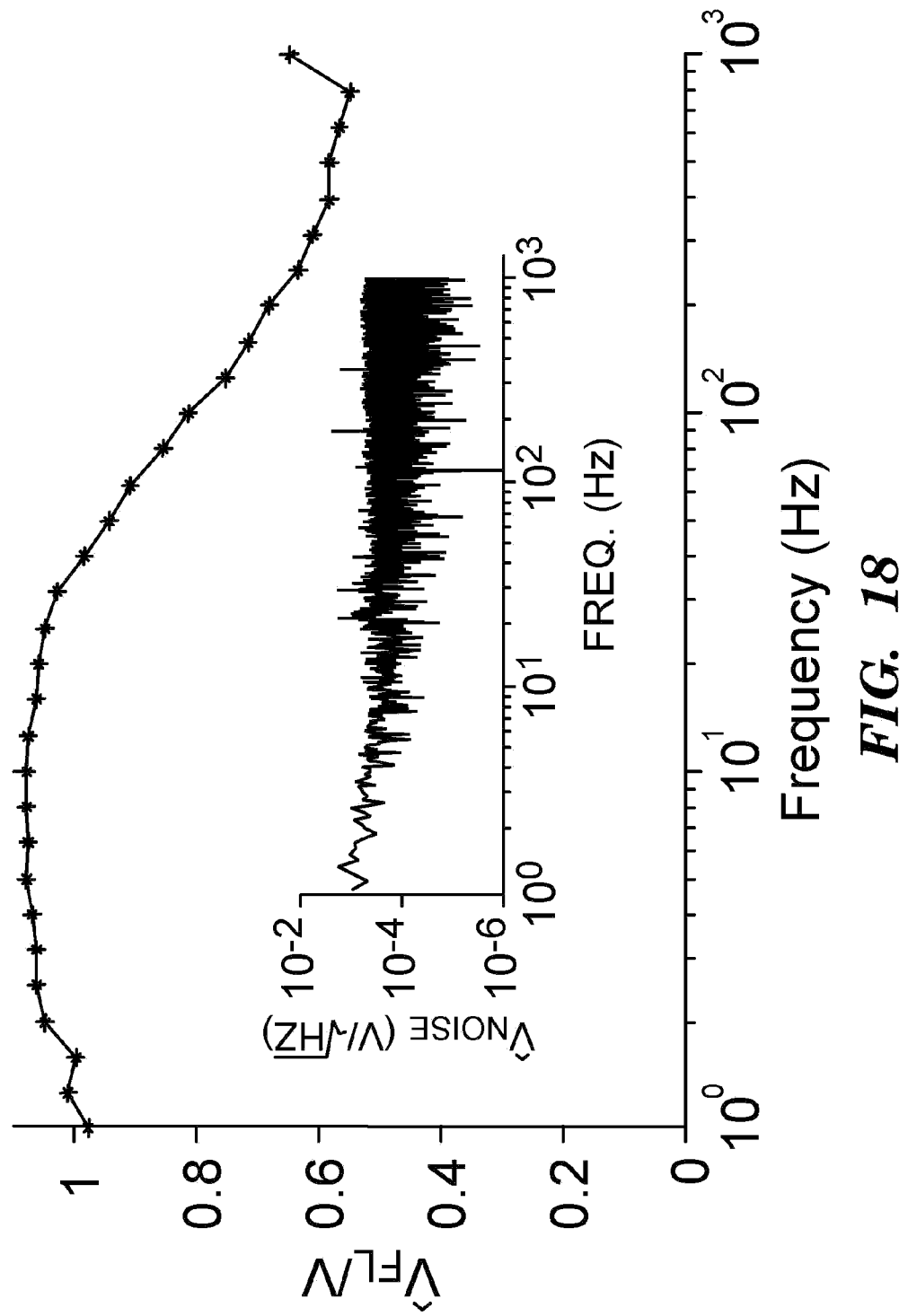

FIG. 18 shows frequency response of Arch 3 WT. A chirped sine wave with amplitude 50 mV and frequency from 1 Hz-1 kHz was applied to a HEK cell expressing Arch 3 WT (wild type). Membrane potential $\hat{V}_{FL}$ was determined from fluorescence and the Fourier transform of $\hat{V}_{FL}$ was calculated. The uptick at 1 kHz is an artifact of electronic compensation circuitry. Inset: power spectrum of noise in $\hat{V}_{FL}$, under voltage clamp at constant V=0 mV shows a shot-noise limited noise floor of 470 µV/(Hz) ½ at frequencies above 10 Hz. The noise figures reported here are specific to our imaging system and serve primarily as an indicator of the possible sensitivity of Arch 3.

Figure 19:
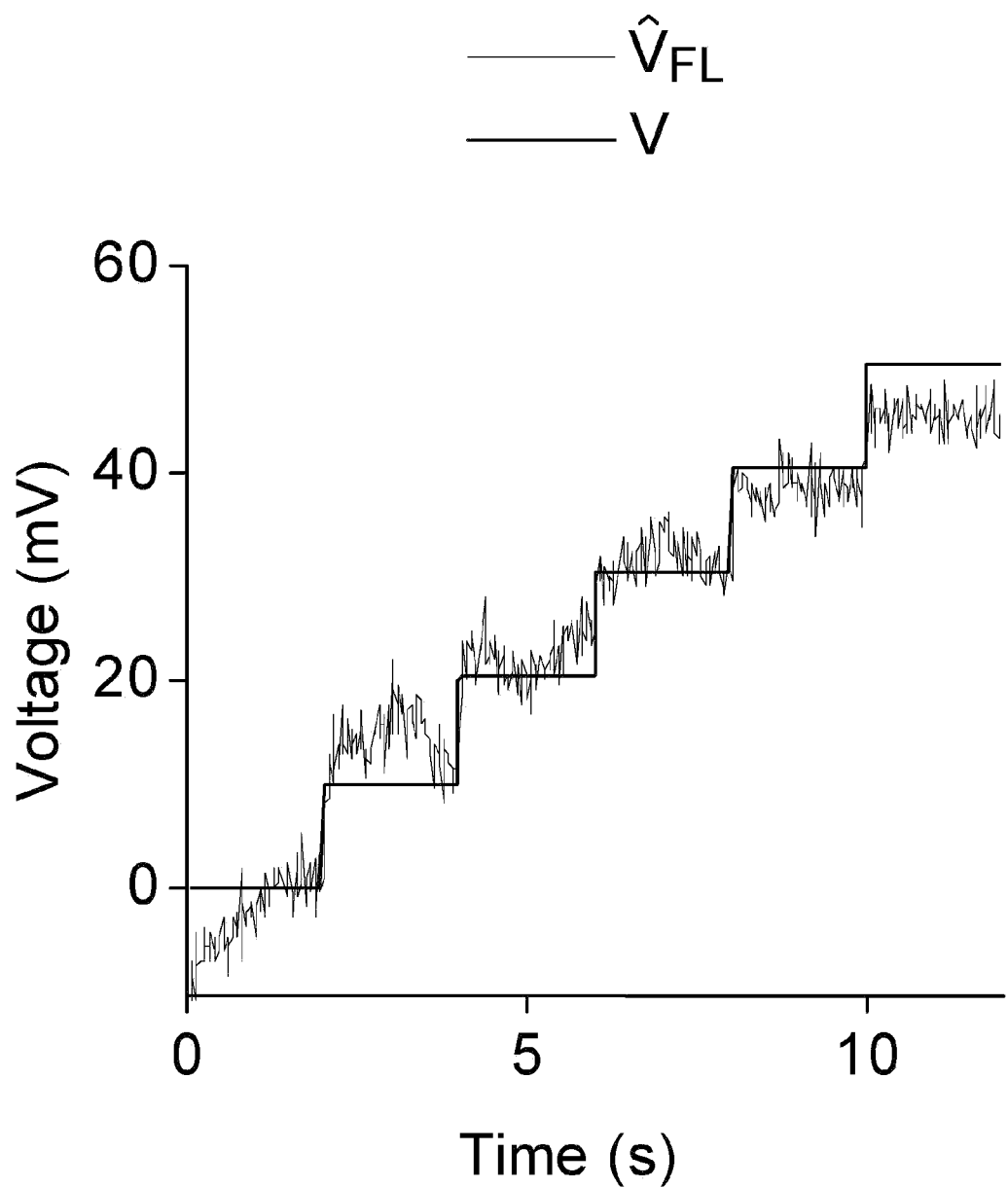

FIG. 19 shows sensitivity of Arch 3 WT to voltage steps of 10 mV. Whole-cell membrane potential determined via direct voltage recording, V, (bolded black line, showing step-like line on the graph) and weighted Arch 3 fluorescence, $\hat{V}_{FL}$, (solid narrower line showing serrations on the graph).

Figure 20:
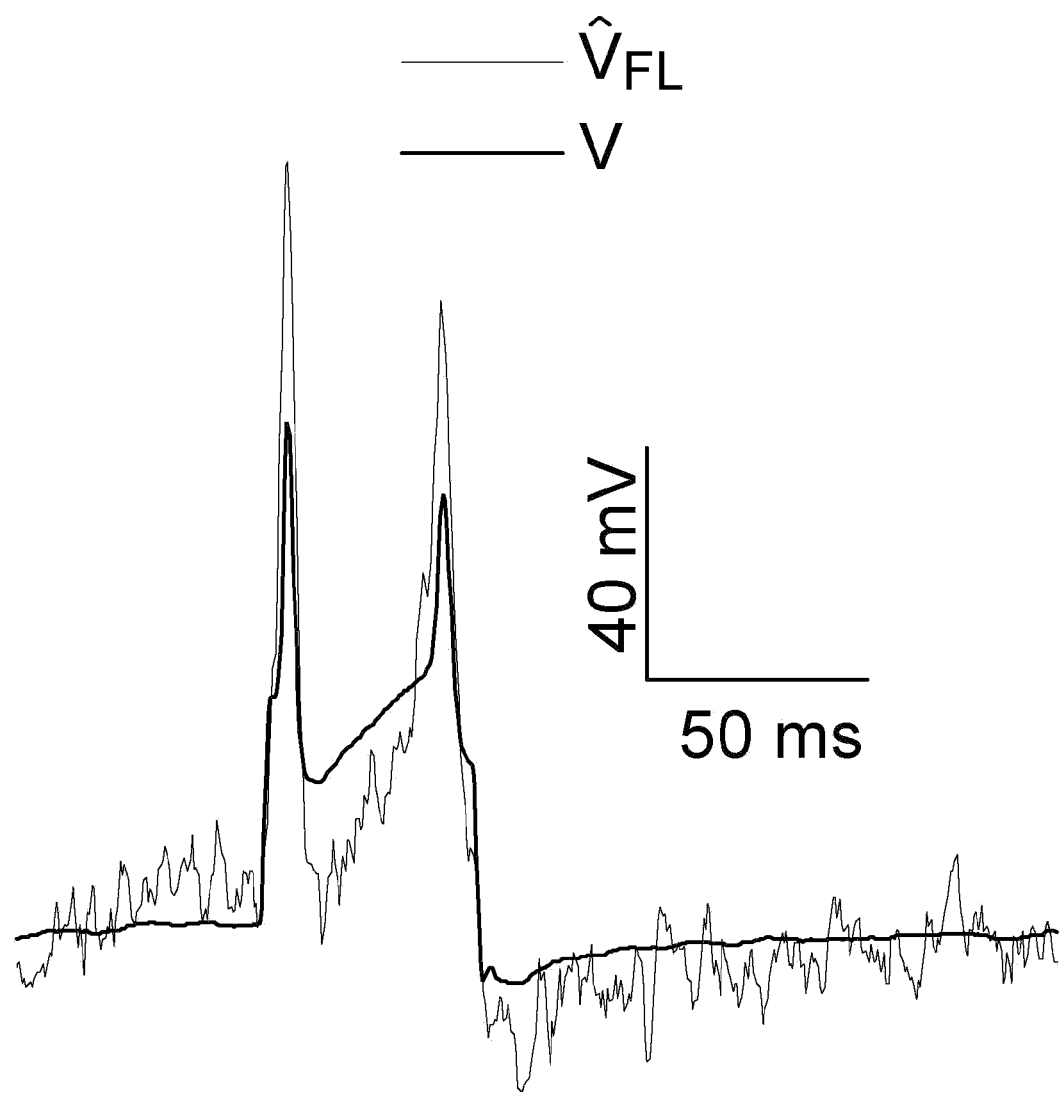

FIG. 20 shows that arch reports action potentials without exogenous retinal. We made an image of 14 day in vitro (DIV) hippocampal neuron imaged via Arch 3 fluorescence with no exogenous retinal. Electrical (bolded solid black line) and fluorescence (non-bolded line, showing serrated line in the graph) records of membrane potential from the neuron during a current pulse. Action potentials are clearly resolved.

Figure 21:
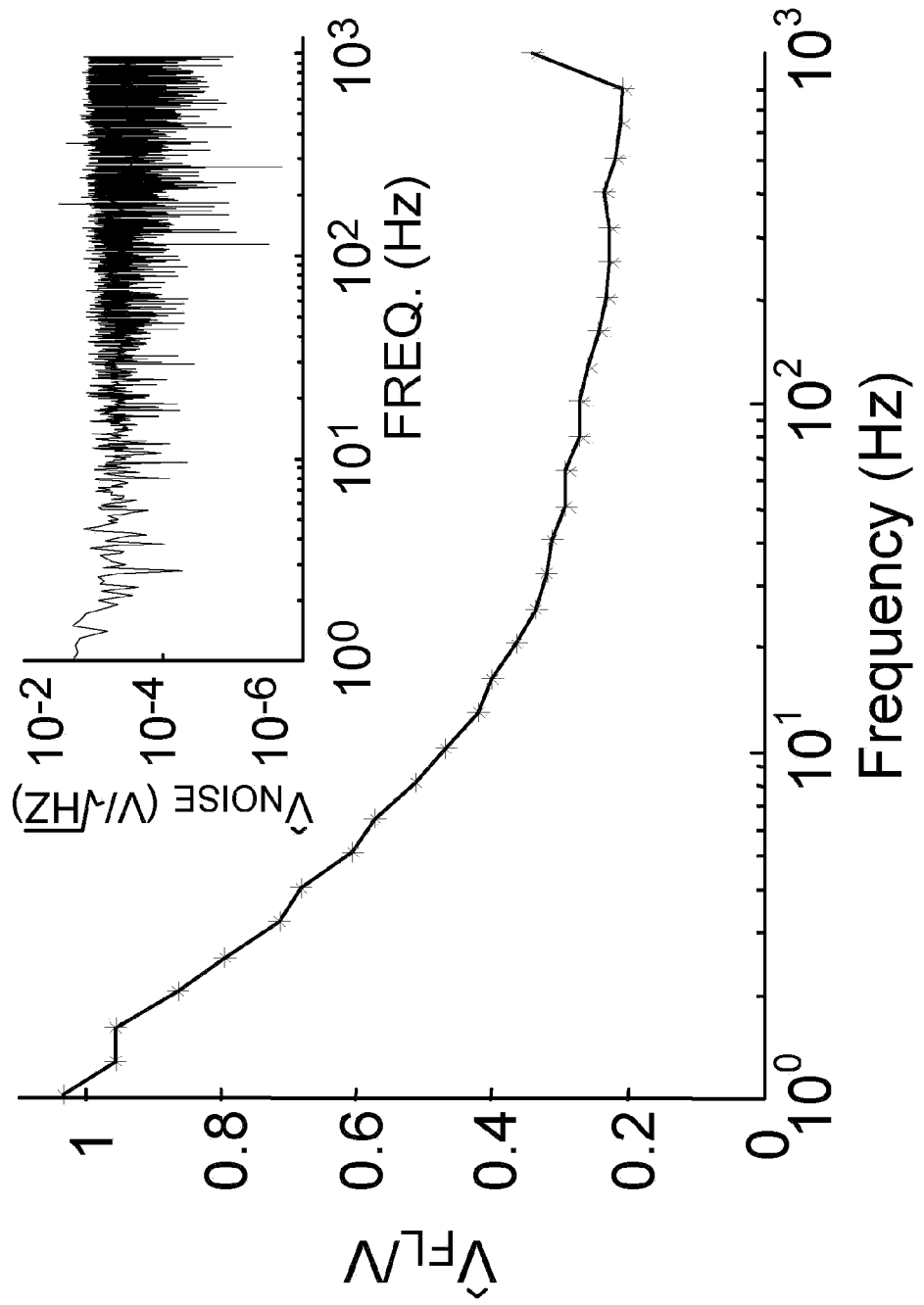

FIG. 21 shows a frequency response of Arch D95N, measured in the same manner as for Arch 3 WT (FIG. 18).

DETAILED DESCRIPTION OF THE INVENTION

The present invention is based, at least in part, on the discovery that microbial rhodopsin proteins or modified microbial rhodopsin proteins that have reduced ion pumping activity, compared to the natural microbial rhodopsin protein from which they are derived, can be used as an optically detectable sensor to sense voltage across membranous structures, such as in cells and sub-cellular organelles when they are present on the cell membrane. That is, the microbial rhodopsin proteins and the modified microbial rhodopsin proteins can be used to measure changes in membrane potential of a cell, including prokaryotic and eukaryotic cells. The optical sensors described herein are not constrained by the need for electrodes and permit electrophysiological studies to be performed in e.g., subcellular compartments (e.g., mitochondria) or in small cells (e.g., bacteria). The optical sensors described herein can be used in methods for drug screening, in research settings, and in in vivo imaging systems.

Microbial Rhodopsins Design of Optical Voltage Sensors

Microbial rhodopsins are a large class of proteins characterized by seven transmembrane domains and a retinilydene chromophore bound in the protein core to a lysine via a Schiff base (Beja, O., et al. Nature 411, 786-789 (2001)). Over 5,000 microbial rhodopsins are known, and these proteins are found in all kingdoms of life. Microbial rhodopsins serve a variety of functions for their hosts: some are light-driven proton pumps (bacteriorhodopsin, proteorhodopsins), others are light-driven ion channels (channelrhodopsins), chloride pumps (halorhodopsins), or serve in a purely photosensory capacity (sensory rhodopsins).

The retinilydene chromophore imbues microbial rhodopsins with unusual optical properties. The linear and nonlinear responses of the retinal are highly sensitive to interactions with the protein host: small changes in the electrostatic environment can lead to large changes in absorption spectrum. These electro-optical couplings provide the basis for voltage sensitivity in microbial rhodopsins.

Some of the optical sensors described herein are natural proteins without modifications and are used in cells that do not normally express the microbial rhodopsin transfected to the cell, such as eukaryotic cells. For example, as shown in the examples, the wild type Arch3 can be used in neural cells to specifically detect membrane potential and changes thereto.

Some of the microbial rhodopsins are derived from a microbial rhodopsin protein by modification of the protein to reduce or inhibit light-induced ion pumping of the rhodopsin protein. Such modifications permit the modified microbial rhodopsin proteins to sense voltage without altering the membrane potential of the cell with its native ion pumping activity and thus altering the voltage of the system. Other mutations impart other advantageous properties to microbial rhodopsin voltage sensors, including increased fluorescence brightness, improved photostability, tuning of the sensitivity and dynamic range of the voltage response, increased response speed, and tuning of the absorption and emission spectra.

Mutations that eliminate pumping in microbial rhodopsins in the present invention generally comprise mutations to the Schiff base counterion; a carboxylic amino acid (Asp or Glu) conserved on the third transmembrane helix (helix C) of the rhodopsin proteins. The amino acid sequence is RYX(DE) where X is a non-conserved amino acid. Mutations to the carboxylic residue directly affect the proton conduction pathway, eliminating proton pumping. Most typically the mutation is to Asn or Gln, although other mutations are possible, and based on the description provided herein, one skilled in the art can make different mutants which also result in reduced or absent ion pumping by the microbial rhodopsin protein. In one embodiment, the modified microbial rhodopsin proteins of the invention and the methods of the invention comprises the Asp to Asn or Gln mutation, or Glu to Asn or Gln mutation. In some embodiments, the protein consist essentially of Asp to Asn or Gln mutation, or Glu to Asn or Gln mutation. In some embodiments, the protein consist of Asp to Asn or Gln mutation, or Glu to Asn or Gln mutation.

Provided herein are illustrative exemplary optical voltage sensors and directions for making and using such sensors. Other sensors that work in a similar manner as optical sensors can be prepared and used based on the description and the examples provided herein.

Table 1a includes exemplary microbial rhodopsins useful according to the present invention. For example, mutations that eliminate pumping in microbial rhodopsins in the present invention generally comprise mutations to the Schiff base counterion; a carboxylic amino acid (Asp or Glu) conserved on the third transmembrane helix (helix C) of the rhodopsin proteins. Table 1a refers to the amino acid position in the sequence provided as the exemplary Genbank number. However, the position may be numbered slightly differently based on the variations in the available amino acid sequences. Based on the description of the motif described herein, a skilled artisan will easily be able to make similar mutations into other microbial rhodopsin genes to achieve the same functional feature, i.e. reduction in the pumping activity of the microbial rhodopsin in question.

TABLE 1a

Exemplary microbial rhodopsins useful according to the present invention.

| Microbial Rhodopsin | Abbreviation | Genbank number | Amino acid mutation |
|---|---|---|---|
| Green-absorbing proteorhodopsin: a light-driven proton pump found in marine bacteria | GPR | AF349983; wild-type, (Nucleotide and protein disclosed as SEQ ID NOS 74-75, respectively) | D99N (SEQ ID NO: 76) in the specification, this mutation is also referred to as D97N |
| Blue-absorbing proteorhodopsin: a light-driven proton pump found in marine bacteria. | BPR | AF349981; wild-type; (Nucleotide and protein disclosed as SEQ ID NOS 77-78, respectively) | D99N (SEQ ID NO: 79) |
| *Natronomonas pharaonis* sensory rhodopsin II: a light-activated signaling protein found in the halophilic bacterium *N. pharaonis*. In the wild the sensory domain is paired with a transducer domain | NpSRII | Z35086.1; In one embodiment only the sensory domain, given by nucleotides 2112-2831 of sequence Z35086, is used (Nucleotide and "sensory domain" protein disclosed as SEQ ID NOS 80-81, respectively) | D75N (SEQ ID NO: 82) |
| Bacteriorhodopsin: a light-driven proton pump found in *Halobacterium salinarum* | BR | NC_010364.1, nucleotides 1082241 to 1083029, or GenBank sequence M11720.1; ("M11720.1" nucleotide and protein disclosed as SEQ ID NOS 83-84, respectively | D98N (SEQ ID NO: 85) |
| Archaerhodopsin Arch 3: a light-driven proton pump found in *Halobacterium sodomense* | Arch 3 (or Ar3) | Chow B. Y. et al., Nature 463: 98-102; ("Arch 3" wild-type protein disclosed as SEQ ID NO: 86) | D95N (SEQ ID NO: 87) |

The following Table 1b includes exemplary additional rhodopsins that can be mutated as indicated in the methods of the invention:

TABLE 1b

| Microbial Rhodopsin | Abbreviation | Genbank number | Nucleic acid mutation | Amino Acid mutation |
|---|---|---|---|---|
| Fungal Opsin Related Protein | Mac | AAG01180 (SEQ ID NO: 60) | G415 to A | D139N (SEQ ID NO: 61) |
| Cruxrhodopsin | Crux | BAA06678 (SEQ ID NO: 62) | G247 to A | D83N (SEQ ID NO: 63) |
| Algal Bacteriorhodopsin | Ace | AAY82897 (SEQ ID NO: 64) | G265 to A | D89N (SEQ ID NO: 65) |
| Archaerhodopsin 1 | Ar1 | P69051 (SEQ ID NO: 66) | G289 to A | D97N (SEQ ID NO: 67) |
| Archaerhodopsin 2 | Ar2 | P29563 (SEQ ID NO: 68) | G286 to A | D96N (SEQ ID NO: 69) |
| Archaerhodopsin 3 | Ar3 | P96787 (SEQ ID NO: 70) | G283 to A | D95N (SEQ ID NO: 71) |
| Archaerhodopsin 4 | Ar4 | AAG42454 (SEQ ID NO: 72) | G292 to A | D98N (SEQ ID NO: 73) |

Voltage Indicating Proteins (VIP)

We have developed a family of fluorescent voltage-indicating proteins (VIPs) based on Achaerhodopsins that function in mammalian cells, including neurons and human stem cell-derived cardiomyocytes. These proteins indicate electrical dynamics with sub-millisecond temporal resolution and sub-micron spatial resolution. We have demonstrated non-contact, high-throughput, and high-content studies of electrical dynamics in mammalian cells and tissues using optical measurement of membrane potential. These VIPs are broadly useful, particularly in eukaryotic, such as mammalian, including human cells.

We have developed VIPs based on Archaerhodopsin 3 (Arch 3) and its homologues. Arch 3 is Archaerhodopsin from *H. sodomense* and it is known as a genetically-encoded reagent for high-performance yellow/green-light neural silencing. Gene sequence at GenBank: GU045593.1 (synthetic construct Arch 3 gene, complete cds. Submitted Sep. 28, 2009). We have shown that these proteins localize to the plasma membrane in eukaryotic cells and show voltage-dependent fluorescence.

We have also shown further improved membrane localization, with comparable voltage sensitivity, in ArchT, gene sequence at GenBank: HM367071.1 (synthetic construct ArchT gene, complete cds. Submitted May 27, 2010). ArchT is Archaerhodopsin from *Halorubrum* sp. TP009: genetically-encoded reagent for high-performance yellow/green-light neural silencing, 3.5× more light sensitive than Arch 3.

Table 1c summarizes exemplary sequences that can be used to create viral constructs that express the voltage indicators based on Archaerhodopsin.

TABLE 1c

Exemplary sequences that can be used to generate virus constructs with Arch 3 and ArchT

| | | |
|---|---|---|
| Virus backbone | Lentivirus | SEQ ID NO: 24 |
| Promoter | CamKII (neuron specific) | SEQ ID NO: 25 |
| | CAG enhancer (pan cellular) | SEQ ID NO: 26 |
| | CMV (pan cellular) | SEQ ID NO: 27 |
| | Ubiquitin (pan cellular) | SEQ ID NO: 28 |
| Voltage-sensing domain | Arch D95N | SEQ ID NO: 29 |
| | ArchT D95N | SEQ ID NO: 30 |

Figure 10:
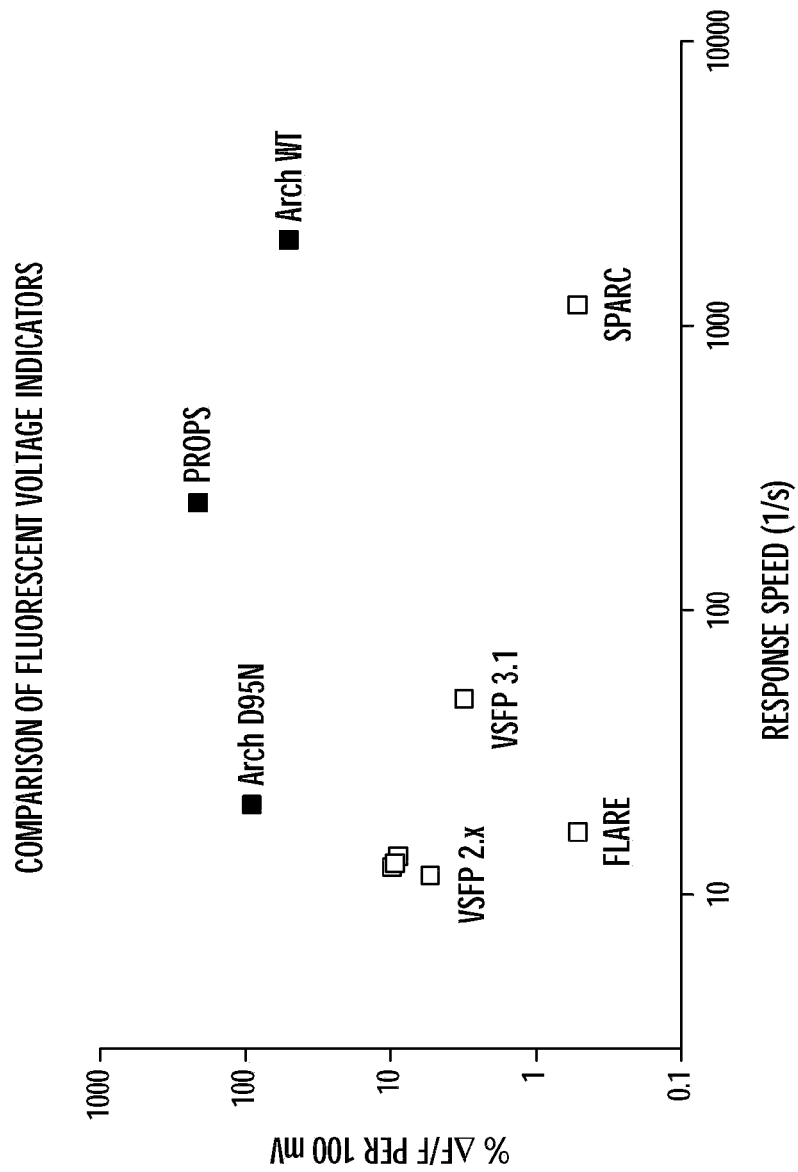
FIG. 10 shows existing genetically encoded fluorescent voltage indicators classified according to their sensitivity and speed-the two key parameters that determine the performance of an indicator. VSFPs, FLARE and SPARC represent indicators based on fusions of GFP homologues to membrane proteins. The exemplary proteins we have developed are the Proteorhodopsin Optical Proton Sensor (PROPS), Arch3 WT, and Arch3 D95N, shown on the upper right. PROPS functions in bacteria, while Arch3 WT and Arch3 D95N function in mammalian cells. Note the logarithmic axes. Microbial rhodopsin-based voltage indicators are much faster and far more sensitive than other indicators.
Figure 11B:
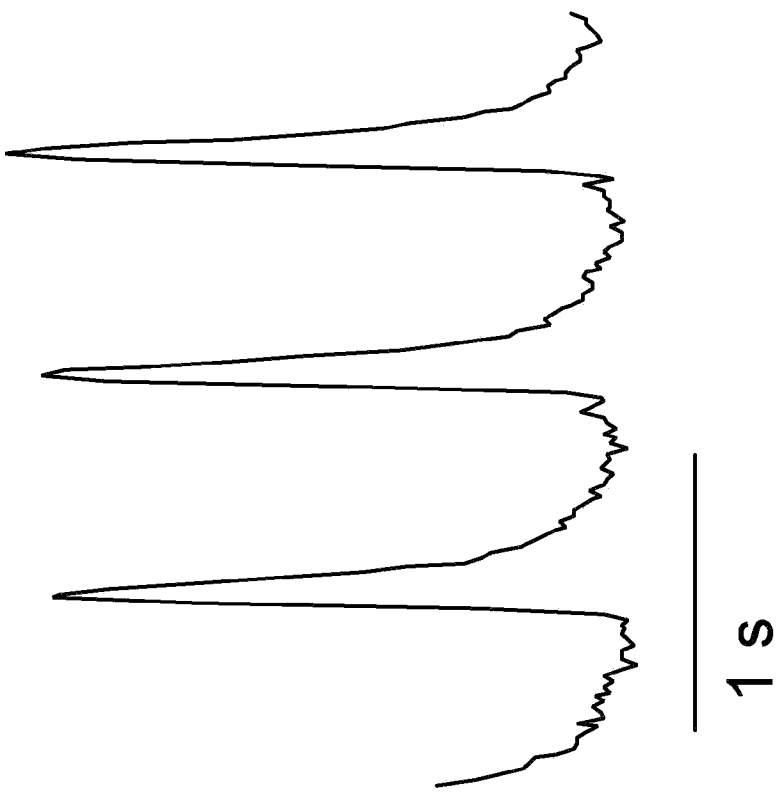
FIGS. 11A-11D show optical recordings of action potentials in a single HL-1 mouse cardiomyocyte expressing Arch3 D95N-eGFP. Action potentials were recorded for up to 1000 s, with no signs of phototoxicity. This experiment is the first quantitative measurement of cardiac action potentials with a genetically encoded voltage indicator. We showed an overlay showing fluorescence of Arch D95N and GFP in a Arch D95N-GFP fusion.
Figure 11A:
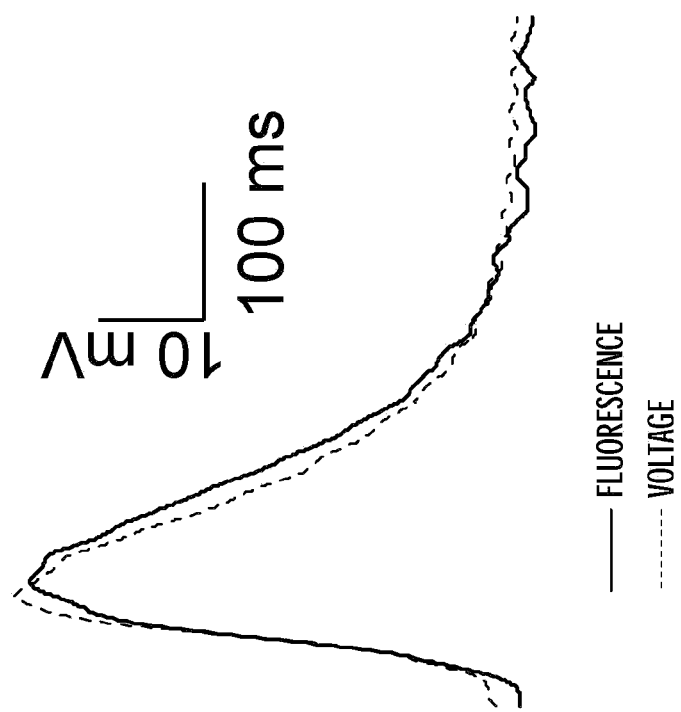
Figure 11C:
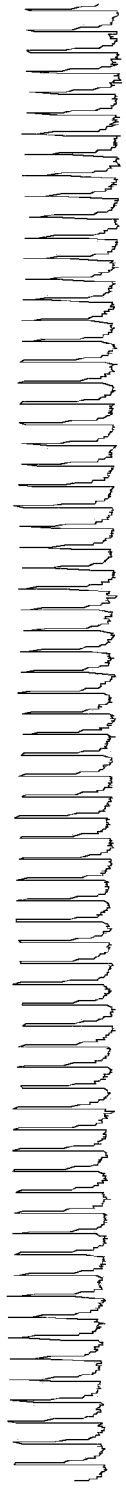
Figure 11D:
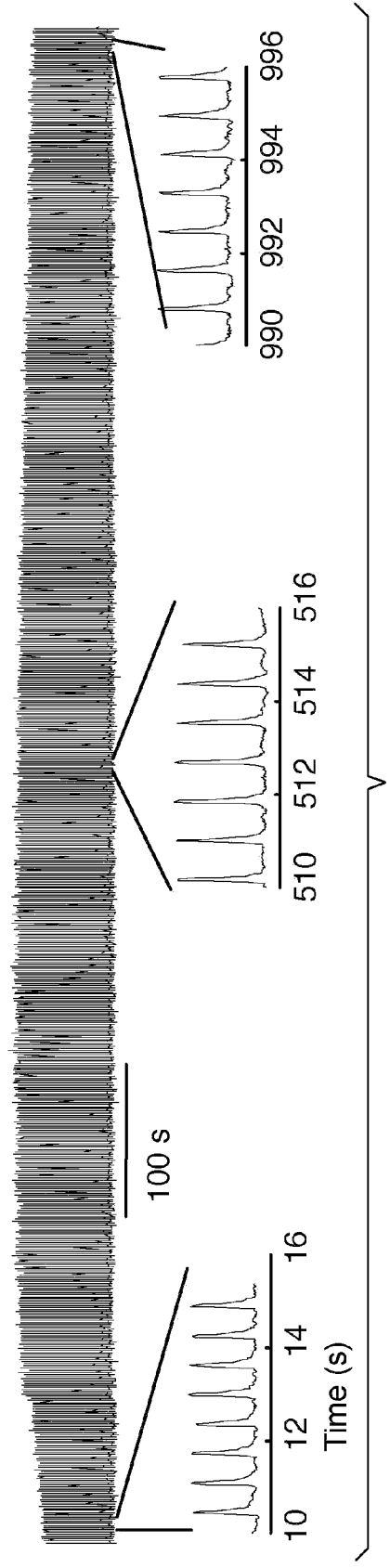

FIG. 10 shows existing genetically encoded fluorescent voltage indicators classified according to their sensitivity and speed—the two key parameters that determine the performance of an indicator. The proteins we developed are the Proteorhodopsin Optical Proton Sensor (PROPS), Arch 3 WT, and Arch 3 D95N, shown on the upper right. PROPS only functions in bacteria, while Arch 3 WT and Arch 3 D95N function in mammalian cells. We showed that microbial rhodopsin-based voltage indicators are faster and far more sensitive than other indicators.

Table 2 shows exemplary approximate characteristics of fluorescent voltage indicating proteins and contains representative members of all families of fluorescent indicators. Although the list on Table 2 is not comprehensive, one skilled in the art can readily see the characteristics of the types of proteins useful in the present invention.

TABLE 2

Representative members of all families of fluorescent indicators.

| Molecule | Approx ΔF/F per 100 mV | Approx response time | Comments |
|---|---|---|---|
| VSFP 2.3, Knopfel, T. et al. J. Neurosci. 30, 14998-15004 (2010) | 9.5% | 78 ms | Ratiometric (ΔR/R) |
| VSFP 2.4 Knopfel, T. et al. J. Neurosci. 30, 14998-15004 (2010) | 8.9% | 72 ms | Ratiometric (ΔR/R) |
| VSFP 3.1, Lundby, A., et al., PLoS One 3, 2514 (2008) | 3% | 1-20 ms | Protein |

TABLE 2-continued

Representative members of all families of fluorescent indicators.

| Molecule | Approx ΔF/F per 100 mV | Approx response time | Comments |
| --- | --- | --- | --- |
| Mermaid, Perron, A. et al. Front Mol Neurosci. 2, 1-8 (2009) | 9.2% | 76 | Ratiometric (ΔR/R) |
| SPARC, Ataka, K. & Pieribone, V. A. Biophys. J. 82, 509-516 (2002) | 0.5% | 0.8 ms | Protein |
| Flash, Siegel, M. S. & Isacoff, E. Y. Neuron 19, 735-741 (1997) | 5.1% | 2.8-85 ms | Protein |
| PROPS, described herein; SEQ ID NO: | 150% | 5 ms | Protein |
| Arch 3 WT, described herein | 66% | <0.5 ms | Protein |
| Arch D95N | 100% | 41 ms | Protein |

Figure 9A:
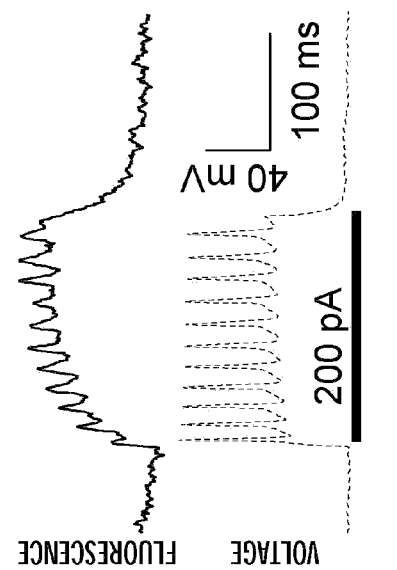
FIGS. 9A-9C show optical recording of action potentials with ArchD95N.

FIG. 9 shows an optical recording of action potentials in a single rat hippocampal neuron. The data represents a single trial, in which spiking was induced by injection of a current pulse. The fluorescence shows clear bursts accompanying individual action potentials. This experiment is the first robust measurement of action potentials in a single mammalian neuron using a genetically encoded voltage indicator.

FIG. 11 shows optical recordings of action potentials in a single HL-1 mouse cardiomyocyte expressing Arch 3 D95N-eGFP. Action potentials were recorded for up to 1000 s, with no signs of phototoxicity. This experiment is the first quantitative measurement of cardiac action potentials with a genetically encoded voltage indicator.

Figure 12:
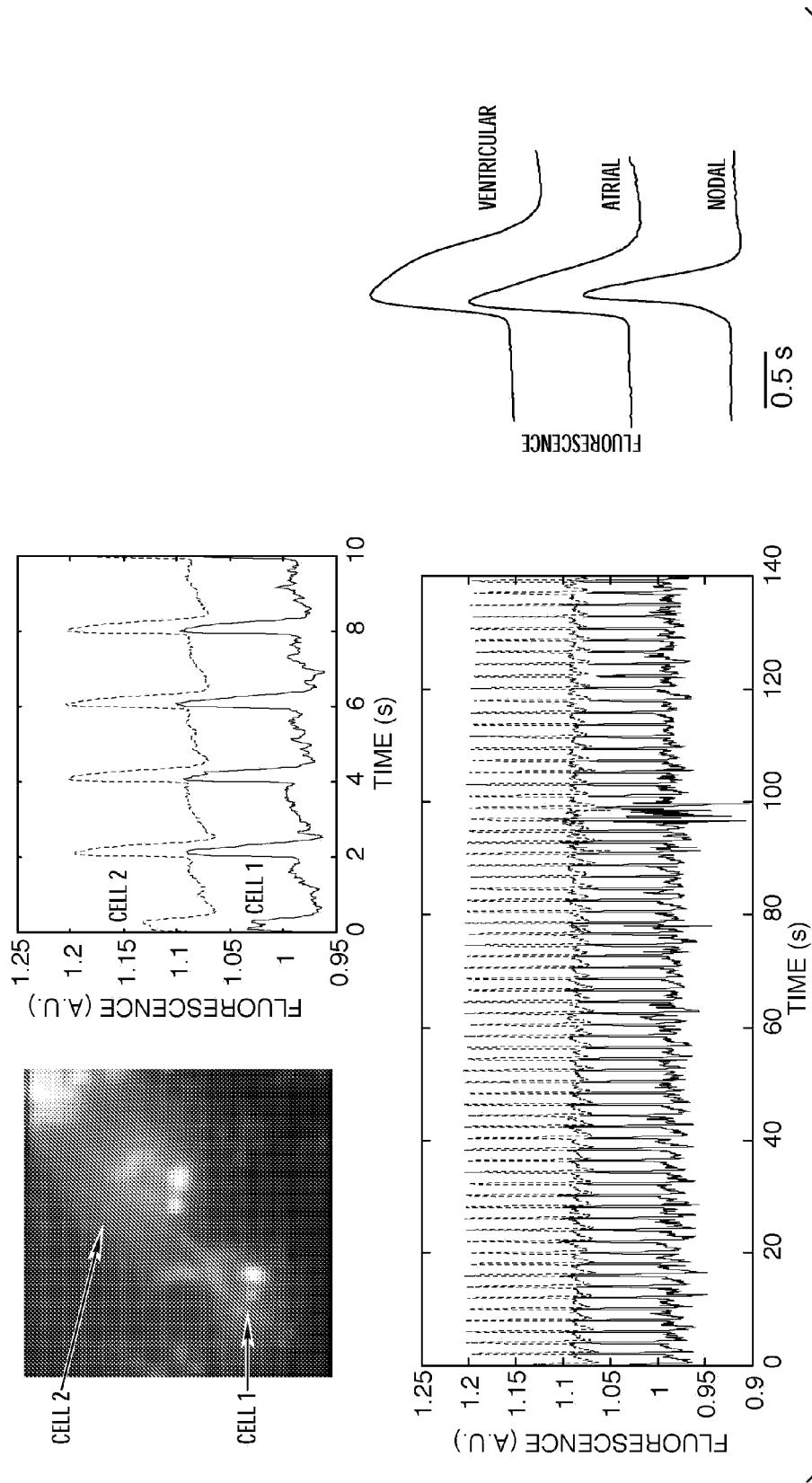
FIG. 12 shows optical recordings of action potentials in human induced pluripotent stem cell (iPS)-derived cardiomyocytes, expressing Arch3 D95N-eGFP. Human induced pluripotent stem cells (hiPSC) were provided by Cellular Dynamics Inc. Cells were plated into MatTek dishes coated in 0.1% gelatin at a density of 20, 50, or 75 thousand cells per square centimeter. These conditions showed cells that were sparse and did not beat spontaneously (20K), a confluent monolayer that did beat spontaneously (50K), and a dense monolayer (75K). iPS cells were plated and maintained for 48 hours in plating medium, and thereafter fed every 48 hours with maintenance medium (both from Cellular Dynamics). iPS cells were transfected using Mirus LT-1 according to the manufacturer directions. To a tube containing 20 uL of OPTI-MEM®, we added 200 ng of DNA and 1.2 uL of the LT-1 transfection reagent. The DNA mixture was incubated at room temperature for 20 minutes. Fresh maintenance medium was added to the iPS cells during the incubation and the DNA mixture was added dropwise over the plate. Cells were imaged 48 to 96 hours after transfection. We observed synchronized beating of adjoining cells, indicating that VIPs can probe intercellular conduction. We recorded for more than 10 minutes continuously, with little phototoxicity. Within the population of cells we observed cells with action potentials matching those of ventricular, atrial, and nodal cells, as expected for this population. Addition of drugs led to changes in the action potential waveform that matched changes reported by conventional patch clamp. Cell 1 fluorescence information is indicated as a solid line and Cell 2 fluorescence as a dashed line on the photos fluorescence vs. time.

FIG. 12 shows optical recordings of action potentials in human induced pluripotent stem cell (iPS)-derived cardiomyocytes, expressing Arch 3 D95N-eGFP. Human induced pluripotent stem cells (hiPSC) were provided by Cellular Dynamics Inc. Cells were plated into MatTek dishes coated in 0.1% gelatin at a density of 20, 50, or 75 thousand cells per square centimeter. These conditions showed cells that were sparse and did not beat spontaneously (20K), a confluent monolayer that did beat spontaneously (50K), and a dense monolayer (75K). iPS cells were plated and maintained for 48 hours in plating medium, and thereafter fed every 48 hours with maintenance medium (both from Cellular Dynamics). iPS cells were transfected using Mirus LT-1 according to the manufacturer directions. To a tube containing 20 uL of optimem, we added 200 ng of DNA and 1.2 uL of the LT-1 transfection reagent. The DNA mixture was incubated at room temperature for 20 minutes. Fresh maintenance medium was added to the iPS cells during the incubation and the DNA mixture was added dropwise over the plate. Cells were imaged 48 to 96 hours after transfection.

We observed synchronized beating of adjoining cells, indicating that VIPs can probe intercellular conduction. We recorded for more than 10 minutes continuously, with little phototoxicity. Within the population of cells we observed cells with action potentials matching those of ventricular, atrial, and nodal cells, as expected for this population. Addition of drugs led to changes in the action potential waveform that matched changes reported by conventional patch clamp.

Generation of Fusions Between Microbial Rhodopsins and GFP Homologues with Additional or Improved Properties We fused VIPs with GFP-homologue proteins to develop a series of improved voltage indicators. FIG. 16 illustrates these exemplary constructs and FIG. 16 legend provides the sequences for these constructs. The new capabilities of these newly developed sensors include, for example, a spectral shift FRET (ssFRET) for enhanced brightness and 2-photon imaging, ratiometric voltage imaging, and multimodal sensors for simultaneous measurement of voltage and concentration.

Spectral Shift FRET (ssFRET) for Enhanced Brightness and 2-Photon Imaging

Figure 13:
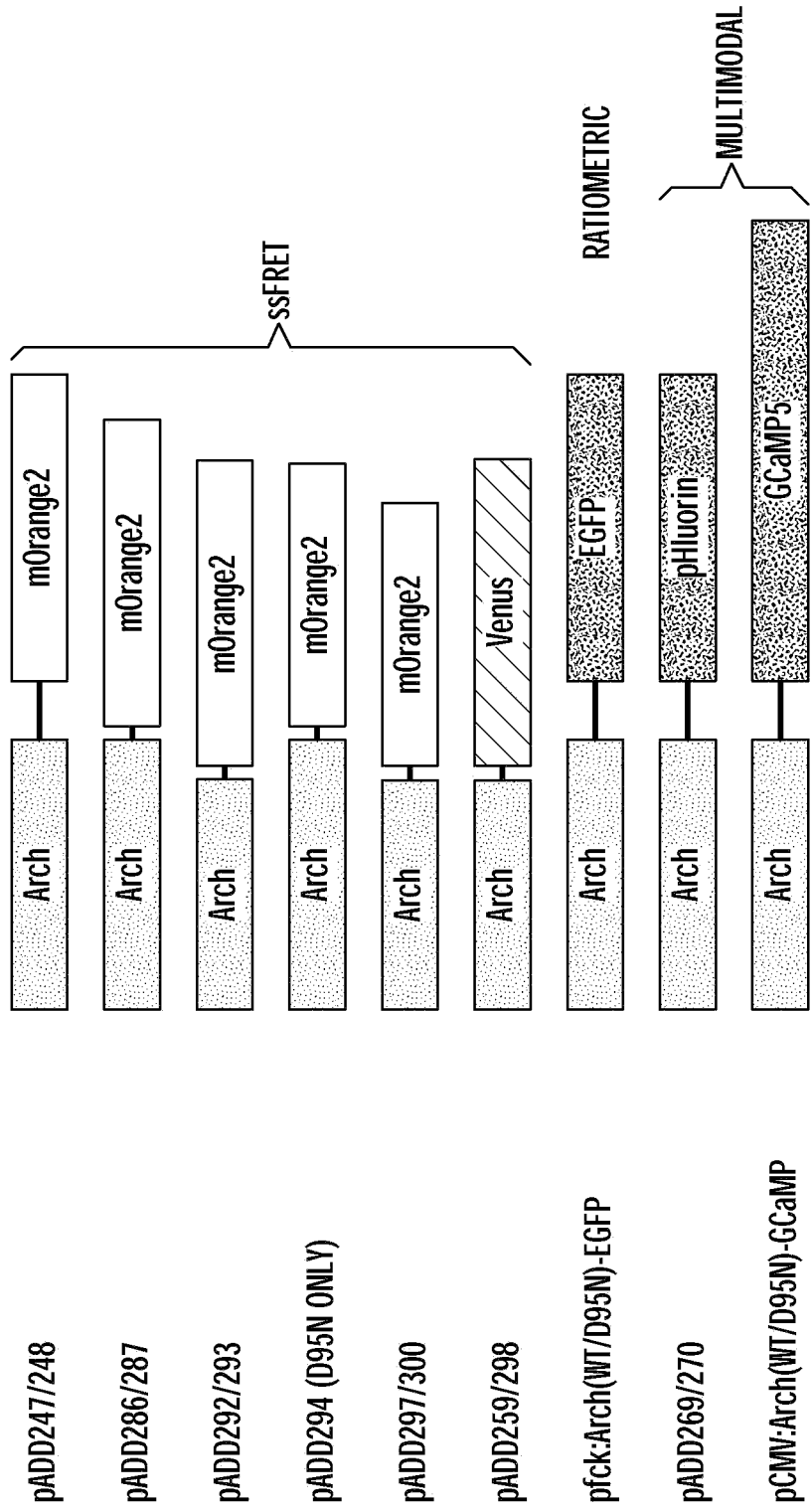
FIG. 13 illustrates constructs of fused VIPs with GFP-homologue proteins to develop a series of improved voltage indicators. The length of each bar indicates the length of the protein sequence or linker region. The color indicates the color of the fluorescence of the corresponding protein. All constructs were constructed with both Arch WT and Arch D95N backbones. The sequences for the constructs are provided in the Sequence Listing as follows.

A key limitation of the first generation of VIPs was that the endogenous fluorescence of the retinal was dim. Imaging required a specialized system comprising an intense red laser, a high numerical aperture objective, and an electron-multiplying CCD (EMCCD) camera. Ideally one would like an indicator bright enough to image on a conventional wide-field or confocal fluorescence microscope, or a 2-photon confocal microscope for in vivo applications.

ssFRET provides a path to brighter VIPs as shown in FIG. 10. A GFP-homologue (generically referred to as GFP) is fused to the microbial rhodopsin (see, e.g., FIG. 13). Voltage-dependent changes in the absorption spectrum of the retinal lead to voltage-dependent rates of nonradiative fluorescence resonance energy transfer (FRET) between the GFP and the retinal. Retinal in its absorbing, fluorescent state quenches the GFP, while retinal in the non-absorbing, non-fluorescent state does not quench the GFP. Thus one obtains anti-correlated fluorescence emission of the GFP and the retinal.

Thus in one embodiment, the invention provides a fusion protein comprising a GFP that is fused to a microbial rhodopsin or a modified microbial rhodopsin, such as a proteorhdopsin or archaerhodopsin. Such fusion proteins can be used in any and all of the methods of the present invention.

To maximize the degree of ssFRET between the GFP and the retinal we selected a GFP-homologue, mOrange2, whose emission overlaps maximally with the absorption of Arch 3 in its protonated state. The rate of FRET falls off very quickly with increasing distance between chromophores, so we constructed a series of truncated constructs in which the linker and non-essential elements of the Arch 3 and mOrange2 were removed. FIG. 15 shows that as the distance between the mOrange2 and the Arch 3 decreased, the ssFRET signal increased. This same strategy can be applied to generate ssFRET signals from other microbial rhodopsins and GFP homologues.

We have shown that the time response of fluorescence from mOrange2 to a step in Vm matches the time response of fluorescence from Arch D95N. This observation is consistent with ssFRET. Similar results can be seen for FIGS. 9A and 11 for fusions to Arch 3 WT.

Ratiometric Voltage Imaging

A key challenge in application of VIPs is to extract accurate values of the membrane potential, without systematic artifacts from photobleaching, variation in illumination intensity, cell movement, or variations in protein expression level. In cells that are accessible to patch clamp, one can calibrate the fluorescence as a function of membrane potential by varying the membrane potential under external control. However, a benefit of VIPs is that they function in systems that are inaccessible to patch clamp. In these cases direct calibration is not possible.

The Arch 3 (WT or D95N) fusion with eGFP enables ratiometric determination of membrane potential. Similar ratiometric determinations may be made using other rhodopsins such as those described in this application using the identical concept. The eGFP fluorescence is independent of membrane potential, The ratio of Arch 3 fluorescence to eGFP fluorescence provides a measure of membrane potential that is independent of variations in expression level, illumination, or movement. This construct does not undergo ssFRET due to the long linker between the eGFP and the Arch 3, and because the emission of eGFP has little spectral overlap with the absorption of Arch 3.

Multimodal Sensors for Simultaneous Measurement of Voltage and Concentration

Membrane potential is only one of several mechanisms of signaling within cells. One often wishes to correlate changes in membrane potential with changes in concentration of other species, such as Ca++, H+ (i.e. pH), Na+, ATP, cAMP. We constructed fusions of Arch with pHluorin (a fluorescent pH indicator) and GCaMP3 (a fluorescent Ca++ indicator). One can also use fusions with other protein-based fluorescent indicators to enable other forms of multimodal imaging using the concept as taught herein. Concentration of ions such as sodium, potassium, chloride, and calcium can be simultaneously measured when the nucleic acid encoding the microbial rhodopsin is operably linked to or fused with an additional fluorescent ion sensitive indicator.

Additional Fluorescent Proteins

The term "additional fluorescent molecule" refers to fluorescent proteins other then microbial rhodopsins. Such molecules may include, e.g., green fluorescent proteins and their homologs.

Fluorescent proteins that are not microbial rhodopsins are well known and commonly used, and examples can be found, e.g., in a review The Family of GFP-Like Proteins: Structure, Function, Photophysics and Biosensor Applications. Introduction and Perspective, by Rebekka M. Wachter (Photochemistry and Photobiology Volume 82, Issue 2, pages 339-344, March 2006). Also, a review by Nathan C Shaner, Paul A Steinbach, & Roger Y Tsien, entitled A guide to choosing fluorescent proteins (Nature Methods—2, 905-909 (2005)) provides examples of additional useful fluorescent proteins.

Targeting VIPs to Intracellular Organelles

We have shown targeting VIPs to intracellular organelles, including mitochondria, the endoplasmic reticulum, the sarcoplasmic reticulum, synaptic vesicles, and phagosomes. Accordingly, in one embodiment, the invention provides constructs, such as expression constructs, such as viral constructs comprising a microbial rhodopsin operably linked to a sequence targeting the protein to an intracellular organelle, including a mitochondrium, an endoplasmic reticulum, a sarcoplasmic reticulum, a synaptic vesicle, and a phagosome.

The invention further provides cells expressing the constructs, and further methods of measuring membrane potential changes in the cells expressing such constructs as well as methods of screening for agents that affect the membrane potential of one or more of the intracellular membranes.

The Key Advantages of Voltage Indicating Proteins (VIPs)

The newly developed VIPs show high sensitivity. In mammalian cells VIPs show about 3-fold increase in fluorescence between −150 mV and +150 mV. The response is linear over most of this range. We can measure membrane voltage with a precision of <1 mV in a 1 s interval.

The newly developed VIPs show high speed. Arch 3 WT shows 90% of its step response in <0.5 ms. A neuronal action potential lasts 1 ms, so this speed meets the benchmark for imaging electrical activity of neurons. However, Arch 3 WT retains the photoinduced proton-pumping, so illumination slightly hyperpolarizes the cell.

The modified microbial rhodopsin, Arch 3 D95N, has a 40 ms response time and lacks photoinduced proton pumping. Although the slower response time of this construct hampers detection of membrane potential and changes thereto in neurons, the Arch 3 D95N is fast enough to indicate membrane potential and action potentials in other types of cells, for example, in cardiomyocytes and does not perturb membrane potential in the cells wherein it is used.

The newly developed VIPs also show high photostability. VIPs are comparable to GFP in the number of fluorescence photons produced prior to photobleaching. We routinely watch VIPs in mammalian cells for many minutes, without signs of photobleaching or phototoxicity. VIPs have no homology to GFP, nor to any other known fluorescent protein.

The newly developed VIPs also show far red spectrum. VIPs are excited with a 633 nm laser, and the emission is in the near infrared, peaked at 710 nm. The emission is farther to the red than any existing fluorescent protein. These wavelengths coincide with low cellular autofluorescence and good transmission through tissue. This feature makes these proteins particularly useful in optical measurements of action potential as the spectrum facilitates imaging with high signal-to-noise, as well as multi-spectral imaging in combination with other fluorescent probes.

The newly developed VIPs further show high targetability. We have imaged VIPs in primary neuronal cultures, cardiomyocytes (HL-1 and human iPSC-derived), HEK cells, and Gram positive and Gram negative bacteria. We targeted a VIP to the endoplasmic reticulum, and to mitochondria. The ocnstructs are useful also for in vivo imaging in *C. elegans*, zebrafish, and mice.

With the microbial rhodopsin constructs of the invention further comprising a cell type- and/or a time-specific promotors, one can image membrane potential in any optically accessible cell type or organelle in a living organism.

In one embodiment, the design of a voltage sensor comprises, consists of, or consists essentially of selecting at least three elements: a promoter, a microbial rhodopsin voltage sensor, one or more targeting motifs, and an optional accessory fluorescent protein. Some non-limiting examples for each of these elements are listed in Tables 1a and 1b, and Table 3 below. In one embodiment, at least one element from each column is selected to create an optical voltage sensor with the desired properties. In some embodiments, methods and compositions for voltage sensing as described herein involves selecting: 1) A microbial rhodopsin protein, 2) one or more mutations to imbue the protein with sensitivity to voltage or to other quantities of interest and to eliminate light-driven charge pumping, 3) codon usage appropriate to the host species, 4) a promoter and targeting sequences to express the protein in cell types of interest and to target the protein to the sub-cellular structure of interest, 5) an optional fusion with a conventional fluorescent protein to provide ratiometric imaging, 6) a chromophore to insert into the microbial rhodopsin, and 7) an optical imaging scheme.

bacteriorhodopsin these residues include, but are not limited to, L92, W86, W182, D212, I119, and M145. Homologous

TABLE 3

Exemplary optical sensor combinations

| Promoter | Voltage sensor | Targeting motif | Accessory fluorescent protein |
|---|---|---|---|
| CMV (SEQ ID NO: 31) | hGPR (D97N)(SEQ ID NO: 35) | SS((β2nAChR)(SEQ ID NO: 39) | Venus(SEQ ID NO: 43) |
| 14x UAS-E1b (SEQ ID NO: 32) | hGPR (D97N, ±E108Q, ±E142Q, ±L217D) (SEQ ID NO: 36) | SS(PPL)(SEQ ID NO: 40) | EYFP (SEQ ID NO: 44) |
| HuC(SEQ ID NO: 33) | hBPR (D99N)(SEQ ID NO: 37) | ER export motif(SEQ ID NO: 41) | TagRFP(SEQ ID NO: 45) |
| ara(SEQ ID NO: 34) | hNpSRII (D75N)(SEQ ID NO: 38) | TS from Kir2.1 (SEQ ID NO: 42) | |
| lac | | MS | |

In one embodiment, the optical sensor gene is encoded by a delivery vector. Such vectors include but are not limited to: plasmids (e.g. pBADTOPO, pCI-Neo, pcDNA3.0), cosmids, and viruses (such as a lentivirus, an adeno-associated virus, or a baculovirus).

In one embodiment, the green-absorbing proteorhodopsin (GPR) is used as the starting molecule. This molecule is selected for its relatively red-shifted absorption spectrum and its ease of expression in heterologous hosts such as *E. coli*. In another embodiment, the blue-absorbing proteorhodopsin (BPR) is used as an optical sensor of voltage. It is contemplated herein that a significant number of the microbial rhodopsins found in the wild can be engineered as described herein to serve as optical voltage sensors.

Microbial rhodopsins are sensitive to quantities other than voltage. Mutants of GPR and BPR, as described herein, are also sensitive to intracellular pH. It is also contemplated that mutants of halorhodopsin may be sensitive to local chloride concentration.

In one embodiment, the voltage sensor is selected from a microbial rhodopsin protein (wild-type or mutant) that provides a voltage-induced shift in its absorption or fluorescence. The starting sequences from which these constructs can be engineered include, but are not limited to, sequences listed in Tables 1a-1b, that list the rhodopsin and an exemplary mutation that can be made to the gene to enhance the performance of the protein product.

Mutations to minimize the light-induced charge-pumping capacity. The retinal chromophore is linked to a lysine by a Schiff base. A conserved aspartic acid serves as the proton acceptor adjacent to the Schiff base. Mutating this aspartic acid to asparagine suppresses proton pumping. Thus, in some embodiments, the mutations are selected from the group consisting of: D97N (green-absorbing proteorhodopsin), D99N (blue-absorbing proteorhodopsin), D75N (sensory rhodopsin II), and D85N (bacteriorhodopsin). In other embodiments, residues that can be mutated to inhibit pumping include (using bacteriorhodopsin numbering) D96, Y199, and R82, and their homologues in other microbial rhodopsins. In another embodiment, residue D95 can be mutated in archaerhodopsin to inhibit proton pumping (e.g., D95N).

Mutations are introduced to shift the absorption and emission spectra into a desirable range. Residues near the binding pocket can be mutated singly or in combination to tune the spectra to a desired absorption and emission wavelength. In residues may be mutated in other microbial rhodopsins. Thus, in some embodiments, the mutation to modify the microbial rhodopsin protein is performed at a residue selected from the group consisting of L92, W86, W182, D212, I119, M145.

Mutations are introduced to shift the dynamic range of voltage sensitivity into a desired band. Such mutations function by shifting the distribution of charge in the vicinity of the Schiff base, and thereby changing the voltage needed to add or remove a proton from this group. Voltage-shifting mutations in green-absorbing proteorhodopsin include, but are not limited to, E108Q, E142Q, L217D, either singly or in combination using green-absorbing proteorhodopsin locations as an example, or a homologous residue in another rhodopsin. In one embodiment, a D95N mutation is introduced into archaerhodopsin 3 to adjust the pKa of the Schiff base towards a neutral pH.

Optionally mutations are introduced to enhance the brightness and photostability of the fluorescence. Residues which when mutated may restrict the binding pocket to increase fluorescence include (using bacteriorhodopsin numbering), but are not limited to, Y199, Y57, P49, V213, and V48.

Codon Usage

A large number of mammalian genes, including, for example, murine and human genes, have been successfully expressed in various host cells, including bacterial, yeast, insect, plant and mammalian host cells. Nevertheless, despite the burgeoning knowledge of expression systems and recombinant DNA technology, significant obstacles remain when one attempts to express a foreign or synthetic gene in a selected host cell. For example, translation of a synthetic gene, even when coupled with a strong promoter, often proceeds much more slowly than would be expected. The same is frequently true of exogenous genes that are foreign to the host cell. This lower than expected translation efficiency is often due to the protein coding regions of the gene having a codon usage pattern that does not resemble those of highly expressed genes in the host cell. It is known in this regard that codon utilization is highly biased and varies considerably in different organisms and that biases in codon usage can alter peptide elongation rates. It is also known that codon usage patterns are related to the relative abundance of tRNA isoacceptors, and that genes encoding proteins of high versus low abundance show differences in their codon preferences.

Codon-optimization techniques have been developed for improving the translational kinetics of translationally inefficient protein coding regions. These techniques are based on the replacement of codons that are rarely or infrequently used in the host cell with those that are host-preferred. Codon frequencies can be derived from literature sources for the highly expressed genes of many organisms (see, for example, Nakamura et al., 1996, Nucleic Acids Res 24: 214-215). These frequencies are generally expressed on an 'organism-wide average basis' as the percentage of occasions that a synonymous codon is used to encode a corresponding amino acid across a collection of protein-encoding genes of that organism, which are preferably highly expressed. In one embodiment, the codons of a microbial rhodopsin protein are optimized for expression in a eukaryotic cell. In one embodiment, the eukaryotic cell is a human cell.

It is preferable but not necessary to replace all the codons of the microbial polynucleotide with synonymous codons having higher translational efficiencies in eukaryotic (e.g., human) cells than the first codons. Increased expression can be accomplished even with partial replacement. Typically, the replacement step affects at least about 5%, 10%, 15%, 20%, 25%, 30%, more preferably at least about 35%, 40%, 50%, 60%, 70% or more of the first codons of the parent polynucleotide. Suitably, the number of, and difference in translational efficiency between, the first codons and the synonymous codons are selected such that the protein of interest is produced from the synthetic polynucleotide in the eukaryotic cell at a level which is at least about 110%, suitably at least about 150%, preferably at least about 200%, more preferably at least about 250%, even more preferably at least about 300%, even more preferably at least about 350%, even more preferably at least about 400%, even more preferably at least about 450%, even more preferably at least about 500%, and still even more preferably at least about 1000%, of the level at which the protein is produced from the parent polynucleotide in the eukaryotic cell.

Generally, if a parent polynucleotide has a choice of low and intermediate translationally efficient codons, it is preferable in the first instance to replace some, or more preferably all, of the low translationally efficient codons with synonymous codons having intermediate, or preferably high, translational efficiencies. Typically, replacement of low with intermediate or high translationally efficient codons results in a substantial increase in production of the polypeptide from the synthetic polynucleotide so constructed. However, it is also preferable to replace some, or preferably all, of the intermediate translationally efficient codons with high translationally efficient codons for optimized production of the polypeptide.

Replacement of one codon for another can be achieved using standard methods known in the art. For example codon modification of a parent polynucleotide can be effected using several known mutagenesis techniques including, for example, oligonucleotide-directed mutagenesis, mutagenesis with degenerate oligonucleotides, and region-specific mutagenesis. Exemplary in vitro mutagenesis techniques are described for example in U.S. Pat. Nos. 4,184,917, 4,321,365 and 4,351,901 or in the relevant sections of Ausubel, et al. (CURRENT PROTOCOLS IN MOLECULAR BIOLOGY, John Wiley & Sons, Inc. 1997) and of Sambrook, et al., (MOLECULAR CLONING. A LABORATORY MANUAL, Cold Spring Harbor Press, 1989). Instead of in vitro mutagenesis, the synthetic polynucleotide can be synthesized de novo using readily available machinery as described, for example, in U.S. Pat. No. 4,293,652. However, it should be noted that the present invention is not dependent on, and not directed to, any one particular technique for constructing the synthetic polynucleotide.

The genes for microbial rhodopsins (e.g., GPR) express well in E. coli, but less well in eukaryotic hosts. In one embodiment, to enable expression in eukaryotes a version of the gene with codon usage appropriate to eukaryotic (e.g., human) cells is designed and synthesized. This procedure can be implemented for any gene using publicly available software, such as e.g., the Gene Designer 2.0 package (available on the world wide web at dna20.com/genedesigner2/). Some of the "humanized" genes are referred to herein by placing the letter "h" in front of the name, e.g. hGPR. The Arch 3 rhodopsins and mutants thereof described herein and in the examples are all optimized for human codon usage.

Applications for VIPs in Screens for Drugs that Target the Following Tissues or Processes The constructs disclosed in the present application can be used in methods for drug screening, e.g., for drugs targeting the nervous system. In a culture of cells expressing specific ion channels, one can screen for agonists or antagonists without the labor of applying patch clamp to cells one at a time. In neuronal cultures one can probe the effects of drugs on action potential initiation, propagation, and synaptic transmission. Application in human iPSC-derived neurons will enable studies on genetically determined neurological diseases, as well as studies on the response to environmental stresses (e.g. anoxia).

Similarly, the optical voltage sensing using the constructs provided herein provides a new and much improved methods to screen for drugs that modulate the cardiac action potential and its intercellular propagation. These screens will be useful both for determining safety of candidate drugs and to identify new cardiac drug leads. Identifying drugs that interact with the hERG channel is a particularly promising direction because inhibition of hERG is associated with ventricular fibrillation in patients with long QT syndrome. Application in human iPSC-derived cardiomyocytes will enable studies on genetically determined cardiac conditions, as well as studies on the response to environmental stresses (e.g. anoxia).

Additionally, the constructs of the present invention can be used in methods to study of development and wound healing. The role of electrical signaling in normal and abnormal development, as well as tissue repair, is poorly understood. VIPs enable studies of voltage dynamics over long times in developing or healing tissues, organs, and organisms, and lead to drugs that modulate these dynamics.

In yet another embodiment, the invention provides methods to screen for drugs that affect membrane potential of mitochondria. Mitochondria play an essential role in ageing, cancer, and neurodegenerative diseases. Currently there is no good probe for mitochondrial membrane potential. VIPs provide such a probe, enabling searches for drugs that modulate mitochondrial activity.

The invention further provides methods to screen for drugs that modulate the electrophysiology of a wide range of medically, industrially, and environmentally significant microorganisms.

Prior to our discovery of VIPs, no measurement of membrane potential had been made in any intact prokaryote. We discovered that bacteria have complex electrical dynamics. VIPs enable screens for drugs that modulate the electrophysiology of a wide range of medically, industrially, and environmentally significant microorganisms. For instance, we found that electrical activity is correlated with efflux pumping in E. coli.

Changes in membrane potential are also associated with activation of macrophages. However, this process is poorly understood due to the difficulty in applying patch clamp to motile cells. VIPs enable studies of the electrophysiology of macrophages and other motile cells, including sperm cells for fertility studies. Thus the VIPs of the invention can be used in methods to screen for drugs or agents that affect, for example, immunity and immune diseases, as well as fertility.

The examples describe expression of VIPs in rat hippocampal neurons, mouse HL-1 cardiomyocytes, and human iPS-derived cardiomyocytes. In all cell types, single action potentials (APs) were readily observed. We tested the effects of drugs on the AP waveform.

For example, in one embodiment, the invention provides a method wherein the cell expressing a microbial rhodopsin is further exposed to a stimulus capable of or suspected to be capable of changing membrane potential.

Stimuli that can be used include candidate agents, such as drug candidates, small organic and inorganic molecules, larger organic molecules and libraries of molecules and any combinations thereof. One can also use a combination of a known drug, such as an antibiotic with a candidate agent to screen for agents that may increase the effectiveness of the one or more of the existing drugs, such as antibiotics.

The methods of the invention are also useful for vitro toxicity screening and drug development. For example, using the methods described herein one can make a human cardiomyocyte from induced pluripotent cells that stably express a modified archaerhodopsin wherein the proton pumping activity is substantially reduced or abolished. Such cells are particularly useful for in vitro toxicity screening in drug development.

PROPS: An Exemplary Optogenetic Voltage Sensor Derived from GPR

GPR has seven spectroscopically distinguishable states that it passes through in its photocycle. In principle the transition between any pair of states is sensitive to membrane potential. In one embodiment, the acid-base equilibrium of the Schiff base was chosen as the wavelength-shifting transition, hence the name of the sensor: Proteorhodopsin Optical Proton Sensor (PROPS). Characterization of the properties of PROPS and its uses are described herein in the Examples section. A brief discussion of PROPS is provided herein below.

The absorption spectrum of wild-type GPR is known to depend sensitively on the state of protonation of the Schiff base. When protonated, the absorption maximum is at 545 nm, and when deprotonated the maximum is at 412 nm. When GPR absorbs a photon, the retinal undergoes a 13-trans to cis isomerization, which causes a proton to hop from the Schiff base to nearby Asp97, leading to a shift from absorption at 545 nm to 412 nm. The PROPS design described herein seeks to recapitulate this shift in response to a change in membrane potential.

Two aspects of wild-type GPR can be changed for it to serve as an optimal voltage sensor. First, the pKa of the Schiff base can be be shifted from its wild-type value of ~12 to a value close to the ambient pH. When pKa~pH, the state of protonation becomes maximally sensitive to the membrane potential. Second, the endogenous charge-pumping capability can be be eliminated, because optimally, a voltage probe should not perturb the quantity under study. However, in some situations, a wild type microbial rhodopsin can be used, such as Arch 3 WT, which functions in neurons to measure membrane potential as shown in our examples.

In one embodiment, a single point mutation induces both changes in GPR. Mutating Asp97 to Asn eliminates a negative charge near the Schiff base, and destabilizes the proton on the Schiff base. The pKa shifts from ~12 to 9.8. In wild-type GPR, Asp97 also serves as the proton acceptor in the first step of the photocycle, so removing this amino acid eliminates proton pumping. This mutant of GPR is referred to herein as PROPS.

Similarly, in an analogous voltage sensor derived from BPR, the homologous mutation Asp99 to Asn lowers the pKa of the Schiff base and eliminates the proton-pumping photocycle. Thus, in one embodiment the optical sensor is derived from BPR in which the amino acid residue Asp99 is mutated to Asn.

In GPR, additional mutations shift the pKa closer to the physiological value of 7.4. In particular, mutations Glu108 to Gln and Glu142 to Gln individually or in combination lead to decreases in the pKa and to further increases in the sensitivity to voltage. Many mutations other than those discussed herein may lead to additional changes in the pKa and improvements in the optical properties of PROPS and are contemplated herein.

Expression Vectors and Targeting Sequences

Optical sensors can be expressed in a cell using an expression vector. The term "vector" refers to a carrier DNA molecule into which a nucleic acid sequence can be inserted for introduction into a host cell. An "expression vector" is a specialized vector that contains the necessary regulatory regions needed for expression of a gene of interest in a host cell. In some embodiments the gene of interest is operably linked to another sequence in the vector. In some embodiments, it is preferred that the viral vectors are replication defective, which can be achieved for example by removing all viral nucleic acids that encode for replication. A replication defective viral vector will still retain its infective properties and enters the cells in a similar manner as a replicating vector, however once admitted to the cell a replication defective viral vector does not reproduce or multiply. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

Many viral vectors or virus-associated vectors are known in the art. Such vectors can be used as carriers of a nucleic acid construct into the cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors. The inserted material of the vectors described herein may be operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence. In some examples, transcription of an inserted material is under the control of a promoter sequence (or other transcriptional regulatory sequence) which controls the expression of the recombinant gene in a cell-type in which expression is intended. It will also be understood that the inserted material can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

An "inducible promoter" is a promoter that is capable of directly or indirectly activating transcription of one or more DNA sequences or genes in response to a "regulatory agent" (e.g., doxycycline), or a "stimulus" (e.g., heat). In the absence of a "regulatory agent" or "stimulus", the DNA sequences or genes will not be substantially transcribed. The term "not substantially transcribed" or "not substantially expressed" means that the level of transcription is at least 100-fold lower than the level of transcription observed in the presence of an appropriate stimulus or regulatory agent; preferably at least 200-fold, 300-fold, 400-fold, 500-fold or more. As used herein, the terms "stimulus" and/or "regulatory agent" refers to a chemical agent, such as a metabolite, a small molecule, or a physiological stress directly imposed upon the organism such as cold, heat, toxins, or through the action of a pathogen or disease agent. A recombinant cell containing an inducible promoter may be exposed to a regulatory agent or stimulus by externally applying the agent or stimulus to the cell or organism by exposure to the appropriate environmental condition or the operative pathogen. Inducible promoters initiate transcription only in the presence of a regulatory agent or stimulus. Examples of inducible promoters include the tetracycline response element and promoters derived from the β-interferon gene, heat shock gene, metallothionein gene or any obtainable from steroid hormone-responsive genes. Inducible promoters which may be used in performing the methods of the present invention include those regulated by hormones and hormone analogs such as progesterone, ecdysone and glucocorticoids as well as promoters which are regulated by tetracycline, heat shock, heavy metal ions, interferon, and lactose operon activating compounds. For review of these systems see Gingrich and Roder, 1998, Annu Rev Neurosci 21, 377-405. Tissue specific expression has been well characterized in the field of gene expression and tissue specific and inducible promoters are well known in the art. These promoters are used to regulate the expression of the foreign gene after it has been introduced into the target cell.

The promoter sequence may be a "cell-type specific promoter" or a "tissue-specific promoter" which means a nucleic acid sequence that serves as a promoter, i.e., regulates expression of a selected nucleic acid sequence operably linked to the promoter, and which affects expression of the selected nucleic acid sequence in specific cells or tissues where membrane potential is desired to be measured. In some embodiments, the cell-type specific promoter is a leaky cell-type specific promoter. The term "leaky" promoter refers to a promoter which regulates expression of a selected nucleic acid primarily in one cell type, but cause expression in other cells as well. For expression of an exogenous gene specifically in neuronal cells, a neuron-specific enolase promoter can be used (see Forss-Petter et al., 1990, Neuron 5: 187-197). For expression of an exogenous gene in dopaminergic neurons, a tyrosine hydroxylase promoter can be used. For expression in pituitary cells, a pituitary-specific promoter such as POMC may be used (Hammer et al., 1990, Mol. Endocrinol. 4:1689-97). Examples of muscle specific promoters include, for example α-myosin heavy chain promoter, and the MCK promoter. Other cell specific promoters active in mammalian cells are also contemplated herein. Such promoters provide a convenient means for controlling expression of the exogenous gene in a cell of a cell culture or within a mammal.

In some embodiments, the expression vector is a lentiviral vector. Lentiviral vectors useful for the methods and compositions described herein can comprise a eukaryotic promoter. The promoter can be any inducible promoter, including synthetic promoters, that can function as a promoter in a eukaryotic cell. For example, the eukaryotic promoter can be, but is not limited to, ecdysone inducible promoters, E1a inducible promoters, tetracycline inducible promoters etc., as are well known in the art. In addition, the lentiviral vectors used herein can further comprise a selectable marker, which can comprise a promoter and a coding sequence for a selectable trait. Nucleotide sequences encoding selectable markers are well known in the art, and include those that encode gene products conferring resistance to antibiotics or anti-metabolites, or that supply an auxotrophic requirement. Examples of such sequences include, but are not limited to, those that encode thymidine kinase activity, or resistance to methotrexate, ampicillin, kanamycin, chloramphenicol, puromycin or zeocin, among many others.

In some embodiments the viral vector is an adeno-asscoated virus (AAV) vector. AAV can infect both dividing and non-dividing cells and may incorporate its genome into that of the host cell.

The type of vector one selects will also depend on whether the expression is intended to be stable or transient.

The invention also provides cells that are genetically engineered to express the microbial rhodopsin, such as VIPs or PROPS. The cell may be engineered to express the VIP or PROPS transiently or stably.

The invention provides methods of making both transiently expressing cells and cells and cell lines that express the microbial rhodopsins stably.

Transient expression. One of ordinary skill in the art is well equipped to engineer cells that are transiently transfected to express the VIPs or PROPS as described herein. Transduction and transformation methods for transient expression of nucleic acids are well known to one skilled in the art.

Transient transfection can be carried out, e.g., using calcium phosphate, by electroporation, or by mixing a cationic lipid with the material to produce liposomes, cationic polymers or highly branched organic compounds. All these are in routine use in genetic engineering.

Stable expression of VIP or PROP in an eukaryotic cell. One of ordinary skill in the art is well equipped to engineer cells that stably express the VIPs or PROPS as described herein. These methods are also in routine use in genetic engineering. Exemplary protocols can be found, e.g., in Essential Stem Cell Methods, edited by Lanza and Klimanskaya, published in 2008, Academic Press. For example, one can generate a virus that integrates into the genome and comprises a selectable marker, and infect the cells with the virus and screen for cells that express the marker, which cells are the ones that have incorporated the virus into their genome. For example, one can generate a VSV-g psuedotyped lenti virus with a puromycin selectable marker in HEK cells according to established procedures. Generally, one can use a stem cell specific promoter to encode a GFP if FACS sorting is necessary. The hiPS cultures are cultivated on embryonic fibroblast (EF) feeder layers or on Matrigel in fibroblast growth factor supplemented EF conditioned medium. The cells are dissociated by trypsinization to a single cell suspension The cells can be plated, e.g., $1 \times 10^5$ cells on a tissue culture 6-well plate pretreated with, e.g., Matrigel. To maintain the cells in an undifferentiated state, one can use, e.g., EF conditioned medium. About 6 hours after plating, one can add virus supernatant to adhered cells (use 5×10⁶ IU virus per 1×10⁵ cells). Add 6 µg/mL protamine sulfate to enhance virus infection. Cells are cultured with the virus for 24 hours; washed, typically with PBS, and fresh media is added with a selection marker, such as 1 µg/mL puromycin. The medium is replaced about every 2 days with additional puromycin. Cells surviving after 1 week are re-plated, e.g., using the hanging drop method to form EBs with stable incorporation of gene.

In some embodiments, it is advantageous to express an optical voltage sensor (e.g., Arch 3 D94N) in only a single cell-type within an organism, and further, if desired, to direct the sensor to a particular subcellular structure within the cell. Upstream promoters control when and where the gene is expressed. Constructs are made that optimize expression in all eukaryotic cells. In one embodiment, the optical voltage sensor is under the control of a neuron-specific promoter.

The promoter sequence can be selected to restrict expression of the protein to a specific class of cells and environmental conditions. Common promoter sequences include, but are not limited to, CMV (cytomegalovirus promoter; a universal promoter for mammalian cells), 14×UAS-E1b (in combination with the transactivator Gal4, this promoter allows combinatorial control of transgene expression in a wide array of eukaryotes. Tissue-specific expression can be achieved by placing Gal4 under an appropriate promoter, and then using Gal4 to drive the UAS-controlled transgene), HuC (drives pan-neuronal expression in zebrafish and other teleosts), ara (allows regulation of expression with arabinose in bacteria) and lac (allows regulation of expression with IPTG in bacteria).

In some embodiments, the optical voltage sensor further comprises a localization or targeting sequence to direct or sort the sensor to a particular face of a biological membrane or subcellular organelle. Preferred localization sequences provide for highly specific localization of the protein, with minimal accumulation in other subcellular compartments. Example localization sequences that direct proteins to specific subcellular structures are shown below in Table 4.

TABLE 4

Exemplary protein localization sequences

| Subcellular compartment | Sequence | SEQ ID NO. |
|---|---|---|
| Nuclear (import signal) | PPKKKRKV | 1 |
| Endoplasmic reticulum (import signal) | MSFVSLLLVGILFWATGAENLTKCEVFN | 2 |
| Endoplasmic reticulum (retention signal) | KDEL | 3 |
| Peroxisome (import signal) | SKL | 4 |
| Peroxisome (import signal) | (R/K)-(L/V/I)-XXXXX-(H/Q)-(L/A/F) (where X can be any amino acid). | 5 |
| Mitochondrial inner membrane | MLSLRNSIRFFKPATRTLCSSRYLL | 6 |
| Mitochondrial outer membrane | MLRTSSLFTRRVQPSLFRNILRLQST | 7 |
| plasma membrane (cytosolic face) | MGCIKSKRKDNLNDDGVDMKT | 8 |
| plasma membrane (cytosolic face) | KKKKKKKSKTKCVIM | 9 |
| mitochondrial targeting sequence: human PINK1 | MAVRQALGRGLQLGRALLLR FTGKPGRAYGLGRPGPAAGC VRGERPGWAAGPGAEPRRVG LGLPNRLRFFRQSVAGL | 10 |
| mitochondrial targeting sequence: human serine protease HTRA2 | MAAPRAGRGAGWSLRAWRAL GGIRWGRRPRL | 11 |
| mitochondrial targeting sequence: human cytochrome oxidase 1 | MFADRWLFST NHKDIGTLY | 12 |
| mitochondrial targeting sequence: human cytochrome oxidase 2 | MAHAAQVGLQ DATSPIMEEL ITFHDH | 13 |
| mitochondrial targeting sequence: human protein phospatase 1K | MSTAALITLVRSGGNQVRRR VLLSSRLLQ | 14 |

TABLE 4-continued

Exemplary protein localization sequences

| Subcellular compartment | Sequence | SEQ ID NO. |
|---|---|---|
| mitochondrial targeting sequence: human ATP synthase alpha | MLSVRVAAAVVRALPRRAGL VSRNALGSSFIAARNFHASNTHL | 15 |
| mitochondrial targeting sequence: human frataxin | MWTLGRRAVAGLLASPSPAQ AQTLTRVPRPAELAPLCGRRG | 16 |

Other examples of localization signals are described in, e.g., "Protein Targeting", chapter 35 of Stryer, L., Biochemistry (4th ed.). W. H. Freeman, 1995 and Chapter 12 (pages 551-598) of Molecular Biology of the Cell, Alberts et al. third edition, (1994) Garland Publishing Inc. In some embodiments, more than one discrete localization motif is used to provide for correct sorting by the cellular machinery. For example, correct sorting of proteins to the extracellular face of the plasma membrane can be achieved using an N-terminal signal sequence and a C-terminal GPI anchor or transmembrane domain.

Typically, localization sequences can be located almost anywhere in the amino acid sequence of the protein. In some cases the localization sequence can be split into two blocks separated from each other by a variable number of amino acids. The creation of such constructs via standard recombinant DNA approaches is well known in the art, as for example described in Maniatis, et al., Molecular Cloning A Laboratory Manual, Cold Spring Harbor Laboratory, N.Y, 1989).

Targeting to the plasma membrane: In some embodiments, constructs are designed to include signaling sequences to optimize localization of the protein to the plasma membrane. These can include e.g., a C-terminal signaling sequence from the □2 nicotinic acetylcholine receptor (MRGTPLLLVVS-LFSLLQD (SEQ ID NO: 17), indicated with the one-letter amino acid code), and/or an endoplasmic reticulum export motif from Kir2.1, (FCYENEV) (SEQ ID NO: 18).

Additional improvements in plasma localization can be obtained by adding Golgi export sequences (e.g. from Kir2.1: RSRFVKKDGHCNVQFINV (SEQ ID NO: 19)) and membrane localization sequences (e.g. from Kir2.1: KSRITSEG-EYIPLDQIDINV (SEQ ID NO: 20)) (Gradinaru, V. et al. Cell (2010)). In some embodiments, the targeting sequence is selected to regulate intracellular transport of the protein to the desired subcellular structure. In one embodiment the protein is targeted to the plasma membrane of a eukaryotic cell. In this case the targeting sequence can be designed following the strategy outlined in e.g., Gradinaru et al., "Molecular and Cellular Approaches for Diversifying and Extending Optogenetics," Cell 141, 154-165 (2010). The term "signal sequence" refers to N-terminal domains that target proteins into a subcellular locale e.g., the endoplasmic reticulum (ER), and thus are on their way to the plasma membrane. Signal sequences used in optogenetic voltage sensors can be derived from the proteins β2-n-acetylcholine receptor (SS B2nAChR) and PPL. In addition, there is an endogenous signaling sequence on microbial rhodopsin proteins that can be harnessed for appropriate subcellular targeting. A trafficking signal (TS) can optionally be inserted into the genome C-terminal to the microbial rhodopsin and N-terminal to the accessory fluorescent protein. In one embodiment, the trafficking signal is derived from the Kir2.1 protein as specified in Gradinaru et al. In another embodiment, an ER export motif is inserted at the C-terminus of the accessory fluorescent protein.

Targeting mitochondria: For measuring mitochondrial membrane potential or for studying mitochondria, one may wish to localize PROPS to the mitochondrial inner membrane or mitochondrial outer membrane, in which case appropriate signaling sequences can be added to the rhodopsin protein.

Optogenetic voltage sensors can be targeted to the inner mitochondrial membrane, following a procedure such as that described in e.g., A. Hoffmann, V. Hildebrandt, J. Heberle, and G. Büldt, "Photoactive mitochondria: in vivo transfer of a light-driven proton pump into the inner mitochondrial membrane of *Schizosaccharomyces pombe*," Proc. Natl. Acad. Sci. USA 91, PNAS 9367-9371 (1994).

Cells

Cells that are useful according to the invention include eukaryotic and prokaryotic cells. Eukaryotic cells include cells of non-mammalian invertebrates, such as yeast, plants, and nematodes, as well as non-mammalian vertebrates, such as fish and birds. The cells also include mammalian cells, including human cells. The cells also include immortalized cell lines such as HEK, HeLa, CHO, 3T3, which may be particularly useful in applications of the methods for drug screens. The cells also include stem cells, pluripotent cells, progenotir cells, and induced pluripotent cells. Differentiated cells including cells differentiated from the stem cells, pluripotent cells and progenotir cells are included as well.

In some embodiments, the cells are cultured in vitro or ex vivo. In some embodiments, the cells are part of an organ or an organism.

In some embodiment, the cell is an "artificial cell" or a "synthetic cell" created by bioengineering (see, e.g., Creation of a Bacterial Cell Controlled by a Chemically Synthesized Genome, Daniel G. Gibson et al., Science 2 Jul. 2010: Vol. 329 no. 5987 pp. 52-56; Cans, Ann-Sofie, Andes-Koback, Meghan, and Keating, Christine D. Positioning Lipid Membrane Domains in Giant Vesicles by Micro-organization of Aqueous Cytoplasm Mimic. J. Am. Chem. Soc., 2008).

The methods can also be applied to any other membrane-bound structure, which may not necessarily be classified as a cell. Such membrane bound structures can be made to carry the microbial rhodopsin proteins of the invention by, e.g., fusing the membranes with cell membrane fragments that carry the microbial rhodopsin proteins of the invention.

Cells include also zebrafish cardiomyocytes; immune cells (primary murine and human cultures and iPS-derived lines for all, in addition to the specific lines noted below), including B cells (e.g., human Raji cell line, and the DT40 chicken cell line), T cells (e.g., human Jurkat cell line), Macrophages, Dendritic cells, and Neutrophils (e.g., HL-60 line). Additionally, one can use glial cells: astrocytes and oligodendrocytes;

pancreatic beta cells; hepatocytes; non-cardiac muscle cells; endocrine cells such as parafollicular and chromaffin; and yeast cells. Cells further include neuronal cells, such as neurons.

The cell can also be a Gram positive or a Gram negative bacteria, as well as pathogenic bacteria of either Gram type. The pathogenic cells are useful for applications of the method to, e.g., screening of novel antibiotics that affect membrane potential to assist in destruction of the bacterial cell or that affect membrane potential to assist destruction of the bacterial cell in combination with the membrane potential affecting agent; or in the search for compounds that suppress efflux of antibiotics.

The membrane potential of essentially any cell, or any phospholipid bilayer enclosed structure, can be measured using the methods and compositions described herein. Examples of the cells that can be assayed are a primary cell e.g., a primary hepatocyte, a primary neuronal cell, a primary myoblast, a primary mesenchymal stem cell, primary progenitor cell, or it may be a cell of an established cell line. It is not necessary that the cell be capable of undergoing cell division; a terminally differentiated cell can be used in the methods described herein. In this context, the cell can be of any cell type including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. The cell can be a cell line, a stem cell, or a primary cell isolated from any tissue including, but not limited to brain, liver, lung, gut, stomach, fat, muscle, testes, uterus, ovary, skin, spleen, endocrine organ and bone, etc. Where the cell is maintained under in vitro conditions, conventional tissue culture conditions and methods can be used, and are known to those of skill in the art. Isolation and culture methods for various cells are well within the knowledge of one skilled in the art. The cell can be a prokaryotic cell, a eukaryotic cell, a mammalian cell or a human cell. In one embodiment, the cell is a neuron or other cell of the brain. In some embodiment, the cell is a cardiomyocyte. In some embodiments, the cell is cardiomyocyte that has been differentiated from an induced pluripotent cell.

Reference Value

The invention provides method for measuring membrane potential in a cell expressing a nucleic acid encoding a microbial rhodopsin protein, the method comprising the steps of (a) exciting at least one cell comprising a nucleic acid encoding a microbial rhodopsin protein with light of at least one wave length; and (b) detecting at least one optical signal from the at least one cell, wherein the level of fluorescence emitted by the at least one cell compared to a reference is indicative of the membrane potential of the cell.

The term "reference" as used herein refers to a baseline value of any kind that one skilled in the art can use in the methods. In some embodiments, the reference is a cell that has not been exposed to a stimulus capable of or suspected to be capable of changing membrane potential. In one embodiment, the reference is the same cell transfected with the microbial rhodopsin but observed at a different time point. In another embodiment, the reference is the fluorescence of a homologue of Green Fluorescent Protein (GFP) operably fused to the microbial rhodopsin.

Detecting Fluorescence from a Modified Microbial Rhodopsin

In the methods of the invention, the cells are excited with a light source so that the emitted fluorescence can be detected. The wavelength of the excitation light depends on the fluorescent molecule. For example, the archerhodopsin constructs in the examples are all excitable using light with wavelengths varying between $\lambda=594$ nm and $\lambda=645$ nm. Alternatively, the range may be between $\lambda=630$-645 nm. For example a commonly used Helium Neon laser emits at $\lambda=632.8$ nm and can be used in excitation of the fluorescent emission of these molecules.

In some embodiments a second light is used. For example, if the cell expresses a reference fluorescent molecule or a fluorescent molecule that is used to detect another feature of the cell, such a pH or Calcium concentration. In such case, the second wavelength differs from the first wavelength. Examples of useful wavelengths include wavelengths in the range of $\lambda=447$-594 nm, for example, $\lambda=473$ nm, $\lambda=488$ nm, $\lambda=514$ nm, $\lambda=532$ nm, and $\lambda=561$ nm.

The hardware and software needed to take maximal advantage of VIPs depends on the type of assay, and can be easily optimized and selected by a skilled artisan based on the information provided herein. Existing instrumentation can be easily used or adapted for the detection of VIPs and PROPs. The factors that determine the type of instrumentation include, precision and accuracy, speed, depth penetration, multiplexing and throughput.

Precision and accuracy: In determining the detection system, one should evaluate whether one needs absolute or relative measurement of voltage. Absolute measurements of membrane potential are typically done ratiometrically, with either two excitation wavelengths or two emission wavelengths. Relative voltage changes in a single cell can be performed with single-band excitation and detection.

Speed: To measure action potentials in a neuron one needs sub-millisecond temporal resolution. This requires either high-speed CCDs, or high-speed confocal microscopes which can scan custom trajectories. Slower dynamics and quasi steady state voltages can be measured with conventional cameras. These measurements can be used, for example, in methods and assays that are directed to screening of agents in cardiac cells, such as cardiomyocytes.

Depth penetration: Imaging in deep tissue may require confocal microscopy or lateral sheet illumination microscopy. Alternatively, deep imaging may require the development of nonlinear microscopies, including two-photon fluorescence or second harmonic generation. Conventional epifluorescence imaging works well for cells in culture, and total internal reflection fluorescence (TIRF) provides particularly high signal-to-noise ratios in images of adherent cells.

Multiplexing with other optical imaging and control: One can combine imaging of VIPs with other structural and functional imaging, of e.g. pH, calcium, or ATP. One may also combine imaging of VIPs with optogenetic control of membrane potential using e.g. channelrhodopsin, halorhodopsin, and archaerhodopsin. If optical measurement and control are combined in a feedback loop, one can perform all-optical patch clamp to probe the dynamic electrical response of any membrane.

Throughput: One can also integrate robotics and custom software for screening large libraries or large numbers of conditions which are typically encountered in high throughput drug screening methods.

Spectroscopic Readouts of Voltage-Induced Shifts in Microbial Rhodopsins

The spectroscopic states of microbial rhodopsins are typically classified by their absorption spectrum. However, in some cases there is insufficient protein in a single cell to detect spectral shifts via absorbance alone. Any of the following several optical imaging techniques can be used to probe other state-dependent spectroscopic properties.

a) Fluorescence

It was found that many microbial rhodopsin proteins and their mutants produce measurable fluorescence. For example, PROPS fluorescence is excited by light with a wavelength between wavelength of 500 and 650 nm, and emission is peaked at 710 nm. The rate of photobleaching of PROPS decreases at longer excitation wavelengths, so one preferable excitation wavelength is in the red portion of the spectrum, near 633 nm. These wavelengths are further to the red than the excitation and emission wavelengths of any other fluorescent protein, a highly desirable property for in vivo imaging. Furthermore, the fluorescence of PROPS shows negligible photobleaching, in stark contrast to all other known fluorophores. When excited at 633 nm, PROPS and GFP emit a comparable numbers of photons prior to photobleaching. Thus microbial rhodopsins constitute a new class of highly photostable, membrane-bound fluorescent markers.

It was further found that the fluorescence of PROPS is exquisitely sensitive to the state of protonation of the Schiff base in that only the protonated form fluoresces. Thus voltage-induced changes in protonation lead to changes in fluorescence.

In some embodiments, the fluorescence of PROPS is detected using e.g., a fluorescent microscope, a fluorescent plate reader, FACS sorting of fluorescent cells, etc.

b) Spectral Shift Fluorescence Resonance Energy Transfer (FRET)

FRET is a useful tool to quantify molecular dynamics in biophysics and biochemistry, such as protein-protein interactions, protein-DNA interactions, and protein conformational changes. For monitoring the complex formation between two molecules (e.g., retinal and microbial rhodopsin), one of them is labeled with a donor and the other with an acceptor, and these fluorophore-labeled molecules are mixed. When they are dissociated, the donor emission is detected upon the donor excitation. On the other hand, when the donor and acceptor are in proximity (1-10 nm) due to the interaction of the two molecules, the acceptor emission is predominantly observed because of the intermolecular FRET from the donor to the acceptor.

A fluorescent molecule appended to a microbial rhodopsin can transfer its excitation energy to the retinal, but only if the absorption spectrum of the retinal overlaps with the emission spectrum of the fluorophore. Changes in the absorption spectrum of the retinal lead to changes in the fluorescence brightness of the fluorophore. To perform spectral shift FRET, a fluorescent protein is fused with the microbial rhodopsin voltage sensor, and the fluorescence of the protein is monitored. This approach has the advantage over direct fluorescence that the emission of fluorescent proteins is far brighter than that of retinal, but the disadvantage of being an indirect readout, with smaller fractional changes in fluorescence.

In some embodiments, voltage-induced changes in the absorption spectrum of microbial rhodopsins are detected using spectral shift FRET c) Rhodopsin Optical Lock-in Imaging (ROLI)

The absorption spectrum of many of the states of retinal is temporarily changed by a brief pulse of light. In ROLI, periodic pulses of a "pump" beam are delivered to the sample. A second "probe" beam measures the absorbance of the sample at a wavelength at which the pump beam induces a large change in absorbance. Thus the pump beam imprints a periodic modulation on the transmitted intensity of the probe beam. These periodic intensity changes are detected by a lock-in imaging system. In contrast to conventional absorption imaging, ROLI provides retinal-specific contrast. Modulation of the pump at a high frequency allows detection of very small changes in absorbance.

In some embodiments, the fluorescence of PROPS is detected using rhodopsin optical lock-in imaging.

d) Raman

Raman spectroscopy is a technique that can detect vibrational, rotational, and other low-frequency modes in a system. The technique relies on inelastic scattering of monochromatic light (e.g., a visible laser, a near infrared laser or a near ultraviolet laser). The monochromatic light interacts with molecular vibrations, phonons or other excitations in the system, resulting in an energy shift of the laser photons. The shift in energy provides information about the phonon modes in the system.

Retinal in microbial rhodopsin molecules is known to have a strong resonant Raman signal. This signal is dependent on the electrostatic environment around the chromophore, and therefore is sensitive to voltage.

In some embodiments, voltage-induced changes in the Raman spectrum of microbial rhodopsins are detected using Raman microscopy.

e) Second Harmonic Generation (SHG)

Second harmonic generation, also known in the art as "frequency doubling" is a nonlinear optical process, in which photons interacting with a nonlinear material are effectively "combined" to form new photons with twice the energy, and therefore twice the frequency and half the wavelength of the initial photons.

SHG signals have been observed from oriented films of bacteriorhodopsin in cell membranes. SHG is an effective probe of the electrostatic environment around the retinal in optical voltage sensors. Furthermore, SHG imaging involves excitation with infrared light which penetrates deep into tissue. Thus SHG imaging can be used for three-dimensional optical voltage sensing using the optical sensors described herein.

In some embodiments, voltage-induced changes in the second harmonic spectrum of microbial rhodopsins are detected using SHG imaging.

Fusion Protein with a Moiety that Produces an Optical Signal

Although microbial rhodopsin proteins are themselves fluorescent in response to changes in voltage, in some applications it may desired or necessary to enhance the level of fluorescence or provide another optical signal (e.g., a colorimetric signal) to permit detection of voltage changes. Further, a moiety that produces an optical signal can be attached to the microbial rhodopsin to monitor the subcellular localization of the rhodopsin protein. Thus, in some embodiments, the modified microbial rhodopsin proteins further comprise a moiety that produces an optical signal, thereby enhancing the optical signal measured from the modified microbial rhodopsin protein or permitting localization studies to be performed for the rhodopsin protein.

For example, a gene for a fluorescent protein of the GFP family or a homolog thereof can optionally be appended or as referred to in the claims "operably linked" to the nucleic acid encoding the microbial rhodopsin. In one embodiment, the identity of the fluorescent protein, its linker to the voltage-sensing complex, and the location of this linker in the overall protein sequence are selected for one of two functions: either to serve as an indicator of the level and distribution of gene expression products; or to serve as an alternative readout of voltage, independent of the endogenous fluorescence of the retinal.

For example, when the fluorescent protein serves as an indicator of protein localization, it enables quantitative optical voltage measurements that are not confounded by cell-tocell variation in expression levels. The fluorescence of the fluorescent protein and the microbial rhodopsin can be measured simultaneously and the ratio of these two signals provides a concentration-independent measure of membrane potential.

In one embodiment, the microbial rhodopsin protein is a PROPS fusion protein comprising a fluorescent protein. For example, an N-terminal fusion of PROPS with the fluorescent protein Venus. This protein provides a stable reference indicating localization of PROPS within the cell and permitting ratiometric imaging of Venus and PROPS fluorescence. Ratiometric imaging permits quantitative measurements of membrane potential because this technique is insensitive to the total quantity of protein within the cell. Other fluorescent proteins may be used in lieu of Venus with similar effects. In some embodiments, the fluorescent polypeptide is selected from the group consisting of GFP, YFP, EGFP, EYFP, EBFB, DsRed, RFP and fluorescent variants thereof.

In one embodiment, the microbial rhodopsin is an archaerhodopsin fused with or operably linked to an additional fluorescent protein, such as a GFP or a homolog thereof.

Chromophore

In the wild, microbial rhodopsins contain a bound molecule of retinal which serves as the optically active element. These proteins will also bind and fold around many other chromophores with similar structure, and possibly preferable optical properties. Analogues of retinal with locked rings cannot undergo trans-cis isomerization, and therefore have higher fluorescence quantum yields (Brack, T. et al. *Biophys. J.* 65, 964-972 (1993)). Analogues of retinal with electron-withdrawing substituents have a Schiff base with a lower pKa than natural retinal and therefore may be more sensitive to voltage (Sheves, M., et al. *Proc. Nat. Acad. Sci. U.S.A.* 83, 3262-3266 (1986); Rousso, I., et al. *Biochemistry* 34, 12059-12065 (1995)). Covalent modifications to the retinal molecule may lead to optical voltage sensors with significantly improved optical properties and sensitivity to voltage.

Advantages of the Methods and Compositions Described Herein

The key figures of merit for an optical voltage sensor are its response speed and its sensitivity (fractional change in fluorescence per 100 mV change in membrane potential). FIG. 10 compares these attributes for previous protein-based fluorescent voltage indicators and those contemplated herein. Additional important attributes include the ability to target the indicator to a particular cell type or sub-cellular structure, photostability, and low phototoxicity.

Previous protein-based efforts focused on fusing one or more fluorescent proteins to transmembrane voltage sensing domains. A change in voltage induces a conformational change in the voltage sensing domain, which moves the fluorescent proteins, and changes their fluorescence. The reliance on conformational motion of multiple large protein domains makes these approaches unavoidably slow. Furthermore, the conformational shifts of most voltage sensing domains are small, leading to small changes in fluorescence.

The most sensitive indicators from the VSFP 2.x family have a change in fluorescence of $\Delta F/F=10\%$ per 100 mV. VSFP 2.x proteins respond in approximately 100 milliseconds, far too slow to detect a 1 ms action potential in a neuron (Perron, A. et al. *Front Mol. Neurosci.* 2 (2009); Mutoh, H. et al. *PLoS One* 4, e4555 (2009)). The SPARC family of voltage sensors has a 1 ms response time, but shows a fluorescence change of <1% per 100 mV (Baker, B. J. et al. *J. Neurosci. Methods* 161, 32-38 (2007); Ataka, K. & Pieribone, V. A. *Biophys. J.* 82, 509-516 (2002)). Prior to the present study described herein, two decades of research on fluorescent voltage sensors had not yet yielded a protein that could signal individual neuronal action potentials in vivo.

Scientists have also developed small organic dyes that show voltage-sensitive fluorescence. These lipophilic molecules incorporate into the cell membrane where voltage leads to shifts in conformation or electronic energy levels and thereby to changes in optical properties. These molecules respond quickly (less than 1 ms, typically), and have sensitivities as large as 34% per 100 mV, but cannot be targeted, are often difficult to deliver, and are highly toxic (Krauthamer, V., et al. *J. Fluoresc.* 1, 207-213 (1991); Fromherz, P., et al. *Eur. Biophys. J.* 37, 509-514 (2008); Sjulson, L. & Miesenbock, G. *J. Neurosci.* 28, 5582 (2008)), see e.g. U.S. Pat. Nos. 7,867,282, 6,107,066, and 5,661,035). None of these optical voltage sensors employs a microbial rhodopsin protein that is configured to run "backwards" to convert changes in membrane potential into changes in an optically detectable signal.

The approach to optical voltage sensing described herein is different from previous efforts. As described herein a protein is used that has a strong electro-optical coupling in the wild. Microbial rhodopsins in the wild serve to transduce sunlight into a membrane potential. The optical voltage sensors described herein use this function in reverse, transducing a membrane potential into a readily detectable optical signal. As FIG. 12 shows, the exemplary microbial rhodopsin voltage sensors (PROPS, Arch 3 WT, Arch 3 D95N) exceed other protein-based indicators on the key figures of merit.

Membrane Fusion Mediated Delivery of an Optical Sensor

Membrane fusion reactions are common in eukaryotic cells. Membranes are fused intracellularly in processes including endocytosis, organelle formation, inter-organelle traffic, and constitutive and regulated exocytosis. Intercellularly, membrane fusion occurs during sperm-egg fusion and myoblast fusion.

Membrane fusion has been induced artificially by the use of liposomes, in which the cell membrane is fused with the liposomal membrane, and by various chemicals or lipids, which induce cell-cell fusion to produce heterokaryons. Naturally occurring proteins shown to induce fusion of biological membranes are mainly fusion proteins of enveloped viruses. Thus, in some embodiments, the optical sensor is administered using a liposome comprising a fusogenic protein.

It is generally believed that membrane fusion under physiological conditions is protein-mediated. This has led to the development of liposomes that contain fusion-promoting proteins (proteoliposomes), with decreased cytotoxicity (see, for example, Cheng, Hum. Gene Ther. 7:275-282 (1996); Hara et al., Gene 159:167-174 (1995); and Findeis et al., Trends Biotechnol., 11:202-205 (1993)).

The only proteins conclusively shown to induce intercellular fusion of biological membranes are those of enveloped viruses and two proteins from nonenveloped viruses. All enveloped viruses encode proteins responsible for fusion of the viral envelope with the cell membrane. These viral fusion proteins are essential for infection of susceptible cells. The mechanism of action of fusion proteins from enveloped viruses have served as a paradigm for protein-mediated membrane fusion (see, for example, White, Ann. Rev. Physiol., 52:675-697 (1990); and White, Science, 258:917-924 (1992)).

Most enveloped virus fusion proteins are relatively large, multimeric, type I membrane proteins, as typified by the influenza virus HA protein, a low pH-activated fusion protein, and the Sendai virus F protein, which functions at neutral pH. These are structural proteins of the virus with the majority of the fusion protein oriented on the external surface of the virion to facilitate interactions between the virus particle and the cell membrane.

According to the mechanism of action of fusion proteins from enveloped viruses, fusion of the viral envelope with the cell membrane is mediated by an amphipathic alpha-helical region, referred to as a fusion peptide motif, that is present in the viral fusion protein. This type of fusion peptide motif is typically 17 to 28 residues long, hydrophobic (average hydrophobicity of about 0.6±0.1), and contains a high content of glycine and alanine, typically 36%±7% (White, Annu. Rev. Physiol., 52:675-697 (1990).

All of the enveloped virus fusion proteins are believed to function via extensive conformational changes that, by supplying the energy to overcome the thermodynamic barrier, promote membrane fusion. These conformational changes are frequently mediated by heptad repeat regions that form coiled coil structures (see Skehel and Wiley, Cell, 95:871-874 (1998)). Recognition of the importance of fusion peptide motifs in triggering membrane fusion has resulted in the use of small peptides containing fusion peptide motifs to enhance liposome-cell fusion (see, for example, Muga et al., Biochemistry 33:4444-4448 (1994)).

Enveloped virus fusion proteins also trigger cell-cell fusion, resulting in the formation of polykaryons (syncytia). Synthesis of the viral fusion protein inside the infected cell results in transport of the fusion protein through the endoplasmic reticulum and Golgi transport system to the cell membrane, an essential step in the assembly and budding of infectious progeny virus particles from the infected cell (Petterson, Curr. Top. Micro. Immunol., 170:67-106 (1991)). The synthesis, transport, and folding of the fusion protein is facilitated by a variety of components, including signal peptides to target the protein to the intracellular transport pathway, glycosylation signals for N-linked carbohydrate addition to the protein, and a transmembrane domain to anchor the protein in the cell membrane. These proteins have been used in reconstituted proteoliposomes ('virosomes') for enhanced, protein-mediated liposome-cell fusion in both cell culture and in vivo (see, for example, Ramani et al., FEBS Lett., 404:164-168 (1997); Scheule et al., Am. J. Respir. Cell Mol. Biol., 13:330-343 (1995); and Grimaldi, Res. Virol., 146:289-293 (1995)).

Thus, in some embodiments of the methods and compositions described herein, a micelle, liposome or other artificial membrane comprising the modified microbial rhodopsin and a fusion protein is administered to a cell or a subject to mediate delivery of the optical sensor protein to the cell by membrane fusion. In a preferred embodiment, the composition further comprises a targeting sequence to target the delivery system to a particular cell-type. If desired, the exogenous lipid of an artificial membrane composition can further comprise a targeting moiety (e.g., ligand) that binds to mammalian cells to facilitate entry. For example, the composition can include as a ligand an asialoglycoprotein that binds to mammalian lectins (e.g., the hepatic asialoglycoprotein receptor), facilitating entry into mammalian cells. Single chain antibodies, which can target particular cell surface markers, are also contemplated herein for use as targeting moieties. Targeting moieties can include, for example, a drug, a receptor, an antibody, an antibody fragment, an aptamer, a peptide, a vitamin, a carbohydrate, a protein, an adhesion molecule, a glycoprotein, a sugar residue or a glycosaminoglycan, a therapeutic agent, a drug, or a combination of these. A skilled artisan can readily design various targeting moieties for modifying an artificial membrane based on the intended target cell to be assessed using an optical sensor as described herein.

For methods using membrane fusion mediated delivery, it is contemplated that the optical sensor to be used is expressed and produced in a heterologous expression system. Different expression vectors comprising a nucleic acid that encodes an optical sensor or derivative as described herein for the expression of the optical sensor can be made for use with a variety of cell types or species. The expression vector should have the necessary 5' upstream and 3' downstream regulatory elements such as promoter sequences, ribosome recognition and binding TATA box, and 3' UTR AAUAAA transcription termination sequence for efficient gene transcription and translation in the desired cell. In some embodiments, the optical sensors are made in a heterologous protein expression system and then purified for production of lipid-mediated delivery agents for fusion with a desired cell type. In such embodiments, the expression vector can have additional sequences such as 6×-histidine (SEQ ID NO: 21), V5, thioredoxin, glutathione-S-transferase, c-Myc, VSV-G, HSV, FLAG, maltose binding peptide, metal-binding peptide, HA and "secretion" signals (e.g., Honeybee melittin Pho, BiP), which are incorporated into the expressed recombinant optical sensor for ease of purification. In addition, there can be enzyme digestion sites incorporated after these sequences to facilitate enzymatic removal of additional sequence after they are not needed. These additional sequences are useful for the detection of optical sensor expression, for protein purification by affinity chromatography, enhanced solubility of the recombinant protein in the host cytoplasm, for better protein expression especially for small peptides and/or for secreting the expressed recombinant protein out into the culture media, into the periplasm of the prokaryote bacteria, or to the spheroplast of yeast cells. The expression of recombinant optical sensors can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose, depending on the host and vector system chosen.

Examples of other expression vectors and host cells are the pET vectors (Novagen), pGEX vectors (Amersham Pharmacia), and pMAL vectors (New England labs. Inc.) for protein expression in *E. coli* host cells such as BL21, BL21(DE3) and AD494(DE3)pLysS, Rosetta (DE3), and Origami(DE3) (Novagen); the strong CMV promoter-based pcDNA3.1 (Invitrogen) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™ HT (Invitrogen) for the expression in Spodopera frugiperda 9 (Sf9) and Sf11 insect cell lines; pMT/BiP/V5-His (Invitrogen) for the expression in *Drosophila* Schneider S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYD1 (Invitrogen) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol. Med. 94:191-5. Foreign heterologous coding sequences are inserted into the genome of the nucleus, chloroplast and mitochondria by homologous recombination. The chloroplast expression vector p64 carrying the versatile chloroplast selectable marker aminoglycoside adenyl transferase (aadA), which confers resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. An example of a cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. As an example, large scale cell-free production of the integral membrane protein EmrE multidrug transporter is described by Chang G. el. al., Science 310:1950-3 (2005). Other commercially available cell-free expression systems include the Expressway™ Cell-Free Expression Systems (Invitrogen) which utilize an *E. coli*-based in-vitro system for efficient, coupled transcription and translation reactions to produce up to milligram quantities of active recombinant protein in a tube reaction format; the Rapid Translation System (RTS) (Roche Applied Science) which also uses an *E. coli*-based in-vitro system; and the TNT Coupled Reticulocyte Lysate Systems (Promega) which uses a rabbit reticulocyte-based in-vitro system.

Applications of Optical Voltage Sensors

Provided herein are areas in which an improved optical voltage indicator can be applied both in commercial and scientific endeavors.

Drug Screens

A recent article reported that "Among the 100 top-selling drugs, 15 are ion-channel modulators with a total market value of more than \$15 billion." (Molokanova, E. & Savchenko, A. *Drug Discov. Today* 13, 14-22 (2008)). However, searches for new ion-channel modulators are limited by the absence of good indicators of membrane potential (Przybylo, M., et al. *J. Fluoresc.*, 1-19 (2010)). In some embodiments, the optical sensors described herein are used to measure or monitor membrane potential changes in response to a candidate ion channel modulator. Such screening methods can be performed in a high throughput manner by simultaneously screening multiple candidate ion channel modulators in cells.

Stem Cells

Many genetically determined diseases of the nervous system and heart lack good animal models. In some embodiments, the optical sensors described herein are expressed in stem cells, either induced pluripotent or stem cells isolated from cord blood or amniotic fluid, or embryonic stem cells derived from humans or fetuses known to carry or be affected with a genetic defect. In some embodiments, the embryonal stem cells are of non-human origin. Alternatively the optical sensors are expressed in progeny of the stem cells, either progenitor cells or differentiated cell types, such as cardiac or neuronal cells. Expression of voltage indicators in these cell types provides information on the electrophysiology of these cells and the response of membrane potential to candidate agents or to changes in ambient conditions (e.g. anoxia). Additionally, expression of voltage indicators in stem cells enables studies of the differentiation and development of stem cells into electrically active cell types and tissues.

The genetic defect may be a single gene alteration, or a deletion, insertion, duplication or a rearrangement or one or more nucleic acids, including large chromosomal alterations.

Stem cells may be isolated and manipulated according to methods known to one skilled in the art. Patents describing methods of making and using, e.g., primate embryonic stem cells are described in, e.g., U.S. Pat. Nos. 7,582,479; 6,887,706; 6,613,568; 6,280,718; 6,200,806; and 5,843,780. Additionally, for example, human cord blood derived unrestricted somatic stem cells are described in U.S. Pat. No. 7,560,280 and progenitor cells from wharton's jelly of human umbilical cord in U.S. Pat. No. 7,547,546.

Induced pluripotent stem cells may be produced by methods described, for example, in U.S. Patent Application Publication No. 20110200568, European Patent Application Publication No. 01970446, and U.S. Paten Application Publication No. US2008/0233610. Additional methods for making and using induced pluripotent stem cells are also described in application U.S. Ser. No. 10/032,191, titled "Methods for cloning mammals using reprogrammed donor chromatin or donor cells," and Ser. No. 10/910,156, "Methods for altering cell fate." These patent applications relate to technology to alter the state of a cell, such as a human skin cell, by exposing the cell's DNA to the cytoplasm of another reprogramming cell with differing properties. Detailed description of the reprogramming factors used in making induced pluripotent stem cells, including expression of genes OCT4, SOX2, NANOG, cMYC, LIN28 can also be found, for example, in PCT/US2006/030632.

Methods for differentiating stem cells or pluripotent cells into differentiated cells are also well known to one skilled in the art.

Brain Imaging

The human brain functions by sending electrical impulses along its ~$10^{11}$ neurons. These patterns of firing are the origin of every human thought and action. Yet there is currently no good way to observe large-scale patterns of electrical activity in an intact brain (Baker, B. J. et al. *J. Neurosci. Methods* 161, 32-38 (2007); Baker, B. J. et al. *Brain Cell Biology* 36, 53-67 (2008)).

An improved optical voltage sensor can lead to unprecedented insights in neuroscience. The device can allow mapping of brain activity in patients and/or cells of patients with psychiatric and neurological diseases, and in victims of traumatic injuries or animal models modeling such diseases and injuries.

Optical imaging of neuronal activity can also form the basis for improved brain-machine interfaces for people with disabilities. For imaging in the brain, the optical sensor is administered by direct injection into the site to be analyzed (with or without accompanying electroporation) or the optical sensor is delivered using a viral vector. Alternatively the optical sensor may be administered through the formation of a transgenic organism, or through application of the Cre-Lox recombination system.

Microbiology

Bacteria are host to dozens of ion channels of unknown function (Martinac, B., et al. *Physiol. Rev.* 88, 1449 (2008)). Most bacteria are too small for direct electrophysiological measurements, so their electrical properties are almost entirely unknown.

Upon expressing PROPS in *E. coli*, it was found that *E. coli* undergo a previously unknown electrical spiking behavior. The data described herein in the Examples section is the first report of spontaneous electrical spiking in any bacterium. This result establishes the usefulness of voltage sensors in microbes.

Furthermore, we found that electrical spiking in *E. coli* is coupled to efflux of a cationic membrane permeable dye. It is thus plausible that electrical spiking is correlated to efflux of other cationic compounds, including antibiotics. Optical voltage indicators may prove useful in screens for inhibitors of antibiotic efflux.

Optical voltage sensors will unlock the electrophysiology of the millions of species of microorganisms which have proven too small to probe via conventional electrophysiology. This information will be useful for understanding the physiology of bacteria with medical, industrial, and ecological applications.

Mitochondria and Metabolic Diseases

Mitochondria are membrane-bound organelles which act as the ATP factories in eukaryotic cells. A membrane voltage powers the mitochondrial ATP synthase. Dysfunction of mitochondria has been implicated in a variety of neurodegenerative diseases, diabetes, cancer, cardiovascular disease, and aging. Thus there is tremendous interest in measuring mitochondrial membrane potential in vivo, although currently available techniques are severely limited (Verburg, J. & Hollenbeck, P. J. *J. Neurosci.* 28, 8306 (2008); Ichas, F., et al. *Cell* 89, 1145-1154 (1997); Johnson, L. V., et al. *Proc. Natl. Acad. Sci. U.S.A.* 77, 990 (1980)).

The exemplary optical voltage sensor described herein (PROPS) can be tagged with peptide sequences that direct it to the mitochondrial inner membrane (Hoffmann, A., et al. *Proc. Nat. Acad. Sci. U.S.A.* 91, 9367 (1994)) or the mitochondrial outer membrane, where it serves as an optical indicator of mitochondrial membrane potential.

Imaging in Human Cells and Vertebrate Models (e.g., Rat, Mouse, Zebrafish)

Figure 1:
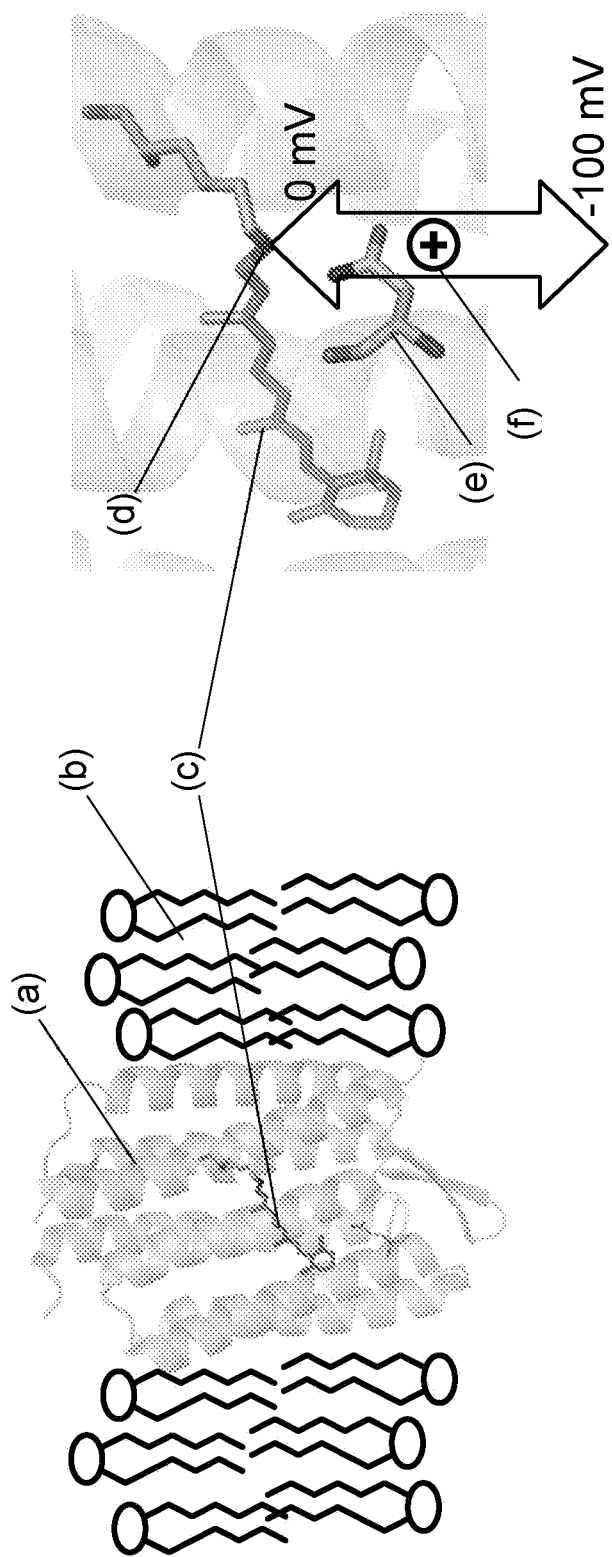
FIG. 1 shows a mechanism of voltage sensitivity in the D97N mutant of Green Proteorhodopsin. Left: Green Proteorhodopsin (a) spans a lipid bilayer membrane (b). Right: Close-up showing a chromophore, retinal (c), covalently linked to the protein backbone via a Schiff Base (d). Aspartic acid 97 in the wild-type structure has been mutated to asparagine (e) to decrease the pKa of the Schiff Base from the wild-type value of >12 to the value 9.8 and to eliminate the proton-pumping photocycle. A change in the voltage drop across the membrane changes the local electrochemical potential for a proton (f) to reside on the Schiff Base, and thereby changes the acid-base equilibrium. The absorption spectrum and fluorescence of the retinal depend on the state of protonation of the Schiff Base: the protonated form is fluorescent, the deprotonated form is not. The voltage across the membrane is determined by measuring the fluorescence.
Figure 2A:
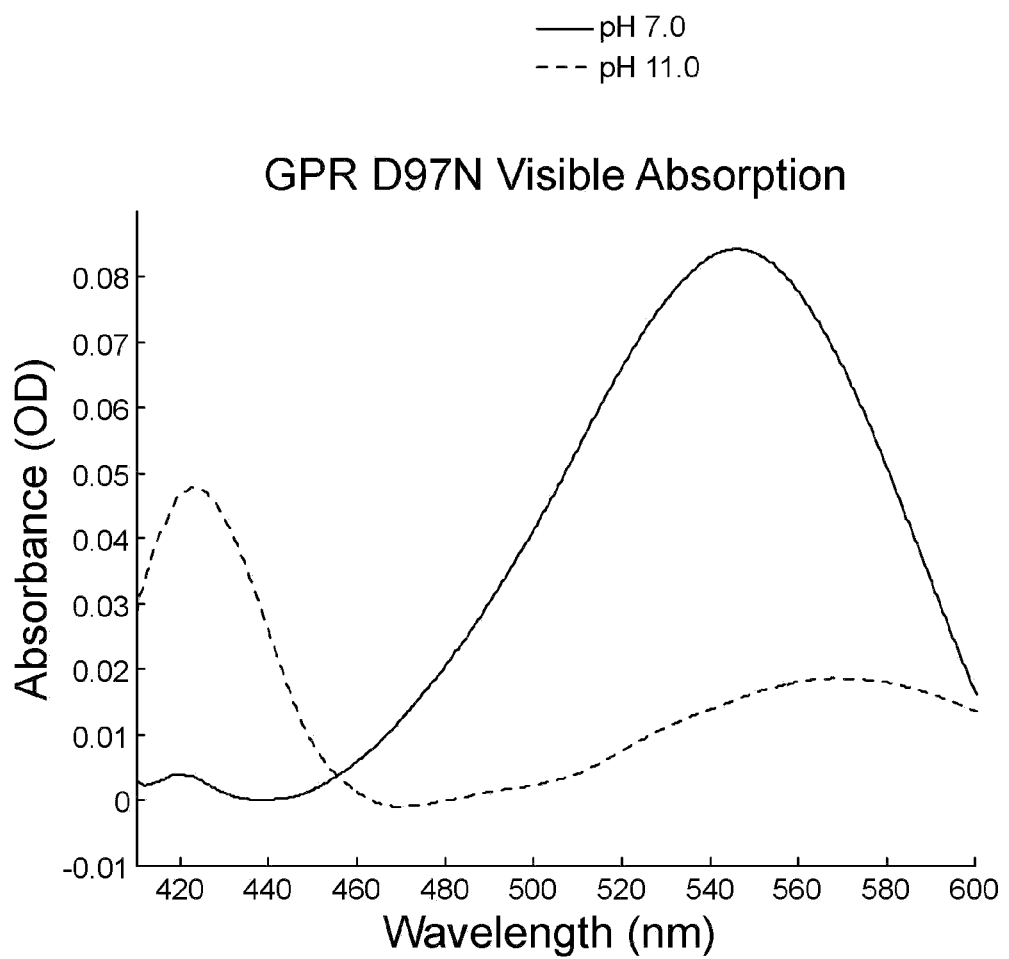
FIGS. 2A-2D show that GPR D97N is a transmembrane protein that shows highly photostable and environmentally sensitive fluorescence. *E. Coli* cells expressing GPR D97N were excited at a wavelength of 633 nm and imaged via fluorescence emission of GPR D97N between 660-760 nm. The protein is localized in the cell periphery as expected for a transmembrane protein.
Figure 2B:
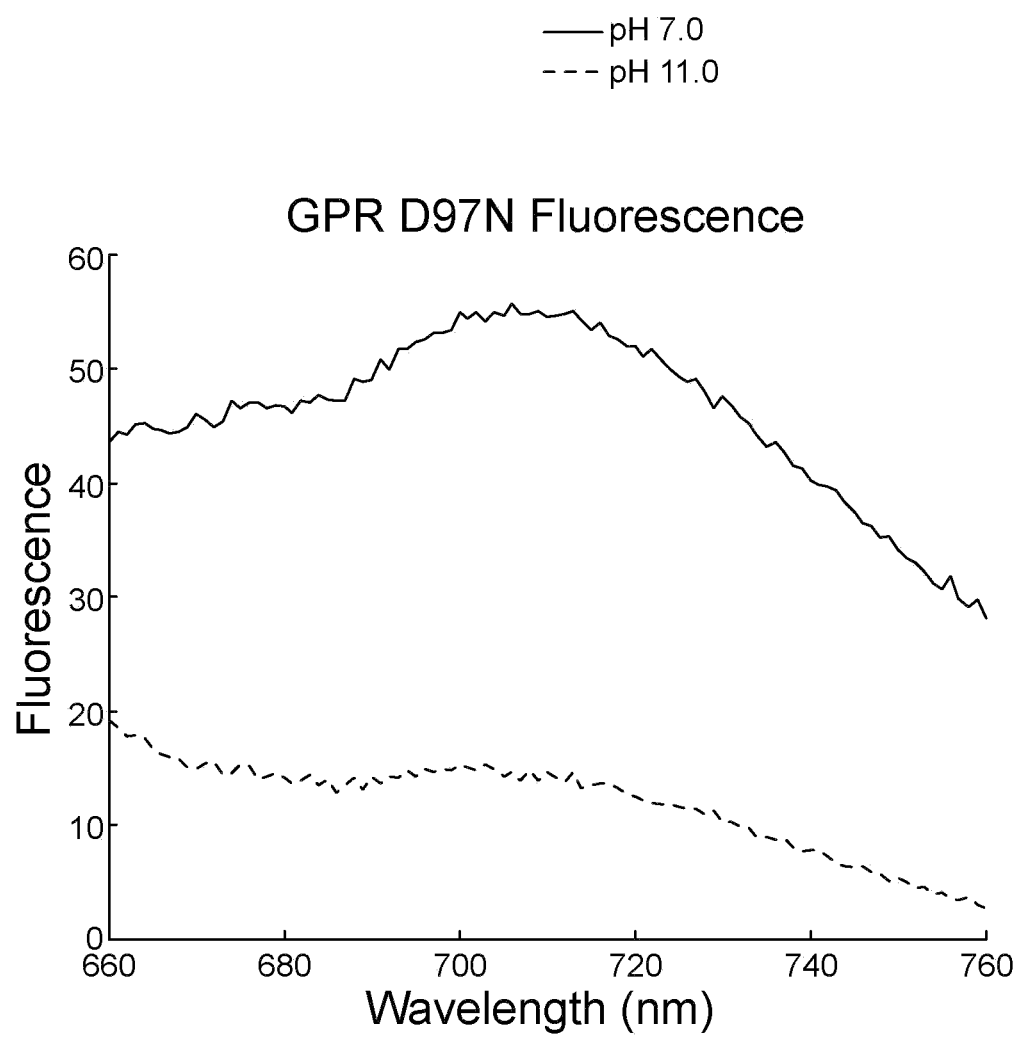
Figure 2C:
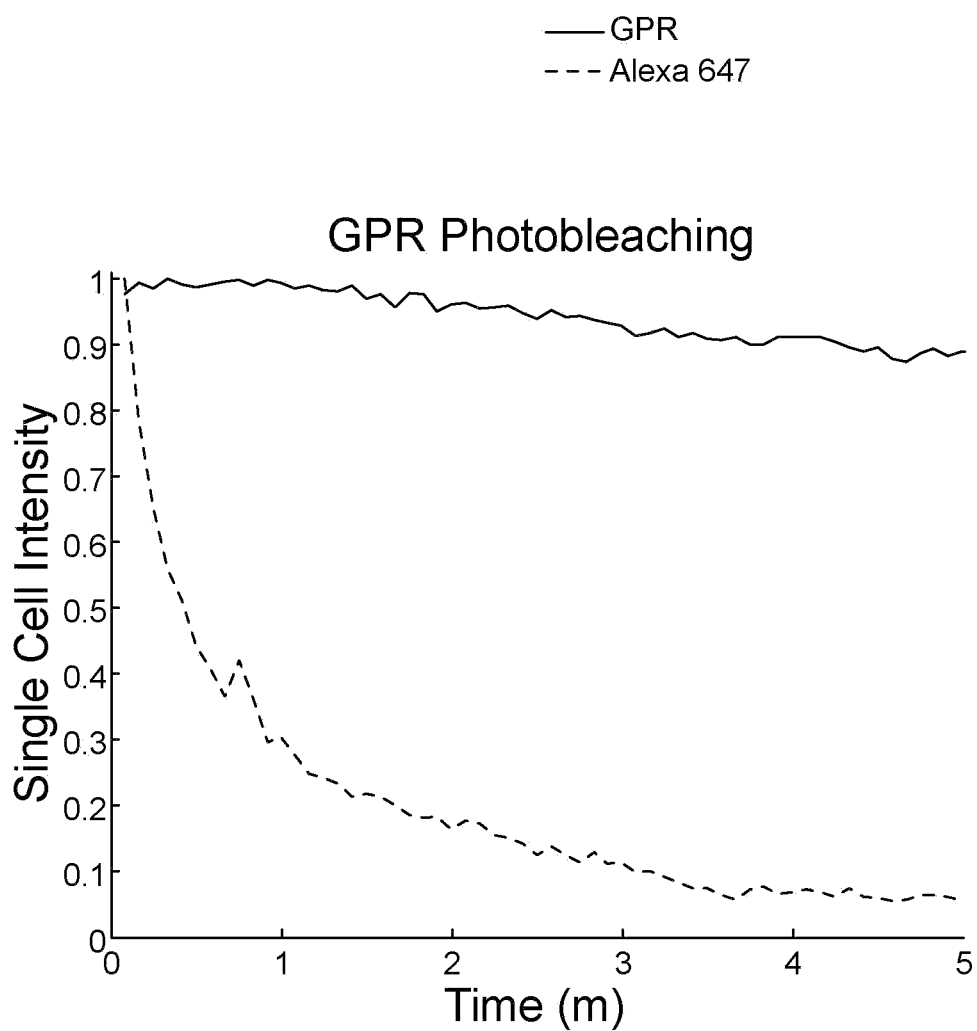
Figure 2D:
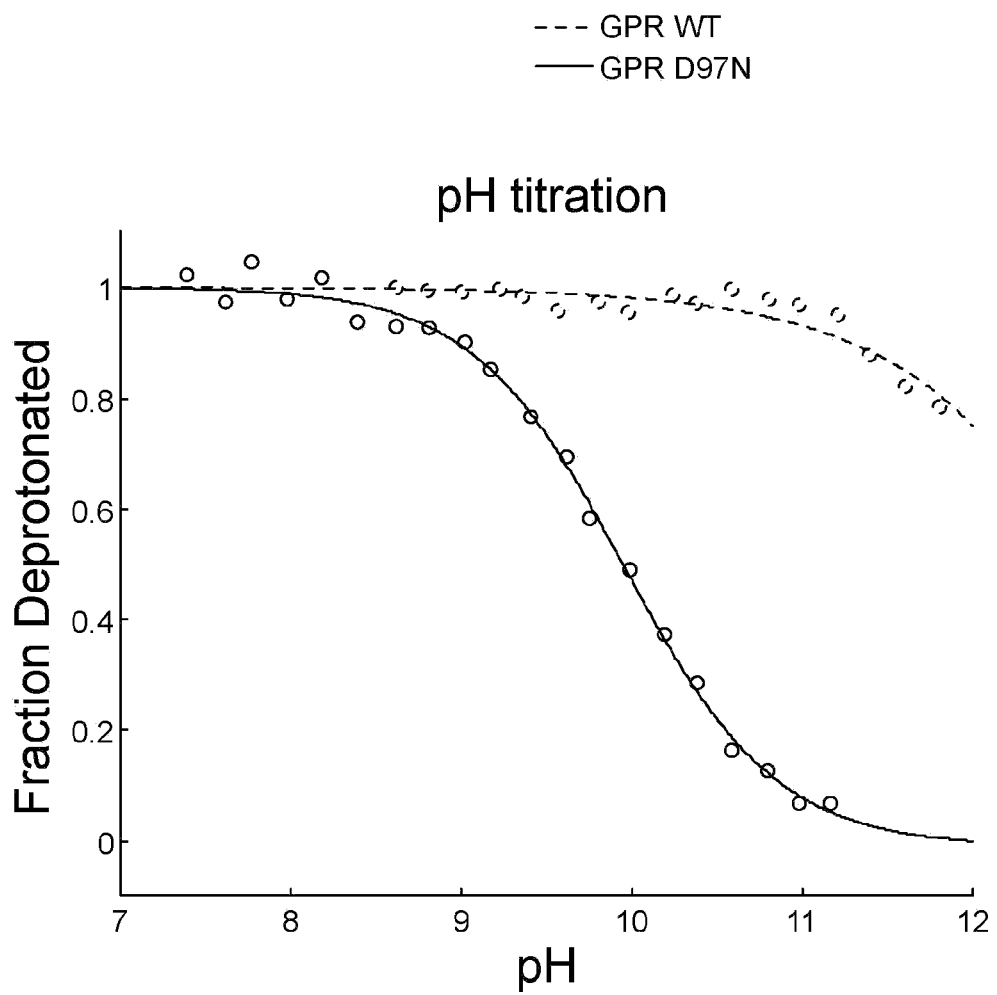
Figure 3:
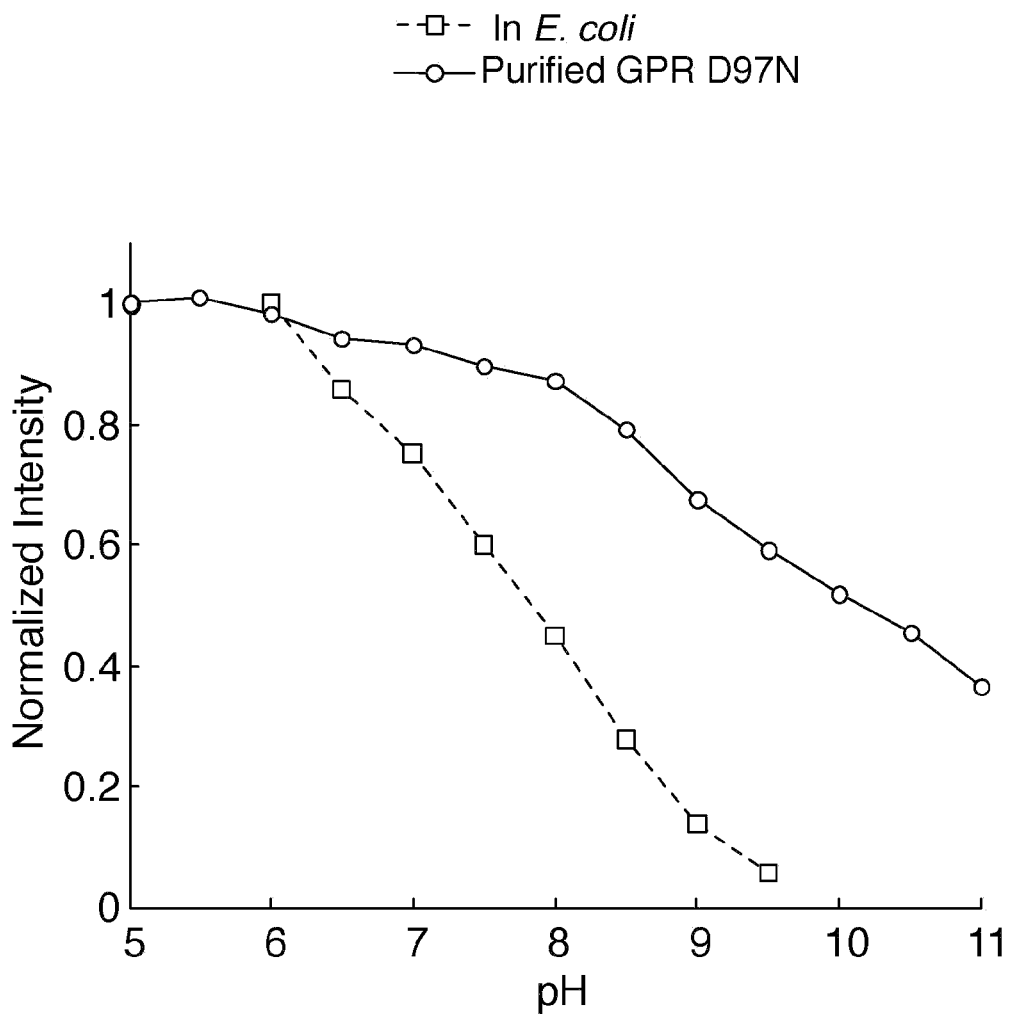
FIG. 3 shows fluorescence brightness of GPR D97N as a function of pH in vivo and in vitro. In both cases the fluorescence decreases at high pH due to the deprotonation of the Schiff Base. The pKa in *E. coli* is measured in cells whose membrane has been made permeable to protons via addition of Carbonyl cyanide 3-chlorophenylhydrazone (CCCP). This treatment is necessary because the proton binds to the Schiff Base from the cytoplasmic side and in the absence of CCCP the cells maintain a nearly constant cytoplasmic pH in the presence of swings in the external pH. The pKa in the cells and in the purified protein differ due to the local environmental effects in the cell.
Figure 4A:
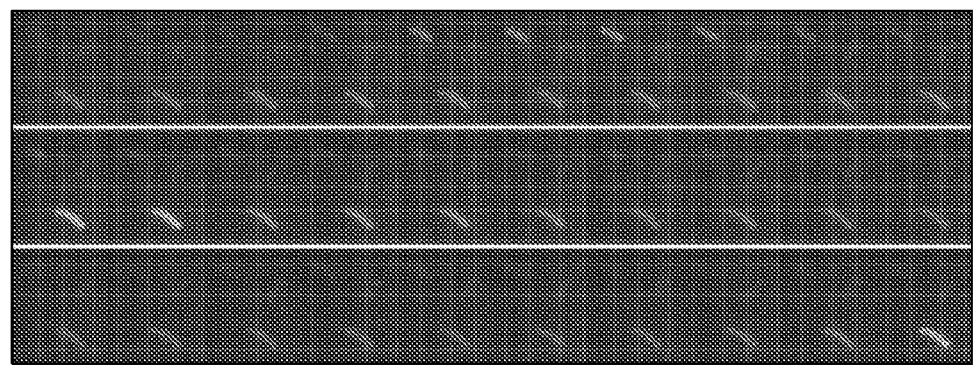
FIGS. 4A and 4B show fluorescence blinking in *E. coli* expressing GPR D97N.
Figure 4B:
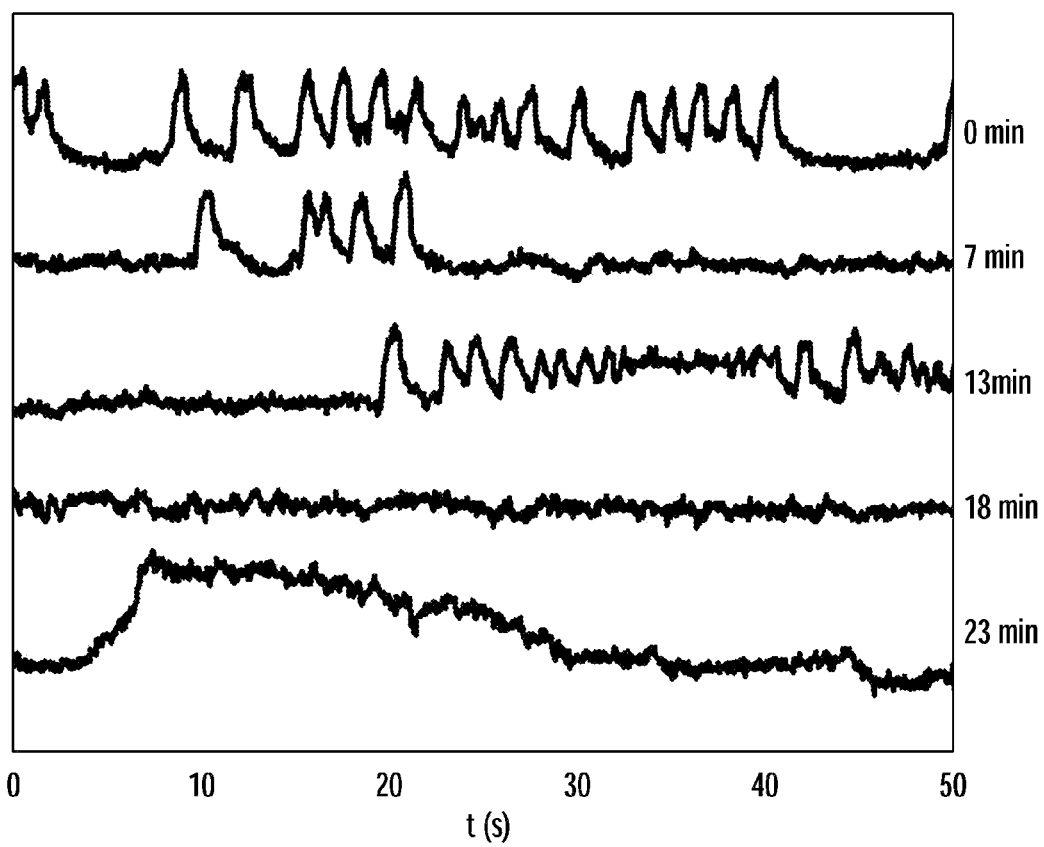
Figure 5:
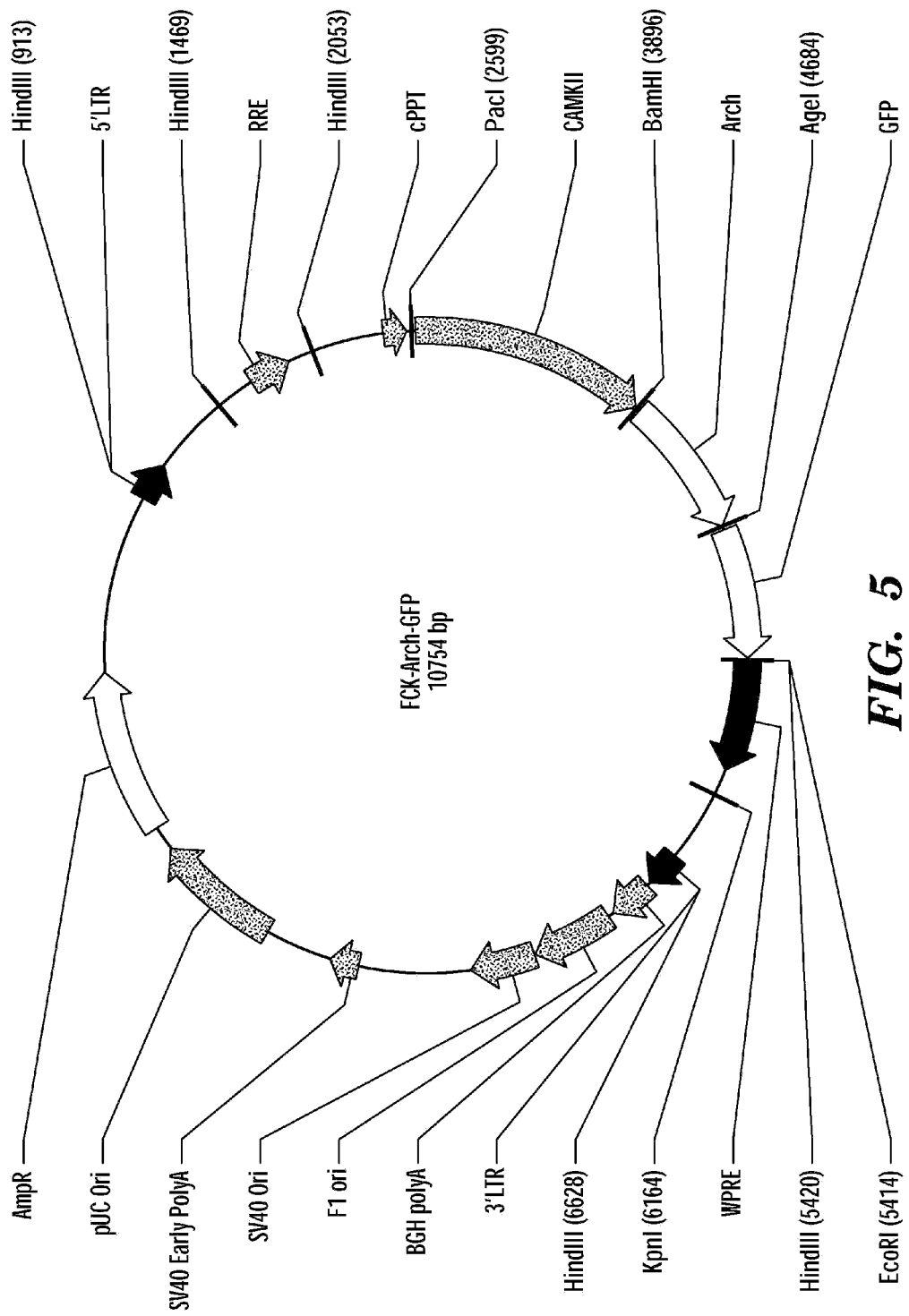
FIG. 5 shows a map of the plasmid containing Archaerhodopsin 3(Arch3, also referred to in some instances herein as Ar-3) as described in the syntheticbiology web site (world wide web at syntheticneurobiology.org/protocols/protocoldetail/36/10).
Figure 6A:
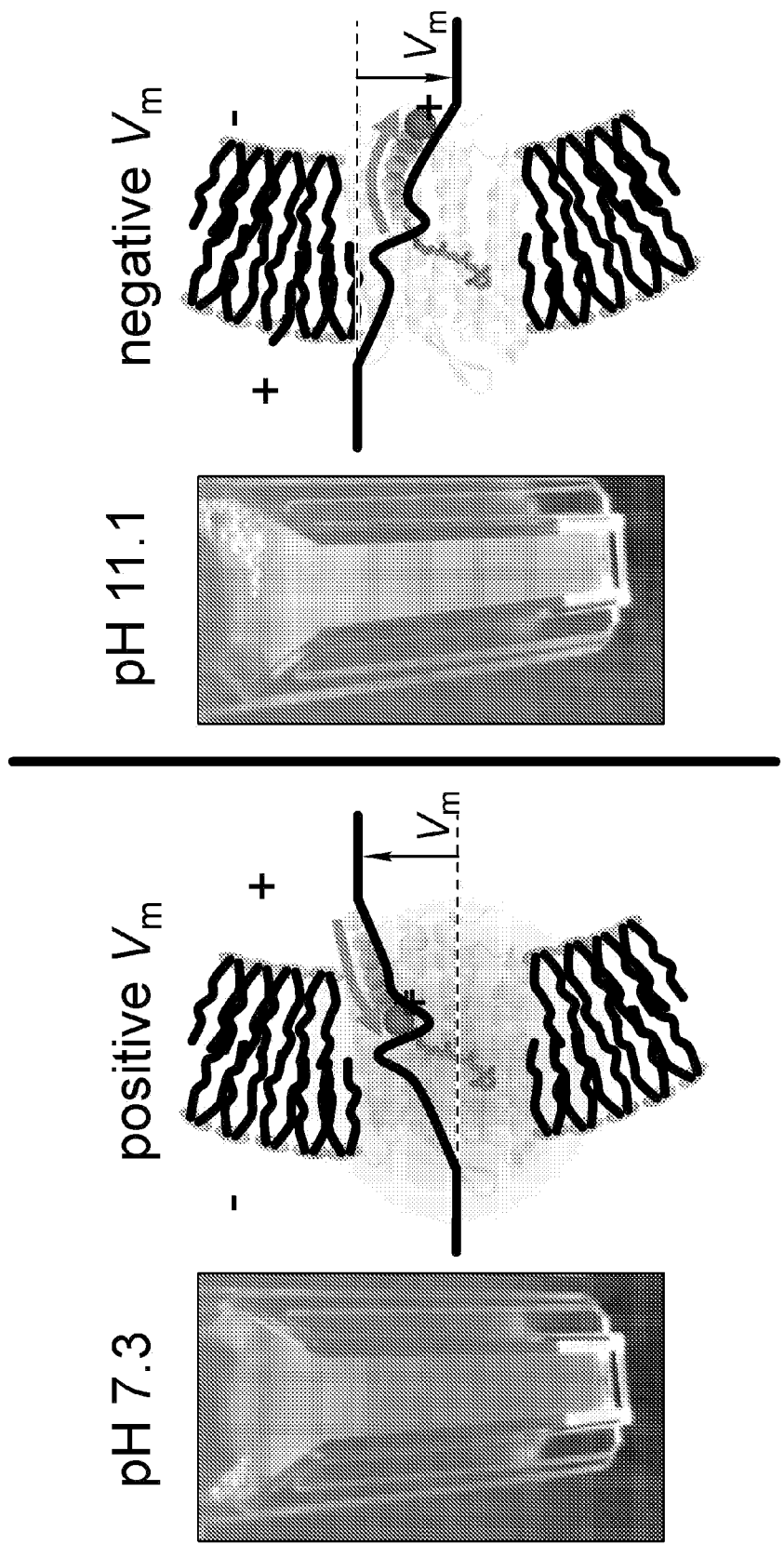
Figure 6C:
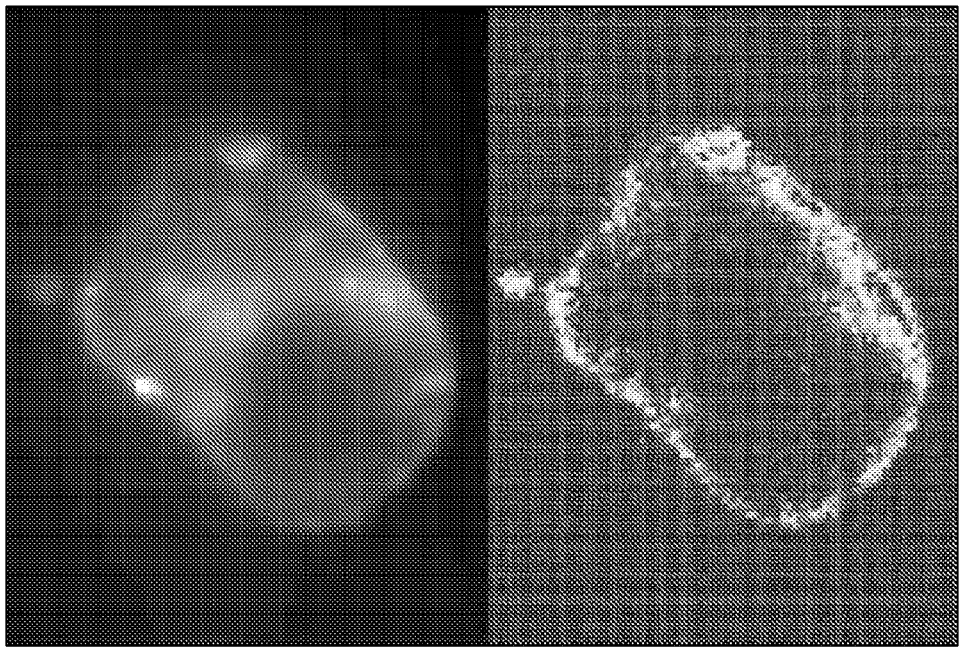

As described in Example 2, we also expressed Arch 3 in HEK293T cells. Fluorescence of Arch 3 in HEK 293T cells was readily imaged in an inverted fluorescence microscope with red illumination ($\lambda$=640 nm, I=540 W/cm2), a high numerical aperture objective, a Cy5 filter set, and an EMCCD camera. The cells exhibited fluorescence predominantly localized to the plasma membrane (FIG. 6C). Cells not expressing Arch 3 were not fluorescent. Cells showed 17% photobleaching over a continuous 10-minute exposure, and retained normal morphology during this interval.

The fluorescence of HEK cells expressing Arch 3 was highly sensitive to membrane potential, as determined via whole-cell voltage clamp. We developed an algorithm to combine pixel intensities in a weighted sum such that the output, was a nearly optimal estimate of membrane potential V determined by conventional electrophysiology. FIG. 6C shows an example of a pixel-weight matrix, indicating that the voltage-sensitive protein was localized to the cell membrane; intracellular Arch 3 contributed fluorescence but no voltage-dependent signal. The fluorescence increased by a factor of 2 between −150 mV and +150 mV, with a nearly linear response throughout this range (FIG. 6D). The response of fluorescence to a step in membrane potential occurred within the 500 µs time resolution of our imaging system on both the rising and falling edge (FIG. 6E). Application of a sinusoidally varying membrane potential led to sinusoidally varying fluorescence; at f=1 kHz, the fluorescence oscillations retained 55% of their low-frequency amplitude (FIG. 18). Arch 3 reported voltage steps as small as 10 mV, with an accuracy of 625 µV/(Hz)$^{1/2}$ over timescales<12 s (FIG. 19).

Figure 7A:
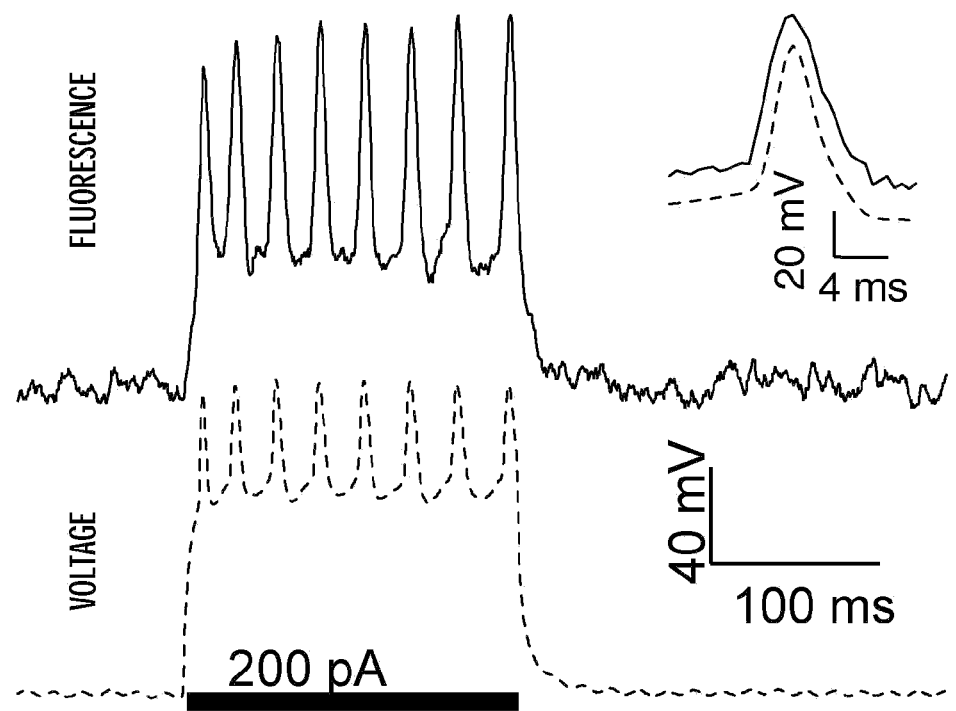
FIGS. 7A-7D show optical recording of action potentials with Arch3 WT. Cultured rat hippocampal neuron expressing Arch-GFP were imaged via fluorescence of GFP. Arch fluorescence was shown in cyan and regions of voltage-dependent fluorescence were shown in red.
Figure 7B:
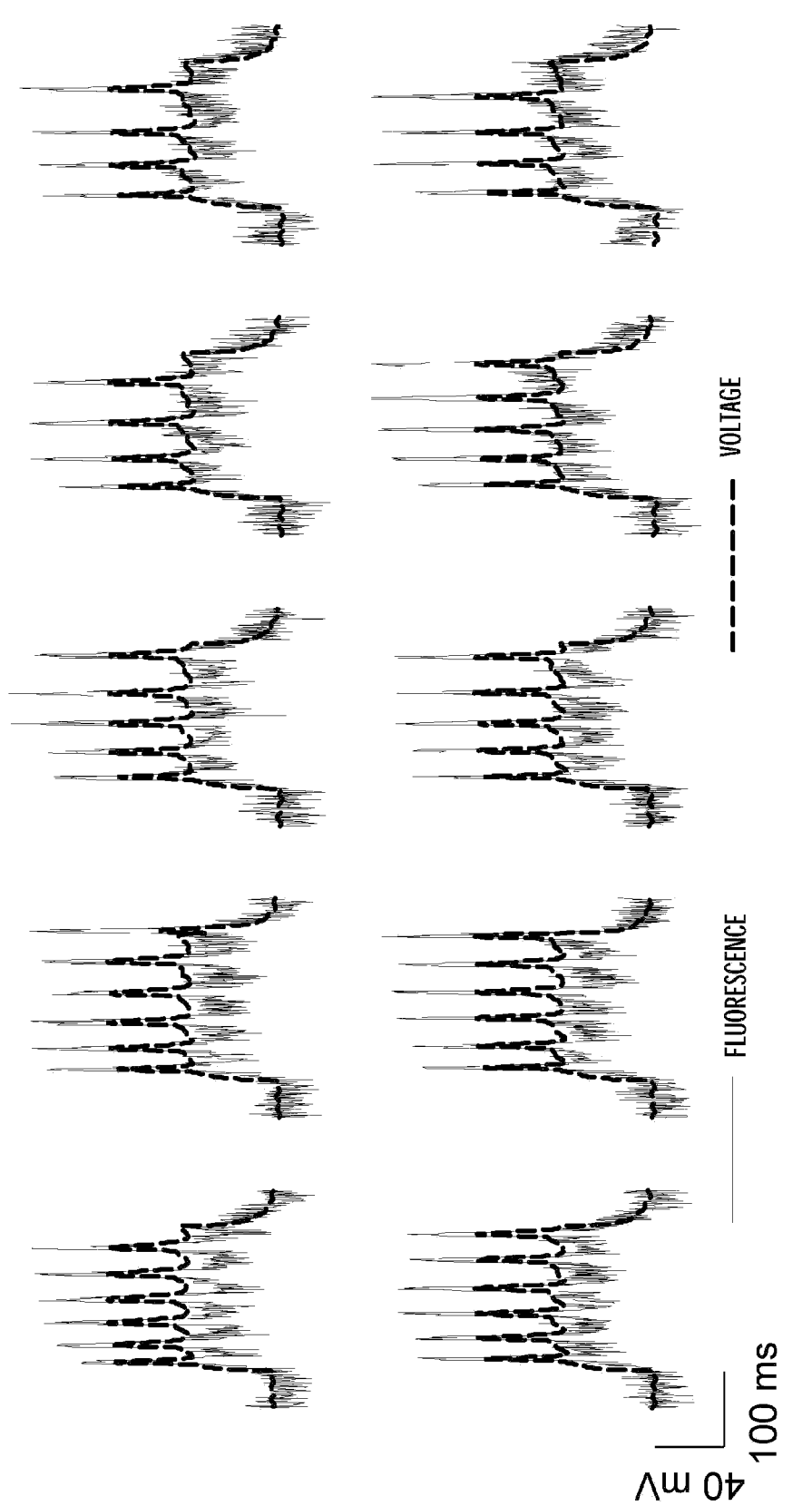

We tested Arch 3 as a voltage indicator in cultured rat hippocampal neurons, using viral delivery. Neurons expressing Arch 3 showed voltage-dependent changes in fluorescence localized to the cell membrane. Under whole cell current clamp, cells exhibited spiking upon injection of current pulses of 200 pA. Individual spikes were accompanied by clearly identifiable increases of fluorescence (FIG. 7A). At a 2 kHz image acquisition rate, the signal-to-noise ratio in the fluorescence (spike amplitude:baseline noise) was 10.5. A spike-finding algorithm correctly identified 99.6% of the spikes (based on comparison to simultaneously recorded membrane potential), with a false-positive rate of 0.7% (n=269 spikes) (FIG. 7B). Single cells were observed for up to 4 minutes of cumulative exposure, with no detectable change in resting potential or spike frequency.

Figure 7C:
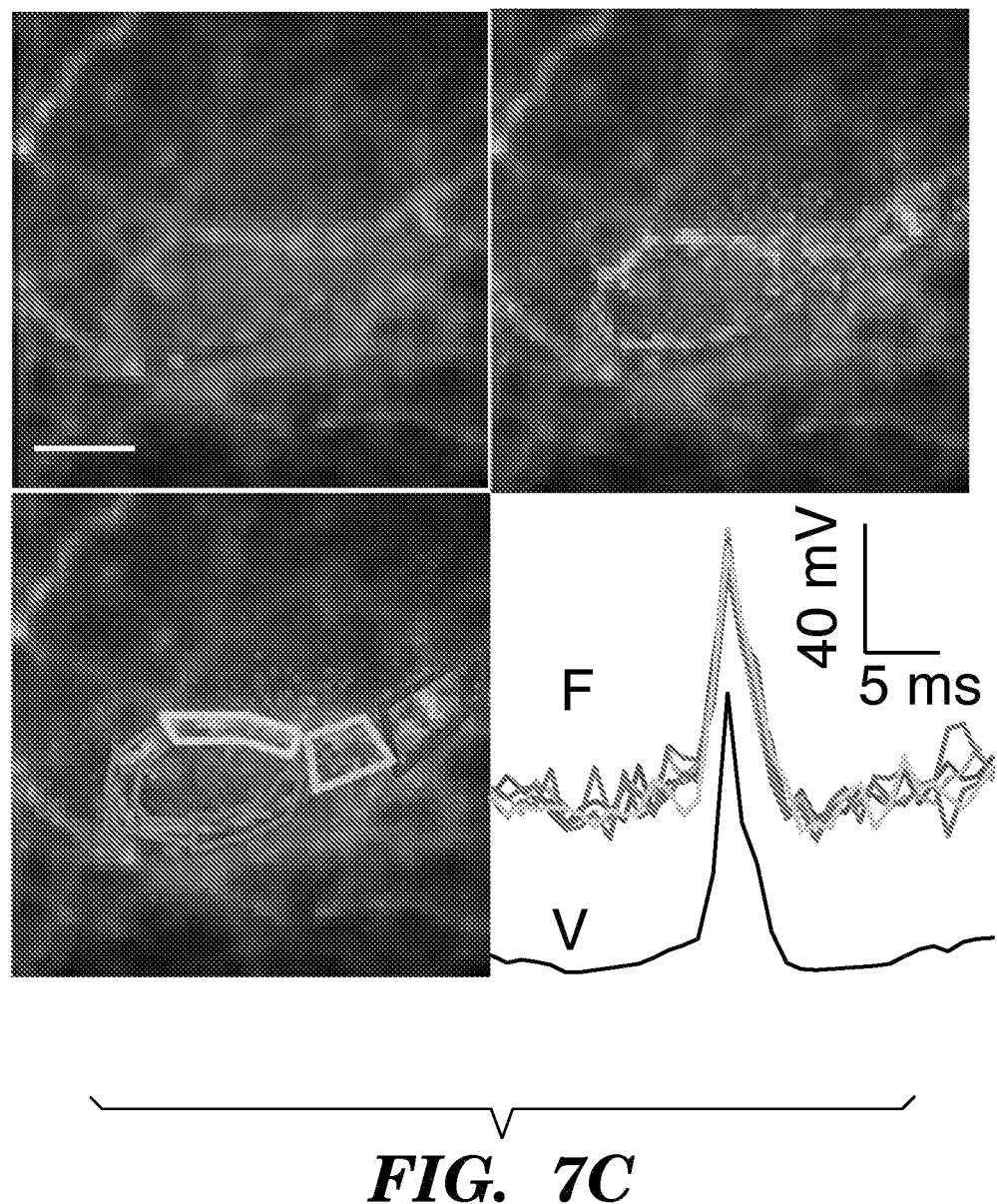
Figure 7D:
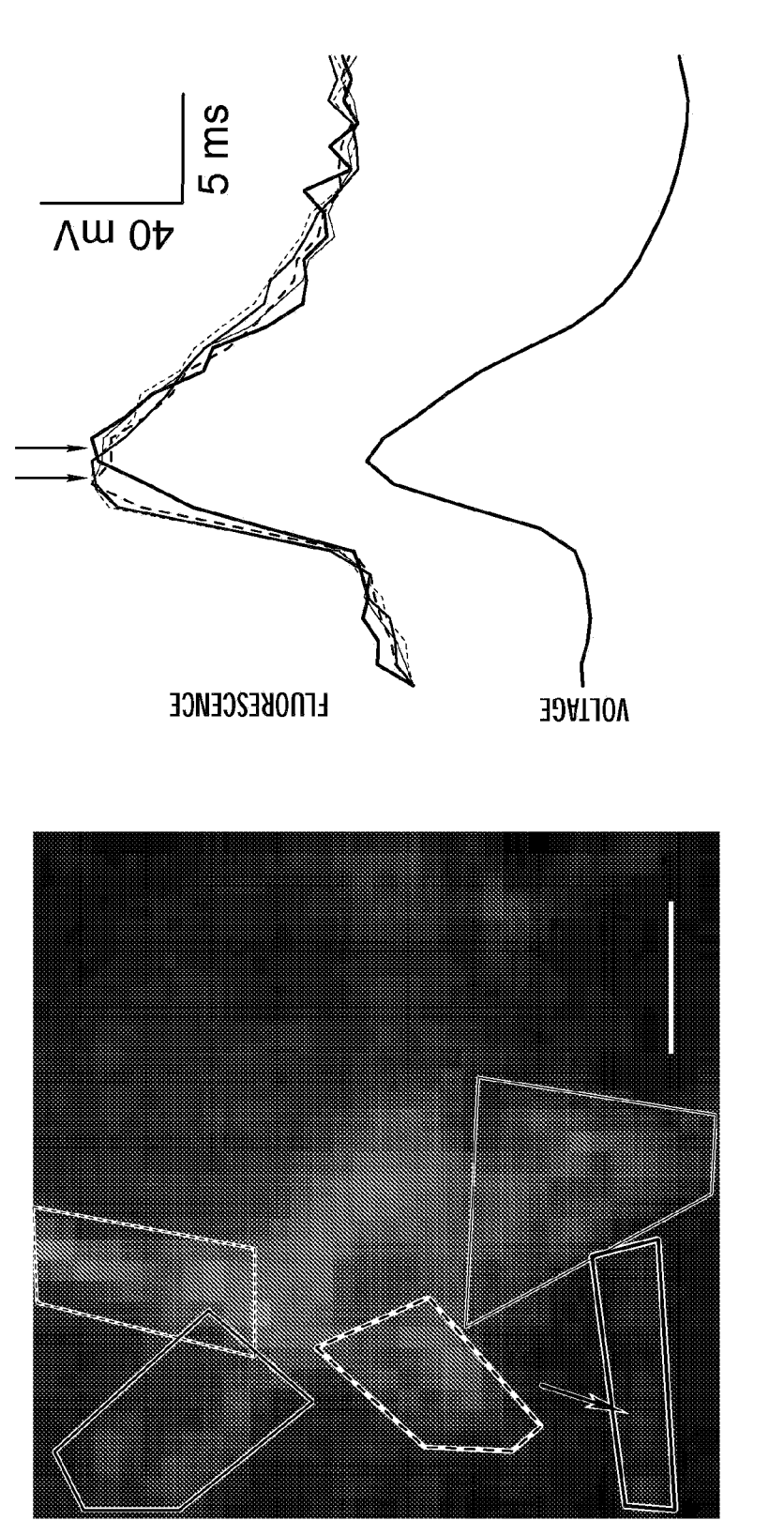

We imaged the dynamics of action potentials with subcellular resolution by averaging multiple temporally registered movies of single spikes (FIG. 7C). In and near the soma, the optically determined waveform of the action potential was uniform and matched the electrically recorded waveform. However in very thin processes the peak of the action potential lagged by up to 1 ms (FIG. 7D). These observations are consistent with multiple-patch recordings on single neurons (Stuart, G. J. & Sakmann, B. Active propagation of somatic action potentials into neocortical pyramidal cell dendrites. *Nature* 367, 69-72 (1994)); but such recordings are technically demanding and only probe the variation in membrane potential at a small number of points. We show that Arch 3 may be used to map intracellular dynamics of action potentials. Similarly, other archaerhodopsins can be expected to work in a eukaryotic cell as membrane potential indicators.

Thus, using a model system of Arch 3, we showed that the membrane potential of a mammalian cell can be detected using archaerhodopsins and modified archaerhodopsins.

Gene Delivery Methods

The nucleic acids encoding the microbial rhodopsin proteins of the invention are introduced to the cell or organ or organism of interest uding routine gene delivery methods. are administered to a subject for the purpose of imaging membrane potential changes in cells of a subject. In one embodiment, the optical sensors are introduced to the cell via expression vectors.

The various gene delivery methods currently being applied to stem cell engineering include viral and non viral vectors, as well as biological or chemical methods of transfection. The methods can yield either stable or transient gene expression in the system used.

Viral Gene Delivery Systems

Because of their high efficiency of transfection, genetically modified viruses have been widely applied for the delivery of genes into stem cells.

DNA Virus Vectors (i) Adenovirus

Adenoviruses are double stranded, nonenveloped and icosahedral viruses containing a 36 kb viral genome (Kojaoghlanian et al., 2003). Their genes are divided into early (E1A, E1B, E2, E3, E4), delayed (IX, IVa2) and major late (L1, L2, L3, L4, L5) genes depending on whether their expression occurs before or after DNA replication. More than 51 human adenovirus serotypes have been described which can infect and replicate in a wide range of organs. The viruses are classified into the following subgroups: A—induces tumor with high frequency and short latency, B—are weakly oncogenic, and C—are non-oncogenic (Cao et al., 2004; Kojaoghlanian et al., 2003).

These viruses have been used to generate a series of vectors for gene transfer cellular engineering. The initial generation of adenovirus vectors were produced by deleting the E1 gene (required for viral replication) generating a vector with a 4 kb cloning capacity. An additional deletion of E3 (responsible for host immune response) allowed an 8 kb cloning capacity (Bett et al., 1994; Danthinne and Imperiale, 2000; Danthinne and Werth, 2000). The second generation of vectors was produced by deleting the E2 region (required for viral replication) and/or the E4 region (participating in inhibition of host cell apoptosis) in conjunction with E1 or E3 deletions. The resultant vectors have a cloning capacity of 10-13 kb (Armentano et al., 1995). The third "gutted" generation of vectors was produced by deletion of the entire viral sequence with the exception of the inverted terminal repeats (ITRs) and the cis acting packaging signals. These vectors have a cloning capacity of 25 kb (Kochanek et al., 2001) and have retained their high transfection efficiency both in quiescent and dividing cells.

Importantly, the adenovirus vectors do not normally integrate into the genome of the host cell, but they have shown efficacy for transient gene delivery into adult stem cells. These vectors have a series of advantages and disadvantages. An important advantage is that they can be amplified at high titers and can infect a wide range of cells (Benihoud et al., 1999; Kanerva and Hemminki, 2005). The vectors are generally easy to handle due to their stability in various storing conditions. Adenovirus type 5 (Ad5) has been successfully used in delivering genes in human and mouse stem cells (Smith-Arica et al., 2003). The lack of adenovirus integration into host cell genetic material can in many instances be seen as a disadvantage, as its use allows only transient expression of the therapeutic gene.

The following provides examples to show that a skilled artisan can readily transducer cells with contructs expressing microbial rhodopsins of the present invention to eukaryotic, such as mammalian cells. For example in a study evaluating the capacity of mesenchymal stem cells to undergo chondrogenesis when TGF-beta1 and bone morphogenic protein-2 (BMP-2) were delivered by adenoviral-mediated expression, the chondrogenesis was found to closely correlated with the level and duration of the transiently expressed proteins. Transgene expression in all aggregates was highly transient, showing a marked decrease after 7 days. Chondrogenesis was inhibited in aggregates modified to express >100 ng/ml TGF-beta1 or BMP-2; however, this was partly due to the inhibitory effect of exposure to high adenoviral loads (Mol. Ther. 2005 August; 12 (2):219-28. Gene-induced chondrogenesis of primary mesenchymal stem cells in vitro. Palmer G D, Steinert A, Pascher A, Gouze E, Gouze J N, Betz O, Johnstone B, Evans C H, Ghivizzani S C). In a second model using rat adipose derived stem cells transduced with adenovirus carrying the recombinant human bone morphogenic protein-7 (BMP-7) gene showed promising results for an autologous source of stem cells for BMP gene therapy. However, activity assessed by measuring alkaline phosphatase in vitro was transient and peaked on day 8. Thus the results were similar to those found in the chondrogenesis model (Cytotherapy. 2005; 7 (3):273-81).

Thus for experiments that do not require stable gene expression adenovirus vectors is a good option.

Adenovirus vectors based on Ad type 5 have been shown to efficiently and transiently introduce an exogenous gene via the primary receptor, coxsackievirus, and adenovirus receptor (CAR). However, some kinds of stem cells, such as MSC and hematopoietic stem cells, cannot be efficiently transduced with conventional adenovirus vectors based on Ad serotype 5 (Ad5), because of the lack of CAR expression. To overcome this problem, fiber-modified adenovirus vectors and an adenovirus vector based on another serotype of adenovirus have been developed. (Mol. Pharm. 2006 March-April; 3 (2):95-103. Adenovirus vector-mediated gene transfer into stem cells. Kawabata K, Sakurai F, Koizumi N, Hayakawa T, Mizuguchi H. Laboratory of Gene Transfer and Regulation, National Institute of Biomedical Innovation, Osaka 567-0085, Japan).

Such modifications can be readily applied to the use of the microbial rhodopsin constructs described herein, particularly in the applications relating to stem cells.

(ii) Adeno-Associated Virus

Adeno-Associated viruses (AAV) are ubiquitous, noncytopathic, replication-incompetent members of ssDNA animal virus of parvoviridae family (G. Gao et al., New recombinant serotypes of AAV vectors. Curr Gene Ther. 2005 June; 5 (3):285-97). AAV is a small icosahedral virus with a 4.7 kb genome. These viruses have a characteristic termini consisting of palindromic repeats that fold into a hairpin. They replicate with the help of helper virus, which are usually one of the many serotypes of adenovirus. In the absence of helper virus they integrate into the human genome at a specific locus (AAVS1) on chromosome 19 and persist in latent form until helper virus infection occurs (Atchison et al., 1965, 1966). AAV can transduce cell types from different species including mouse, rat and monkey. Among the serotypes, AAV2 is the most studied and widely applied as a gene delivery vector. Its genome encodes two large opening reading frames (ORFs) rep and cap. The rep gene encodes four proteins Rep 78, Rep 68, Rep 52 and Rep 40 which play important roles in various stages of the viral life cycle (e.g. DNA replication, transcriptional control, site specific integration, accumulation of single stranded genome used for viral packaging). The cap gene encodes three viral capsid proteins VP1, VP2, VP3 (Becerra et al., 1988; Buning et al., 2003). The genomic 3' end serves as the primer for the second strand synthesis and has terminal resolution sites (TRS) which serve as the integration sequence for the virus as the sequence is identical to the sequence on chromosome 19 (Young and Samulski, 2001; Young et al., 2000).

These viruses are similar to adenoviruses in that they are able to infect a wide range of dividing and non-dividing cells. Unlike adenovirus, they have the ability to integrate into the host genome at a specific site in the human genome. Unfortunately, due to their rather bulky genome, the AAV vectors have a limited capacity for the transfer of foreign gene inserts (Wu and Ataai, 2000).

RNA Virus Vectors (i) Retroviruses

Retroviral genomes consist of two identical copies of single stranded positive sense RNAs, 7-10 kb in length coding for three genes; gag, pol and env, flanked by long terminal repeats (LTR) (Yu and Schaffer, 2005). The gag gene encodes the core protein capsid containing matrix and nucleocapsid elements that are cleavage products of the gag precursor protein. The pol gene codes for the viral protease, reverse transcriptase and integrase enzymes derived from gag-pol precursor gene. The env gene encodes the envelop glycoprotein which mediates viral entry. An important feature of the retroviral genome is the presence of LTRs at each end of the genome. These sequences facilitate the initiation of viral DNA synthesis, moderate integration of the proviral DNA into the host genome, and act as promoters in regulation of viral gene transcription. Retroviruses are subdivided into three general groups: the oncoretroviruses (Maloney Murine Leukenmia Virus, MoMLV), the lentiviruses (HIV), and the spumaviruses (foamy virus) (Trowbridge et al., 2002).

Retroviral based vectors are the most commonly used integrating vectors for gene therapy. These vectors generally have a cloning capacity of approximately 8 kb and are generated by a complete deletion of the viral sequence with the exception of the LTRs and the cis acting packaging signals.

The retroviral vectors integrate at random sites in the genome. The problems associated with this include potential insertional mutagenesis, and potential oncogenic activity driven from the LTR. The U3 region of the LTR harbors promoter and enhancer elements, hence this region when deleted from the vector leads to a self-inactivating vector where LTR driven transcription is prevented. An internal promoter can then be used to drive expression of the transgene.

The initial studies of stem cell gene transfer in mice raised the hope that gene transfer into humans would be equally as efficient (O'Connor and Crystal, 2006). Gene transfer using available retroviral vector systems to transfect multi-lineage long-term repopulating stem cells is still significantly more efficient in the mouse.

(ii) Lentivirus

Lentiviruses are members of Retroviridae family of viruses (M. Scherr et al., Gene transfer into hematopoietic stem cells using lentiviral vectors. Curr Gene Ther. 2002 February; 2 (1):45-55). They have a more complex genome and replication cycle as compared to the oncoretroviruses (Beyer et al., 2002). They differ from simpler retroviruses in that they possess additional regulatory genes and elements, such as the tat gene, which mediates the transactivation of viral transcription (Sodroski et al., 1996) and rev, which mediates nuclear export of unspliced viral RNA (Cochrane et al., 1990; Emerman and Temin, 1986).

Lentivirus vectors are derived from the human immunodeficiency virus (HIV-1) by removing the genes necessary for viral replication rendering the virus inert. Although they are devoid of replication genes, the vector can still efficiently integrate into the host genome allowing stable expression of the transgene. These vectors have the additional advantage of a low cytotoxicity and an ability to infect diverse cell types. Lentiviral vectors have also been developed from Simian, Equine and Feline origin but the vectors derived from Human Immunodeficiency Virus (HIV) are the most common (Young et al., 2006).

Lentivirus vectors are generated by deletion of the entire viral sequence with the exception of the LTRs and cis acting packaging signals. The resultant vectors have a cloning capacity of about 8 kb. One distinguishing feature of these vectors from retroviral vectors is their ability to transduce dividing and non-dividing cells as well as terminally differentiated cells (Kosaka et al., 2004). The lentiviral delivery system is capable of high infection rates in human mesenchymal and embryonic stem cells. In a study by Clements et al., the lentiviral backbone was modified to express mono- and bi-cistronic transgenes and was also used to deliver short hairpin ribonucleic acid for specific silencing of gene expression in human stem cells. (Tissue Eng. 2006 July; 12 (7): 1741-51. Lentiviral manipulation of gene expression in human adult and embryonic stem cells. Clements M O, Godfrey A, Crossley J, Wilson S J, Takeuchi Y, Boshoff C).

Table below summarizes some of the qualities of the viral vectors.

| Vector | Insert capacity (kb) | Tropism | Vector genome form | Expression | Efficiency |
|---|---|---|---|---|---|
| Enveloped | | | | | |
| Retrovirus | 8 | Dividing cells only | Integrated | Stable | High |
| Lentivirus | 8 | Dividing and non-dividing | Integrated | Stable | High |
| Non-enveloped | | | | | |
| Adeno-associated virus | <5 | Dividing and non-dividing | Episomal and integrated | Stable | High |
| Adenovirus | 2-24 | Dividing and non-dividing | Episomal | Transient | High |

Non-Viral Gene Delivery Systems (i) Methods for the Facilitated Integration of Genes In addition to the viral based vectors discussed above, other vector systems that lack viral sequence can be used. The alternative strategies include conventional plasmid transfer and the application of targeted gene integration through the use of integrase or transposase technologies. These represent important new approaches for vector integration and have the advantage of being both efficient, and often site specific in their integration. Currently three recombinase systems are available for genetic engineering: cre recombinase from phage P1 (Lakso et al., 1992; Orban et al., 1992), FLP (flippase) from yeast 2 micron plasmid (Dymecki, 1996; Rodriguez et al., 2000), and an integrase isolated from streptomyces phage I C31 (Ginsburg and Calos, 2005). Each of these recombinases recognize specific target integration sites. Cre and FLP recombinase catalyze integration at a 34 bp palindromic sequence called lox P (locus for crossover) and FRT (FLP recombinase target) respectively. Phage integrase catalyzes site-specific, unidirectional recombination between two short att recognition sites in mammalian genomes. Recombination results in integration when the att sites are present on two different DNA molecules and deletion or inversion when the att sites are on the same molecule. It has been found to function in tissue culture cells (in vitro) as well as in mice (in vivo).

The Sleeping Beauty (SB) transposon is comprised of two inverted terminal repeats of 340 base pairs each (Izsvak et al., 2000). This system directs the precise transfer of specific constructs from a donor plasmid into a mammalian chromosome. The excision and integration of the transposon from a plasmid vector into a chromosomal site is mediated by the SB transposase, which can be delivered to cells as either in a cis or trans manner (Kaminski et al., 2002). A gene in a chromosomally integrated transposon can be expressed over the lifetime of a cell. SB transposons integrate randomly at TA-dinucleotide base pairs although the flanking sequences can influence integration.

Physical Methods to Introduce Vectors into Cells (i) Electroporation

Electroporation relies on the use of brief, high voltage electric pulses which create transient pores in the membrane by overcoming its capacitance. One advantage of this method is that it can be utilized for both stable and transient gene expression in most cell types. The technology relies on the relatively weak nature of the hydrophobic and hydrophilic interactions in the phospholipid membrane and its ability to recover its original state after the disturbance. Once the membrane is permeabilized, polar molecules can be delivered into the cell with high efficiency. Large charged molecules like DNA and RNA move into the cell through a process driven by their electrophoretic gradient. The amplitude of the pulse governs the total area that would be permeabilized on the cell surface and the duration of the pulse determines the extent of permeabilization (Gabriel and Teissie, 1997). The permeabilized state of the cell depends on the strength of the pulses. Strong pulses can lead to irreversible permeabilization, irreparable damage to the cell and ultimately cell death. For this reason electroporation is probably the harshest of gene delivery methods and it generally requires greater quantities of DNA and cells. The effectiveness of this method depends on many crucial factors like the size of the cell, replication and temperature during the application of pulse (Rols and Teissie, 1990).

The most advantageous feature of this technique is that DNA can be transferred directly into the nucleus increasing its likelihood of being integrated into the host genome. Even cells difficult to transfect can be stably transfected using this method (Aluigi et al., 2005; Zernecke et al., 2003). Modification of the transfection procedure used during electroporation has led to the development of an efficient gene transfer method called nucleofection. The Nucleofector™ technology, is a non-viral electroporation-based gene transfer technique that has been proven to be an efficient tool for transfecting hard-to-transfect cell lines and primary cells including MSC (Michela Aluigi, Stem Cells Vol. 24, No. 2, February 2006, pp. 454-461).

Biomolecule-Based Methods (i) Protein Transduction Domains (PTD)

PTD are short peptides that are transported into the cell without the use of the endocytotic pathway or protein channels. The mechanism involved in their entry is not well understood, but it can occur even at low temperature (Derossi et al. 1996). The two most commonly used naturally occurring PTDs are the trans-activating activator of transcription domain (TAT) of human immunodeficiency virus and the homeodomain of Antennapedia transcription factor. In addition to these naturally occurring PTDs, there are a number of artificial peptides that have the ability to spontaneously cross the cell membrane (Joliot and Prochiantz, 2004). These peptides can be covalently linked to the pseudo-peptide backbone of PNA (peptide nucleic acids) to help deliver them into the cell.

(ii) Liposomes

Liposomes are synthetic vesicles that resemble the cell membrane. When lipid molecules are agitated with water they spontaneously form spherical double membrane compartments surrounding an aqueous center forming liposomes. They can fuse with cells and allow the transfer of "packaged" material into the cell. Liposomes have been successfully used to deliver genes, drugs, reporter proteins and other biomolecules into cells (Felnerova et al., 2004). The advantage of liposomes is that they are made of natural biomolecules (lipids) and are nonimmunogenic.

Diverse hydrophilic molecules can be incorporated into them during formation. For example, when lipids with positively charged head group are mixed with recombinant DNA they can form lipoplexes in which the negatively charged DNA is complexed with the positive head groups of lipid molecules. These complexes can then enter the cell through the endocytotic pathway and deliver the DNA into lysosomal compartments. The DNA molecules can escape this compartment with the help of dioleoylethanolamine (DOPE) and are transported into the nucleus where they can be transcribed (Tranchant et al., 2004).

Despite their simplicity, liposomes suffer from low efficiency of transfection because they are rapidly cleared by the reticuloendothelial system due to adsorption of plasma proteins. Many methods of stabilizing liposomes have been used including modification of the liposomal surface with oligosaccharides, thereby sterically stabilizing the liposomes (Xu et al., 2002).

(iii) Immunoliposomes

Immunoliposomes are liposomes with specific antibodies inserted into their membranes. The antibodies bind selectively to specific surface molecules on the target cell to facilitate uptake. The surface molecules targeted by the antibodies are those that are preferably internalized by the cells so that upon binding, the whole complex is taken up. This approach increases the efficiency of transfection by enhancing the intracellular release of liposomal components. These antibodies can be inserted in the liposomal surface through various lipid anchors or attached at the terminus of polyethylene glycol grafted onto the liposomal surface. In addition to providing specificity to gene delivery, the antibodies can also provide a protective covering to the liposomes that helps to limit their degradation after uptake by endogenous RNAses or proteinases (Bendas, 2001). To further prevent degradation of liposomes and their contents in the lysosomal compartment, pH sensitive immunoliposomes can be employed (Torchilin, 2006). These liposomes enhance the release of liposomal content into the cytosol by fusing with the endosomal membrane within the organelle as they become destabilized and prone to fusion at acidic pH.

In general non-viral gene delivery systems have not been as widely applied as a means of gene delivery into stem cells as viral gene delivery systems. However, promising results were demonstrated in a study looking at the transfection viability, proliferation and differentiation of adult neural stem/progenitor cells into the three neural lineages neurons. Non-viral, non-liposomal gene delivery systems (ExGen500 and FuGene6) had a transfection efficiency of between 16% (ExGen500) and 11% (FuGene6) of cells. FuGene6-treated cells did not differ from untransfected cells in their viability or rate of proliferation, whereas these characteristics were significantly reduced following ExGen500 transfection. Importantly, neither agent affected the pattern of differentiation following transfection. Both agents could be used to genetically label cells, and track their differentiation into the three neural lineages, after grafting onto ex vivo organotypic hippocampal slice cultures (J Gene Med. 2006 January; 8 (1): 72-81. Efficient non-viral transfection of adult neural stem/progenitor cells, without affecting viability, proliferation or differentiation. Tinsley R B, Faijerson J, Eriksson P S).

(iv) Polymer-Based Methods

The protonated .epsilon.-amino groups of poly L-lysine (PLL) interact with the negatively charged DNA molecules to form complexes that can be used for gene delivery. These complexes can be rather unstable and showed a tendency to aggregate (Kwoh et al., 1999). The conjugation of polyethylene glycol (PEG) was found to lead to an increased stability of the complexes (Lee et al., 2005, Harada-Shiba et al., 2002). To confer a degree of tissue-specificity, targeting molecules such as tissue-specific antibodies have also been employed (Trubetskoy et al., 1992, Suh et al., 2001).

An additional gene carrier that has been used for transfecting cells is polyethylenimine (PEI) which also forms complexes with DNA. Due to the presence of amines with different pKa values, it has the ability to escape the endosomal compartment (Boussif et al., 1995). PEG grafted onto PEI complexes was found to reduce the cytotoxicity and aggregation of these complexes. This can also be used in combination with conjugated antibodies to confer tissue-specificity (Mishra et al., 2004, Shi et al., 2003, Chiu et al., 2004, Merdan et al., 2003).

Targeted Gene Delivery—Site-Specific Recombinations

In certain embodiments, a non-human, transgenic animal comprising a targeting vector that further comprises recombination sites (e.g., Lox sites, FRT sites) can be crossed with a non-human, transgenic animal comprising a recombinase (e.g., Cre recombinase, FLP recombinase) under control of a particular promoter. It has been shown that these site-specific recombination systems, although of microbial origin for the majority, function in higher eukaryotes, such as plants, insects and mice. Among the site-specific recombination systems commonly used, there may be mentioned the Cre/Lox and FLP/FRT systems. The strategy normally used consists of inserting the loxP (or FRT) sites into the chromosomes of ES cells by homologous recombination, or by conventional transgenesis, and then of delivering Cre (or FLP) for the latter to catalyze the recombination reaction. The recombination between the two loxP (or FRT) sites may be obtained in ES cells or in fertilized eggs by transient expression of Cre or using a Cre transgenic mouse. Such a strategy of somatic mutagenesis allows a spatial control of the recombination because the expression of the recombinase is controlled by a promoter specific for a given tissue or for a given cell.

A detailed description of the FRT system can be found, e.g., in U.S. Pat. No. 7,736,897.

The P1 bacteriophage uses Cre-lox recombination to circularize and facilitate replication of its genomic DNA when reproducing. Since being discovered, the bacteriophage's recombination strategy has been developed as a technology for genome manipulation. Because the cre gene and loxP sites are not native to the mouse genome, they are introduced by transgenic technology into the mouse genomes (Nagy A. 2000. Cre recombinase: the universal reagent for genome tailoring. Genesis 26:99-109). The orientation and location of the loxP sites determine whether Cre recombination induces a deletion, inversion, or chromosomal translocation (Nagy A. 2000. Cre recombinase: the universal reagent for genome tailoring. Genesis 26:99-109). The cre/lox system has been successfully applied in mammalian cell cultures, yeasts, plants, mice, and other organisms (Araki K, Imaizumi T, Okuyama K, Oike Y, Yamamura K. 1997. Efficiency of recombination by Cre transient expression in embryonic stem cells: comparison of various promoters. J Biochem (Tokyo) 122:977-82). Much of the success of Cre-lox is due to its simplicity. It requires only two components: (a) Cre recombinase: an enzyme that catalyzes recombination between two loxP sites; and (b) LoxP sites: a specific 34-base pair bp) sequences consisting of an 8-bp core sequence, where recombination takes place, and two flanking 13-bp inverted repeats.

Cell-mediated Delivery

In one embodiment, the optical sensors of the present invention are delivered using e.g., a cell expressing the optical sensor. A variety of means for administering cells to subjects are known to those of skill in the art. Such methods can include systemic injection, for example i.v. injection or implantation of cells into a target site in a subject. Cells may be inserted into a delivery device which facilitates introduction by injection or implantation into the subjects. Such delivery devices may include tubes, e.g., catheters, for injecting cells and fluids into the body of a recipient subject. In one preferred embodiment, the tubes additionally have a needle, e.g., a syringe, through which the cells of the invention can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention may be prepared by incorporating cells as described herein in a pharmaceutically acceptable carrier or diluent and, as required, other ingredients enumerated above, followed by filtered sterilization. It is preferred that the mode of cell administration is relatively non-invasive, for example by intravenous injection, pulmonary delivery through inhalation, oral delivery, buccal, rectal, vaginal, topical, or intranasal administration.

However, the route of cell administration will depend on the tissue to be treated and may include implantation or direct injection. Methods for cell delivery are known to those of skill in the art and can be extrapolated by one skilled in the art of medicine for use with the methods and compositions described herein. Direct injection techniques for cell administration can also be used to stimulate transmigration through the entire vasculature, or to the vasculature of a particular organ, such as for example liver, or kidney or any other organ. This includes non-specific targeting of the vasculature. One can target any organ by selecting a specific injection site, such as e.g., a liver portal vein. Alternatively, the injection can be performed systemically into any vein in the body. This method is useful for enhancing stem cell numbers in aging patients. In addition, the cells can function to populate vacant stem cell niches or create new stem cells to replenish the organ, thus improving organ function. For example, cells may take up pericyte locations within the vasculature. Delivery of cells may also be used to target sites of active angiogenesis. If so desired, a mammal or subject can be pre-treated with an agent, for example an agent is administered to enhance cell targeting to a tissue (e.g., a homing factor) and can be placed at that site to encourage cells to target the desired tissue. For example, direct injection of homing factors into a tissue can be performed prior to systemic delivery of ligand-targeted cells.

Method of using stem cells, such as neural stem cells to deliver agents through systemic administration and via intracranial administration to home in on a tumor or to an injured parts of brain have been described (see, e.g., U.S. Pat. Nos. 7,655,224; and 7,393,526). Accordingly, one can also modify such cells to express the desired voltage sensor for delivery into the organs, such as the brain.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Some Definitions

As used herein the term "optical sensor" refers to a microbial rhodopsin protein employed to yield an optical signal indicative of the voltage drop across the membrane in which it is embedded As used herein the phrase "reduced ion pumping activity" means a decrease in the endogenous ion pumping activity of a modified microbial rhodopsin protein of at least 10% compared to the endogenous pumping activity of the natural microbial rhodopsin protein from which the modified rhodopsin is derived. The ions most commonly pumped by microbial rhodopsins are $H^+$ and $Cl^{--}$. In some embodiments, the ion pumping activity of a modified rhodopsin protein is at least 20% lower, at least 30%, at least 40%, at least 50%, at least 60%, at least 70%, at least 80%, at least 90%, at least 95%, or at least 99% lower than the endogenous ion pumping activity of the corresponding native microbial rhodopsin protein.

In some embodiments, the modified microbial rhodopsin has no detectable ion pumping activity.

As used herein, the term "endogenous ion pumping activity" refers to the movement of ions through a native microbial rhodopsin protein that occurs in response to light stimuli.

As used herein, the term "native microbial rhodopsin protein" or "natural microbial rhodopsin protein" refers to a rhodopsin protein prepared or isolated from a microbial (e.g., bacterial, archaeal, or eukaryotic) source. Such natural microbial rhodopsin proteins, when isolated, retain characteristics (e.g., pKa, ion pumping activity etc) that are substantially similar to the microbial rhodopsin protein in its native environment (e.g., in a microbial cell). Some non-limiting examples of microbial rhodopsin proteins useful with the methods described herein include green-absorbing proteorhodopsin (GPR; GenBank accession number AF349983), blue-absorbing proteorhodopsin (BPR, GenBank accession number AF349981), *Natromonas pharaonis* sensory rhodopsin II (NpSR11; GenBank accession number Z35086.1), and bacteriorhodopsin (BR; the protein encoded by GenBank sequence NC_010364.1, nucleotides 1082241-1083029, wherein 1082241 is designated as 1 herein, GenBank accession number M11720.1, or as described by e.g., Beja O, et al., (2000). *Science* 289 (5486): 1902-1904), and archaerhodopsin (see e.g., Chow B. Y. et al., Nature 463:98-102 (2010) and the Examples in this application).

As used herein, the term "modified microbial rhodopsin protein" refers to a native microbial rhodopsin protein comprising at least one mutation. Mutations can be in the nucleic acid sequence (e.g., genomic or mRNA sequence), or alternatively can comprise an amino acid substitution. Such amino acid substitutions can be conserved mutations or non-conserved mutations. As well-known in the art, a "conservative substitution" of an amino acid or a "conservative substitution variant" of a polypeptide refers to an amino acid substitution which maintains: 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine. "Positively charged residues" relate to lysine, arginine or histidine. "Negatively charged residues" refer to aspartic acid or glutamic acid. Residues having "bulky side chains" refer to phenylalanine, tryptophan or tyrosine. To avoid doubt as to nomenclature, the term "D97N" or similar terms specifying other specific amino acid substitutions means that the Asp (D) at position 97 of the protein sequence is substituted with Asn (N). A "conservative substitution variant" of D97N would substitute a conservative amino acid variant of Asn (N) that is not D.

The terminology "conservative amino acid substitutions" is well known in the art, which relates to substitution of a particular amino acid by one having a similar characteristic (e.g., similar charge or hydrophobicity, similar bulkiness). Examples include aspartic acid for glutamic acid, or isoleucine for leucine. A list of exemplary conservative amino acid substitutions is given in the Table 5 below. A conservative substitution mutant or variant will 1) have only conservative amino acid substitutions relative to the parent sequence, 2) will have at least 90% sequence identity with respect to the parent sequence, preferably at least 95% identity, 96% identity, 97% identity, 98% identity or 99%; and 3) will retain voltage sensing activity as that term is defined herein.

TABLE 5

Conservative Amino Acid Substitutions

| For Amino Acid | Code | Replace With |
|---|---|---|
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |

TABLE 5-continued

Conservative Amino Acid Substitutions

| For Amino Acid | Code | Replace With |
|---|---|---|
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. 4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

A non-conservative mutation is any other amino acid substitution other than the conservative substitutions noted in the above table.

Methods of making conservative amino acid substitutions are also well known to one skilled in the art and include but are not limited to site-specific mutagenesis using oligonucleotide primers and polymerase chain reactions. Optical sensor variants can be expressed and assayed for voltage sensing activity, pKa, and fluorescence detection by methods known in the art and/or described herein to verify that the desired activities of the optical sensor are retained or augmented by the amino acid substitutions. It is contemplated that conservative amino acid substitution variants of the optical sensors described herein can have enhanced activity or superior characteristics for sensing voltage relative to the parent optical sensor. Certain silent or neutral missense mutations can also be made in the nucleic acid encoding an optical sensor by a mutation that does not change the encoded amino acid sequence of the encoded optical sensor. These types of mutations are useful to optimize codon usage which improve recombinant protein expression and production in the desired cell type. Specific site-directed mutagenesis of a nucleic acid encoding an optical sensor in a vector can be used to create specific amino acid mutations and substitutions. Site-directed mutagenesis can be carried out using, e.g. the QUICK-CHANGE® site-directed mutagenesis kit from STRAT-AGENE® according to manufacture's instructions, or by any method known in the art.

As used herein, the term "membrane potential" refers to a calculated difference in voltage between the interior and exterior of a cell. In one embodiment membrane potential, $\Delta V$, is determined by the equation $\Delta V = V_{interior} - V_{exterior}$. For example, if the outside voltage is 100 mV, and the inside voltage is 30 mV, then the difference is −70 mV. Under resting conditions, the membrane potential is predominantly determined by the ion having the greatest conductance across the membrane. In many cells, the membrane potential is determined by potassium, which yields a resting membrane potential of approximately −70 mV. Thus by convention, a cell under resting conditions has a negative membrane potential. In some cells when a membrane potential is reached that is equal to or greater than a threshold potential, an action potential is triggered and the cell undergoes depolarization (i.e., a large increase in the membrane potential). Often, when a cell undergoes depolarization, the membrane potential reverses and reaches positive values (e.g., 55 mV). During resolution of the membrane potential following depolarization towards the resting membrane potential, a cell can "hyperpolarize." The term "hyperpolarize" refers to membrane potentials that are more negative than the resting membrane potential, while the term "depolarize" refers to membrane potentials that are less negative (or even positive) compared to the resting membrane potential. Membrane potential changes can arise by movement of ions through ion channels or ion pumps embedded in the membrane. Membrane potential can be measured across any cellular membrane that comprises ion channels or ion pumps that can maintain an ionic gradient across the membrane (e.g., plasma membrane, mitochondrial inner and outer membranes etc.).

As used herein, the term "change in the membrane potential" refers to an increase (or decrease) in $\Delta V$ of at least 1 mV that is either spontaneous or in response to e.g., environmental or chemical stimuli (e.g., cell-to-cell communication, ion channel modulation, contact with a candidate agent etc.) compared to the resting membrane potential measured under control conditions (e.g., absence of an agent, impaired cellular communication, etc.). In some embodiments, the membrane potential $\Delta V$ is increased by at least 10 mV, at least 15 mV, at least 20 mV, at least 25 mV, at least 30 mV, at least 35 mV, at least 40 mV, at least 45 mV, at least 50 mV, at least 55 mV, at least 60 mV, at least 65 mV, at least 70 mV, at least 75 mV, at least 80 mV, at least 85 mV, at least 90 mV, at least 95 mV, at least 100 mV, at least 105 mV, at least 110 mV, at least 115 mV, at least 120 mV, at least 125 mV, at least 130 mV, at least 135 mV, at least 140 mV, at least 145 mV, at least 150 mV, at least 155 mV, at least 160 mV, at least 165 V, at least 170 mV, at least 180 mV, at least 190 mV, at least 200 mV or more compared to the membrane potential of a similar cell under control conditions. In other embodiments, the membrane potential is decreased by at least 3 mV, at least 5 mV, at least 10 mV, at least 15 mV, at least 20 mV, at least 25 mV, at least 30 mV, at least 35 mV, at least 40 mV, at least 45 mV, at least 50 mV, at least 55 mV, at least 60 mV, at least 65 mV, at least 70 mV, at least 75 mV, at least 80 mV, at least 85 mV, at least 90 mV, at least 95 mV, at least 100 mV, at least 105 mV, at least 110 mV, at least 115 mV, at least 120 mV, at least 125 mV, at least 130 mV, at least 135 mV, at least 140 mV, at least 145 mV, at least 150 mV or more compared to the membrane potential of a similar cell under control conditions.

As used herein, the phrase "localizes to a membrane of the cell" refers to the preferential localization of the modified microbial rhodopsin protein to the membrane of a cell and can be achieved by e.g., modifying the microbial rhodopsin to comprise a signal sequence that directs the rhodopsin protein to a membrane of the cell (e.g., the plasma membrane, the mitochondrial outer membrane, the mitochondrial inner membrane etc.). In some embodiments, at least 40% of the modified microbial rhodopsin protein in the cell is localized to the desired cellular membrane compartment (e.g., plasma membrane, mitochondrial membrane etc); in other embodiments, at least 50%, at least 60%, at least 70%, at least 75%, at least 80%, at least 85%, at least 90%, at least 95%, at least 99% of the modified microbial rhodopsin protein is localized to the desired cellular membrane compartment. Similarly, the phrase "localized to a subcellular compartment" refers to the preferential localization of the microbial rhodopsin protein to a particular subcellular compartment (e.g., mitochondria, endoplasmic reticulum, peroxisome etc.). In some embodiments, at least 40% of the modified microbial rhodopsin protein in the cell is localized to the desired subcellular compartment; in other embodiments, at least 50%, at least 60%, at least 70%, at least 75%, at least 80%, at least 85%, at least 90%, at least 95%, or at least 99% of the modified microbial rhodopsin protein is localized to the desired subcellular compartment.

In some embodiment, about 100% is localized to the desired cellular membrane or compartment.

As used herein, the term "introducing to a cell" refers to any method for introducing either an expression vector encoding an optical sensor or a recombinant optical sensor protein described herein into a host cell. Some non-limiting examples of introducing an expression vector into a cell include, for example, calcium phosphate transfection, electroporation, lipofection, or a method using a gene gun or the like. In one embodiment, a recombinant optical sensor protein is introduced to a cell by membrane fusion using a lipid mediated delivery system, such as micelles, liposomes, etc.

As used herein, the phrase "a moiety that produces an optical signal" refers to a molecule (e.g., retinal), or moiety of a molecule, capable of producing a detectable signal such as e.g., fluorescence, chemiluminescence, a colorimetric signal etc. In one embodiment, the modified microbial rhodopsin comprises a fusion molecule with a moiety that produces an optical signal.

As used herein, the phrases "change in the level of fluorescence" or "a change in the level of the optical signal" refer to an increase or decrease in the level of fluorescence from the modified microbial rhodopsin protein or an increase or decrease in the level of the optical signal induced by a change in voltage or membrane potential. In some embodiments, the level of fluorescence or level of optical signal in a cell is increased by at least at least 2%, at least 5%, at least 10%, 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 50-fold, at least 100-fold, at least 500-fold, at least 600-fold, at least 700-fold, at least 800-fold, at least 900-fold, at least 1000-fold, at least 2000-fold, at least 5000-fold, at least 10000-fold or more compared to the same cell or a similar cell under control conditions. Alternatively, the level of fluorescence or level of optical signal in a cell is decreased by at least by at least 20%, at least 30%, at least 40%, at least 50%, at least 60%, at least 70%, at least 80%, at least 90%, at least 95%, at least 99%, or even 100% (i.e., no detectable signal) compared to the same cell or a similar cell under control culture conditions.

As used herein, the phrase "modulates ion channel activity" refers to an increase or decrease in one or more properties of an ion channel that manifests as a change in the membrane potential of a cell. These properties include, e.g., open- or closed-state conductivity, threshold voltage, kinetics and/or ligand affinity. In some embodiments, the one or more properties of interest of an ion channel of a cell as measured by e.g., a change in membrane potential of the cell. In some embodiments, the activity of an ion channel is increased by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 20-fold, at least 50-fold, at least 100-fold, at least 1000-fold or more in the presence of an agent compared to the activity of the ion channel in the absence of the agent. In other embodiments, the parameter of interest of an ion channel is decreased by at least 20%, at least 30%, at least 40%, at least 50%, at least 60%, at least 70%, at least 80%, at least 90%, at least 95%, or at least 99% in the presence of an agent compared to the activity of the ion channel in the absence of the agent. In some embodiments, the parameter of an ion channel is absent in the presence of an agent compared to the activity of the ion channel in the absence of the agent.

As used herein, the term "inhibitor of antibiotic efflux" refers to an agent that decreases the level of antibiotic efflux from a bacterial cell by at least 20% compared to the level of antibiotic efflux in the absence of the agent. In some embodiments, antibiotic efflux is decreased by at least 30%, at least 40%, at least 50%, at least 60%, at least 70%, at least 80%, at least 90%, at least 95%, at least 99%, or even 100% (i.e., absent) in the presence of an agent compared to the level of antibiotic efflux in the absence of the agent.

As used herein, the term "targeting sequence" refers to a moiety or sequence that homes to or preferentially associates or binds to a particular tissue, cell type, receptor, organelle, or other area of interest. The addition of a targeting sequence to an optical sensor composition will enhance the delivery of the composition to a desired cell type or subcellular location. The addition to, or expression of, a targeting sequence with the optical sensor in a cell enhances the localization of the optical sensor to a desired location within an animal or subject.

As used herein, the phrase "homologous mutation in another microbial rhodopsin that corresponds to the amino acid mutation in bacteriorhodopsin" refers to mutation of a residue in a desired microbial rhodopsin that is expected to have a similar effect to a substantially similar mutation in bacteriorhodopsin. One of skill in the art can easily locate a homologous residue in their desired microbial rhodopsin by performing an alignment of conserved regions of the desired microbial rhodopsin with a bacteriorhodopsin sequence using a computer program such as ClustalW.

Examples of homologous mutations include the mutations made in the Examples set forth in this application.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Provided herein are optical sensors comprising a microbial rhodopsin or a modified microbial rhodopsin protein with a reduced ion pumping activity compared to a natural microbial rhodopsin protein from which it is derived. In one embodiment, the composition comprises a vector encoding or an engineered cell comprising the microbial rhodopsin protein or the modified microbial rhodopsin protein with a reduced ion pumping activity compared to a natural microbial rhodopsin protein from which it is derived. In some embodiments, the microbial rhodopsin is directed to a membrane, such as plasma membrane or mitochondrial membrane.

Accordingly, the invention provides a method for measuring membrane potential in a cell expressing a nucleic acid encoding a microbial rhodopsin protein, the method comprising the steps of: (a) exciting, in vitro, ex vivo or in vivo, at least one cell comprising a nucleic acid encoding a microbial rhodopsin protein with light of at least one wave length; and (b) detecting, in vitro, at least one optical signal from the at least one cell, wherein the level of fluorescence emitted by the at least one cell compared to a reference is indicative of the membrane potential of the cell.

In some or any embodiment or aspect of the invention, the he microbial rhodopsin protein is a modified microbial rhodopsin protein with reduced ion pumping activity compared to a natural microbial rhodopsin protein from which it is derived.

In some or any embodiment or aspect of the invention, the modified microbial rhodopsin comprises a mutated proton acceptor proximal to the Schiff Base.

In some or any embodiment or aspect of the invention, the microbial rhodopsin protein is a member of the proteorhodopsin family of proteins.

In some or any embodiment or aspect of the invention the microbial rhodopsin protein is a member of the archaerhodopsin family of proteins.

In some or any embodiment or aspect of the invention the at least one wave length is a wave length between $\lambda=594\text{-}645$ nm.

In some or any embodiment or aspect of the invention the cell is a prokaryotic cell.

In some or any embodiment or aspect of the invention the cell is a eukaryotic cell.

In some or any embodiment or aspect of the invention the eukaryotic cell is a mammalian cell.

In some or any embodiment or aspect of the invention the eukaryotic cell is a stem cell or a pluripotent or a progenitor cell.

In some or any embodiment or aspect of the invention the eukaryotic cell is an induced pluripotent cell.

In some or any embodiment or aspect of the invention the eukaryotic cell is a neuron.

In some or any embodiment or aspect of the invention the eukaryotic cell is a cardiomyocyte.

In some or any embodiment or aspect of the invention the method further comprises a step of transfecting, in vitro, ex vivo or in vivo, the at least one cell with a vector comprising the nucleic acid encoding the microbial rhodopsin protein.

In some or any embodiment or aspect of the invention, the nucleic acid encoding the microbial rhodopsin protein is operably linked to a cell-type specific promoter.

In some or any embodiment or aspect of the invention, the nucleic acid encoding the microbial rhodopsin protein is operably linked to a membrane-targeting nucleic acid sequence.

In some or any embodiment or aspect of the invention, the membrane-targeting nucleic acid is a plasma membrane targeting nucleic acid sequence.

In some or any embodiment or aspect of the invention, the membrane-targeting nucleic acid sequence is a subcellular compartment-targeting nucleic acid sequence.

In some or any embodiment or aspect of the invention, the subcellular compartment is selected from a mitochondrial membrane, an endoplasmic reticulum, a sarcoplastic reticulum, a synaptic vesicle, an endosome and a phagosome.

In some or any embodiment or aspect of the invention, the nucleic acid encoding a microbial rhodopsin protein is operably linked to a nucleic acid encoding at least one additional fluorescent protein or a chromophore.

In some or any embodiment or aspect of the invention, the at least one additional fluorescent protein is a fluorescent protein capable for indicating the ion concentration in the cell.

In some or any embodiment or aspect of the invention, the fluorescent protein capable for indicating ion concentration is a calcium indicator.

In some or any embodiment or aspect of the invention, the fluorescent protein capable for indicating ion concentration is a pH indicator.

In some or any embodiment or aspect of the invention, the at least one additional fluorescent protein is capable of undergoing nonradiative fluorescence resonance energy transfer to the microbial rhodopsin, with a rate of energy transfer dependent on the membrane potential.

In some or any embodiment or aspect of the invention, the at least one additional fluorescent protein is a green fluorescent protein or a homolog thereof.

In some or any embodiment or aspect of the invention, brightness of the fluorescent protein is insensitive to membrane potential and local chemical environment.

In some or any embodiment or aspect of the invention, the method further comprises steps of exciting, in vitro, ex vivo or in vivo, the at least one cell with light of at least a first and a second wavelength; and detecting, in vitro, ex vivo or in vivo, the at least first and the second optical signal resulting from the excitation with the at least the first and the second wavelength from the at least one cell.

In some or any embodiment or aspect of the invention, the at least second wave length is between $\lambda=447\text{-}594$ nm.

In some or any embodiment or aspect of the invention, the method further comprises a step of calculating the ratio of the fluorescence emission from the microbial rhodopsin to the fluorescence emission of the at least one additional fluorescent protein to obtain a measurement of membrane potential independent of variations in expression level.

In some or any embodiment or aspect of the invention, the method further comprises the step of exposing, in vitro, ex vivo or in vivo, the at least one cell to a stimulus capable of, or suspected to be capable of changing membrane potential.

In some or any embodiment or aspect of the invention, the stimulus a candidate agent.

In some or any embodiment or aspect of the invention, the stimulus is a change to the composition of the cell culture medium.

In some or any embodiment or aspect of the invention, the stimulus is an electrical current.

In some or any embodiment or aspect of the invention, further comprising the step of measuring, in vitro, ex vivo or in vivo the at least one optical signal at a first and at least at a second time point.

In some or any embodiment or aspect of the invention, the first time point is before exposing the at least one cell to a stimulus and the at least second time point is after exposing the at least one cell to the stimulus.

In some or any embodiment or aspect of the invention, wherein the method comprises a plurality of cells, for example in a highthroughput assay.

In another embodiment, the invention provides an isolated and purified nucleic acid encoding a modified member of the archaerhodopsin family of proteins with reduced ion pumping activity compared to a natural member of the archaerhodopsin family of proteins from which it is derived.

In some or any embodiment or aspect of the invention, the modified member of an archaerhodopsin family of proteins comprises a mutated proton acceptor proximal to the Schiff Base.

In some or any embodiment or aspect of the invention, the modified member of the archaerhodopsin family of proteins with reduced ion pumping activity compared to a natural member of the archaerhodopsin family of proteins from which it is derived is operably linked to a nucleic acid sequence encoding a membrane-targeting nucleic acid sequence.

In some or any embodiment or aspect of the invention, the membrane-targeting nucleic acid sequence is a plasma membrane targeting nucleic acid sequence.

In some or any embodiment or aspect of the invention, the membrane-targeting nucleic acid sequence is a subcellular membrane-targeting nucleic acid sequence.

In some or any embodiment or aspect of the invention, the subcellular membrane is a mitochondrial membrane, an endoplasmic reticulum, a sarcoplastic reticulum, a synaptic vesicle, an endosome or a phagosome.

In some or any embodiment or aspect of the invention, the modified microbial rhodopsin of the archaerhodopsin family is operably linked to a cell-type specific promoter.

In some or any embodiment or aspect of the invention, the modified microbial rhodopsin of the archaerhodopsin family is operably linked to a nucleic acid encoding at least one additional fluorescent protein or a chromophore.

In some or any embodiment or aspect of the invention, wherein the at least one additional fluorescent protein is a green fluorescent protein or a homolog thereof.

In some or any embodiment or aspect of the invention, the at least one additional fluorescent protein is a fluorescent protein capable for indicating ion concentration in the cell.

In some or any embodiment or aspect of the invention, the fluorescent protein capable for indicating ion concentration is a calcium indicator.

In some or any embodiment or aspect of the invention, the fluorescent protein capable for indicating ion concentration is a pH indicator.

In some or any embodiment or aspect of the invention, the at least one additional fluorescent protein is capable of undergoing nonradiative fluorescence resonance energy transfer to the microbial rhodopsin, with a rate of energy transfer dependent on the membrane potential.

In some or any embodiment or aspect of the invention, the isolated and purified nucleic further comprises a vector.

In some or any embodiment or aspect of the invention, the vector is a viral vector, such as a lentiviral vector or an adeno-associated viral vector.

In another embodiment, the invention provides a kit comprising the isolated and purified nucleic acid encoding the modified microbial proteins of archaerhodopsin family as disclosed herein in a suitable container. The nucleic acids may be provided in dry form or in a suitable buffer.

Another embodiment of the invention provides an isolated cell comprising a nucleic acid encoding a microbial rhodopsin protein, wherein the microbial rhodopsin protein is a modified microbial rhodopsin protein with reduced ion pumping activity compared to a natural microbial rhodopsin protein from which it is derived.

In some or any embodiment or aspect of the invention, the modified microbial rhodopsin protein comprises a mutated proton acceptor proximal to the Schiff Base.

In some or any embodiment or aspect of the invention, the microbial rhodopsin is a member of the proteorhodopsin family.

In some or any embodiment or aspect of the invention, the microbial rhodopsin is a member of the archaerhodopsin family.

In some or any embodiment or aspect of the invention, the cell is a eukaryotic cell.

In some or any embodiment or aspect of the invention, the cell is a prokaryotic cell.

In some or any embodiment or aspect of the invention, the modified microbial rhodopsin gene is operably linked to a promoter.

In some or any embodiment or aspect of the invention, the promoter is a cell-type specific promoter.

In some or any embodiment or aspect of the invention, the nucleic acid encoding the modified microbial rhodopsin protein is operably linked to a membrane-targeting nucleic acid sequence.

In some or any embodiment or aspect of the invention, the membrane-targeting nucleic acid is a plasma membrane targeting nucleic acid sequence.

In some or any embodiment or aspect of the invention, the membrane-targeting nucleic acid is a subcellular compartment-targeting nucleic acid sequence.

In some or any embodiment or aspect of the invention, the subcellular compartment is selected from a mitochondrial membrane, an endoplasmic reticulum, a sarcoplastic reticulum, a synaptic vesicle, an endosome and a phagosome.

In some or any embodiment or aspect of the invention, the nucleic acid encoding the modified microbial rhodopsin protein is operably linked to a nucleic acid encoding at least one additional fluorescent protein or chromophore.

In some or any embodiment or aspect of the invention, the at least one additional fluorescent protein is a green fluorescent protein or a homolog thereof.

In some or any embodiment or aspect of the invention, the at least one additional fluorescent protein is capable of undergoing nonradiative fluorescence resonance energy transfer to the microbial rhodopsin, with a rate of energy transfer dependent on the membrane potential.

In some or any embodiment or aspect of the invention, the least one additional fluorescent protein is a fluorescent protein whose brightness is insensitive to membrane potential and local chemical environment.

In some or any embodiment or aspect of the invention, the at least one additional fluorescent protein is capable of indicating the ion concentration in the cell.

In some or any embodiment or aspect of the invention, the fluorescent protein capable for indicating ion concentration is a calcium indicator.

In some or any embodiment or aspect of the invention, the fluorescent protein capable for indicating ion concentration is a pH indicator.

In some or any embodiment or aspect of the invention, the cell is a stem cell, a pluripotent cell, or an induced pluripotent cell, or differentiated or undifferentiated progeny thereof.

In some or any embodiment or aspect of the invention, the cell is a differentiated cell.

In some or any embodiment or aspect of the invention, the differentiated cell is a neuron.

In some or any embodiment or aspect of the invention, the differentiated cell is a cardiomyocyte.

The invention further provides, in one embodiment, an isolated cell comprising the isolated and purified nucleic acid of any of the isolated and purified nucleic acids or nucleic acid constructs comprising the modified microbial rhodopsin of archaerhodopsin family as described above.

In one embodiment, the invention provides a kit comprising a plurality of cells as described herein in a suitable cell culture medium and a container.

In yet another embodiment, the invention provides a method of making an engineered cell for optical measurement of membrane potential comprising the steps of transducing a cell with a nucleic acid encoding a microbial rhodopsin protein.

In some or any embodiment or aspect of the invention, the microbial rhodopsin protein is a modified microbial rhodopsin protein with reduced ion pumping activity compared to a natural microbial rhodopsin protein.

In some or any embodiment or aspect of the invention, the modified microbial rhodopsin comprises a mutated proton acceptor proximal to the Schiff Base.

In some or any embodiment or aspect of the invention, the nucleic acid encoding a microbial rhodopsin protein is operably linked to a membrane targeting nucleic acid sequence.

In some or any embodiment or aspect of the invention, the membrane targeting nucleic acid sequence is a plasma membrane targeting nucleic acid sequence.

In some or any embodiment or aspect of the invention, the membrane targeting nucleic acid sequence is a subcellular membrane targeting nucleic acid sequence.

In some or any embodiment or aspect of the invention, the subcellular membrane is a mitochondrial membrane, an endoplasmic reticulum, a sarcoplastic reticulum, a synaptic vesicle, an endosome or a phagosome.

In some or any embodiment or aspect of the invention, the nucleic acid encoding the microbial rhodopsin protein is operably linked to a cell-type specific promoter.

In some or any embodiment or aspect of the invention, the nucleic acid encoding the microbial rhodopsin protein is operably linked to an additional nucleic acid encoding at least one additional fluorescent protein or a chromophore.

In some or any embodiment or aspect of the invention, the at least one additional fluorescent protein is a green fluorescent protein or a homolog thereof.

In some or any embodiment or aspect of the invention, the at least one additional fluorescent protein is capable of indicating ion concentration in the cell.

In some or any embodiment or aspect of the invention, the at least one additional fluorescent protein is capable of indicating ion concentration in the cell is a calcium indicator.

In some or any embodiment or aspect of the invention, the at least one additional fluorescent protein is capable of indicating ion concentration in the cell is a pH indicator.

In some or any embodiment or aspect of the invention, the cell is a differentiated cell.

In some or any embodiment or aspect of the invention, the differentiated cell is a neuron.

In some or any embodiment or aspect of the invention, the differentiated cell is a cardiomyocyte.

In some or any embodiment or aspect of the invention, the cell is a pluripotent cell, a stem cell or an induced pluripotent stem cell.

In some or any embodiment or aspect of the invention, the method further comprises a step of differentiating the pluripotent cell, the stem cell or the induced pluripotent stem cell into a differentiated cell.

The method of any one of the claims 80-97, wherein the transducing is performed using a transient transfection.

In some or any embodiment or aspect of the invention, the transducing is performed using a stable transfection.

In some or any embodiment or aspect of the invention, the cell is transduced with the isolated and purified nucleic acid as described herein.

In some embodiments, the method is performed to a non-human cells.

In some embodiments and aspects, the invention provides a cell that has been genetically engineered to express a microbial rhodopsin that is not naturally present in the cell, and methods of using such cells.

Also provided herein are methods for making an optical sensor comprising: (a) modifying a microbial rhodopsin protein to reduce the ion pumping activity compared to a natural microbial rhodopsin protein from which it is derived, and (b) introducing the modified microbial rhodopsin protein into a cell, thereby producing a genetically encoded optical sensor.

In one embodiment, the step of introducing comprises introducing a gene for the modified microbial rhodopsin protein into the cell.

In another aspect, the invention provides for a method for measuring a change in a membrane potential of a cell, the method comprising: measuring an optical signal in a cell, wherein the cell comprises a natural microbial rhodopsin or a modified microbial rhodopsin protein with reduced ion pumping activity compared to a natural microbial rhodopsin protein from which it is derived, wherein the microbial rhodopsin or the modified microbial rhodopsin protein localizes to a membrane of the cell and, wherein a change in the level of fluorescence of the rhodopsin or the modified microbial rhodopsin is indicative of a change in the membrane potential of the cell.

Also described herein is a method of screening for an agent that modulates membrane potential, either directly or through an effect on ion channel activity, the method comprising: (a) contacting a cell with a candidate agent, wherein the cell comprises a microbial rhodopsin or a modified microbial rhodopsin protein with reduced ion pumping activity compared to a natural microbial rhodopsin protein from which it is derived, wherein the microbial rhodopsin or the modified microbial rhodopsin protein localizes to a membrane of the cell, and (b) measuring the optical signal, wherein a change in the level of fluorescence of the rhodopsin or the modified microbial rhodopsin in the presence of the candidate agent is indicative of a change in the membrane potential across the membrane of the cell, thereby indicating that the candidate agent modulates membrane potential directly or through an effect on ion channel activity.

In addition, provided herein is a method of screening for a modulator of antibiotic efflux in a bacterial cell, the method comprising: (a) contacting a bacterial cell with a candidate agent, wherein the cell comprises a microbial rhodopsin or a modified microbial rhodopsin protein having reduced ion pumping activity compared to a natural microbial rhodopsin protein from which it is derived, wherein the microbial rhodopsin or the modified microbial rhodopsin protein localizes to a membrane of the cell, and (b) measuring the time-dependent fluctuations in the level of fluorescence of the microbial rhodopsin or the modified microbial rhodopsin, wherein a change in the fluctuations in the presence of the candidate agent is indicative of a change in fluctuations in the membrane potential across the membrane of the cell, thereby indicating that the candidate agent is a modulator of antibiotic efflux in the bacterial cell. In one embodiment, the candidate agent is an inhibitor of antibiotic efflux. In an alternate embodiment, the candidate agent enhances antibiotic efflux.

Also described herein are nucleic acid constructs for expressing a microbial rhodopsin and a modified microbial rhodopsin protein with a reduced ion pumping activity compared to the natural microbial rhodopsin protein from which it is derived comprising at least one nucleic acid sequence encoding the modified microbial rhodopsin protein that is modified for codon usage appropriate for the eukaryotic cell.

In another embodiment, described herein are vectors comprising at least one nucleic acid encoding a voltage indicator protein operably linked to a promoter, e.g., a tissue-specific promoter, such as a neuron-specific promoter or a cardiac tissue, such as cardiomyocyte-specific promoter.

In some embodiments, the vector also comprises a membrane-targeting signal sequence to membranes such as the plasma membrane, mitochondria, the endoplasmic reticulum, the sarcoplasmic reticulum, synaptic vesicles, and phagosomes. In some embodiments, the vector comprises at least two nucleic acids each encoding a different voltage indicator protein. In some embodiments, the vector further comprises a nucleic acids encoding, e.g., a pH indicator (e.g., pHluorin) or a calcium indicator (e.g., GCaMP3). Use of such a combination enables simultaneous monitoring of voltage and ion concentration (pH or $Ca^{2+}$, respectively).

In another embodiment, the invention provides a cell expressing, either stably or transiently, at least one nucleic acid construct or vector encoding a microbial rhodopsin or a modified microbial rhodopsin described in the specification.

In another aspect, methods are provided for measuring a change in the membrane potential of at least one cell in a cellular circuit, the method comprising: measuring the level of fluorescence of the microbial rhodopsin or the modified microbial rhodopsin in at least one cell in a cellular circuit, wherein the at least one cell in a cellular circuit comprises a microbial rhodopsin or a modified microbial rhodopsin protein having reduced ion pumping activity compared to a natural microbial rhodopsin protein from which it is derived, wherein the microbial rhodopsin or the modified microbial rhodopsin protein localizes to a membrane of the cell, and wherein a change in the level of fluorescence is indicative of a change in the membrane potential across a membrane of the at least one cell in said cellular circuit. In some and in all aspects of the invention, the microbial rhodopsin targets the plasma membrane of the cell.

Another aspect provided herein is a high-throughput system for optically measuring membrane potential, the system comprising: (a) a plurality of engineered cells comprising on their membrane at least one modified microbial rhodopsin protein having reduced ion pumping activity compared to a natural microbial rhodopsin protein from which it is derived, and, (b) means for detecting fluorescence of the modified microbial rhodopsin protein.

In one embodiment of the cells or methods described above, the cell is a eukaryotic cell or a prokaryotic cell.

In one embodiment, the eukaryotic cell is a mammalian cell.

In another embodiment of the cell is a stem cell or a pluripotent cell, including an induced pluripotent cell or a stem cell.

In some embodiments, the cell is a progenitor cell, such as a neural progenitor or a cardiac progenitor cell.

In some embodiments, the cell is a differentiated cell, such as a neural cell or a cardiomyocyte.

In another embodiment of the cells or methods described above, the prokaryotic cell is a bacterial cell.

In one embodiment, the step of introducing comprises introducing a gene for the microbial rhodopsin or the modified rhodopsin protein into the cell.

In one and all aspects of the embodiments described herein, the cell is a eukaryotic cell. In one and all embodiments described herein, the cell does not naturally express a microbial rhodopsin.

In another embodiment of the cells or methods described above, the introducing is performed using a viral vector.

In another embodiment of the cells or methods described above, the introducing is performed using electroporation.

In other embodiments of the cells or methods described herein, the introducing is performed using lipofection, $CaPO_4$, lipid-mediated delivery (e.g., liposome, micelle etc.), transfection or transformation.

In another embodiment of the cells or methods described above, the introducing is performed in vivo into at least one cell in a subject.

In another embodiment of the cells or methods described above, the cell is genetically engineered to encode the modified microbial rhodopsin protein.

In another embodiment of the cells or methods described above, the cell is a stem cell.

In another embodiment of the cells or methods described above, the stem cell selected from the group consisting of an induced pluripotent cell, an embryonic stem cell, an adult stem cell, and a neuronal stem cell.

In another embodiment of the cells or methods described above, the modified microbial rhodopsin protein further comprises a moiety that produces an optical signal.

In another embodiment of the cells or methods described above, the modified microbial rhodopsin protein comprises an amino acid mutation compared to the natural microbial rhodopsin protein from which it is derived.

In some embodiments, the microbial rhodopsin is a proteorhodopsin.

In some embodiments, the microbial rhodopsin is Archaerhodopsin. In some embodiments, the Archaerhodopsin is Archaerhodopsin 3 (Arch3) or any of its homologues.

In another embodiment of the cells or methods described above, the modified microbial rhodopsin protein comprising a mutation is green-absorbing proteorhodopsin.

In another embodiment of the cells or methods described above, the mutation is selected from the group consisting of: D97N, E108Q, E142Q, and L217D.

In another embodiment of the cells or methods described above, the modified microbial rhodopsin protein comprising a mutation is blue-absorbing proteorhodopsin.

In another embodiment of the cells or methods described above, the mutation is D85N in bacteriorhodopsin or D99N in blue-absorbing proteorhodopsin.

In another embodiment of the cells or methods described above, the amino acid mutation is at residue V48, P49, Y57, L92, W86, I119, M145, W182, Y199, D212, and V213 in bacteriorhodopsin (e.g., a protein encoded by the nucleic acid sequence GenBank NC_010364.1, sequences 1082241-1083029, wherein the nucleotides 1082241 is designated herein as nucleic acid residue 1 or GenBank accession sequence M11720.1) or the homologous mutations in another microbial rhodopsin.

In one embodiment, the microbial rhodopsin is archaerhodopsin, such as Arh-3 (see e.g., Chow, B. Y. et al., Nature 463:98-102 (2010), which is herein incorporated by reference in its entirety). In another embodiment, the archaerhodopsin Arh-3 comprises a D95N amino acid mutation or a mutation in a homologous location of another archaerhodopsin. Other achaerhodopsins include, but are not limited to archaerhodopsin-1 and -2 found in *Halorubrum* sp. (see, e.g., Enami et al. J Mol. Biol. 2006 May 5; 358(3):675-85. Epub 2006 Mar. 3)

In another embodiment of the cells or methods described above, the modified microbial rhodopsin protein is localized to a subcellular compartment.

In another embodiment of the cells or methods described above, the modified microbial rhodopsin protein is localized to the plasma membrane, the mitochondrial inner membrane, or the mitochondrial outer membrane.

In another embodiment of the cells or methods described above, the modified microbial rhodopsin protein further comprises a targeting sequence.

In another embodiment of the cells or methods described above, the modified microbial rhodopsin protein comprises a Golgi export sequence, a membrane localization sequence, and/or an endoplasmic reticulum export sequence.

In another embodiment of the cells or methods described above, the membrane localization sequence comprises a C-terminal signaling sequence from the β2 nicotinic acetylcholine receptor.

In another embodiment of the cells or methods described above, the modified microbial rhodopsin protein further comprises a fluorescent moiety or a chromophore.

In another embodiment of the cells or methods described above, the fluorescence or optical signal is detected by fluorescence, spectral shift fluorescence resonance energy transfer (FRET), rhodopsin optical lock-in imaging (ROLI), Raman, or second harmonic generation (SHG).

In another embodiment of the cells or methods described above, the eukaryotic cell is a neuronal cell.

In another embodiment of the cells or methods described above, the modified microbial rhodopsin protein is expressed in the cell.

In another embodiment of the cells or methods described above, the modified microbial rhodopsin protein is expressed from a nucleic acid sequence encoding the modified microbial rhodopsin protein having a modified codon usage such that the codon usage is appropriate for the eukaryotic cell but the amino acid sequence remains substantially similar to the modified microbial rhodopsin protein.

In another embodiment of the cells or methods described above, the bacterial cell is an antibiotic insensitive strain of bacteria.

In another embodiment of the cells or methods described above, the rhodopsin protein further comprises a moiety that produces an optical signal.

In another embodiment of the cells or methods described above, the moiety that produces an optical signal comprises a fluorescent moiety or a chromophore.

In another embodiment of the cells or methods described above, the construct further comprises a eukaryotic promoter.

In another embodiment of the cells or methods described above, the eukaryotic promoter is an inducible promoter, or a tissue-specific promoter.

In another embodiment of the cells or methods described above, the cellular circuit comprises at least two neuronal cells.

In another embodiment of the cells or methods described above, the ion pumping activity of the modified microbial rhodopsin protein is inhibited.

In another embodiment of the cells or methods described above, the modified microbial rhodopsin has no measurable ion pumping activity.

In another embodiment of the cells or methods described above, the candidate agent inhibits, increases, or reduces the ion channel activity.

EXAMPLES

Voltage is used by biological systems to convey information on both cellular and organismal scales. Traditional voltage probes rely on electrodes to make physical contact with the cell and can be used in limited numbers. Described herein is a new class of fluorescent proteins based on microbial rhodopsins, whose fluorescence is exquisitely sensitive to the membrane potential of a cell. The probes, have a far red fluorescent excitation, a near infrared emission, a millisecond response time, and are extremely photostable.

Example 1

Proteorhodopsin as a Fluorescent Sensor of Protons

Proteorhodopsins are a large family of photoactive transmembrane proteins recently discovered in marine bacteria. Green-absorbing proteorhodopsin (GPR) is a light-driven proton pump that converts solar energy into a proton-motive force used by its host to power cellular machinery. The directional motion of a proton through GPR is accompanied by a series of dramatic color shifts in the protein. The approach of the study was to determine whether GPR could be run backward: could a transmembrane potential drive a proton through the protein and thereby alter its color? Described herein is a protein-based colorimetric indicator of membrane potential using such an approach.

A covalently bound retinylidene is the visible chromophore of GPR. A Schiff base (SB) links the retinal to the $\epsilon$-amino group of lysine 231. Early in the wild-type photocycle, a proton leaves the SB, causing a shift in the peak absorption from $\lambda_{max}$=535 nm to $\lambda_{max}$=421 nm. An increase in pH also induces this color shift and indicates that the SB has a $pK_a$>12. It was reasoned that a change in membrane potential would alter the electrochemical potential of the proton on the SB, and thereby affect the $pK_a$. The Nernst equation indicates that a $\Delta V$ of 59 mV at the SB corresponds to a $\Delta pK_a$ of 1 pH unit. If the $pK_a$ became lower than the ambient pH, the SB loses its proton and a color change would ensue. Electrochromic responses were shown to occur in bulk in the closely related protein bacteriorhodopsin when a point mutation was made to the SB counterion Asp85.

A mutation of the GPR counterion, Asp97Asn, was constructed. The mutant has been reported to not pump protons in response to light, and has a SB with $pK_a$=9.9 which is much closer to physiological pH. The purified protein undergoes a visible color change between pH 8.4 and 10.4. Although the $pK_a$ was still >2 pH units above ambient, the protein was tested as a voltage sensor. This engineered protein is referred to herein as a Proteorhodopsin Optical Proton Sensor (PROPS).

Optical absorption is insufficiently sensitive to detect color changes in the small amount of PROPS in a single cell. Therefore, a different spectroscopic readout was sought. Surprisingly, PROPS expressed in E. coli showed clearly visible fluorescence ($\lambda_{exc}$=633 nm, $\lambda_{em}$=700-750 nm) localized to the membrane. Furthermore the fluorescence of purified PROPS vanished at high pH, indicating that only the protonated SB is fluorescent with a 633 nm excitation. E. coli –PROPS/+retinal, or +PROPS/–retinal exhibited 100-fold lower fluorescence than cells +PROPS/+retinal (SOM) confirming the emission is arising from the functional protein.

PROPS has several photophysical properties that are advantageous for imaging. The red excitation and near infrared emission fall in spectral bands of little background autofluorescence. At pH 7.4, purified PROPS has fluorescence quantum yield (QY)=1.0×10$^{-3}$, while WT GPR has QY=1.3×10$^{-3}$. The low QY of PROPS is partially offset by its remarkable photostability. At a laser intensity of 350 mW/cm$^2$, PROPS photobleaches to 50% of its initial intensity in >30 minutes, while under the same measurement conditions the organic fluorophore Alexa 647 photobleaches to 50% in 24s. PROPS constitutes a new class of far-red fluorescent protein with no homology to GFP.

PROPS is Sensitive to the Local Concentration of Protons

To test the sensitivity of PROPS to protons, the protein was simultaneously imaged with the pH sensitive dye, BCECF, inside intact E. coli treated with CCCP to equalize internal and external pH. A pH titration of the fluorescence of both fluorophores shows that PROPS is indeed sensitive to protons with the fluorescence decreasing at increasing pH.

To test the response of PROPS to voltage, E. coli membranes were rendered permeable to K$^+$ by treatment with EDTA and valinomycin and subjected to shocks of KCl using a homebuilt flow chamber. Intensity differences were calculated as a function of the imposed membrane voltage. PROPS shows a clear decrease in fluorescence upon a KCl up-shock consistent with the model that higher membrane voltage lowers the fluorescence from the protonated state. Using these measurements, a ΔF/F per 100 mV of 500% was calculated. These experiments confirm that PROPS is sensitive to a linear combination of the internal pH and voltage.

E. Coli Expressing PROPS have Periodic Flashes of Fluorescence

PROPS was expressed in E. coli, the cells were immobilized on a glass coverslip, and imaged in an inverted epifluorescence microscope while gently flowing minimal medium at pH 7 over the cells. Many cells exhibited cell-wide flashes in fluorescence in which the fluorescence increased by a factor of up to 8. The flashes occurred simultaneously (to within the 10 ms imaging resolution) and homogeneously over the extent of a cell. Flashes were uncorrelated between neighboring cells.

Within a nominally homogeneous population of cells in a single microscope field of view, a variety of temporal dynamics were observed. The most common flashes had a rise time of 350 ms, a duration of 1 s and a return to baseline over 1000 ms. Many cells flashed periodically, with a typical frequency of 0.2 Hz. Some cells occasionally had "slow flashes", lasting from 20 s to 40 s. The fast and slow flashes reached the same maximum intensity. A third motif was a "ringing pattern" in which the fluorescence oscillations became smaller in amplitude and higher in frequency until the cell settled at an intermediate intensity. Some cells were quiescent for many minutes, flashed once, and then returned to darkness; others had periods of quiescence punctuated by brief bursts of flashing. Some cells were permanently bright, and some were permanently dark. Four strains of E. coli showed blinks with two different plasmids encoding PROPS (arabinose or IPTG induction). Flashing occurred in cells immobilized via poly-L-lysine, cells left to settle on an uncoated coverslip, and cells immobilized on an agarose pad. Flashing was observed on two independent microscopic imaging systems.

It was sought to determine whether flashing was induced by the expression of PROPS and/or by the laser used in imaging. The same field of cells was monitored under increasing laser power over 2 orders of magnitude. The blinking was unchanged until a threshold intensity of 100 W/cm$^2$ at which point the blinking rose dramatically. The cause of the increased blinking is unclear. The sharp increase in blinking allows two regimes of PROPS (i) monitoring endogenous activity at low powers (<50 W/cm$^2$) and (ii) enhancing activity at high powers (>100 W/cm$^2$). To increase the fraction of cells undergoing blinking, the rest of the studies were conducted in the high power regime.

It was also observed that strain JY29 showed some "sub-threshold" flashes with rise and fall times as brief as 4 ms. This observation is significant because it establishes that PROPS responds to voltage fluctuations on a timescale comparable to the duration of a neuronal action potential (1 ms). At present it is not clear whether the observed 4 ms timescale is set by the response speed of PROPS or by the intrinsic voltage dynamics in E. coli.

Flashes are Due to Swings in Voltage, not pH

PROPS are sensitive to both voltage and pH, but the transient blinks in fluorescence could be a function of the internal pH ($pH_i$), the external pH ($pH_o$), and the membrane potential (ΔV). The study sought to determine this unknown response function, and furthermore to determine whether flashing was caused by changes in $pH_i$, ΔV, or both. Independent measures of these quantities were deemed necessary.

To measure $pH_i$, cells were incubated with EDTA and a fluorescent indicator of pH, BCECF-AM. This dye is taken up by the cells and converted to a fluorescent membrane-impermeable form. The fluorescence of the BCECF and of the PROPS was simultaneously measured. The BCECF fluorescence was largely constant as $pH_o$ was varied from 6.5-9, consistent with earlier findings that E. coli maintain homeostasis of $pH_i$~7.8 over this range of $pH_o$. The PROPS baseline (non-blinking) fluorescence was also largely constant over this range of $pH_o$, indicating that the SB in PROPS is not exposed to the extracellular medium. The ionophore carbonyl cyanide m-chlorophenyl hydrazone (CCCP) was then added, which renders the cell membrane permeable to protons so that changes in $pH_o$ induce corresponding changes in $pH_i$. Both the BCECF and the PROPS fluorescence changed much more in response to changed $pH_o$, indicating that PROPS is sensitive to $pH_i$. CCCP treated cells with BCECF responded to step changes in $pH_o$ fast enough that if there were a change in $pH_i$ during a flash, a change in BCECF fluorescence would be detectable.

A fresh sample of blinking cells was prepared with EDTA and BCECF and two-color movies were recorded showing simultaneous fluorescence of BCECF and PROPS (data not shown). These cells continued to flash in the PROPS channel, but the BCECF fluorescence remained constant to within measurement error. This indicates that there is little or no change in $pH_i$ during a blink.

To correlate flashing with ΔV, PROPS fluorescence and flagellar rotation of E. coli strain JY29 were simultaneously observed. These cells have a sticky flagellum which binds to a glass coverslip, causing the cell body to rotate at an angular velocity proportional to the cellular PMF. Strain JY29 lacks CheY and thus its flagellar motor does not reverse direction. Flashes were associated with slowing or pauses of the rotation indicating that blinks occur as a lowering of the cellular PMF. Since $pH_o$ and $pH_i$ remain constant, the membrane potential must be reduced to account for the change in PMF.

Blinks are Sensitive to pH, Benzoate, and [Na$^+$] and [K$^+$].

Flashing cells were subjected to chemical perturbations in an effort to deduce the mechanism of the voltage changes. In unstirred medium in a sealed chamber, the flashing ceased over ~15 minutes; but re-started upon addition of freshly oxygenated medium. Removal of oxygen from the medium using Oxyrase also reversibly eliminated flashing. From these experiments it was concluded that flashing requires aerobic respiration. Under continuous gentle flow of aerated minimal medium, cells flashed continuously for >1 hr. Cells stored in minimal media for several days at 4° C. started flashing when warmed to room temperature.

Flashing was highly sensitive to $pH_o$, occurring only between pH 7 and 9. Flashing frequencies increased and on-time decreased at lower pH. Flashing was more likely to be periodic at lower pH. Extremes of pH (<6 or >9.5) irreversibly eliminated flashing, causing cells to enter the bright state in an abrupt transition. Addition of CCCP (20 μg/mL) rapidly and irreversibly eliminated the blinking, causing all cells to become bright.

Ionic shocks were tested to determine the ions conducted during the voltage swing. Cells in buffer containing just Na$^+$, K$^+$, Cl$^-$, and PO$_4$ were able to blink for >30 minutes at pH 7.5. Removal of just Na$^+$ or K$^+$ did not immediately stop blinking, but removal of both ions caused dramatic fluorescence changes. Likewise, a 2 M KCl shock induced dramatic effects, but a 2 M NaCl shock did not. The evidence does not point to specific ions, but rather a channel that is capable of transporting multiple types of ions. Further tests on the mechanisms of blinking and efflux are being conducted with genetic knockouts.

The development of PROPS represents an important step in molecular probes. With the advent of the optogenetic tools for controlling neural activity based on channel rhodopsin II and halorhodopsin, microbial rhodopsins have gained interest as tools for neuroscience. PROPS adds an important tool in neuroscience through its ability to probe electrical activity with light. The far red shifted excitation and emission spectra of PROPS can combine easily with current efforts of channel rhodopsin to provide fully optical control and read-out of membrane potentials.

Using the unique capabilities of PROPS spontaneous electrical activity in respiring *E. coli* was discovered. The discrete nature of the spikes is reminiscent of localization of the Crz1 protein to the nucleus of yeast during $Ca^{++}$ adaption, although the localization on yeast occurs on a much slower timescale (minutes rather than seconds.) The biological significance of electrical spiking in *E. coli* is at present unclear.

PROPS can also be used to determine (i) the molecular components and mechanisms behind bacterial blinking, (ii) the biological role that each of the three types of blinks serve, (iii) other cellular behaviors, and (iv) blinking patterns of other bacterial strains. In one embodiment, GPR is engineered to have a higher fluorescent quantum yield. GPR, its mutants, and other microbial rhodopsins are a promising family of fluorescent indicators of membrane potential. In one embodiment, PROPS and its variants may be used to monitor changes in membrane potential in other types of electrically active cells, such as neurons.

Example 2

Arch 3 can be Run Backward and Thereby Provide a Voltage Sensor

Archaerhodopsin 3 (Arch 3) from Halorubrum sodomense is a light-driven outward proton pump, capturing solar energy for its host (Ihara, K. et al. Evolution of the archaeal rhodopsins: evolution rate changes by gene duplication and functional differentiation. J. Mol. Biol. 285, 163-174 (1999)). Recently Arch 3 was expressed in mammalian neurons, wherein it enabled optical silencing of neural activity, and was shown to be minimally perturbative to endogenous function in the dark (Chow, B. Y. et al. High-performance genetically targetable optical neural silencing by light-driven proton pumps. Nature 463, 98-102 (2010)). We have now demonstrated that Arch 3 can be run backward: that a membrane potential can alter the optical properties of the protein, and thereby provide a voltage sensor that function through a mechanism similar to PROPS.

At neutral pH Arch 3 was pink, but at high pH the protein turned yellow (FIG. 8A), with a pKa for the transition of 10.1. Based on homology to other microbial rhodopsins (Lanyi, J. K. Bacteriorhodopsin. Annu. Rev. Physiol. 66, 665-688 (2004); Friedrich, T. et al. Proteorhodopsin is a light-driven proton pump with variable vectoriality. J. Mol. Biol. 321, 821-838 (2002)), we attributed the pH-induced color change to deprotonation of the Schiff Base (SB) which links the retinal chromophore to the protein core (Dioumaev, A. K. et al. Proton transfers in the photochemical reaction cycle of proteorhodopsin. Biochemistry 41, 5348-5358 (2002)). We reasoned that a change in membrane potential might change the local electrochemical potential of the proton at the SB, tipping the acid-base equilibrium and inducing a similar color shift (FIG. 6A). This mechanism of voltage-induced color shift has previously been reported in dried films of bacteriorhodopsin (Kolodner, P., Lukashev, E. P., Ching, Y. & Rousseau, D. L. Electric-field-induced Schiff-base deprotonation in D85N mutant bacteriorhodopsin. Proc. Nat. Acad. Sci. U.S.A. 93, 11618-11621 (1996)), and formed the basis of voltage sensitivity in PROPS (Kralj, J. M., Hochbaum, D. R., Douglass, A. D. & Cohen, A. E. Electrical spiking in *Escherichia coli* probed with a fluorescent voltage indicating protein. Science 333, 345-348 (2011)).

Figure 6B:
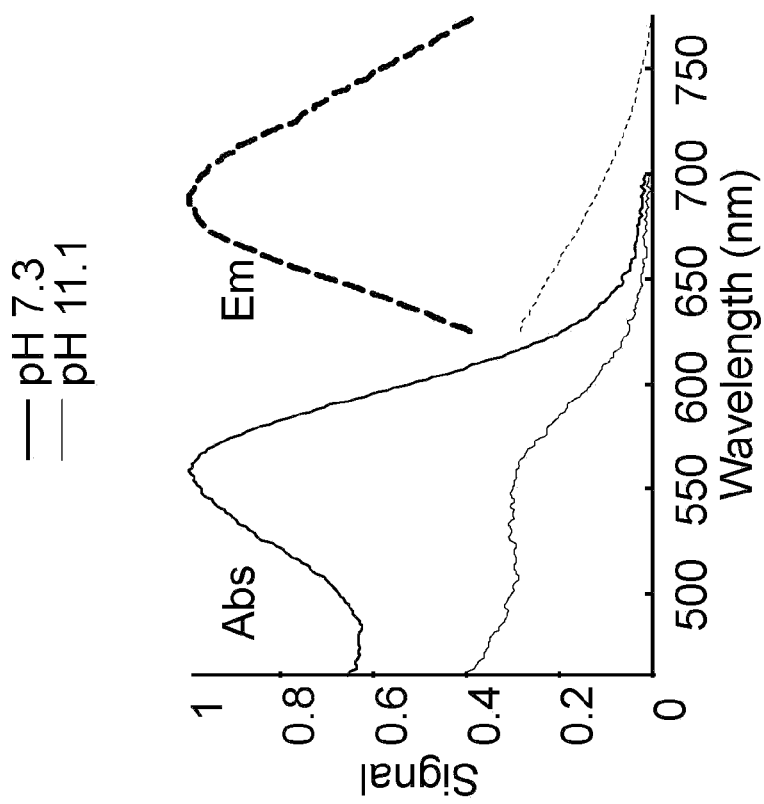

Changes in optical absorption would be challenging to detect in a single cell, due to the small quantity of protein available. However, most microbial rhodopsins are weakly fluorescent (Lenz, M. O. et al. First steps of retinal photoisomerization in proteorhodopsin. Biophys. J. 91, 255-262 (2006)), so we characterized purified Arch 3 as a prospective fluorescent indicator (Table 6). At neutral pH, Arch emitted far red fluorescence ($\lambda$em=687 nm), while at high pH Arch was not fluorescent (FIG. 6B, FIG. 17). The fluorescence quantum yield of Arch was low (9×10-4) but the photostability was comparable to members of the GFP family (Shaner, N. C., Steinbach, P. A. & Tsien, R. Y. A guide to choosing fluorescent proteins. Nat. Meth. 2, 905 (2005)), yielding approximately 25% as many photons prior to photobleaching as eGFP. The broad absorption peak enabled excitation at $\lambda$=640 nm, a wavelength where few other cellular components absorb, and the far red emission occurred in a spectral region of little background autofluorescence.

Fluorescence of Arch 3 in HEK 293 cells was readily imaged in an inverted fluorescence microscope with red illumination ($\lambda$=640 nm, I=540 W/cm$^2$), a high numerical aperture objective, a Cy5 filter set, and an EMCCD camera. The cells exhibited fluorescence predominantly localized to the plasma membrane (FIG. 6C). Cells not expressing Arch were not fluorescent. Cells showed 17% photobleaching over a continuous 10-minute exposure, and retained normal morphology during this interval.

The fluorescence of HEK cells expressing Arch was highly sensitive to membrane potential, as determined via whole-cell voltage clamp. We developed an algorithm to combine pixel intensities in a weighted sum such that the output, was a nearly optimal estimate of membrane potential V determined by conventional electrophysiology. FIG. 6C shows an example of a pixel-weight matrix, indicating that the voltage-sensitive protein was localized to the cell membrane; intracellular Arch contributed fluorescence but no voltage-dependent signal. The fluorescence increased by a factor of 2 between −150 mV and +150 mV, with a nearly linear response throughout this range (FIG. 6D). The response of fluorescence to a step in membrane potential occurred within the 500 µs time resolution of our imaging system on both the rising and falling edge (FIG. 6E). Application of a sinusoidally varying membrane potential led to sinusoidally varying fluorescence; at f=1 kHz, the fluorescence oscillations retained 55% of their low-frequency amplitude (FIG. 18). Arch reported voltage steps as small as 10 mV, with an accuracy of 625 µV/(Hz)$^{1/2}$ over timescales <12 s (FIG. 19). Over longer timescales laser power fluctuations and cell motion degraded the accuracy.

We tested Arch 3 as a voltage indicator in cultured rat hippocampal neurons, using viral delivery. Neurons expressing Arch showed voltage-dependent changes in fluorescence localized to the cell membrane. Under whole cell current clamp, cells exhibited spiking upon injection of current pulses of 200 pA. Individual spikes were accompanied by clearly identifiable increases of fluorescence (FIG. 7A). At a 2 kHz image acquisition rate, the signal-to-noise ratio in the fluorescence (spike amplitude:baseline noise) was 10.5. A spike-finding algorithm correctly identified 99.6% of the spikes (based on comparison to simultaneously recorded membrane potential), with a false-positive rate of 0.7% (n=269 spikes) (FIG. 7B). Single cells were observed for up to 4 minutes of cumulative exposure, with no detectable change in resting potential or spike frequency.

We imaged the dynamics of action potentials with subcellular resolution by averaging multiple temporally registered movies of single spikes (FIG. 7C). In and near the soma, the optically determined waveform of the action potential was uniform and matched the electrically recorded waveform. However in very thin processes the peak of the action potential lagged by up to 1 ms (FIG. 7D). These observations are consistent with multiple-patch recordings on single neurons (Stuart, G. J. & Sakmann, B. Active propagation of somatic action potentials into neocortical pyramidal cell dendrites. Nature 367, 69-72 (1994)); but such recordings are technically demanding and only probe the variation in membrane potential at a small number of points. The present results suggest that Arch may be used to map intracellular dynamics of action potentials.

In the absence of added retinal, neurons expressing Arch showed clearly identifiable fluorescence flashes accompanying individual spikes (FIG. 20), indicating that neurons contained sufficient endogenous retinal to populate some of the protein. Experiments with Arch and other microbial rhodopsins in vivo have shown that endogenous retinal is sufficient for optogenetic control of neural activity 25. Thus Arch may function as a voltage indicator in vivo without exogenous retinal.

Figure 8B:
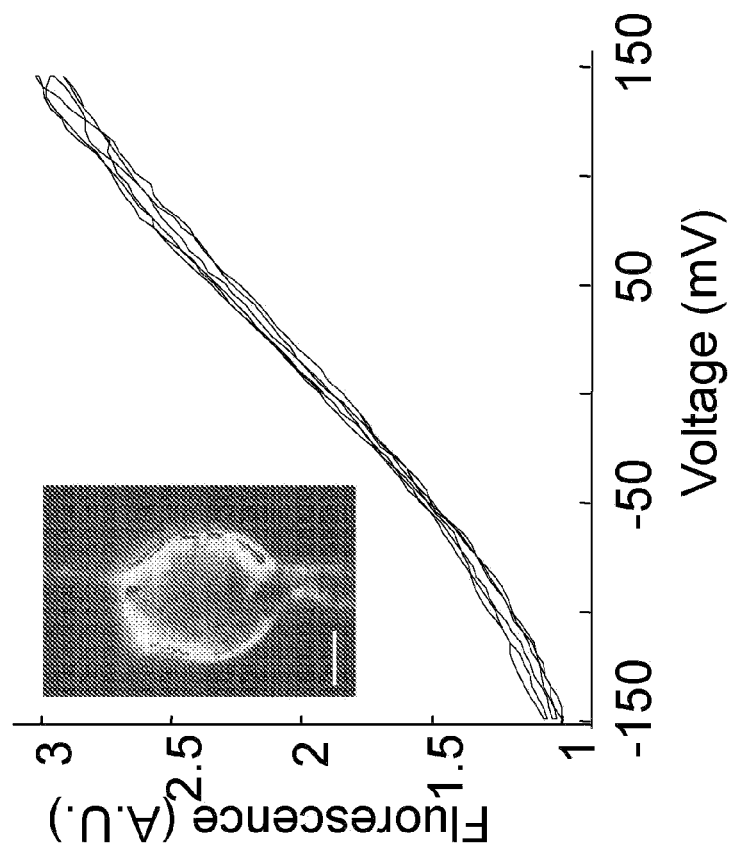
Figure 8A:
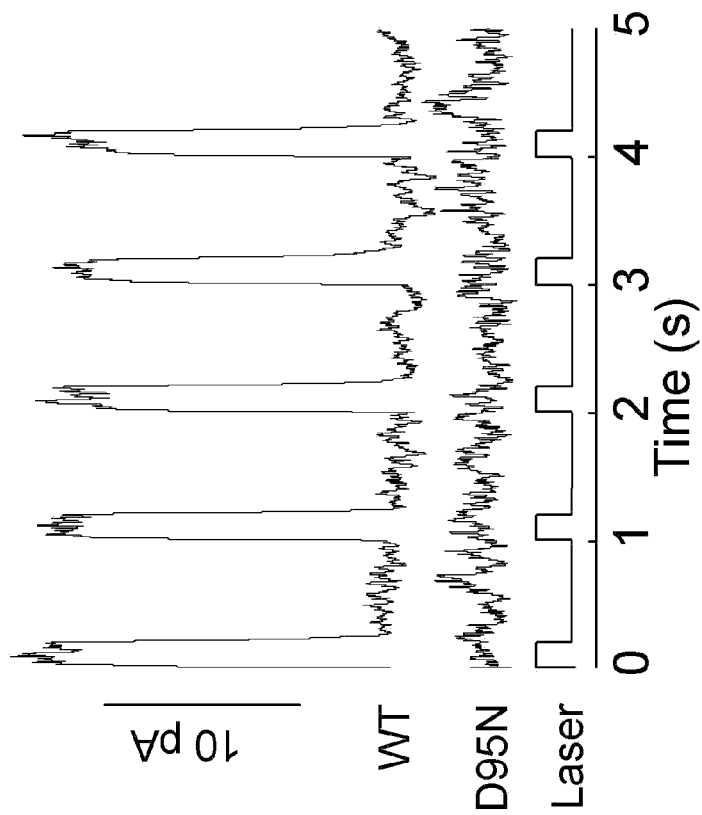

Illumination at 640 nm was far from the peak of the Arch absorption spectrum ($\lambda$=558 nm), but the imaging laser nonetheless induced photocurrents of 10-20 pA in HEK cells expressing Arch 3 (FIG. 8A). We sought to develop a mutant which did not perturb the membrane potential, yet which maintained voltage sensitivity. The mutation D85N in bacteriorhodopsin eliminated proton pumping 26, so we introduced the homologous mutation, D95N, into Arch 3. This mutation eliminated the photocurrent (FIG. 8A) and shifted several other photophysical properties of importance to voltage sensing (Table 6, FIG. 8, FIG. 21). Movies of the fluorescence response to changes in membrane potential were also taken and showed the result visually. Arch D95N was more sensitive and brighter than Arch 3 WT, but had a slower response (FIG. 8A-8C).

Figure 9B:
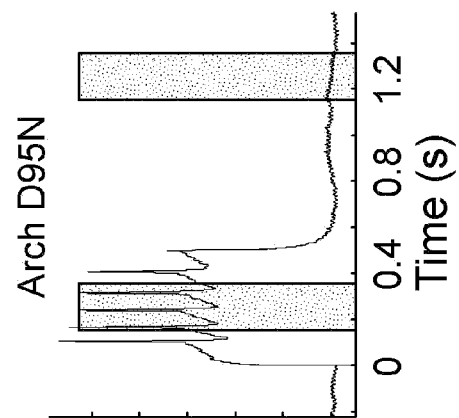

Under illumination conditions typically used for imaging neural activity (I=1800 W/cm2 in total internal reflection (TIR) mode), the light-induced outward photocurrent was typically 10 pA in neurons expressing Arch 3 WT. Under current-clamp conditions this photocurrent shifted the resting potential of the neurons by up to −20 mV. For neurons near their activation threshold, this photocurrent could suppress firing (FIG. 9A), so we explored the non-pumping variant D95N as a voltage indicator in neurons. Illumination of Arch D95N did not perturb membrane potential in neurons (FIG. 9B).

Figure 9C:
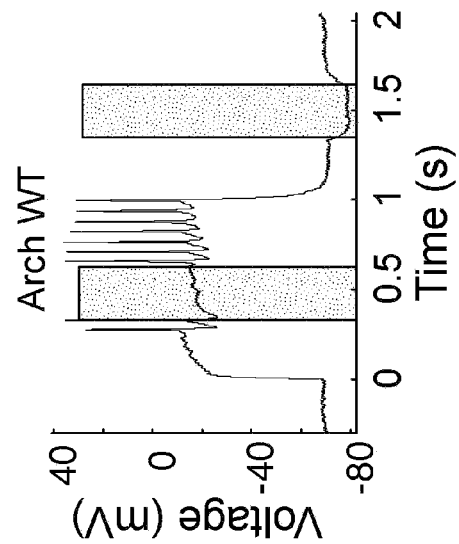

Arch 3 D95N reported neuronal action potentials on a single-trial basis (FIG. 9C). The response to a depolarizing current pulse was dominated by the slow component of the step response; yet the fast component of the response was sufficient to indicate action potentials.

Protein Purification

A lentiviral backbone plasmid encoding Arch 3-EGFP (FCK:Arch 3-EGFP) was a generous gift from Dr. Edward Boyden (MIT). The gene for the rhodopsin was cloned into pet28b vector using the restriction sites EcoRI and NcoI. The D95N mutation was created using the QuikChange11 kit (Agilent) using the forward primer (5'-TTATGCCAGGTACGC-CAACTGGCTGTTTACCAC) (SEQ ID NO: 22) and the reverse primer (5'-GTGGTAAACAGCCAGTTGGCGTAC-CTGGCATAA) (SEQ ID NO: 23).

Arch and its D95N mutant were expressed and purified from E. coli, following Bergo, V., et al. (Conformational changes detected in a sensory rhodopsin II-transducer complex. J. Biol. Chem. 278, 36556-36562 (2003)). Briefly, E. coli (strain BL21, pet28b plasmid) was grown in 1 L of LB with 100 µg/mL kanamycin, to an O.D 600 of 0.4 at 37° C. All-trans retinal (5 µM) and inducer (IPTG 0.5 mM) were added and cells were grown for an additional 3.5 hours in the dark. Cells were harvested by centrifugation and resuspended in 50 mM Tris, 2 mM $MgCl_2$ at pH 7.3 and lysed with a tip sonicator for 5 minutes. The lysate was centrifuged and the pellet was resuspended in PBS supplemented with 1.5% dodecyl maltoside (DM). The mixture was homogenized with a glass/teflon Potter Elvehjem homogenizer and centrifuged again. The supernatant was concentrated and washed using a centricon 30k MWCO filter to a final volume of 3 mL.

Spectroscopic Characterization of Arch WT and D95N

The absorption spectra of purified Arch 3 WT and D95N were determined using an Ocean Optics USB4000 spectrometer with a DT-MINI-2-GS light source. Absorption spectra, for Arch 3 WT and D95N, were measured as a function of pH between pH 6 and 11. To determine the fluorescence emission spectra, proteins in a quartz cuvette were illuminated with the uncollimated beam of a 100 mW, 532 nm laser (Dragon Lasers, 532GLM100) or a 25 mW, 633 nm HeNe laser (Spectra-Physics). Scattered laser light was blocked with a 532 nm Raman notch filter (Omega Optical, XR03) or a 710/100 emission filter (Chroma), and fluorescence was collected perpendicular to the illumination with a 1000 micron fiber, which passed the light to an Ocean Optics QE65000 spectrometer. Spectra were integrated for 2 seconds.

The fluorescence quantum yields of Arch 3 WT and D95N were determined by comparing the integrated emission intensity to emission of a sample of the dye ALEXA FLUOR® 647 Conjugate. Briefly, the concentrations of micromolar solutions of dye and protein were determined using a visible absorption spectrum. We used the extinction coefficients of 270,000 $M^{-1}$ $cm^{-1}$ for ALEXA FLUOR® 647 and 63,000 $M^{-1}$ $cm^{-1}$ for Arch 3 WT and D95N, assuming that these microbial rhodopsins have the same extinction coefficient as bacteriorhodopsin. The dye solution was then diluted 1:1000 to yield a solution with comparable fluorescence emission to the Arch 3. The fluorescence emission spectra of dye and protein samples were measured with 633 nm excitation. The quantum yield was then determined by the formula $$QY_{Arch} = \frac{Fl_{Arch}}{Fl_{Alexa}} * \frac{\varepsilon_{Alexa}}{\varepsilon_{Arch}} * \frac{c_{Alexa}}{c_{Arch}} * QY_{Alexa}$$

where Fl is the integrated fluorescence from 660 to 760 nm, $\varepsilon$ is the extinction coefficient at 633 nm and c is the concentration.

Relative Photostability of Arch 3 and eGFP

To perform a direct comparison of photostability of Arch 3 and eGFP we studied the photobleaching of the Arch 3-eGFP fusion. This strategy guaranteed a 1:1 stoichiometry of the two fluorophores, simplifying the analysis. The experiments were performed on permeabilized cells, in the microscope, with video recording as the cells photobleached. We first recorded a movie of photobleaching of Arch 3 under 640 nm illumination; then on the same field of view we recorded photobleaching of eGFP under 488 nm illumination, with illumination intensity adjusted to yield approximately the same initial count rate as for Arch 3. Fluorescence background levels were obtained from nearby protein-free regions of each movie and were subtracted from the intensity of the protein-containing regions. The area under each photobleaching timetrace was calculated, yielding an estimate of the total number of detected photons from each fluorophore. The eGFP emission ($\lambda_{max}$=509 nm) and the Arch emission ($\lambda_{max}$=687 nm) were collected through different emission filters, so the raw counts were corrected for the transmission spectra of the filters and the wavelength-dependent quantum yield of the EMCCD camera. The result was that the relative number of photons emitted prior to photobleaching for eGFP: Arch 3 WT was 3.9:1, and for eGFP:Arch D95N this ratio was 10:1.

HEK Cell Culture

HEK-293 cells were grown at 37° C., 5% $CO_2$, in DMEM supplemented with 10% FBS and penicillin-streptomycin. Plasmids were transfected using LIPOFECTAMINE™ and PLUS reagent (Invitrogen) following the manufacturer's instructions, and assayed between 48-72 hours later. The day before recording, cells were re-plated onto glass-bottom dishes (MatTek) at a density of ~5000 cells/cm².

The concentration of endogenous retinal in the HEK cells was not known, so the cells were supplemented with retinal by diluting stock retinal solutions (40 mM, DMSO) in growth medium to a final concentration of 5 μM, and then placing the cells back in the incubator for 1-3 hours. All imaging and electrophysiology were performed in Tyrode's buffer (containing, in mM: 125 NaCl, 2 KCl, 3 $CaCl_2$, 1 $MgCl_2$, 10 HEPES, 30 glucose pH 7.3, and adjusted to 305-310 mOsm with sucrose). Only HEK cells having reversal potentials between −10 and −40 mV were included in the analysis.

Microscopy

Simultaneous fluorescence and whole-cell patch clamp recordings were acquired on a home-built, inverted epifluorescence microscope at room temperature. A diode laser operating at 100 mW, 640 nm (CrystaLaser, DL638-100-O) provided wide-field illumination at an intensity typically between 500-2000 W/cm². To minimize background signal from out-of-focus debris, illumination was often performed in through-the-objective total internal reflection fluorescence (TIRF) mode. Fluorescence emission was collected using a 60×, 1.45 NA oil immersion objective (Olympus), and separated from scattered excitation using a 660-760 nm bandpass emission filter (Chroma). For fast imaging of dynamic fluorescence responses and action potentials, images were acquired on an Andor iXon⁺ 860 camera operating at up to 2,000 frames/s (using a small region of interest and pixel binning). Slower images with higher spatial resolution were acquired on an Andor iXon⁺ 897 EMCCD. Custom software written in LabView (National Instruments) was used to synchronize illumination, collection of images, recording of membrane potential and cell current, and application of electrical stimuli to the cell.

Electrophysiology

Filamented glass micropipettes (WPI) were pulled to a tip resistance of 3-10 MΩ, fire polished, and filled with internal solution (containing, in mM: 125 Potassium gluconate, 8 NaCl, 0.6 $MgCl_2$, 0.1 $CaCl_2$, 1 EGTA, 10 HEPES, 4 Mg-ATP, 0.4 Na-GTP, pH 7.3; adjusted to 295 mOsm with sucrose). The micropipettes were positioned with a Burleigh PCS 5000 micromanipulator. Whole-cell, voltage clamp recordings were acquired using an AxoPatch 200B amplifier (Molecular Devices), filtered at 2 kHz with the internal Bessel filter, and digitized with a National Instruments PCIE-6323 acquisition board at 10 kHz. Ambient 60 Hz noise was removed using a HumBug Noise Eliminator (AutoMate Scientific). For experiments requiring rapid modulation of transmembrane potential, series resistance and whole-cell capacitance were predicted to 95% and corrected to ~50%. Electrical stimuli were generated using the PCIE-6323 acquisition board and sent to the AXOPATCH™, which then applied these signals in either constant current or constant voltage mode.

Measurements of photocurrents were performed on HEK cells held in voltage clamp at 0 mV while being exposed to brief (200 ms) pulses of illumination at 640 nm at an intensity of 1800 W/cm².

All experiments were performed at room temperature.

Estimates of Membrane Potentials from Fluorescence Images

A common practice in characterizing fluorescent voltage indicators is to report a value of ΔF/F per 100 mV of membrane potential. We feel that this parameter is of limited use, for several reasons. First, the value of ΔF/F is highly sensitive to the method of background subtraction, particularly for indicators in which F approaches zero at some voltage. Second, ΔF/F contains no information about signal-to-noise ratio: one indicator may have small values of F and of ΔF and another may have large values, but the ratio ΔF/F might be the same. Third, the ratio ΔF/F contains no information about the temporal stability of the fluorescence. Fluctuations may arise due to intracellular transport, photobleaching, or other photophysics.

We therefore sought a measure of the performance of a voltage indicator which reported the information content of the fluorescence signal. We sought an algorithm to infer membrane potential from a series of fluorescence images. We used the accuracy with which the estimated membrane potential matched the true membrane potential (as reported by patch clamp recording) as a measure of indicator performance.

The estimated membrane potential, $\hat{V}_{FL}(t)$, was determined from the fluorescence in two steps. First we trained a model relating membrane potential to fluorescence at each pixel. We used the highly simplified model that the fluorescence signal, $S_i(t)$, at pixel i and time t, is given by:

$$S_i(t)=a_i+b_i V(t)+\epsilon_i(t), \quad [S1]$$

where $a_i$ and $b_i$ are position-dependent but time-independent constants, the membrane potential V(t) is time-dependent but position independent, and $\epsilon_i(t)$ is spatially and temporally uncorrelated Gaussian white noise with pixel-dependent variance:

$$\langle \epsilon_i(t_1)\epsilon_j(t_2)\rangle = \sigma_i^2 \delta_{i,j}\delta(t_1-t_2),$$

where $\langle\ \rangle$ indicates an average over time.

This model neglects nonlinearity in the fluorescence response to voltage, finite response time of the protein to a change in voltage, photobleaching, cell-motion or stage drift, and the fact that if $\epsilon_i(t)$ is dominated by shot-noise then its variance should be proportional to $S_i(t)$, and its distribution should be Poisson, not Gaussian. Despite these simplifications, the model of Eq. S1 provided good estimates of membrane potential when calibrated from the same dataset to which it was applied.

The pixel-specific parameters in Eq. 1 are determined by a least-squares procedure, as follows. We define the deviations from the mean fluorescence and mean voltage by $$\delta S_i(t)=S_i(t)-\langle S_i(t)\rangle$$

$$\delta V(t)=V(t)-\langle V(t)\rangle.$$

Then the estimate for the slope $\hat{b}_i$ is:

$$\hat{b}_i = \frac{\langle \delta S_i \delta V\rangle}{\langle \delta V^2\rangle},$$

and the offset is:

$$\hat{a}_i = \langle S_i \rangle - \hat{b}_i \langle V \rangle.$$

A pixel-by-pixel estimate of the voltage is formed from:

$$\hat{V}_i(t) = \frac{S_i(t)}{\hat{b}_i} - \frac{\hat{a}_i}{\hat{b}_i}.$$

The accuracy of this estimate is measured by $$\varsigma_i^2 = \langle (\hat{V}_i(t) - V(t))^2 \rangle.$$

A maximum likelihood weight matrix is defined by:

$$w_i \equiv \frac{1/\varsigma_i^2}{\sum_i 1/\varsigma_i^2}. \quad [S2]$$

This weight matrix favors pixels whose fluorescence is an accurate estimator of voltage in the training set.

To estimate the membrane potential, the pixel-by-pixel estimates are combined according to:

$$\hat{V}_{FL}(t) = \sum_i w_i \hat{V}_i(t) \quad [S3]$$

Within the approximations underlying Eq. S1, Eq. S3 is the maximum likelihood estimate of V(t).

Ramp and Step-Response of Arch 3 WT and D95N

To measure fluorescence as a function of membrane potential, a triangle wave was applied, with amplitude from −150 mV to +150 mV and period 12 s, with video recording at 100 ms per frame. A pixel weight matrix was calculated according to Eq. S2 and applied to the movie images to generate a fluorescence number for each frame. These fluorescence values were divided by their minimum value (at V=−150 mV). The result is plotted as a function of V in FIGS. 7 and 8. This procedure preferentially weighted data from pixels at the cell membrane, but did not entail any background subtraction. Comparable results were obtained by manually selecting pixels corresponding to a region of plasma membrane, and plotting their intensity as a function of V, without background subtraction. Background subtraction from the raw fluorescence would have yielded considerably larger values of ΔF/F.

The step response was measured in a similar manner, except that test waveforms consisted of a series of voltage pulses, from −70 mV to +30 mV with duration 300 ms and period 1 s. Cells were subjected to 20 repetitions of the waveform, and the fluorescence response was averaged over all iterations.

Frequency-dependent Response Functions of Arch 3 WT and D95N

Test waveforms consisted of a concatenated series of sine waves, each of duration 2 s, amplitude 100 mV, zero mean, and frequencies uniformly spaced on a logarithmic scale between 1 Hz and 1 kHz (31 frequencies total). The waveforms were discretized at 10 kHz and applied to the cell, while fluorescence movies were acquired at a frame rate of 2 kHz.

The model parameters for extracting $\hat{V}_{FL}(t)$ were calculated from the fluorescence response to low frequency voltages. These parameters were then used to calculate an estimated voltage at all frequencies.

The applied voltage was downsampled to 2 kHz to mimic the response of a voltage indicator with instantaneous response. For each applied frequency, the Fourier transform of $\hat{V}_{FL}(t)$ was calculated and divided by the Fourier transform of the downsampled V(t). The amplitude of this ratio determined the response sensitivity. It was crucial to properly compensate pipette resistance and cell membrane capacitance to obtain accurate response spectra. Control experiments on cells expressing membrane-bound GFP showed no voltage-dependent fluorescence.

The power spectrum of $\hat{V}_{FL}(t)$ under constant V=0 was also measured to enable calculations of signal-to-noise ratio for any applied V(t).

Molecular Biology and Virus Production

Plasmids encoding Arch-EGFP (FCK:Arch-EGFP) were either used directly for experiments in HEK cells, or first used to produce VSVg-pseudotyped virus according to published methods (Chow, B. Y. et al. High-performance genetically targetable optical neural silencing by light-driven proton pumps. Nature 463, 98-102 (2010)). For pseudotyping, HEK-293 cells were co-transfected with pDelta 8.74, VSVg, and either of the Arch backbone plasmids using LIPO-FECTAMINE and PLUS reagent (Invitrogen). Viral supernatants were collected 48 hours later and filtered using a 0.45 μm membrane. The virus medium was used to infect neurons without further concentration.

The D95N mutation was introduced using the QUICK-CHANGE® kit (Stratagene), according to the manufacturer's instructions using the same primers as the *E. coli* plasmid.

Neuronal Cell Culture

E18 rat hippocampi were purchased from BrainBits and mechanically dissociated in the presence of 1 mg/mL papain (Worthington) before plating at 5,000-30,000 cells per dish on poly-L-lysine and Matrigel-coated (BD Biosciences) glass-bottom dishes. Cells were incubated in N+ medium (100 mL Neurobasal medium, 2 mL B27 supplement, 0.5 mM glutamine, 25 μM glutamate, penicillin-streptomycin) for 3 hours. An additional 300 μL virus medium was added to the cells and incubated overnight, then brought to a final volume of 2 mL N+ medium. After two days, cells were fed with 1.5 mL N+ medium. Cells were fed with 1 mL N+ medium without glutamate at 4 DIV, and fed 1 mL every 3-4 days after. Cells were allowed to grow until 10-14 DIV at which point they were used for experiments.

Whole-cell current clamp recordings were obtained from mature neurons under the same conditions used for HEK cells recordings. Series resistance and pipette capacitance were corrected. Only neurons having resting potentials between −50 and −70 mV were used in the analysis.

Spike Sorting

A spike identification algorithm was developed that could be applied either to electrically recorded V(t) or to optically determined $\hat{V}(t)$. The input trace was convolved with a reference spike of duration 10 ms. Sections of the convolved waveform that crossed a user-defined threshold were identified as putative spikes. Multiple spikes that fell within 10 ms (a consequence of noise-induced glitches near threshold) were clustered and identified as one.

Table 6 shows Optical and electrical response of Arch 3 WT and Arch D95N.

TABLE 6

| | $\lambda_{max}$ abs (nm) | $\lambda_{max}$ em[1] (nm) | $\epsilon_{633}$[2] (M$^{-1}$cm$^{-1}$) | QY[3] | Photostability relative to eGFP[4] | pK$_a$ of SB[5] | $\tau_{response}$[6] (ms) | Noise in $\hat{V}_{FL}$[7] ($\mu$V/Hz$^{1/2}$) | Photo-current |
|---|---|---|---|---|---|---|---|---|---|
| Arch WT | 558 | 687 | 6,300 | $9 \times 10^{-4}$ | 0.25 | 10.1 | <0.5 | 625 | yes |
| Arch D95N | 585 | 687 | 37,500 | $4 \times 10^{-4}$ | 0.1 | 8.9 | 41 | 260 | no |

[1]Excitation at X = 532 nm.
[2]Absorption spectra calibrated assuming the same peak extinction coefficient as Bacteriorhodopsin, 63,000 M$^{-1}$ cm$^{-1}$ (Ref.[32]).
[3]Determined via comparison to Alexa 647 with excitation at $\lambda$ = 633 nm.
[4]Measured in a 1:1 fusion with eGFP.
[5]Determined via singular value decomposition on absorption spectra.
[6]Determined from step-response. Arch D95N has a minor component of its response (20%) that is fast (<0.5 ms).
[7]$\hat{V}_{FL}$ is the membrane potential estimated from fluorescence. Noise determined at frequencies f ≥ 0.1 Hz in HEK cells.

The references cited throughout the specification and examples are hereby incorporated by reference in their entirety.

We claim:

1. A method for measuring membrane potential in a cell expressing a nucleic acid encoding a microbial rhodopsin protein, the method comprising the steps of:

a. exciting, in vitro, at least one cell comprising a nucleic acid encoding a microbial rhodopsin protein with light of at least one wave length; and b. detecting, in vitro, at least one optical signal from the at least one cell, wherein the level of fluorescence emitted by the at least one cell compared to a reference is indicative of the membrane potential of the cell.

2. The method of claim 1, wherein the microbial rhodopsin protein comprises: a mutation to a carboxylic amino acid on a third transmembrane helix of the microbial rhodopsin protein; and reduced ion pumping activity compared to a natural microbial rhodopsin protein from which it is derived.

3. The method of claim 2, wherein the carboxylic amino acid on the third transmembrane helix of the natural microbial rhodopsin comprises a proton acceptor proximal to a Schiff base.

4. The method of claim 1, wherein the microbial rhodopsin protein is a member of the proteorhodopsin family of proteins or a member of the archaerhodopsin family of proteins.

5. The method of claim 1, wherein the at least one wavelength is a wavelength between $\lambda=594-645$ nm.

6. The method of claim 1, wherein the cell is selected from the group consisting of a prokaryotic cell, a eukaryotic cell, a mammalian cell, a stem cell or a pluripotent or a progenitor cell, an induced pluripotent cell, a neuron, and a cardiomyocyte.

7. The method of claim 1 further comprising a step of transfecting, in vitro, the at least one cell with a vector comprising the nucleic acid encoding the microbial rhodop sin protein.

8. The method of claim 1, wherein the nucleic acid encoding the microbial rhodopsin protein is operably linked to a cell-type specific promoter.

9. The method of claim 1, wherein the nucleic acid encoding the microbial rhodopsin protein is operably linked to a membrane-targeting nucleic acid sequence.

10. The method of claim 9, wherein the membrane-targeting nucleic acid is a plasma membrane targeting nucleic acid sequence or a subcellular compartment-targeting nucleic acid sequence.

11. The method of claim 1, wherein the nucleic acid encoding a microbial rhodopsin protein is operably linked to a nucleic acid encoding at least one additional fluorescent protein or a chromophore.

12. The method of claim 11, wherein the at least one additional fluorescent protein is selected from the group consisting of: a green fluorescent protein, mOrange2, and eGFP.

13. The method of claim 11 further comprising steps of exciting, in vitro, the at least one cell with light of at least a first and a second wavelength; and detecting, in vitro, the at least first and the second optical signal resulting from the excitation with the at least the first and the second wavelength from the at least one cell.

14. The method of claim 13, wherein the at least second wave length is between $\lambda=447-594$ nm.

15. The method of claim 1, further comprising a step of calculating the ratio of the fluorescence emission from the microbial rhodopsin to the fluorescence emission of the at least one additional fluorescent protein to obtain a measurement of membrane potential independent of variations in expression level.

16. The method of claim 1 further comprising the step of exposing, in vitro, the at least one cell to a stimulus capable of, or suspected to be capable of changing membrane potential.

17. The method of claim 1 further comprising the step of measuring, in vitro, the at least one optical signal at a first and at least at a second time point.

18. The method of claim 17, wherein the first time point is before exposing the at least one cell to a stimulus and the at least second time point is after exposing the at least one cell to the stimulus.

19. A method for measuring membrane potential in a cell expressing a nucleic acid encoding a microbial rhodopsin protein, the method comprising the steps of:
   a. exciting at least one cell comprising a nucleic acid encoding a microbial rhodopsin protein with light of at least one wave length; and
   b. detecting at least one optical signal from the at least one cell, wherein the level of fluorescence emitted by the at least one cell compared to a reference is indicative of the membrane potential of the cell.

20. The method of claim 19, wherein the microbial rhodop sin protein comprises: a mutation to a carboxylic amino acid on a third transmembrane helix of the microbial rhodopsin protein; and reduced ion pumping activity compared to a natural microbial rhodopsin protein from which it is derived.

21. The method of claim 20, wherein the carboxylic amino acid on the third transmembrane helix of the natural microbial rhodopsin comprises a proton acceptor proximal to a Schiff Base.

22. The method of claim 19, wherein the microbial rhodopsin protein is a member of the proteorhodop sin family of proteins or a member of the archaerhodop sin family of proteins.

23. The method of claim 19, wherein the at least one wave length is a wave length between $\lambda=594-645$ nm.

24. The method of claim 19, wherein the cell is a eukaryotic cell.

25. The method of claim 24, wherein the eukaryotic cell is a mammalian cell.

26. The method of claim 24, wherein the eukaryotic cell is selected from a stem cell, a pluripotent cell, a progenitor cell, an induced pluripotent cell, a neuronal cell, and a cardiomyocyte.

27. The method of claim 19, wherein the nucleic acid encoding a microbial rhodopsin protein is operably linked to a nucleic acid encoding at least one additional fluorescent protein or a chromophore.

28. The method of claim 27, wherein the at least one additional fluorescent protein is a fluorescent protein capable for indicating the ion concentration in the cell.

29. The method of claim 27, wherein the at least one additional fluorescent protein is selected from the group consisting of: a green fluorescent protein, mOrange2, and eGFP.

30. The method of claim 27 further comprising steps of exciting the at least one cell with light of at least a first and a second wavelength; and detecting the at least first and the second optical signal resulting from the excitation with the at least the first and the second wavelength from the at least one cell.

31. The method of claim 30, wherein the at least second wave length is between $\lambda=447-594$ nm.

32. The method of claim 27, further comprising a step of calculating the ratio of the fluorescence emission from the microbial rhodopsin to the fluorescence emission of the at least one additional fluorescent protein to obtain a measurement of membrane potential independent of variations in expression level.

33. The method of claim 19 further comprising the step of exposing the at least one cell to a stimulus capable of, or suspected to be capable of changing membrane potential.

34. The method of claim 19, further comprising the step of measuring, in vitro, the at least one optical signal at a first and at least at a second time point.

35. The method of claim 34, wherein the first time point is before exposing the at least one cell to a stimulus and the at least second time point is after exposing the at least one cell to the stimulus.

* * * * *